United States Patent
Jin

(10) Patent No.: US 10,724,049 B2
(45) Date of Patent: Jul. 28, 2020

(54) CONTROLLING FUNGAL PATHOGENS BY DISABLING THEIR SMALL RNA PATHWAYS USING RNAI-BASED STRATEGY

(71) Applicant: The Regents of the University of California, Oakland, CA (US)

(72) Inventor: Hailing Jin, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 630 days.

(21) Appl. No.: 14/809,063

(22) Filed: Jul. 24, 2015

(65) Prior Publication Data

US 2016/0032314 A1    Feb. 4, 2016

Related U.S. Application Data

(60) Provisional application No. 62/028,776, filed on Jul. 24, 2014, provisional application No. 62/153,440, filed on Apr. 27, 2015.

(51) Int. Cl.
C12N 15/82    (2006.01)
C12N 15/113    (2010.01)

(52) U.S. Cl.
CPC ........ *C12N 15/8282* (2013.01); *C12N 15/113* (2013.01); *C12N 15/8218* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 6,353,155 B1 * | 3/2002 | Kloti | C12N 15/8205 435/419 |
| 6,495,133 B1 | 12/2002 | Xue et al. | |
| 6,653,535 B1 | 11/2003 | Tarczynski | |
| 7,834,243 B2 | 11/2010 | Schweizer | |
| 8,148,604 B2 * | 4/2012 | Niblett | C12N 15/8218 800/279 |
| 8,865,968 B2 * | 10/2014 | Van De Craen | A01N 63/02 536/24.5 |
| 2003/0221211 A1 | 11/2003 | Rottmann | |
| 2004/0029283 A1 | 2/2004 | Fillatti | |
| 2009/0300796 A1 * | 12/2009 | Raemaekers | C12N 15/8218 800/279 |
| 2011/0061128 A1 * | 3/2011 | Roberts | C12N 15/8282 800/279 |
| 2011/0119788 A1 | 5/2011 | Rodriguez Baixauli et al. | |
| 2014/0283211 A1 | 9/2014 | Crawford et al. | |
| 2015/0089688 A1 | 3/2015 | Jacobs et al. | |
| 2015/0203865 A1 | 7/2015 | Jin | |

FOREIGN PATENT DOCUMENTS

| | | |
|---|---|---|
| EP | 1 888 754 | 5/2011 |
| EP | 2698379 A1 | 2/2014 |
| WO | 2012155109 A1 | 11/2012 |
| WO | 2013/025670 A1 | 2/2013 |
| WO | 2014/033723 A1 | 3/2014 |

OTHER PUBLICATIONS

Nicolas et al (Fungal Genet Biol., 2007, 44: 504-516).*
Kadotani et al (J Biol Chem., 2004, 279: 44467-44474).*
Bernstein et al (PNAS, 2012, 109: 523-528).*
Segers et al (PNAS, 2007, 104:12902-12906).*
Drinnenberg et al (Science, 2009, 326: 544-550).*
Catalanotto et al (Mol Cell Biol., 2004, 24(6): 2536-2545).*
Weiberg et al (Science, 2013, 342(6154), 118-123; and supplemental materials).*
GenBank XM_001551139 (published 2008; see alignment in Office action).*
GenBank XP_001551189 (published 2008; see sequence appended below).*
Yoshinari et al (Nucleic Acid Res. 2004, 32(2): 691-699) (Year: 2004).*
UniProt M7U651_BOTF1 (published May 29, 2013; see sequence in Office Action) (Year: 2013).*
UniProt G2WQ29_VERDV (published online Nov. 16, 2011; see sequence in Office Action) (Year: 2011).*
UniProt G2XA42_VERDV (published online Nov. 16, 2011; see sequence in Office Action) (Year: 2011).*
UniProt M7U4R4_BOTF1 (published May 29, 2013; see sequence in Office Action) (Year: 2013).*
Deleris et al., "Hierarchical Action and Inhibition of Plant Dicer-Like Proteins in Antiviral Defense", Science AAAS, vol. 313, No. 5783;, Jun. 1, 2006, pp. 68-71. PCT/US2016/029560 , "International Search Report and Written Opinion", dated Jul. 14, 2016, 10 pages.
Ashida H. et al., "Shigella deploy multiple countermeasures against host innate immune responses" *Curr. Opin. Microbiol.* 14, 16-23 (2011).
Bozkurt T.O. et al., "Oomycetes, effectors, and all that jazz" *Curr. Opin. Plant Biol.* 15, 483-492 (2012).
Dean et al., "The Top 10 fungal pathogens in molecular plant pathology," Mol Plant Pathol (2012) 13(4):414-430.
Ellendorff U. et al., "RNA silencing is required for *Arabidopsis* defence against Verticillium wilt disease" *J. Exp. Bot.* 60, 591 (2009).

(Continued)

*Primary Examiner* — Stephen Uyeno
(74) *Attorney, Agent, or Firm* — Kilpatrick Townsend & Stockton LLP

(57) ABSTRACT

The present invention relates to pathogen-resistant plants. In one aspect, plants comprising a heterologous expression cassette are provided, wherein the expression cassette comprises a polynucleotide that inhibits expression of a fungal pathogen dicer-like (DCL) gene and wherein the plant has increased resistance to a fungal pathogen compared to a control plant lacking the expression cassette. Methods of making and cultivating pathogen-resistant plants are also provided.

21 Claims, 18 Drawing Sheets
(18 of 18 Drawing Sheet(s) Filed in Color)
Specification includes a Sequence Listing.

(56) References Cited

OTHER PUBLICATIONS

Gan et al., "Bacterially expressed dsRNA protects maize against SCMV infection," *Plant Cell Reports* 29(11):1261-1268 (2010).
Govindarajulu et al., "Host-induced gene silencing inhibits the biotrophic pathogen causing downy mildew of lettuce," *Plant Biotechnology Journal* (2015) 13(7):875-883.
Hilbi H. et al., "Secretive Bacterial Pathogens and the Secretory Pathway" *Traffic* 13, 1187 (2012).
Jiang N, Yan Y, Janbon G, Pan J, Zhu X."Identification and functional demonstration of miRNAs in the fungus *Cryptococcus neoformans*" *PLoS One*. 2012; 7:e52734.
Katiyar-Agarwal S, Jin H., "Role of small RNAs in host-microbe interactions" *Annu Rev Phytopathol.* 2010; 48:225-226.
Lee HC et al. "Diverse pathways generate microRNA-like RNAs and Dicer-independent small interfering RNAs in fungi" *Mol Cell.* 2010; 38:803-814.
Lu et al., "RNA silencing in plants by the expression of siRNA duplexes," *Nucleic Acids Res*. 32(21):e171 (2004).
Mi S.J. et al., "Sorting of Small RNAs into *Arabidopsis* Argonaute Complexes is Directed by the 50 Terminal Nucleotide" Cell 133, 116 (2008).
Montgomery T.A. et al., "Specificity of ARGONAUTE7-miR390 Interaction and Dual Functionality in TAS3 Trans-Acting siRNA Formation" *Cell* 133, 128 (2008).
Nowara et al., "HIGS: Host-Induced Gene Silencing in the Obligate Biotrophic Fungal Pathogen Blumeria graminis," *Plant Cell* (2010) 22(9):3130-3141.
Nunes CC et al. "Diverse and tissue-enriched small RNAs in the plant pathogenic fungus, *Magnaporthe oryzae*" *MBC Genomics*. 2011; 12:288.
Nunes et al., "Host-induced gene silencing: a tool for understanding fungal host interaction and for developing novel disease control strategies," *Mol Plant Pathol* (2012) 13(5):519-529.
Qutob D, Patrick Chapman B, Gijzen M., "Transgenerational gene silencing causes gain of virulence in a plant pathogen" *Nature Comm.* 2013; 4:1349.
Rafiqi M. et al., "Challenges and progress towards understanding the role of effectors in plant—fungal interactions" *Curr. Opin. Plant Biol*. 15, 477-482 (2012).
Raman V et al. "Physiological stressors and invasive plant infections alter the small RNA transcriptome of the rice blast fungus, *Magnaporthe oryzae*" *MBC Genomics.* 2011; 14:326.
Ruiz-Ferrer V, Voinnet O. "Roles of plant small RNAs in biotic stress responses" *Annu Rev Plant Biol*. 2009, 60:485-510.
Tang et al., "Construction of short tandem target mimic (STTM) to block the functions of plant and animal microRNAs" *Methods* 58:118-125 (2012).
Wessner B, Gryadunov-Masutti L, Tschan H, Bachl N, Roth E. "Is there a role for microRNAs in exercise immunology? A synopsis of current literature and future developments" *Exerc Immunol Rev*. 2010;16:22-29.
Yan et al., "Effective Small RNA Destruction by the Expression of a Short Tandem Target Mimic in *Arabidopsis*" *Plant Cell* 24:415-427 (2012).
Zhang X et al. "*Arabidopsis* Argonaute 2 regulates innate immunity via miRNA393(*)-mediated silencing of a Golgi-localized SNARE gene, MEMB12" *Mol Cell*. 2011; 42:356-366.
Zhou J et al., "Identification of microRNA-like RNAs in a plant pathogenic fungus *Sclerotinia sclerotiorum* by high-throughput sequencing" *Mol Gen Genet*. 2012;287-282.
Amselem et al., "Genomic Analysis of the Necrotrophic Fungal Pathogens *Sclerotinia sclerotiorum* and *Botrytis cinerea*" PLoS Genetics, August 2011, vol. 7, Issue 8, e1002230, pp. 1-27.
Chen et al., "Characterization of RNA silencing components in the plant pathogenic fungus *Fusarium graminearum*," www.nature.com/ Scientific Reports, Published Jul. 27, 2015, 5:12500, DOI:10.1038/ srep12500, pp. 1-13.
Starkel, "Host Induced Gene Silencing—strategies for the improvement of resistance against *Cercospora beticola* in sugar beet (*B. vulgaris* L.) and against *Fusarium graminearum* in wheat (*T. aestivum* L.) and maize (*Z. mays* L.)," Thesis submitted 2011 to the Biology Dept, the Faculty of Mathematics, Informatics and Natural Sciences, University of Hamburg, pp. 1-130.
EP16787063.3, Extended European Search Report, dated Sep. 7, 2018, 9 pages.
Wang et al., "Pathogen small RNAs: a new class of effectors for pathogen attacks," Molecular Plant Pathology, 2015, 16(3):219-223.
Weiberg et al., "Conversations between kingdoms: small RNAs," Current Opinion in Biotechnology, 2015, 32:207-215.
Weiberg et al., "Small RNAs: A New Paradigm in Plant-Microbe Interactions," Ann. Rev. Phytopathol., 2014, 52:495-516.
Yang et al., "Roles of small RNAs in plant disease resistance," J. Integrative Plant Biology, Oct. 2014, 56(10):962-970.

* cited by examiner

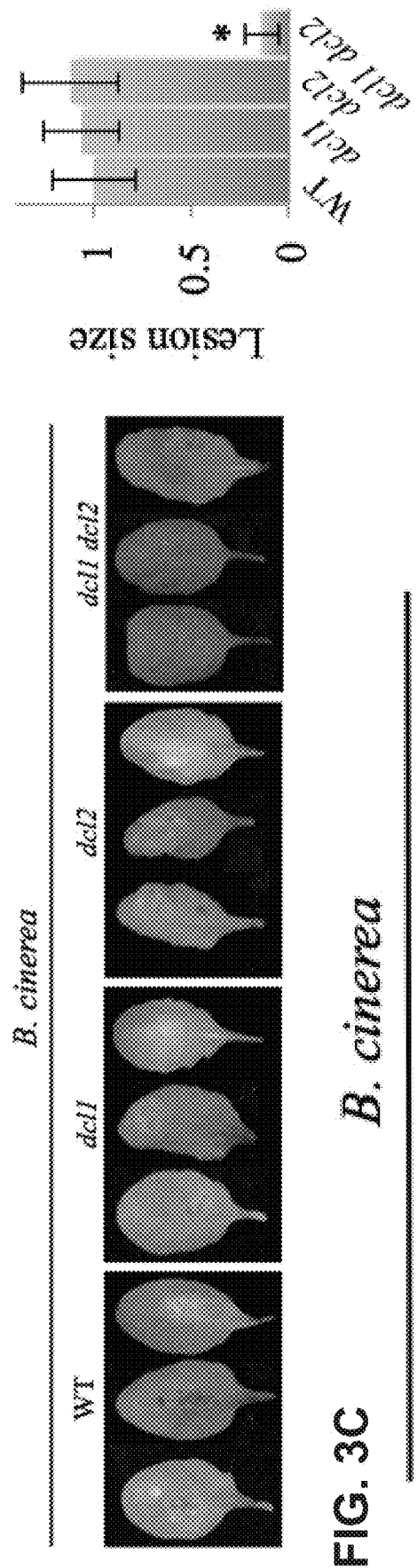
FIG. 3A
FIG. 3B
FIG. 3C
FIG. 3D

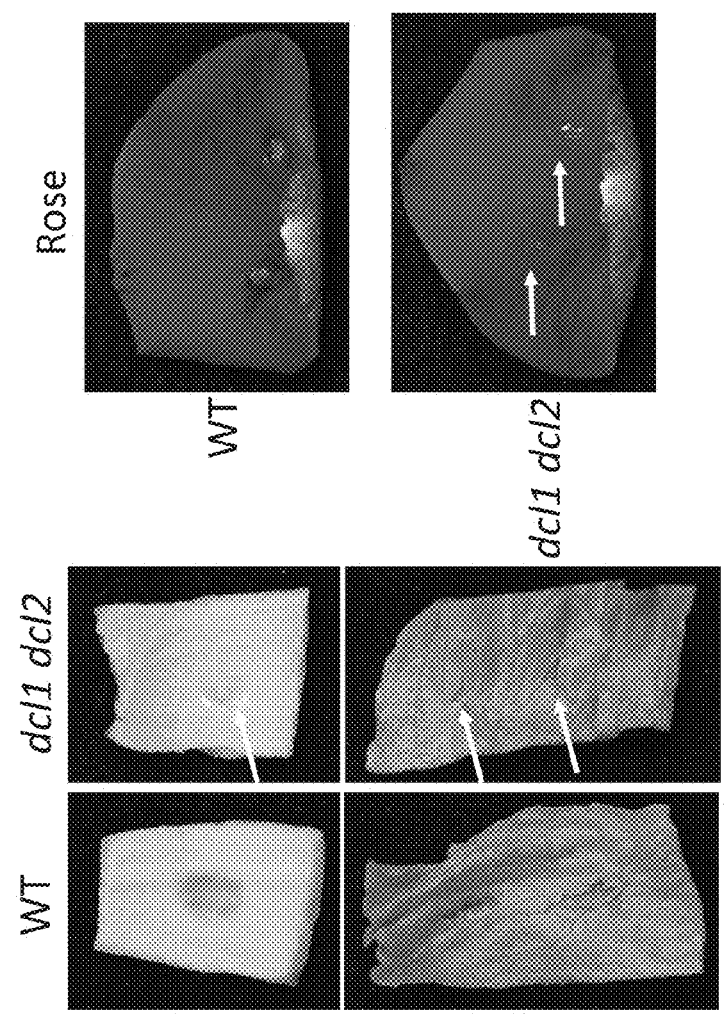
FIG. 4C
FIG. 4B
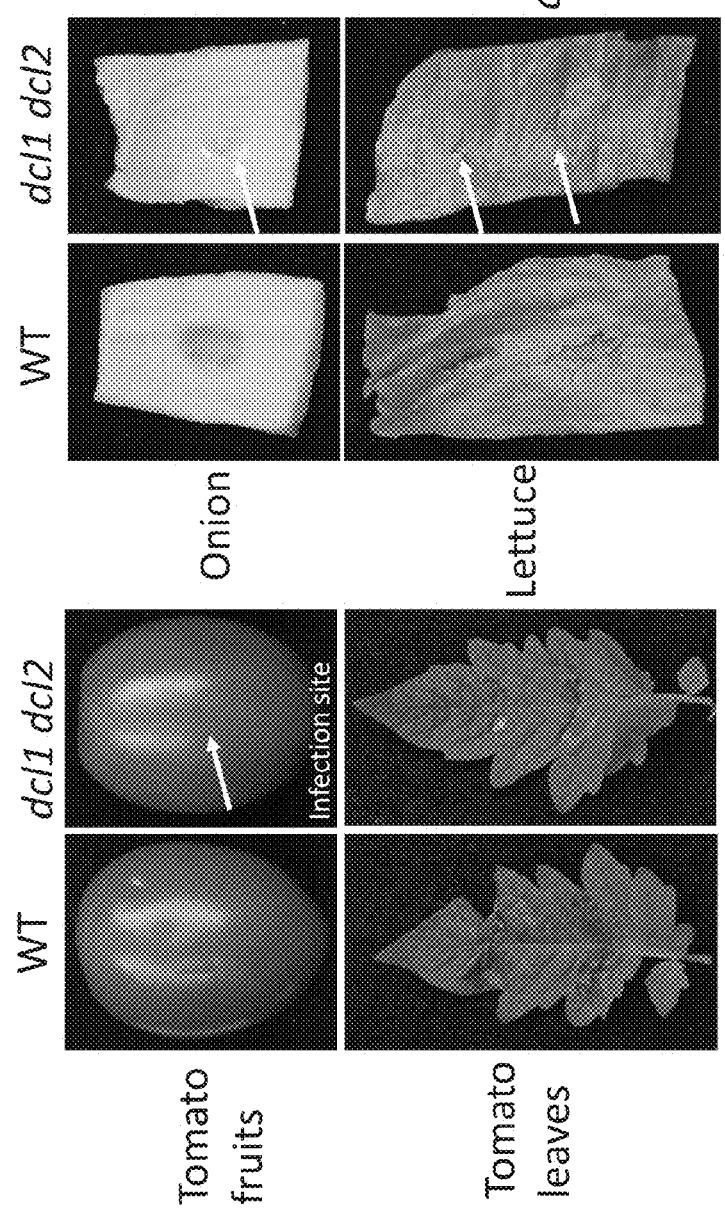
FIG. 4A

Absolute sRNA numbers at different genomic regions

| | | WT | dcl1dcl2 | ratio |
|---|---|---|---|---|
| IGR | S | 2,014,017 | 3,818,294 | 1.88 |
| Coding gene | S | 6,797,713 | 7,057,318 | 1.04 |
| | AS | 12,889,611 | 13,316,060 | 0.41 |
| LTR | S | 23,557 | 3,892 | 0.16 |
| | AS | | | |
| Total | | 41,977,871 | 24,199,411 | |
| rRNA | S | 38,989,023 | 14,619,918 | 0.52 |
| | AS | 75903 | 29387 | 0.37 |
| Total | | 39,064,926 | 14,695,305 | |
| tRNA | S | 2,919,709 | 14,029,210 | 4.81 |
| | AS | 14,865 | 4,558 | 0.31 |
| Total | | 2,934,574 | 14,033,768 | |
| Absolute | | 83,977,371 | 52,892,484 | |

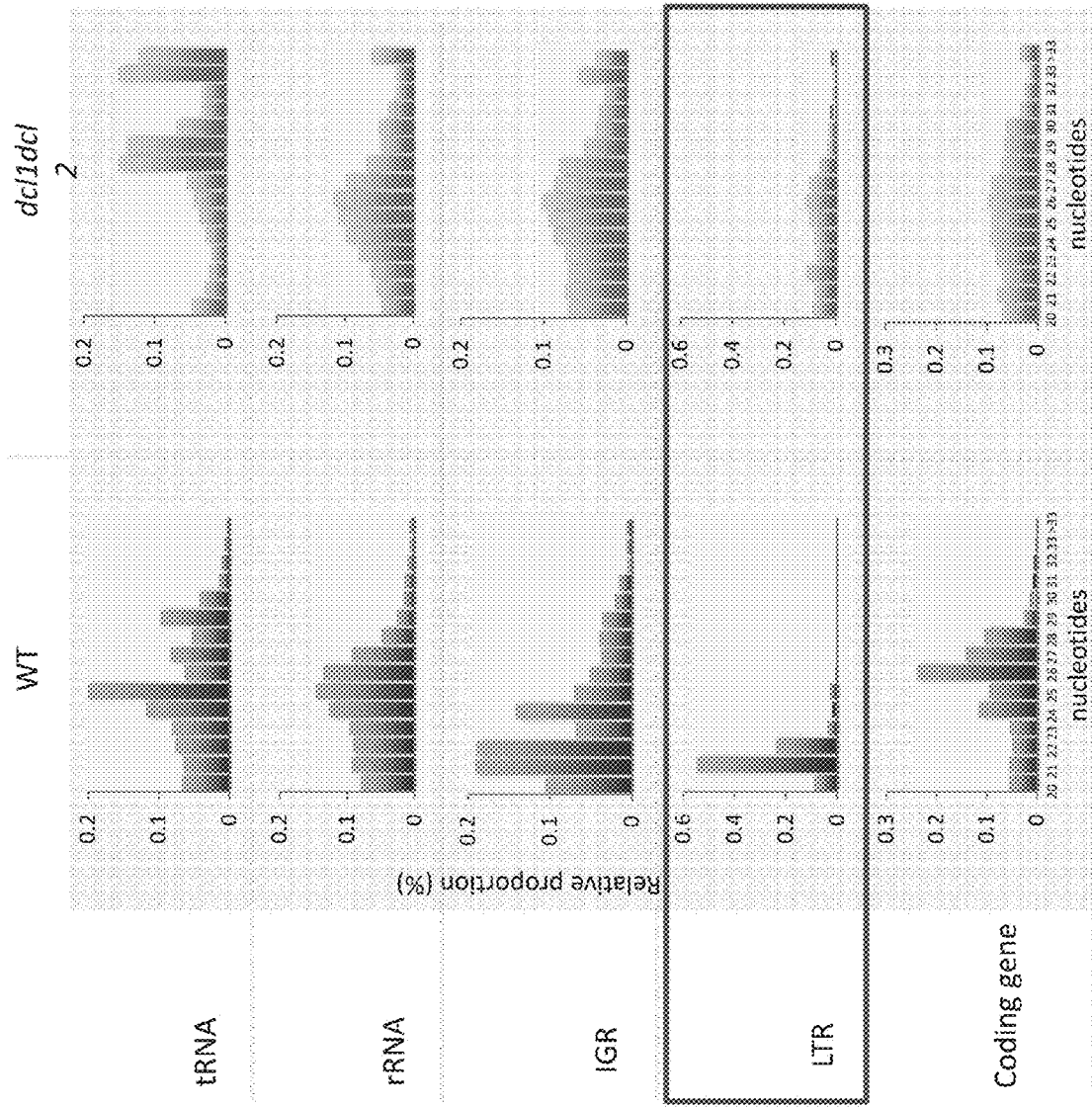

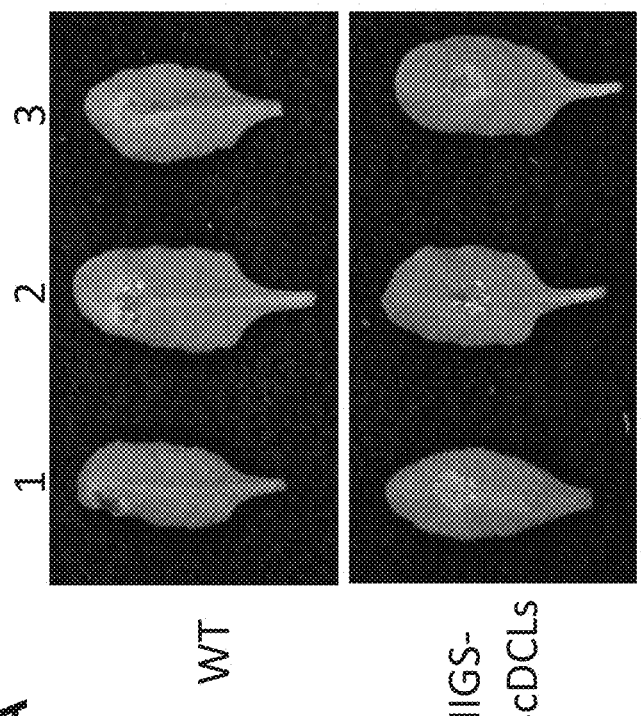
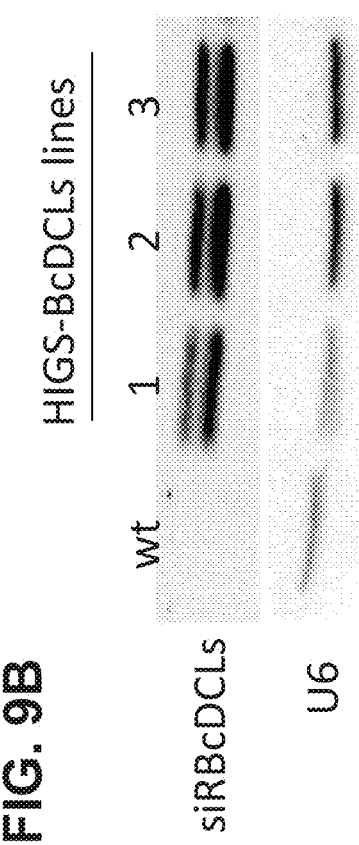
FIG. 9A
FIG. 9B

VIGS-
RB

VIGS-
BcDCLs siRBcDCLs

U6

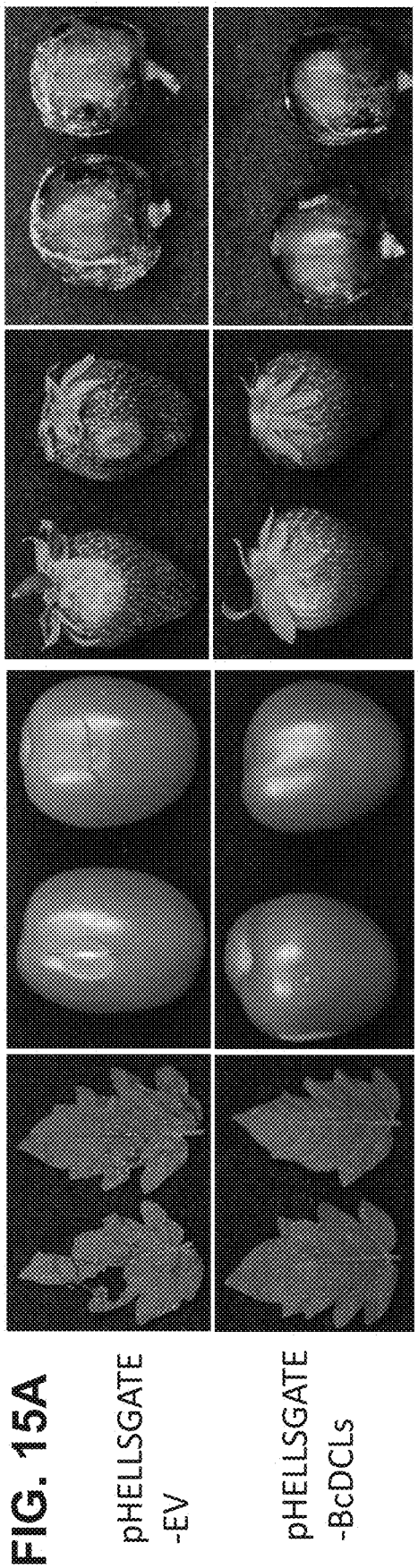
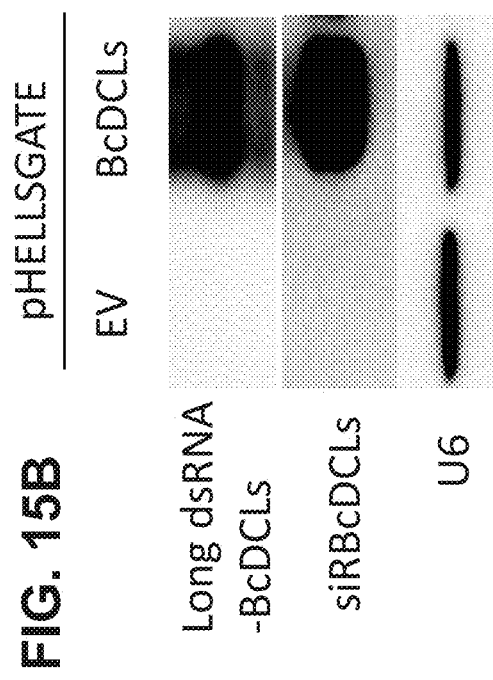
FIG. 15A
pHELLSGATE -EV
pHELLSGATE -BcDCLs
FIG. 15B

SEQUENCE LISTING

<160> NUMBER OF SEQ ID NOS: 66

<210> SEQ ID NO 1
<211> LENGTH: 5529
<212> TYPE: DNA
<213> ORGANISM: Botrytis cinerea

<400> SEQUENCE: 1
atgacgagag acgcagcagc agcaaaaagt ctctaccatt ggcgaagaaa aggcgtcact 60
ccttcagccg aagaggatct tctatcgttt gatgatattg ttactgccgt tccacctaca 120
atcttgtctt cgtctgtcgc tccatatact tctcgagata agataccttc tgcatctggc 180
aacggagatg ctatagcaga tgttagcagt ggttacctca aacaggctac cgtatcttct 240
cattctgctc aagtccgatc atcttcaaac ggcaatcaag gtgatgccaa aagttctccc 300
tctctttcac ctgatagtaa actggaattc atctttgggc ctcctttaag ggagccagag 360
aagccattct ttaataaatc ttcttattcg tttcgagatt cgagagggtt gagcagaaat 420
cgggcttctt cttctatgga aaattcgaga actctcgatc caaagatact caaaccagtt 480
atcatcaata atcaccaggg cgaatgcttc caagaggctt ccagaacagg tatacctcag 540
gctgatactt ttgataaatc ttcccttgct aagactgcgg atatggattt gtcaccagtt 600
tctcaccatg cggatgtgct tgcgacgacg gtcactgcac agcattctgc aatagccgcc 660
cagaacgcag ctcaaagctc taagatgcca ggtcctgaag cttttttact tgccgaaaag 720
gacgaggcag gttctcccgt tgttatatca ctgggttctg caaaccaaat tccttctgga 780
aacatttctt tgcagcttga ttcaccatct ctggaaaacc attctccaaa tgtgacccca 840
atcaacaaag tccctacacc attcgcactt tctacaagga caaccgatga cgttttcgca 900
gaacttaggc ggcctttgca tccccaagct attcagagcc agattgatat caagacttcc 960
tcttgtgttg atagttataa cacgaatgat gagattctag acaacaatca aggttccaat 1020
caaaaagatc tgcatgttgt tgaaaaggat aaggaagagg aagaggaaga ggatatgaac 1080
caagccatac ccgatatcaa acgtatctca gcacgaaaac aaaagaacgc tgccatattt 1140
gacgtttttc ttaaggaagc taccaaacta ccaaagacag aaaagacttc acatgcgaat 1200
gatgaagcaa ttcagtctac taggtggttg attgaccaag cagaaaaaca gcatattata 1260
gaaagtccca gggactatca acttgaattg tttgagaagg caaagaaaca gaacattata 1320
gctgtacttg atacaggatc tggcaagaca ttcattgcag ttctcttact tcggtggatc 1380
atagaccaag agcttgaaga tagagctatt ggcaagcctc atcgtgtttc attcttcctg 1440
tggaagaaac gactggatac gaatatggtc attgtctgca ctgcagaaat tttgcgccaa 1500
tgcctgcacc attcgtttgt tacaatggct caaataaatc tgctaatttt cgatgaagcc 1560

```
caccatgcaa agaaggatca tccttatgct aggattatta aagattttta tcgcaatgac    1620
acggaaaagg atatcgctct gcctaaaata tttgggatga cagcatcacc ggtagatgct    1680
agagataatg tcaagaaagc tgcggaagaa cttgaaggtt tgctacacag tcaaatatgt    1740
actgcagaag atcccagctt gctgcagtac tcaatcaaag gtaaacctga gactcttgcc    1800
tactatgatc ccttgggccc gaaattcaat actcctcttt atcttcaaat gctcccgctt    1860
ctaaaagaca atcctatctt tcggaagcca tttgtatttg ggacagaagc cagtagaact    1920
ctaggatctt ggtgtgttga ccagatctgg actttctgtc ttcaagaaga agagtctaag    1980
aaactacaag caaggacgga gcaggcgcat cataagaaga gagtcccgga gccacttgaa    2040
gtgctagaga acgcaagga acaacttgaa caagccaaat ccattgtcga aaatcacact    2100
ttcgagccac cacactttgc atcaagatta ttggatgatt tcacaacaaa agttcactat    2160
tcgaataatt tatctactaa agtcgttgct ctcttgagta ttctcaaaga tcgtttccaa    2220
cgacccacca atgacaagtg tattgtattt gtcaaagaaa gatacaccgc acgccttcta    2280
gcctcacttc tctccacacc tgaagctggg acaccattct tgaaggctgc accgctggtt    2340
ggtactacgt ctgcttcagc cggggaaatg catatcacat ttagatcaca aactcttact    2400
atgcacaact ttcgcaatgg taaaatcaac tgccttatcg caacatcagt tgctgaagaa    2460
ggtcttgaca ttcctgactg taacctcgtt gtcagattcg atttgtacaa tacagtcatt    2520
cagtacattc aatctagagg tcgtgctagg catatcaatt caaggtacta ccatatggta    2580
gagagccaca acgaggaaca gattcgtaca atcaagagg ttttgaagca tgagaaaatg    2640
ctaaagcttt ttgcttctgc tcttccagaa gatcgaaaat tgaccggaaa caacttcaat    2700
atggattact tcctcagaaa agaacgaggc cacagaattt accctgtccc gaatagtgac    2760
gcaaaactta cttacagaat gagcttaacg gtcctatctg ccttcgttga ctcacttcct    2820
cgagccccag agtcggttct tcgagtggat tatgtcgtca caactgtcga taagcagttt    2880
atctgtgagg ccattttgcc agaagaagca cccatacgcg gagcaattgg tcggccagca    2940
acaactaaac aagtggccaa atgctcagca gcctttgaaa cttgtgtgat tctgcaccag    3000
aaaggataca tcaacgacta cctactttct acatttaaaa gatcagcaca catgatgaga    3060
aatgcacttt tggctgtgga tggaaagaag caagaagctt atgatatgca gactaaacca    3120
actttatggt cttcgaaagg gaaacaaggc atattttata tgactgtctt gtctctcaaa    3180
tctccagata atcttgacag agcatctcag ccattgggct tactgacaag atcacccttg    3240
cctgatttgc cagaatttgt tcttcatttc ggagcagggc gaaactctcc aacctcgtgc    3300
gtacctctcg cttcctcaat tacgctcgaa aaaaacaagc ttgaccaagt taatatgttc    3360
accctatgtt tattccaaga tgtgttcagt aaagcataca aatcagatcc ggatagtatg    3420
ccatactttc tggttcctat caactgcctg aatgctattg tcgactggaa atcacaaaac    3480
ccaatgtcaa taatcgattg ggagacagtt gaatatgtcc aagacttcga gaataagcaa    3540
gctgataagc catgggagca caagccatgg ttaggaaagc ctgacgatta tttcaaagac    3600
aaattcataa ctgatcccct tgacgggtct cgaaaattgt ggtccgttgg aatcacaaaa    3660
gaatacagac cattggatcc agtcccacca aacacggcgc ccaggaaggg agctagaaag    3720
aacaatagta atatcatgga gtatagttgt agtctctggg caaaggctag agcaaaacga    3780
acttttgatg aagaacagcc tgttattgaa gcaacctaca tttcacttcg gagaaatttg    3840
cttgatgaat ttgatggagg tgagctcgag acttcaaaga gagttttat tattttagaa    3900 ccattgaagg tatcacctct tccaactacc gtgggtgcaa tggcctatct tttacctgca    3960
```

```
attattcatc gagttgagtc atatctcatt gctcttgaag caacagactt gttacatctt   4020
gatatccgtc ctgatcttgc gctagaggct gttaccaagg attccgacaa ttctggagag   4080
catggtgagg aacagacaaa ctttcaacgt ggaatgggca ataattatga acgattggaa   4140
tttcttgggg actgcttctt gaagatggga acgtcaatat ctctatacgg tctaaatcct   4200
gatagtgatg aattccgcta ccatgttgat cgtatgtgtc tgatttgcaa caaaaatctg   4260
ttcaatacgg ctttgaaatt agagctttac aaatacattc ggtcggcagc cttcaaccga   4320
cgagcttggt atcccgaagg ccccgaatta ttaagaggaa agacagccac ggcaccaaat   4380
acccacaagc tcggcgataa gtcagttgca gatgtttgtg aagcaatgat tggagctgct   4440
ttactaagcc accacgaaag caagtccatg gataatgcgg ttcgcgccgt tactgaagtt   4500
gtcaatagtg acaaccacaa tgctgttgta tggtctgatt attacaaatt gtatgagaaa   4560
ccaaaatggc aaactgctac agctacagct gcacaaatag atatggcaag acaagttgaa   4620
atgaaacatc catatcattt caaacaccca cgcctgttaa gatcagcttt catccatccg   4680
gcatacttgt tcatctatga acaaattcct tgttatcaac gtctcgaatt tttgggtgat   4740
tcgctactcg atatggcatg tgtcaacttc ctttttcaca accacccaac aaaagatcct   4800
cagtggctca ctgagcacaa gatggctata gtatccaatc agtttcttgg agctctttgt   4860
gtcaaattag gcttccacaa acatctactg acactcgatt ctcaagttca aaaaatgatt   4920
gcagattact cctcagatat caatgaagct ctcattcaag ccaaaacgga cgcaaagaga   4980
gtcggcaaag tagaagatga ttacgctcgt gattattgga ttgccgtccg tcaacctcct   5040
aaatgtcttc ccgatattgt agaagcattc attggtgcca tttttgtcga ctctgagtat   5100
gactacggtg aagttgagaa gttctttgaa atgcatatca gatggtactt tgaggatatg   5160
ggcatctacg atacctatgc taacaagcac ccaaccactt tccttactaa tttcttgcaa   5220
aagaacatgg gatgtgagga ctgggcacca gttagtaagg aagtacctgg agaggatggt   5280
agaaagaatg ttgtagtttg cggggtcatc atacacaata aggtggtatc aactgccact   5340
gccgaaagta tgagatatgc tagggtcgga gcagcgagga atgccttgag aaaattggag   5400
ggaatgagtg tccgagaatt cagggatgaa tacgggtgct catgtgaagg tgatgttgtt   5460
gatgaagagg gcaatattga atttgttgaa cgtgaagacg ggatggaggg gatcggtatg   5520
ggatattga                                                           5529
```

<210> SEQ ID NO 2
<211> LENGTH: 1842
<212> TYPE: PRT
<213> ORGANISM: Botrytis cinerea

<400> SEQUENCE: 2

```
Met Thr Arg Asp Ala Ala Ala Ala Lys Ser Leu Tyr His Trp Arg Arg
1               5                   10                  15

Lys Gly Val Thr Pro Ser Ala Glu Glu Asp Leu Leu Ser Phe Asp Asp
            20                  25                  30

Ile Val Thr Ala Val Pro Pro Thr Ile Leu Ser Ser Ser Val Ala Pro
        35                  40                  45

Tyr Thr Ser Arg Asp Lys Ile Pro Ser Ala Ser Gly Asn Gly Asp Ala
    50                  55                  60

Ile Ala Asp Val Ser Ser Gly Tyr Leu Lys Gln Ala Thr Val Ser Ser
65                  70                  75                  80

His Ser Ala Gln Val Arg Ser Ser Ser Asn Gly Asn Gln Gly Asp Ala
```

```
                85                  90                  95
Lys Ser Ser Pro Ser Leu Ser Pro Asp Ser Lys Leu Glu Phe Ile Phe
                100                 105                 110

Gly Pro Pro Leu Arg Glu Pro Glu Lys Pro Phe Phe Asn Lys Ser Ser
                115                 120                 125

Tyr Ser Phe Arg Asp Ser Arg Gly Leu Ser Arg Asn Arg Ala Ser Ser
    130                 135                 140

Ser Met Glu Asn Ser Arg Thr Leu Asp Pro Lys Ile Leu Lys Pro Val
145                 150                 155                 160

Ile Ile Asn Asn His Gln Gly Glu Cys Phe Gln Glu Ala Ser Arg Thr
                165                 170                 175

Gly Ile Pro Gln Ala Asp Thr Phe Asp Lys Ser Ser Leu Ala Lys Thr
                180                 185                 190

Ala Asp Met Asp Leu Ser Pro Val Ser His His Ala Asp Val Leu Ala
                195                 200                 205

Thr Thr Val Thr Ala Gln His Ser Ala Ile Ala Ala Gln Asn Ala Ala
    210                 215                 220

Gln Ser Ser Lys Met Pro Gly Pro Glu Ala Phe Leu Leu Ala Glu Lys
225                 230                 235                 240

Asp Glu Ala Gly Ser Pro Val Val Ile Ser Leu Gly Ser Ala Asn Gln
                245                 250                 255

Ile Pro Ser Gly Asn Ile Ser Leu Gln Leu Asp Ser Pro Ser Leu Glu
                260                 265                 270

Asn His Ser Pro Asn Val Thr Pro Ile Asn Lys Val Pro Thr Pro Phe
                275                 280                 285

Ala Leu Ser Thr Arg Thr Thr Asp Asp Val Phe Ala Glu Leu Arg Arg
                290                 295                 300

Pro Leu His Pro Gln Ala Ile Gln Ser Gln Ile Asp Ile Lys Thr Ser
305                 310                 315                 320

Ser Cys Val Asp Ser Tyr Asn Thr Asn Asp Glu Ile Leu Asp Asn Asn
                325                 330                 335

Gln Gly Ser Asn Gln Lys Asp Leu His Val Val Glu Lys Asp Lys Glu
                340                 345                 350

Glu Glu Glu Glu Glu Asp Met Asn Gln Ala Ile Pro Asp Ile Lys Arg
                355                 360                 365

Ile Ser Ala Arg Lys Gln Lys Asn Ala Ala Ile Phe Asp Val Phe Leu
                370                 375                 380

Lys Glu Ala Thr Lys Leu Pro Lys Thr Glu Lys Thr Ser His Ala Asn
385                 390                 395                 400

Asp Glu Ala Ile Gln Ser Thr Arg Trp Leu Ile Asp Gln Ala Glu Lys
                405                 410                 415

Gln His Ile Ile Glu Ser Pro Arg Asp Tyr Gln Leu Glu Leu Phe Glu
                420                 425                 430

Lys Ala Lys Lys Gln Asn Ile Ile Ala Val Leu Asp Thr Gly Ser Gly
                435                 440                 445

Lys Thr Phe Ile Ala Val Leu Leu Leu Arg Trp Ile Ile Asp Gln Glu
                450                 455                 460

Leu Glu Asp Arg Ala Ile Gly Lys Pro His Arg Val Ser Phe Phe Leu
465                 470                 475                 480

Trp Lys Lys Arg Leu Asp Thr Asn Met Val Ile Val Cys Thr Ala Glu
                485                 490                 495

Ile Leu Arg Gln Cys Leu His His Ser Phe Val Thr Met Ala Gln Ile
                500                 505                 510
```

```
Asn Leu Leu Ile Phe Asp Glu Ala His His Ala Lys Lys Asp His Pro
            515                 520                 525

Tyr Ala Arg Ile Ile Lys Asp Phe Tyr Arg Asn Asp Thr Glu Lys Asp
        530                 535                 540

Ile Ala Leu Pro Lys Ile Phe Gly Met Thr Ala Ser Pro Val Asp Ala
545                 550                 555                 560

Arg Asp Asn Val Lys Lys Ala Ala Glu Glu Leu Glu Gly Leu Leu His
                565                 570                 575

Ser Gln Ile Cys Thr Ala Glu Asp Pro Ser Leu Leu Gln Tyr Ser Ile
            580                 585                 590

Lys Gly Lys Pro Glu Thr Leu Ala Tyr Tyr Asp Pro Leu Gly Pro Lys
        595                 600                 605

Phe Asn Thr Pro Leu Tyr Leu Gln Met Leu Pro Leu Leu Lys Asp Asn
    610                 615                 620

Pro Ile Phe Arg Lys Pro Phe Val Phe Gly Thr Glu Ala Ser Arg Thr
625                 630                 635                 640

Leu Gly Ser Trp Cys Val Asp Gln Ile Trp Thr Phe Cys Leu Gln Glu
                645                 650                 655

Glu Glu Ser Lys Lys Leu Gln Ala Arg Thr Glu Gln Ala His His Lys
            660                 665                 670

Lys Arg Val Pro Glu Pro Leu Glu Val Leu Glu Lys Arg Lys Glu Gln
        675                 680                 685

Leu Glu Gln Ala Lys Ser Ile Val Glu Asn His Thr Phe Glu Pro Pro
    690                 695                 700

His Phe Ala Ser Arg Leu Leu Asp Asp Phe Thr Lys Val His Tyr
705                 710                 715                 720

Ser Asn Asn Leu Ser Thr Lys Val Val Ala Leu Leu Ser Ile Leu Lys
            725                 730                 735

Asp Arg Phe Gln Arg Pro Thr Asn Asp Lys Cys Ile Val Phe Val Lys
        740                 745                 750

Glu Arg Tyr Thr Ala Arg Leu Leu Ala Ser Leu Leu Ser Thr Pro Glu
    755                 760                 765

Ala Gly Thr Pro Phe Leu Lys Ala Ala Pro Leu Val Gly Thr Thr Ser
770                 775                 780

Ala Ser Ala Gly Glu Met His Ile Thr Phe Arg Ser Gln Thr Leu Thr
785                 790                 795                 800

Met His Asn Phe Arg Asn Gly Lys Ile Asn Cys Leu Ile Ala Thr Ser
            805                 810                 815

Val Ala Glu Glu Gly Leu Asp Ile Pro Asp Cys Asn Leu Val Val Arg
        820                 825                 830

Phe Asp Leu Tyr Asn Thr Val Ile Gln Tyr Ile Gln Ser Arg Gly Arg
    835                 840                 845

Ala Arg His Ile Asn Ser Arg Tyr Tyr His Met Val Glu Ser His Asn
850                 855                 860

Glu Glu Gln Ile Arg Thr Ile Lys Glu Val Leu Lys His Glu Lys Met
865                 870                 875                 880

Leu Lys Leu Phe Ala Ser Ala Leu Pro Glu Asp Arg Lys Leu Thr Gly
            885                 890                 895

Asn Asn Phe Asn Met Asp Tyr Phe Leu Arg Lys Glu Arg Gly His Arg
        900                 905                 910

Ile Tyr Pro Val Pro Asn Ser Asp Ala Lys Leu Thr Tyr Arg Met Ser
    915                 920                 925
```

```
Leu Thr Val Leu Ser Ala Phe Val Asp Ser Leu Pro Arg Ala Pro Glu
    930                 935                 940

Ser Val Leu Arg Val Asp Tyr Val Val Thr Thr Val Asp Lys Gln Phe
945                 950                 955                 960

Ile Cys Glu Ala Ile Leu Pro Glu Glu Ala Pro Ile Arg Gly Ala Ile
                965                 970                 975

Gly Arg Pro Ala Thr Thr Lys Gln Val Ala Lys Cys Ser Ala Ala Phe
            980                 985                 990

Glu Thr Cys Val Ile Leu His Gln Lys Gly Tyr Ile Asn Asp Tyr Leu
        995                 1000                1005

Leu Ser Thr Phe Lys Arg Ser Ala His Met Met Arg Asn Ala Leu
    1010                1015                1020

Leu Ala Val Asp Gly Lys Lys Gln Glu Ala Tyr Asp Met Gln Thr
    1025                1030                1035

Lys Pro Thr Leu Trp Ser Lys Gly Lys Gln Gly Ile Phe Tyr
    1040                1045                1050

Met Thr Val Leu Ser Leu Lys Ser Pro Asp Asn Leu Asp Arg Ala
    1055                1060                1065

Ser Gln Pro Leu Gly Leu Leu Thr Arg Ser Pro Leu Pro Asp Leu
    1070                1075                1080

Pro Glu Phe Val Leu His Phe Gly Ala Gly Arg Asn Ser Pro Thr
    1085                1090                1095

Ser Cys Val Pro Leu Ala Ser Ser Ile Thr Leu Glu Lys Asn Lys
    1100                1105                1110

Leu Asp Gln Val Asn Met Phe Thr Leu Cys Leu Phe Gln Asp Val
    1115                1120                1125

Phe Ser Lys Ala Tyr Lys Ser Asp Pro Asp Ser Met Pro Tyr Phe
    1130                1135                1140

Leu Val Pro Ile Asn Cys Leu Asn Ala Ile Val Asp Trp Lys Ser
    1145                1150                1155

Gln Asn Pro Met Ser Ile Ile Asp Trp Glu Thr Val Glu Tyr Val
    1160                1165                1170

Gln Asp Phe Glu Asn Lys Gln Ala Asp Lys Pro Trp Glu His Lys
    1175                1180                1185

Pro Trp Leu Gly Lys Pro Asp Asp Tyr Phe Lys Asp Lys Phe Ile
    1190                1195                1200

Thr Asp Pro Phe Asp Gly Ser Arg Lys Leu Trp Ser Val Gly Ile
    1205                1210                1215

Thr Lys Glu Tyr Arg Pro Leu Asp Pro Val Pro Pro Asn Thr Ala
    1220                1225                1230

Pro Arg Lys Gly Ala Arg Lys Asn Asn Ser Asn Ile Met Glu Tyr
    1235                1240                1245

Ser Cys Ser Leu Trp Ala Lys Ala Arg Ala Lys Arg Thr Phe Asp
    1250                1255                1260

Glu Glu Gln Pro Val Ile Glu Ala Thr Tyr Ile Ser Leu Arg Arg
    1265                1270                1275

Asn Leu Leu Asp Glu Phe Asp Gly Gly Glu Leu Glu Thr Ser Lys
    1280                1285                1290

Lys Ser Phe Ile Ile Leu Glu Pro Leu Lys Val Ser Pro Leu Pro
    1295                1300                1305

Thr Thr Val Gly Ala Met Ala Tyr Leu Leu Pro Ala Ile Ile His
    1310                1315                1320

Arg Val Glu Ser Tyr Leu Ile Ala Leu Glu Ala Thr Asp Leu Leu
```

-continued

```
            1325                1330                1335

His Leu Asp Ile Arg Pro Asp Leu Ala Leu Glu Ala Val Thr Lys
        1340                1345                1350

Asp Ser Asp Asn Ser Gly Glu His Gly Glu Gln Thr Asn Phe
    1355                1360                1365

Gln Arg Gly Met Gly Asn Asn Tyr Glu Arg Leu Glu Phe Leu Gly
        1370                1375                1380

Asp Cys Phe Leu Lys Met Gly Thr Ser Ile Ser Leu Tyr Gly Leu
    1385                1390                1395

Asn Pro Asp Ser Asp Glu Phe Arg Tyr His Val Asp Arg Met Cys
    1400                1405                1410

Leu Ile Cys Asn Lys Asn Leu Phe Asn Thr Ala Leu Lys Leu Glu
    1415                1420                1425

Leu Tyr Lys Tyr Ile Arg Ser Ala Ala Phe Asn Arg Arg Ala Trp
    1430                1435                1440

Tyr Pro Glu Gly Pro Glu Leu Leu Arg Gly Lys Thr Ala Thr Ala
    1445                1450                1455

Pro Asn Thr His Lys Leu Gly Asp Lys Ser Val Ala Asp Val Cys
    1460                1465                1470

Glu Ala Met Ile Gly Ala Ala Leu Leu Ser His His Glu Ser Lys
    1475                1480                1485

Ser Met Asp Asn Ala Val Arg Ala Val Thr Glu Val Val Asn Ser
    1490                1495                1500

Asp Asn His Asn Ala Val Val Trp Ser Asp Tyr Tyr Lys Leu Tyr
    1505                1510                1515

Glu Lys Pro Lys Trp Gln Thr Ala Thr Ala Thr Ala Ala Gln Ile
    1520                1525                1530

Asp Met Ala Arg Gln Val Glu Met Lys His Pro Tyr His Phe Lys
    1535                1540                1545

His Pro Arg Leu Leu Arg Ser Ala Phe Ile His Pro Ala Tyr Leu
    1550                1555                1560

Phe Ile Tyr Glu Gln Ile Pro Cys Tyr Gln Arg Leu Glu Phe Leu
    1565                1570                1575

Gly Asp Ser Leu Leu Asp Met Ala Cys Val Asn Phe Leu Phe His
    1580                1585                1590

Asn His Pro Thr Lys Asp Pro Gln Trp Leu Thr Glu His Lys Met
    1595                1600                1605

Ala Ile Val Ser Asn Gln Phe Leu Gly Ala Leu Cys Val Lys Leu
    1610                1615                1620

Gly Phe His Lys His Leu Leu Thr Leu Asp Ser Gln Val Gln Lys
    1625                1630                1635

Met Ile Ala Asp Tyr Ser Ser Asp Ile Asn Glu Ala Leu Ile Gln
    1640                1645                1650

Ala Lys Thr Asp Ala Lys Arg Val Gly Lys Val Glu Asp Asp Tyr
    1655                1660                1665

Ala Arg Asp Tyr Trp Ile Ala Val Arg Gln Pro Pro Lys Cys Leu
    1670                1675                1680

Pro Asp Ile Val Glu Ala Phe Ile Gly Ala Ile Phe Val Asp Ser
    1685                1690                1695

Glu Tyr Asp Tyr Gly Glu Val Glu Lys Phe Phe Glu Met His Ile
    1700                1705                1710

Arg Trp Tyr Phe Glu Asp Met Gly Ile Tyr Asp Thr Tyr Ala Asn
    1715                1720                1725
```

| | | | | | | | | | | | |
|---|---|---|---|---|---|---|---|---|---|---|---|
|Lys|His|Pro|Thr|Thr|Phe|Leu|Thr|Asn|Phe|Leu|Gln|Lys|Asn|Met|
| |1730| | | |1735| | | |1740| | |

Lys His Pro Thr Thr Phe Leu Thr Asn Phe Leu Gln Lys Asn Met
        1730              1735              1740

Gly Cys Glu Asp Trp Ala Pro Val Ser Lys Glu Val Pro Gly Glu
        1745              1750              1755

Asp Gly Arg Lys Asn Val Val Cys Gly Val Ile Ile His Asn
        1760              1765              1770

Lys Val Val Ser Thr Ala Thr Ala Glu Ser Met Arg Tyr Ala Arg
        1775              1780              1785

Val Gly Ala Ala Arg Asn Ala Leu Arg Lys Leu Glu Gly Met Ser
        1790              1795              1800

Val Arg Glu Phe Arg Asp Glu Tyr Gly Cys Ser Cys Glu Gly Asp
        1805              1810              1815

Val Val Asp Glu Glu Gly Asn Ile Glu Phe Val Glu Arg Glu Asp
        1820              1825              1830

Gly Met Glu Gly Ile Gly Met Gly Tyr
        1835              1840

<210> SEQ ID NO 3
<211> LENGTH: 4197
<212> TYPE: DNA
<213> ORGANISM: Botrytis cinerea

<400> SEQUENCE: 3

```
atggaataca cttcggaacc tgacactgac ccggatac

```
aaggatcgtt ttaagattgg aaccatggtt ggcacatcct taaatggcaa gcgtacagac    1440
caaataggag agcttgtcga tgttaatcaa caaaaagaca ctttgtcaag tttcaagcgt    1500
ggaaaaattg atatccttat agctacaaat gtattggaag agggaattga tgttcctgcc    1560
tgtaatctag tgatctgctt tagtaaacca gcaaacctca aatctttcgt acaaagacga    1620
gggcgagcaa gacagcaaga ttctaagctg attcttcttg atgcttcagg tgataaagcg    1680
acaaattggc atgagcttga agaaaaatg cgagaggagt acggaaagga atgcgagaa     1740 ttgcaacaca tctacgaaat tgagacagct gatgaacagt cggaagatga tagggtcttg    1800
cgaatagaaa gcactggggc tcaattagac cttgacagtg ctttaccaca tctctatcat    1860
ttctgttcag tcttaacaac aaaagatttt gttgacctca ggccagactt cgtctactcc    1920
tccgaactgg gatcggaata tgttcgagca aaggtcatcc tgcctggatc ggtttctaaa    1980
cccctgcgag tccatgaaag ccgcggatcg tggttgagcg agaggtcggc tgcaaaagat    2040
gcagcgtttg aggcgtattc cgcattatac agggggggct tagtgaatga taacctactg    2100
cccctgatgg tgcacgacaa agtcatcgat gagttgactt caaagcccgt ggatactcgc    2160
gcgtctcttc tggaggtgaa ggaaagatta atccatgga ttgacattgc tagagcatgg     2220
aaagaggcag aacaccatgc tggaattgtt cgcacatcgg taatgatctt caatgggatg    2280
aagctggaac tctgtcttcc aattgatcca ccggcaatac ccccattaaa gctttattgg    2340
gatgctgaca ccgagttctt tgttgacttt acaaacgata tcgagatcgg caccagcgag    2400
aatatgttgg cacaggcgtt gaacgatacc aatctactat tatcagatcg tggtcgtaaa    2460
gttcacatcc agtcacgtcg aacagttgtg caatttatct tgcttcaaga ttcgggctcg    2520
ctcagttcag attgttttcc ggttgacccc aacggtaata ttaaaagtac aggttttatc    2580
agagaagtcg gtaaactaga atcgccctac atctttgaaa aatggttgcc caatgcacca    2640
gaagacgtcc catatctagc tgtggttaaa gtaagtcgcc gtgcagactt tttgcacaag    2700
gtacagaacg aaaaacccc gtcattcact aaacaattct cgtctgttct acctgcctcg    2760
acatgtgtac aggatgtaat gcccgcacag ttgtctcggt tcggcatgat gattccttcc    2820
atcacacacc acattgaggt gcaactcgtt gtagaccgac tatccaggac catcctcaag    2880
gatctcgaaa ttagtgacca gagtcttatt cagaccgcca tcacacatgc cagttattcg    2940
ttagactcga attatcagcg tctcgaattt ctgggcgact caattctcaa attgtgtaca    3000
tcggtacaat tggtggcaga gcatctagat tggcacgaag atatttgtc ggctatgaag     3060 gatcgtatcg tgtccaattc acggtcatca agagcggcgg ctgaagtcgg tttggatgag    3120
tatataatga ccaagaaatt cacaggtgca aaatggcgac caatgtacgt ggatgatctg    3180
gtcgtcacag aacaaaaaac aagagaaatg tcctccaaaa ttctttccga cgttgtggaa    3240
gcactcatcg gcgcatctct ccggcccgtc gagcaaatcc tcgcatatac cttcaccaaa    3300
aaatctctcc tcgtcgaagc catgacgcac ccctcttaca ccagcggcac gcaatccctc    3360
gagcgactcg agttcctcgg cgattccatt ctcgacaaca tcatcgtcac agccatgtgg    3420
tcgcactcga cgccgctctc ccacttccac atgcatctcc tgcgctctgc gctcgtcaac    3480
gccgatttcc tcgcctttct ctgcatggaa atgagcatac caaaacgt caccaatctg     3540 accgaaggaa aaaaccatcg catccacgaa acccactcgc gacgccgcgt ttccctcgtc    3600
agttttctcc gtcactcaag cgttcgtctc tctatctatc aaaagaagc gctttctcgc    3660 catgcagaat tgcgcgatca gatcctcgag gcaaatataca ccggtgatac attccctgg    3720 gctctattat cccgattgga cgcgcggaaa ttttctccg atatgattga gagtttgctg    3780
```

```
ggcgcggtat ggattgatag cggctcgatg gaagtgtgca cgcagctgat cgaaagaatg   3840
ggcgtcctga gatacatgcg acggattttg aaagatggcg tgcgcatcat gcatccgaag   3900
gaggaactgg gcatcgtggc cgattctgaa aacgtcaggt acgttttgcg gcgggagaag   3960
atgggtgggg atgctaccga ggtaaatgcg gacgcggatg aagaggtacg cacggagtac   4020
cggtgcacag tatttgtggg cggggaggaa attgtagagg tgaggggtgg agcgaggaaa   4080
gaggagattc aggcaagggc tgcggagcag gcggtgcgga ttttgaaggc gaggggtcat   4140
gagaagagga atgggggtgc gggggagggg aaaaagagaa aatcgctgga tgaatag      4197
```

<210> SEQ ID NO 4
<211> LENGTH: 1398
<212> TYPE: PRT
<213> ORGANISM: Botrytis cinerea

<400> SEQUENCE: 4

```
Met Glu Tyr Thr Ser Glu Pro Asp Thr Asp Pro Asp Thr Arg Gly Ser
1               5                   10                  15

Leu Ile Asp Gly Arg Asp Gly Ile Glu Gly Asp Leu Ile Ala Leu Thr
            20                  25                  30

Ser Gly Glu Arg Leu Asn Glu Thr Val Glu Asp Leu Cys Ser Asp Ser
        35                  40                  45

Ser Gly Leu Ile Val Glu Asn Glu Asp Asp Asp Asn Ser Ala Gly Glu
    50                  55                  60

Lys Gly Glu Ile Val Ile Val Thr Pro Arg Thr Tyr Gln Leu Glu Met
65                  70                  75                  80

Leu Glu Glu Ser Leu Lys Arg Asn Val Ile Val Ala Met Asp Thr Gly
                85                  90                  95

Ser Gly Lys Thr His Val Ala Val Leu Arg Ile Leu Ala Glu Leu Glu
            100                 105                 110

Arg Met Lys Pro Gly Lys Ile Ile Trp Phe Leu Ala Pro Thr Val Ala
        115                 120                 125

Leu Cys Ala Gln His His Glu Tyr Leu Gln Leu Asn Ile Pro Ser Val
    130                 135                 140

Leu Ile Lys Met Leu Ile Gly Ala Asp Gly Val Asp Arg Trp Thr Glu
145                 150                 155                 160

Gln Arg Gln Trp Asp Thr Val Leu Lys Asp Val Lys Val Val Val Ser
                165                 170                 175

Ser Tyr Gln Val Leu Leu Asp Ala Leu Thr His Gly Phe Val Arg Met
            180                 185                 190

Gly Arg Leu Ser Leu Ile Ile Phe Asp Glu Ala His Asn Cys Val Asn
        195                 200                 205

Lys Ala Pro Gly Ala Lys Ile Met Lys Ser Phe Tyr His Pro Tyr Lys
    210                 215                 220

Ser Ile Phe Pro Leu Pro His Ile Leu Gly Leu Ser Ala Ser Pro Val
225                 230                 235                 240

Met Arg Ser Ser Pro Gln Ser Leu Ser Asp Ile Glu Glu Thr Leu Asp
                245                 250                 255

Ala Ile Cys Cys Thr Pro Lys Ile His Arg Ala Asp Leu Arg Leu Arg
            260                 265                 270

Val Lys Leu Pro Leu Leu Ser Ile Ile Tyr Tyr Thr Pro Glu Ser Asn
        275                 280                 285

Ile Ile Val Thr Lys Thr Val Ala Ser Leu Arg Lys Ile Val Gln Ser
    290                 295                 300
```

```
Leu Asn Ile Phe Glu Asp Pro Tyr Val Leu Thr Leu Lys Arg Ser Asp
305                 310                 315                 320

Ser Glu Lys Ser Gln Arg Glu Leu Ala Lys Val Leu Lys Ser Phe Lys
            325                 330                 335

Thr Tyr Ser Gln Thr Gln Leu Lys Ser Ile Asp Lys Thr Ser Asn Glu
            340                 345                 350

Ile Ile Leu Val Glu Leu Gly Pro Trp Ala Ala Asp Tyr Tyr Ile Ser
            355                 360                 365

Thr Val Val Thr Arg Tyr Leu Lys Ala Met Ser Ala Lys Asp Thr Phe
370                 375                 380

Ile Val Glu Asp Ser Pro Ala Ala Glu Lys Leu Tyr Ile Ala Lys Ala
385                 390                 395                 400

Leu Arg Gln Val Glu Ile Ser Pro Ser Thr Leu Ser Asp Thr Gly Lys
                405                 410                 415

Ile Ser Asn Lys Val Glu Lys Leu Leu Gly Ile Ile Ala Gln Gln Lys
                420                 425                 430

Pro Pro Phe Ser Ala Ile Ile Phe Val Gln Glu Arg Ala Thr Val Ser
            435                 440                 445

Val Leu Ala His Leu Leu Ser His His Pro Leu Thr Lys Asp Arg Phe
            450                 455                 460

Lys Ile Gly Thr Met Val Gly Thr Ser Leu Asn Gly Lys Arg Thr Asp
465                 470                 475                 480

Gln Ile Gly Glu Leu Val Asp Val Asn Gln Gln Lys Asp Thr Leu Ser
                485                 490                 495

Ser Phe Lys Arg Gly Lys Ile Asp Ile Leu Ile Ala Thr Asn Val Leu
                500                 505                 510

Glu Glu Gly Ile Asp Val Pro Ala Cys Asn Leu Val Ile Cys Phe Ser
            515                 520                 525

Lys Pro Ala Asn Leu Lys Ser Phe Val Gln Arg Arg Gly Arg Ala Arg
            530                 535                 540

Gln Gln Asp Ser Lys Leu Ile Leu Leu Asp Ala Ser Gly Asp Lys Ala
545                 550                 555                 560

Thr Asn Trp His Glu Leu Glu Arg Lys Met Arg Glu Glu Tyr Gly Lys
                565                 570                 575

Glu Met Arg Glu Leu Gln His Ile Tyr Glu Ile Glu Thr Ala Asp Glu
            580                 585                 590

Gln Ser Glu Asp Asp Arg Val Leu Arg Ile Glu Ser Thr Gly Ala Gln
            595                 600                 605

Leu Asp Leu Asp Ser Ala Leu Pro His Leu Tyr Phe Cys Ser Val
610                 615                 620

Leu Thr Thr Lys Asp Phe Val Asp Leu Arg Pro Asp Phe Val Tyr Ser
625                 630                 635                 640

Ser Glu Leu Gly Ser Glu Tyr Val Arg Ala Lys Val Ile Leu Pro Gly
                645                 650                 655

Ser Val Ser Lys Pro Leu Arg Val His Glu Ser Arg Gly Ser Trp Leu
                660                 665                 670

Ser Glu Arg Ser Ala Ala Lys Asp Ala Ala Phe Glu Ala Tyr Ser Ala
            675                 680                 685

Leu Tyr Arg Gly Gly Leu Val Asn Asp Asn Leu Leu Pro Leu Met Val
            690                 695                 700

His Asp Lys Val Ile Asp Glu Leu Thr Ser Lys Pro Val Asp Thr Arg
705                 710                 715                 720
```

```
Ala Ser Leu Leu Glu Val Lys Glu Arg Leu Asn Pro Trp Ile Asp Ile
            725                 730                 735

Ala Arg Ala Trp Lys Glu Ala Glu His His Ala Gly Ile Val Arg Thr
            740                 745                 750

Ser Val Met Ile Phe Asn Gly Met Lys Leu Glu Leu Cys Leu Pro Ile
            755                 760                 765

Asp Pro Pro Ala Ile Pro Pro Leu Lys Leu Tyr Trp Asp Ala Asp Thr
            770                 775                 780

Glu Phe Phe Val Asp Phe Thr Asn Asp Ile Glu Ile Gly Thr Ser Glu
785                 790                 795                 800

Asn Met Leu Ala Gln Ala Leu Asn Asp Thr Asn Leu Leu Ser Asp
                805                 810                 815

Arg Gly Arg Lys Val His Ile Gln Ser Arg Arg Thr Val Val Gln Phe
            820                 825                 830

Ile Leu Leu Gln Asp Ser Gly Ser Leu Ser Ser Asp Cys Phe Pro Val
            835                 840                 845

Asp Pro Asn Gly Asn Ile Lys Ser Thr Gly Phe Ile Arg Glu Val Gly
            850                 855                 860

Lys Leu Glu Ser Pro Tyr Ile Phe Glu Lys Trp Leu Pro Asn Ala Pro
865                 870                 875                 880

Glu Asp Val Pro Tyr Leu Ala Val Val Lys Val Ser Arg Arg Ala Asp
                885                 890                 895

Phe Leu His Lys Val Gln Asn Glu Lys Pro Ser Ser Phe Thr Lys Gln
                900                 905                 910

Phe Ser Ser Val Leu Pro Ala Ser Thr Cys Val Gln Asp Val Met Pro
            915                 920                 925

Ala Gln Leu Ser Arg Phe Gly Met Met Ile Pro Ser Ile Thr His His
            930                 935                 940

Ile Glu Val Gln Leu Val Val Asp Arg Leu Ser Arg Thr Ile Leu Lys
945                 950                 955                 960

Asp Leu Glu Ile Ser Asp Gln Ser Leu Ile Gln Thr Ala Ile Thr His
                965                 970                 975

Ala Ser Tyr Ser Leu Asp Ser Asn Tyr Gln Arg Leu Glu Phe Leu Gly
            980                 985                 990

Asp Ser Ile Leu Lys Leu Cys Thr Ser Val Gln Leu Val Ala Glu His
            995                 1000                1005

Leu Asp Trp His Glu Gly Tyr Leu Ser Ala Met Lys Asp Arg Ile
    1010                1015                1020

Val Ser Asn Ser Arg Ser Ser Arg Ala Ala Ala Glu Val Gly Leu
    1025                1030                1035

Asp Glu Tyr Ile Met Thr Lys Lys Phe Thr Gly Ala Lys Trp Arg
    1040                1045                1050

Pro Met Tyr Val Asp Asp Leu Val Val Thr Glu Gln Lys Thr Arg
    1055                1060                1065

Glu Met Ser Ser Lys Ile Leu Ser Asp Val Val Glu Ala Leu Ile
    1070                1075                1080

Gly Ala Ser Leu Arg Pro Val Glu Gln Ile Leu Ala Tyr Thr Phe
    1085                1090                1095

Thr Lys Lys Ser Leu Leu Val Glu Ala Met Thr His Pro Ser Tyr
    1100                1105                1110

Thr Ser Gly Thr Gln Ser Leu Glu Arg Leu Glu Phe Leu Gly Asp
    1115                1120                1125

Ser Ile Leu Asp Asn Ile Ile Val Thr Ala Met Trp Ser His Ser
```

```
                     1130                1135                1140
Thr Pro Leu Ser His Phe His Met His Leu Leu Arg Ser Ala Leu
                1145                1150                1155
Val Asn Ala Asp Phe Leu Ala Phe Leu Cys Met Glu Met Ser Ile
                1160                1165                1170
Asp Gln Asn Val Thr Asn Leu Thr Glu Gly Lys Asn His Arg Ile
                1175                1180                1185
His Glu Thr His Ser Arg Arg Val Ser Leu Val Ser Phe Leu
                1190                1195                1200
Arg His Ser Ser Val Arg Leu Ser Ile Tyr Gln Lys Glu Ala Leu
                1205                1210                1215
Ser Arg His Ala Glu Leu Arg Asp Gln Ile Leu Glu Ala Ile Tyr
                1220                1225                1230
Thr Gly Asp Thr Phe Pro Trp Ala Leu Leu Ser Arg Leu Asp Ala
                1235                1240                1245
Arg Lys Phe Phe Ser Asp Met Ile Glu Ser Leu Leu Gly Ala Val
                1250                1255                1260
Trp Ile Asp Ser Gly Ser Met Glu Val Cys Thr Gln Leu Ile Glu
                1265                1270                1275
Arg Met Gly Val Leu Arg Tyr Met Arg Arg Ile Leu Lys Asp Gly
                1280                1285                1290
Val Arg Ile Met His Pro Lys Glu Glu Leu Gly Ile Val Ala Asp
                1295                1300                1305
Ser Glu Asn Val Arg Tyr Val Leu Arg Arg Glu Lys Met Gly Gly
                1310                1315                1320
Asp Ala Thr Glu Val Asn Ala Asp Ala Asp Glu Glu Val Arg Thr
                1325                1330                1335
Glu Tyr Arg Cys Thr Val Phe Val Gly Gly Glu Glu Ile Val Glu
                1340                1345                1350
Val Arg Gly Gly Ala Arg Lys Glu Glu Ile Gln Ala Arg Ala Ala
                1355                1360                1365
Glu Gln Ala Val Arg Ile Leu Lys Ala Arg Gly His Glu Lys Arg
                1370                1375                1380
Asn Gly Gly Ala Gly Glu Gly Lys Lys Arg Lys Ser Leu Asp Glu
                1385                1390                1395

<210> SEQ ID NO 5
<211> LENGTH: 4692
<212> TYPE: DNA
<213> ORGANISM: Verticillium dahilae

<400> SEQUENCE: 5
atgacgactg acgagctctc tgttggtctg gacgccaccg gcatctcaat cctcgcagat      60
ggaccggaaa acatatcgtc cagcacatca acatctacga ctggaaagga agatggatac    120
ctctgtatca acagattcac tcagaatacc gccacgaccc aggacaacca gagccgagat    180
tctgacgacg atgaggatga ctgcggcagc cacgatgaag ctgacgaaga ttcagacgaa    240
agacagtaca gcatgacccc agaaaggcct cataaaatta ccgagaagaa gcgcgcagat    300
catgctgcct ttcacgactg gcttcagagc aactccagcg agattgctca gtcaaccccc    360
cagccggctc aaaacctcaa ccacacctcc acggccctga tggtacgcga gagtgagaat    420
cgtaagatca tcgaaaatcc tcgggagtat cagattgagc tcttcgagcg ggcgaagcga    480
aagaacatca ttgccgtgtt acccactgga tcaggaagga ccttaatcgc agcccttctt    540
```

```
ctgcgacaca ccctcgaaca agaaaccgcg gatcgacgcg cgggcaagcc caagagaatc    600
gccttttttcc tcgtggaaaa ggttgctctt gccctccaac agcacgcggt tctggagtgc   660
aatctggaat ttcccattga ccgggtatgc ggtgacatgg tacggtcgga ctggatcaag    720
gagtcatgga tgaaaagatg ggatgacaac atggtcatgg tctgcaccgc cgccatcctt    780
cagcaatgcc ttgccagatc attcatccgc atggatcaga tcaacctgct tgtcttcgat    840
gaagcacatc acgccaaggg aaatcatccg tacgcccgga tcatcaagga ctactacatt    900
acggaacctg acaaagaaag gcgccccaag atcttcggca tgactgcctc tccggtggat    960
gccctcaccg acgtcaagat tgctgccgct caactcgaag gtttgttgca tagtgagatt   1020
gcgacaatcg aggaggactc tgtatcattc aaacaaatcc agaagaggt cgtcgaacaa    1080
gactgcaagt accctgccct cgaaccaccc ttcaccacca atcttcataa gaagatccaa    1140
gaacaggtgc gctacaacaa gaacttcgca aaggcgctga gcaattcttt agaaatgtcg    1200
agctcccttg gcagctggtg tgtcgatcgc ttctggcaga tatttctgac cgaagaaacc    1260
ctcgcgagat tggcagcgca aactgcacaa gacaacattt tgccgatcg cgccgaaaag    1320
gagcgcgttg ccattgagga ggtccgcaac atcatcaagc aacatcagtt cctcccaatc    1380
accaaaaccc tgcaagactt gtcgtccaaa gtgctgtgcc tcctcggcca actggaattg    1440
cgcttcagtg cccctaccga tcacaagtgc atcatcttcg tggagaaacg aaacacagcc    1500
atgattctgg ctcacctcct ctccttgcct ggtattggac tctatatct gaaaccggct    1560
gcgcttgtcg ggaacccatc tgacaacagc cctcttgcca tgtcgtacaa agagcaagtg   1620
atgacaataa caaagttcag acgtggtgaa tacaactgtc ttctcgccac ttctgtggcc   1680
gaggagggca ttgacatcgc agactgcaac attgtcattc gattcgatct tttcaactcg   1740
gtgattcagt acatacaatc caaaggccgc gctcggcact tgaactcgga gtatatttgc   1800
atggccgagc taggcaacgg caagcataca agggcgaaga tacaagcaaa ttatgacctc   1860
tccctcatcc gccaattctg cagcacactg ccagaagacc gcaagatcgt gggctgggac   1920
cccgaggcag ctcttcacca tggcgagcgc gaccataagt tccacatcgt tccatccacc   1980
ggggccaaac tcacctggac cggcagcctc gtggttctgt caaattttgc ctcttctcta   2040
caggtgaacg acgaaacact aagtccttcc tatatggtct ctctcatcgg tagcgagtac   2100
atctgcgagg tccagcttcc gagcaagtct cccattttga gcgtgtcagg cacgctccaa   2160
aagaacaaag cagaggccag gtgctccgca gcgtttgaga tgtgcatgaa gctcatcaaa   2220
ggtgggttca tcagcagtca ccttcagccg acgtttacca ggaagctccc ggccatgcga   2280
aacgcacgcc tagccatcag ctccaagaag cgtgaacggt acaatatgag ggtcaagcca   2340
gaggtatggt cacggcgtgg accggcatcc tctctgttcc tcacagtcct gaagcttcgt   2400
acacctggtg cattgaacag accatcacag ccactcgccc tcctcacacg agaggcactg   2460
ccagagcttc caggagttcc gctattttc ggtaactgtg gtcggtccat agcggaggta   2520
gtatctgtgg cgaaacccat gcacttggat gaagtacgtc tagacagcct cagagtattc   2580
accctgcgca ttttcaaaga tgtcttcagc aaggtatacg attctcaagt cgcagacctt   2640
ccatacttcc tggcacctgc tgctcatgac cacagtcatg agttctcacc gaatgaagac   2700
ccagggtcac tgatcgactg gagccatctg ctgtcgacca aagaggttga gtacttgcct   2760
tgggatgaag atcacagtcc cagcttctat caaagcaagt ttgtgattga tccatacacg   2820
ggatcgcgca agctgtttct cagaggtatt cggacagatc tcaagccgac cgacttggtt   2880
ccagatggag ttcccgaacc cacattcagg ctctggaagg acgttgagca taccataaag   2940
```

-continued

```
gaatacagca tcagcctctg ggcaaagagt cgagcccgga gagctggcga atggttggac      3000
actcaacccg tggtagaagc cgagttggtc tcgctgcgcc ggaatcttct cgacgaattt      3060
gccgattcca agcatgaagg gtctagggtc tgttatgtga ttctccagcc gctacagatc      3120
tcaacactcc ctgtcgaggt cgtcgctatg gcctacaact ttcccgccat catccatcgg      3180
attgaatcga atatgatcgc ccttgacgcc tgccgtatgt tgaaccttcg agttcgtccc      3240
gacctggctc tcgaggcgat gaccaaagat caagcaaca gtgaagagca cgatcaggaa       3300
aagattgatt ccaggccgg catgggcaat aattatgagc gactcgagtt tctcggagac       3360
tgctttctca aaatggcaac caccatcgca cttttttactc ggatccctga cagcaacgag     3420
tttgagtgtc acgtcgagcg aatgcttctt atttgcaacc agaatctgtt caatgtcgca     3480
ttaaagaaga acttgcaaga gtacattcga tcaaagcaat tcgatcgacg cagttggtac     3540
ccccagggtc tgaagcagaa ggcgggcaaa gcccaaggag cacaaaactc acactcattg     3600
gccgacaagt ctattgctga tgtatgcgag gccatcattg gcgcctcata tttgtcgtac     3660
actgacgagg gcaactttga catggccgta cgcgctgtga cggccgtcgt gaggaacaaa     3720
aatcacgaca tgaaatcata cgaggactat tacaaagcat ttaagatgcc gatctggcaa     3780
gcggcggagc caagtgctgt gcagatggaa gcgtctttac agattaaaga gcagatggga     3840
tatgagttca gtctcctgc cctgctgcgg agtgccttca agcacccgtc ctaccccgt       3900
cagtttgaga gcgtgcccaa ttatcagcgc ctcgagttcc tcggtgacgc gcttctagac     3960
atggtctgcg tagactttct cttcaggaag tttcccgacg ccgatcctca atggctcact     4020
gaacacaaga tggccatggt ttcgaaccac ttcctcggaa gtctgagtgt agagttgggc     4080
ttctaccggc gtgtccttca ctttaacagc atcatggcca atcaaatcaa ggactacgtc     4140
gacgcactta ctcatgcacg ccaagaagcc gaagcggtgg cccagatctc tggcacagtc     4200
tcgcgagatt actggctcaa cgtgaagcac ccccccaaat tcctctcaga cgtggtcgag    4260
gcatacatcg gtgctatttt cgttgattca ggatacgatt atggccaggt acaggcgttc    4320
ttcgagaagc atatccggcc ttttcttcgca gacatggcgc tatatgattc ctttgccagc   4380
agccaccctg tcacaacgct ggcgcgtatg atgcagcagg actttggctg ccaggactgg   4440
cggcttcttg taagtgaact gccgccgagc tgcgaagacg gcggggcagc tgcgatcact   4500
gagacggaag tgatttgtgg gttcatggtc cacggaagaa tcctgctaca tgccaagtcg   4560
tcgagtggac ggtacgccaa agtgggtgct gcaaagagag cggtcgagaa gctcatgggt   4620
ctcggcaacg acaaagaggt ctttcggacg gacttcggct gtgactgtga ctgtgaaggt   4680
caagcaatct ag                                                          4692
```

<210> SEQ ID NO 6
<211> LENGTH: 1563
<212> TYPE: PRT
<213> ORGANISM: Verticillium dahilae

<400> SEQUENCE: 6

```
Met Thr Thr Asp Glu Leu Ser Val Gly Leu Asp Ala Thr Gly Ile Ser
1               5                   10                  15

Ile Leu Ala Asp Gly Pro Glu Asn Ile Ser Ser Thr Ser Thr Ser
            20                  25                  30

Thr Thr Gly Lys Glu Asp Gly Tyr Leu Cys Ile Asn Arg Phe Thr Gln
        35                  40                  45

Asn Thr Ala Thr Thr Gln Asp Asn Gln Ser Arg Asp Ser Asp Asp Asp
```

```
                50             55                  60
Glu Asp Asp Cys Gly Ser His Asp Glu Ala Asp Glu Asp Ser Asp Glu
65                  70                  75                  80

Arg Gln Tyr Ser Met Thr Pro Glu Arg Pro His Lys Ile Thr Glu Lys
                85                  90                  95

Lys Arg Ala Asp His Ala Ala Phe His Asp Trp Leu Gln Ser Asn Ser
                100                 105                 110

Ser Glu Ile Ala Gln Ser Thr Pro Gln Pro Ala Gln Asn Leu Asn His
                115                 120                 125

Thr Ser Thr Ala Leu Met Val Arg Glu Ser Glu Asn Arg Lys Ile Ile
        130                 135                 140

Glu Asn Pro Arg Glu Tyr Gln Ile Glu Leu Phe Glu Arg Ala Lys Arg
145                 150                 155                 160

Lys Asn Ile Ile Ala Val Leu Pro Thr Gly Ser Gly Lys Thr Leu Ile
                165                 170                 175

Ala Ala Leu Leu Leu Arg His Thr Leu Glu Gln Glu Thr Ala Asp Arg
                180                 185                 190

Arg Ala Gly Lys Pro Lys Arg Ile Ala Phe Phe Leu Val Glu Lys Val
        195                 200                 205

Ala Leu Ala Leu Gln Gln His Ala Val Leu Glu Cys Asn Leu Glu Phe
        210                 215                 220

Pro Ile Asp Arg Val Cys Gly Asp Met Val Arg Ser Asp Trp Ile Lys
225                 230                 235                 240

Glu Ser Trp Met Lys Arg Trp Asp Asp Asn Met Val Met Val Cys Thr
                245                 250                 255

Ala Ala Ile Leu Gln Gln Cys Leu Ala Arg Ser Phe Ile Arg Met Asp
                260                 265                 270

Gln Ile Asn Leu Leu Val Phe Asp Glu Ala His His Ala Lys Gly Asn
            275                 280                 285

His Pro Tyr Ala Arg Ile Ile Lys Asp Tyr Tyr Ile Thr Glu Pro Asp
        290                 295                 300

Lys Glu Arg Arg Pro Lys Ile Phe Gly Met Thr Ala Ser Pro Val Asp
305                 310                 315                 320

Ala Leu Thr Asp Val Lys Ile Ala Ala Ala Gln Leu Glu Gly Leu Leu
                325                 330                 335

His Ser Glu Ile Ala Thr Ile Glu Glu Asp Ser Val Ser Phe Lys Gln
            340                 345                 350

Ile Gln Lys Glu Val Val Glu Gln Asp Cys Lys Tyr Pro Ala Leu Glu
        355                 360                 365

Pro Pro Phe Thr Thr Asn Leu His Lys Lys Ile Gln Glu Gln Val Arg
        370                 375                 380

Tyr Asn Lys Asn Phe Ala Lys Ala Leu Ser Asn Ser Leu Glu Met Ser
385                 390                 395                 400

Ser Ser Leu Gly Ser Trp Cys Val Asp Arg Phe Trp Gln Ile Phe Leu
                405                 410                 415

Thr Glu Glu Thr Leu Ala Arg Leu Ala Ala Gln Thr Ala Gln Asp Asn
                420                 425                 430

Ile Phe Ala Asp Arg Ala Glu Lys Glu Arg Val Ala Ile Glu Glu Val
            435                 440                 445

Arg Asn Ile Ile Lys Gln His Gln Phe Leu Pro Ile Thr Lys Thr Leu
        450                 455                 460

Gln Asp Leu Ser Ser Lys Val Leu Cys Leu Leu Gly Gln Leu Glu Leu
465                 470                 475                 480
```

```
Arg Phe Ser Ala Pro Thr Asp His Lys Cys Ile Ile Phe Val Glu Lys
            485                 490                 495

Arg Asn Thr Ala Met Ile Leu Ala His Leu Leu Ser Leu Pro Gly Ile
            500                 505                 510

Gly Pro Leu Tyr Leu Lys Pro Ala Ala Leu Val Gly Asn Pro Ser Asp
            515                 520                 525

Asn Ser Pro Leu Ala Met Ser Tyr Lys Glu Gln Val Met Thr Ile Thr
            530                 535                 540

Lys Phe Arg Arg Gly Glu Tyr Asn Cys Leu Leu Ala Thr Ser Val Ala
545                 550                 555                 560

Glu Glu Gly Ile Asp Ile Ala Asp Cys Asn Ile Val Ile Arg Phe Asp
            565                 570                 575

Leu Phe Asn Ser Val Ile Gln Tyr Ile Gln Ser Lys Gly Arg Ala Arg
            580                 585                 590

His Leu Asn Ser Glu Tyr Ile Cys Met Ala Glu Leu Gly Asn Gly Lys
            595                 600                 605

His Thr Arg Ala Lys Ile Gln Ala Asn Tyr Asp Leu Ser Leu Ile Arg
            610                 615                 620

Gln Phe Cys Ser Thr Leu Pro Glu Asp Arg Lys Ile Val Gly Trp Asp
625                 630                 635                 640

Pro Glu Ala Ala Leu His His Gly Glu Arg Asp His Lys Phe His Ile
            645                 650                 655

Val Pro Ser Thr Gly Ala Lys Leu Thr Trp Thr Gly Ser Leu Val Val
            660                 665                 670

Leu Ser Asn Phe Ala Ser Ser Leu Gln Val Asn Asp Glu Thr Leu Ser
            675                 680                 685

Pro Ser Tyr Met Val Ser Leu Ile Gly Ser Glu Tyr Ile Cys Glu Val
            690                 695                 700

Gln Leu Pro Ser Lys Ser Pro Ile Leu Ser Val Ser Gly Thr Leu Gln
705                 710                 715                 720

Lys Asn Lys Ala Glu Ala Arg Cys Ser Ala Ala Phe Glu Met Cys Met
            725                 730                 735

Lys Leu Ile Lys Gly Gly Phe Ile Ser Ser His Leu Gln Pro Thr Phe
            740                 745                 750

Thr Arg Lys Leu Pro Ala Met Arg Asn Ala Arg Leu Ala Ile Ser Ser
            755                 760                 765

Lys Lys Arg Glu Arg Tyr Asn Met Arg Val Lys Pro Glu Val Trp Ser
770                 775                 780

Arg Arg Gly Pro Ala Ser Ser Leu Phe Leu Thr Val Leu Lys Leu Arg
785                 790                 795                 800

Thr Pro Gly Ala Leu Asn Arg Pro Ser Gln Pro Leu Ala Leu Leu Thr
            805                 810                 815

Arg Glu Ala Leu Pro Glu Leu Pro Gly Val Pro Leu Phe Phe Gly Asn
            820                 825                 830

Cys Gly Arg Ser Ile Ala Glu Val Ser Val Ala Lys Pro Met His
            835                 840                 845

Leu Asp Glu Val Arg Leu Asp Ser Leu Arg Val Phe Thr Leu Arg Ile
            850                 855                 860

Phe Lys Asp Val Phe Ser Lys Val Tyr Asp Ser Gln Val Ala Asp Leu
865                 870                 875                 880

Pro Tyr Phe Leu Ala Pro Ala Ala His Asp His Ser His Glu Phe Ser
            885                 890                 895
```

-continued

```
Pro Asn Glu Asp Pro Gly Ser Leu Ile Asp Trp Ser His Leu Leu Ser
            900                 905                 910
Thr Lys Glu Val Glu Tyr Leu Pro Trp Asp Glu Asp His Ser Pro Ser
        915                 920                 925
Phe Tyr Gln Ser Lys Phe Val Ile Asp Pro Tyr Thr Gly Ser Arg Lys
    930                 935                 940
Leu Phe Leu Arg Gly Ile Arg Thr Asp Leu Lys Pro Thr Asp Leu Val
945                 950                 955                 960
Pro Asp Gly Val Pro Glu Pro Thr Phe Arg Leu Trp Lys Asp Val Glu
                965                 970                 975
His Thr Ile Lys Glu Tyr Ser Ile Ser Leu Trp Ala Lys Ser Arg Ala
            980                 985                 990
Arg Arg Ala Gly Glu Trp Leu Asp Thr Gln Pro Val Val Glu Ala Glu
        995                 1000                1005
Leu Val Ser Leu Arg Arg Asn Leu Leu Asp Glu Phe Ala Asp Ser
    1010                1015                1020
Lys His Glu Gly Ser Arg Val Cys Tyr Val Ile Leu Gln Pro Leu
    1025                1030                1035
Gln Ile Ser Thr Leu Pro Val Glu Val Val Ala Met Ala Tyr Asn
    1040                1045                1050
Phe Pro Ala Ile Ile His Arg Ile Glu Ser Asn Met Ile Ala Leu
    1055                1060                1065
Asp Ala Cys Arg Met Leu Asn Leu Arg Val Arg Pro Asp Leu Ala
    1070                1075                1080
Leu Glu Ala Met Thr Lys Asp Ser Ser Asn Ser Glu Glu His Asp
    1085                1090                1095
Gln Glu Lys Ile Asp Phe Gln Ala Gly Met Gly Asn Asn Tyr Glu
    1100                1105                1110
Arg Leu Glu Phe Leu Gly Asp Cys Phe Leu Lys Met Ala Thr Thr
    1115                1120                1125
Ile Ala Leu Phe Thr Arg Ile Pro Asp Ser Asn Glu Phe Glu Cys
    1130                1135                1140
His Val Glu Arg Met Leu Leu Ile Cys Asn Gln Asn Leu Phe Asn
    1145                1150                1155
Val Ala Leu Lys Lys Asn Leu Gln Glu Tyr Ile Arg Ser Lys Gln
    1160                1165                1170
Phe Asp Arg Arg Ser Trp Tyr Pro Gln Gly Leu Lys Gln Lys Ala
    1175                1180                1185
Gly Lys Ala Gln Gly Ala Gln Asn Ser His Ser Leu Ala Asp Lys
    1190                1195                1200
Ser Ile Ala Asp Val Cys Glu Ala Ile Ile Gly Ala Ser Tyr Leu
    1205                1210                1215
Ser Tyr Thr Asp Glu Gly Asn Phe Asp Met Ala Val Arg Ala Val
    1220                1225                1230
Thr Ala Val Val Arg Asn Lys Asn His Asp Met Lys Ser Tyr Glu
    1235                1240                1245
Asp Tyr Tyr Lys Ala Phe Lys Met Pro Ile Trp Gln Ala Ala Glu
    1250                1255                1260
Pro Ser Ala Val Gln Met Glu Ala Ser Leu Gln Ile Lys Glu Gln
    1265                1270                1275
Met Gly Tyr Glu Phe Lys Ser Pro Ala Leu Leu Arg Ser Ala Phe
    1280                1285                1290
Lys His Pro Ser Tyr Pro Arg Gln Phe Glu Ser Val Pro Asn Tyr
```

```
    1295                1300                1305

Gln Arg  Leu Glu Phe Leu Gly  Asp Ala Leu Leu Asp  Met Val Cys
    1310                1315                1320

Val Asp  Phe Leu Phe Arg Lys  Phe Pro Asp Ala Asp  Pro Gln Trp
    1325                1330                1335

Leu Thr  Glu His Lys Met Ala  Met Val Ser Asn His  Phe Leu Gly
    1340                1345                1350

Ser Leu  Ser Val Glu Leu Gly  Phe Tyr Arg Arg Val  Leu His Phe
    1355                1360                1365

Asn Ser  Ile Met Ala Asn Gln  Ile Lys Asp Tyr Val  Asp Ala Leu
    1370                1375                1380

Thr His  Ala Arg Gln Glu Ala  Glu Ala Val Ala Gln  Ile Ser Gly
    1385                1390                1395

Thr Val  Ser Arg Asp Tyr Trp  Leu Asn Val Lys His  Pro Pro Lys
    1400                1405                1410

Phe Leu  Ser Asp Val Val Glu  Ala Tyr Ile Gly Ala  Ile Phe Val
    1415                1420                1425

Asp Ser  Gly Tyr Asp Tyr Gly  Gln Val Gln Ala Phe  Phe Glu Lys
    1430                1435                1440

His Ile  Arg Pro Phe Phe Ala  Asp Met Ala Leu Tyr  Asp Ser Phe
    1445                1450                1455

Ala Ser  Ser His Pro Val Thr  Thr Leu Ala Arg Met  Met Gln Gln
    1460                1465                1470

Asp Phe  Gly Cys Gln Asp Trp  Arg Leu Leu Val Ser  Glu Leu Pro
    1475                1480                1485

Pro Ser  Cys Glu Asp Gly Gly  Ala Ala Ala Ile Thr  Glu Thr Glu
    1490                1495                1500

Val Ile  Cys Gly Phe Met Val  His Gly Arg Ile Leu  Leu His Ala
    1505                1510                1515

Lys Ser  Ser Ser Gly Arg Tyr  Ala Lys Val Gly Ala  Ala Lys Arg
    1520                1525                1530

Ala Val  Glu Lys Leu Met Gly  Leu Gly Asn Asp Lys  Glu Val Phe
    1535                1540                1545

Arg Thr  Asp Phe Gly Cys Asp  Cys Asp Cys Glu Gly  Gln Ala Ile
    1550                1555                1560
```

<210> SEQ ID NO 7
<211> LENGTH: 3593
<212> TYPE: DNA
<213> ORGANISM: Verticillium dahilae

<400> SEQUENCE: 7

```
atcactctac gggtaaaagc gctgagagaa tgatcatgat gaatttctat catccacgca      60
aacaatcggc actatctgtt ccccacgtcc tgggactgac cgcaagcccc ataatgcgat     120
ctaggctcga aggccttgag gcactggaac agacactgga ctcggtttgc gttacgccca     180
gattgcaccg agatgactta atgacccatg tcaaaaggcc caccgtctgt tatgtccatt     240
acgaaacgac agatgctaag gatgagccca agccggtcag catttcaagt cttcgcgaag     300
catgcagaaa tatggacatc aggcaagatc catacgttat ctgtctaaga gacaaaggca     360
ctgatcgagc acgacgtgag ctcatcaagg tccttacaag ccataaaaca gattcgcaac     420
agcaaatgaa gtctttcttc aatcaaagct tgcgagtcct gcgagatctc gggccctggg     480
cggccgagta ctacatttgg aaggttgtta cagattttct ggcaatcatt gaagcaagag     540
```

```
atcaccgcat gaatcaacgg aataccgaag aaaagcagta tctggccaac atccttcgac    600
aaatcagtat cagcgagccg ccagtcagca tgttgagtgc tcataacacg tcgaacaaag    660
taatggtgct catggaatac ttgtcatcta aagctaccga tggtactgtc gggatcatat    720
ttgtcaaaga gcgatcaact gcggcgatgc ttgcacacgt gattgagtcg catccactga    780
cacagaatag gcactcgagc gttggggttg ttgttggtgc ttccactcat ctggtaagga    840
agaaagacat gtgggatctg tctcgagcag cccacgagac agagccccctt cttcagttca    900 gatctggcca cctcaatttg ctcatcgcca cgagtgtgct tgaagagggc atcgacgttc    960
ctgcctgcaa cctcgtgatc tgttttgatg agcccgagaa tctcaaagcc tttgtccagc    1020
ggcgcggccg agcccggaag aaggattcta gcctcgtggt tcttctcccc gggacagacc    1080
acgtgcctca ggactgggaa agcatggaag cgacaatgag gacacactac gagagagaac    1140
agcgcgaaat acaaatcatg gagcagatcg aagcatccga gtctgcaaag tacgaagagt    1200
acgttgtcga gagtactaat gccagactcg acttcgagaa cgccaaagcg catctcagca    1260
acttttgtgg gcagctctct cccggggagt ttatagacaa gaggcccgaa tacataccccc    1320 gtgtggtaga caacggagta cctccatctc tgagggtcac ggtactgttg ccaagctatg    1380
ttccagctgc cgtccgccat gctgagagtc gtcgaagctg gaagtcggag catcaggcct    1440
caaaggatgc cgcttttcag gcatacgtgg ctctttacaa agcgggactg gtcaatgaac    1500
acatgcttcc actcacggta aaagatatcg tacccgcaaa cgaacctcga gtagcaacct    1560
tgcaggtcaa tggcctcttg aatgtctggc ttggtattgc ccaggcctgg atcacgagca    1620
ctgaaacctg gttaactcca gtgcacctcc gagacgcgac gggattgacg cgaggaacgt    1680
atatcatgag aatgccggta gcattgccgg cactgccttc cacgccggtg tacttcgatc    1740
gcgaaggacc atggcttctg gattttggcc cacaagaacg aaaggagaat cttgaaatgc    1800
ctgatcatac ttcagtgctg cttgcactcc actttggcca tcactggtct attgctcatg    1860
gtcagcagca ggttatcagc ttcgcttcac aagatggcga actgaatatc aggcaattaa    1920
gtgcacgggg tttcacaacc gcagatgccg accgagagga aatgctgtac ctggtacggg    1980
acgagtcagg atgcccgtat gtgtacgacc actttctaaa tggcaagccg tcacttgaac    2040
ttgttcaacg accttttccgg cgcatcgggg actctccagg ctttcaagac gcacccagta    2100
acatccccta cttggctctc agaaagtggc cgcggtacct ggccctcttg caccaacaga    2160
aggtcaacga tctactgcca caggcgacaa acaagaagcc atatgctagg gtttatccgg    2220
caccgtgggc gaaagtcgac acgattccat tagatcatgc ttactttggg gcgttgatcc    2280
ctttcatttc acacattgtc gaggttcgac tggttgcaga acagctttcc tcgagcctac    2340
ttcgtgacct caatttctca gatccctctc ttgtcctggc ggccattagc actaagggtt    2400
ccttggaagc cacaaactac gagcgccttg agcttttggg tgactctatc ctcaagcttt    2460
gcaccacggc caatgccgcc gctctgcatg gcttagtgtc gaactcgaga ttgtgtaggg    2520
ctgcactgga tgctggcctt gacaaatttg ttctaactga aaacttcact tgtcgcacgt    2580
ggcgccctat ctacgtcaac gacatgatgg aaaagggtgc tcgcgactca ggaccccgta    2640
tcatgtcgac gaagacgctc gccgatattg tggaagcact catagggggcc gcatacattg    2700 acggtggcct cccaaaggca cttgggtgca tttcgatctt cctgagggag ctcgattgga    2760
aaccgttgcc agcttgccag gagatccttt acagtttggc gtcccctgat gtgcctttgc    2820
cgccaatgct tgttccgctg gaggacctga tcggctacac gatgcatctc ctcaagactg    2880
cttcggtcaa cggcgatctt ctaggcttcc ttgcactcga gtgccatgcc gaggaagacg    2940
```

-continued

```
aggtgatcat tgatatcgat ttttctcctt ccgatacgga cttcaatcct caaaattccg    3000
ccggggtgga acagaagctc aaacagacac gccggaaaat ccccctttgg aagtttatgc    3060
gccactcctc aatagaggtt gtgcagcagc agaccaaagc tgccagcgtt catgccgatc    3120
tccgaggaca gatcatgcac gctctggaac atgggtcaag ctaccctgg tctcttctcg     3180 cccgtttaca tcccgcaaag ttcttctccg acatggtcga agctgtactg ggtgccgtct    3240
gggtcgattc gggcgacatg ggcgcgtgca ttcgtgtggc ggaacgactg gcattctgc     3300 ctgtgctctc ccgactggca aaggaggacg ttcatgtgct gcatccgaag caagagctgg    3360
gagagatcgc tggtccccgg acagtcaaat atctcctcac tttgcccgag acgcagccg     3420 gcctgcaaag tgcaacaaga aaatatgcct gcaaggtcat ggtcggggat cgctgtgttg    3480
cagaggtgga tgacggggtc gctcgagatg aggttgagac aaaggctgca gaggttgcgg    3540
tacagacctt gaagaatgaa caggctgacg cgaaacaagt agcagaacac taa           3593
```

<210> SEQ ID NO 8
<211> LENGTH: 1187
<212> TYPE: PRT
<213> ORGANISM: Verticillium dahilae

<400> SEQUENCE: 8

```
Met Ile Met Met Asn Phe Tyr His Pro Arg Lys Gln Ser Ala Leu Ser
1               5                   10                  15

Val Pro His Val Leu Gly Leu Thr Ala Ser Pro Ile Met Arg Ser Arg
            20                  25                  30

Leu Glu Gly Leu Glu Ala Leu Glu Gln Thr Leu Asp Ser Val Cys Val
        35                  40                  45

Thr Pro Arg Leu His Arg Asp Asp Leu Met Thr His Val Lys Arg Pro
    50                  55                  60

Thr Val Cys Tyr Val His Tyr Glu Thr Thr Asp Ala Lys Asp Glu Pro
65                  70                  75                  80

Lys Pro Val Ser Ile Ser Ser Leu Arg Glu Ala Cys Arg Asn Met Asp
                85                  90                  95

Ile Arg Gln Asp Pro Tyr Val Ile Cys Leu Arg Asp Lys Gly Thr Asp
            100                 105                 110

Arg Ala Arg Arg Glu Leu Ile Lys Val Leu Thr Ser His Lys Thr Asp
        115                 120                 125

Ser Gln Gln Gln Met Lys Ser Phe Asn Gln Ser Leu Arg Val Leu
    130                 135                 140

Arg Asp Leu Gly Pro Trp Ala Ala Glu Tyr Tyr Ile Trp Lys Val Val
145                 150                 155                 160

Thr Asp Phe Leu Ala Ile Ile Glu Ala Arg Asp His Arg Met Asn Gln
                165                 170                 175

Arg Asn Thr Glu Glu Lys Gln Tyr Leu Ala Asn Ile Leu Arg Gln Ile
            180                 185                 190

Ser Ile Ser Glu Pro Pro Val Ser Met Leu Ser Ala His Asn Thr Ser
        195                 200                 205

Asn Lys Val Met Val Leu Met Glu Tyr Leu Ser Lys Ala Thr Asp
    210                 215                 220

Gly Thr Val Gly Ile Ile Phe Val Lys Glu Arg Ser Thr Ala Ala Met
225                 230                 235                 240

Leu Ala His Val Ile Glu Ser His Pro Leu Thr Gln Asn Arg His Ser
                245                 250                 255
```

```
Ser Val Gly Val Val Gly Ala Ser Thr His Leu Val Arg Lys Lys
            260                 265                 270

Asp Met Trp Asp Leu Ser Arg Ala Ala His Glu Thr Glu Pro Leu Leu
        275                 280                 285

Gln Phe Arg Ser Gly His Leu Asn Leu Leu Ile Ala Thr Ser Val Leu
    290                 295                 300

Glu Glu Gly Ile Asp Val Pro Ala Cys Asn Leu Val Ile Cys Phe Asp
305                 310                 315                 320

Glu Pro Glu Asn Leu Lys Ala Phe Val Gln Arg Arg Gly Arg Ala Arg
                325                 330                 335

Lys Lys Asp Ser Ser Leu Val Val Leu Leu Pro Gly Thr Asp His Val
            340                 345                 350

Pro Gln Asp Trp Glu Ser Met Glu Ala Thr Met Arg Thr His Tyr Glu
        355                 360                 365

Arg Glu Gln Arg Glu Ile Gln Ile Met Glu Gln Ile Glu Ala Ser Glu
    370                 375                 380

Ser Ala Lys Tyr Glu Glu Tyr Val Val Glu Ser Thr Asn Ala Arg Leu
385                 390                 395                 400

Asp Phe Glu Asn Ala Lys Ala His Leu Ser Asn Phe Cys Gly Gln Leu
                405                 410                 415

Ser Pro Gly Glu Phe Ile Asp Lys Arg Pro Glu Tyr Ile Pro Arg Val
            420                 425                 430

Val Asp Asn Gly Val Pro Pro Ser Leu Arg Val Thr Val Leu Leu Pro
        435                 440                 445

Ser Tyr Val Pro Ala Ala Val Arg His Ala Glu Ser Arg Arg Ser Trp
    450                 455                 460

Lys Ser Glu His Gln Ala Ser Lys Asp Ala Ala Phe Gln Ala Tyr Val
465                 470                 475                 480

Ala Leu Tyr Lys Ala Gly Leu Val Asn Glu His Met Leu Pro Leu Thr
                485                 490                 495

Val Lys Asp Ile Val Pro Ala Asn Glu Pro Arg Val Ala Thr Leu Gln
            500                 505                 510

Val Asn Gly Leu Leu Asn Val Trp Leu Gly Ile Ala Gln Ala Trp Ile
        515                 520                 525

Thr Ser Thr Glu Thr Trp Leu Thr Pro Val His Leu Arg Asp Ala Thr
    530                 535                 540

Gly Leu Thr Arg Gly Thr Tyr Ile Met Arg Met Pro Val Ala Leu Pro
545                 550                 555                 560

Ala Leu Pro Ser Thr Pro Val Tyr Phe Asp Arg Glu Gly Pro Trp Leu
                565                 570                 575

Leu Asp Phe Gly Pro Gln Glu Arg Lys Glu Asn Leu Glu Met Pro Asp
            580                 585                 590

His Thr Ser Val Leu Leu Ala Leu His Phe Gly His His Trp Ser Ile
        595                 600                 605

Ala His Gly Gln Gln Val Ile Ser Phe Ala Ser Gln Asp Gly Glu
    610                 615                 620

Leu Asn Ile Arg Gln Leu Ser Ala Arg Gly Phe Thr Thr Ala Asp Ala
625                 630                 635                 640

Asp Arg Glu Glu Met Leu Tyr Leu Val Arg Asp Glu Ser Gly Cys Pro
                645                 650                 655

Tyr Val Tyr Asp His Phe Leu Asn Gly Lys Pro Ser Leu Glu Leu Val
            660                 665                 670

Gln Arg Pro Phe Arg Arg Ile Gly Asp Ser Pro Gly Phe Gln Asp Ala
```

-continued

```
            675                 680                 685
Pro Ser Asn Ile Pro Tyr Leu Ala Leu Arg Lys Trp Pro Arg Tyr Leu
    690                 695                 700

Ala Leu Leu His Gln Gln Lys Val Asn Asp Leu Leu Pro Gln Ala Thr
705                 710                 715                 720

Asn Lys Lys Pro Tyr Ala Arg Val Tyr Pro Ala Pro Trp Ala Lys Val
                725                 730                 735

Asp Thr Ile Pro Leu Asp His Ala Tyr Phe Gly Ala Leu Ile Pro Phe
                    740                 745                 750

Ile Ser His Ile Val Glu Val Arg Leu Val Ala Glu Gln Leu Ser Ser
                755                 760                 765

Ser Leu Leu Arg Asp Leu Asn Phe Ser Asp Pro Ser Leu Val Leu Ala
770                 775                 780

Ala Ile Ser Thr Lys Gly Ser Leu Glu Ala Thr Asn Tyr Glu Arg Leu
785                 790                 795                 800

Glu Leu Leu Gly Asp Ser Ile Leu Lys Leu Cys Thr Thr Ala Asn Ala
                    805                 810                 815

Ala Ala Leu His Gly Leu Val Ser Asn Ser Arg Leu Cys Arg Ala Ala
                820                 825                 830

Leu Asp Ala Gly Leu Asp Lys Phe Val Leu Thr Glu Asn Phe Thr Cys
                    835                 840                 845

Arg Thr Trp Arg Pro Ile Tyr Val Asn Asp Met Met Glu Lys Gly Ala
850                 855                 860

Arg Asp Ser Gly Pro Arg Ile Met Ser Thr Lys Thr Leu Ala Asp Ile
865                 870                 875                 880

Val Glu Ala Leu Ile Gly Ala Ala Tyr Ile Asp Gly Gly Leu Pro Lys
                    885                 890                 895

Ala Leu Gly Cys Ile Ser Ile Phe Leu Arg Glu Leu Asp Trp Lys Pro
                900                 905                 910

Leu Pro Ala Cys Gln Glu Ile Leu Tyr Ser Leu Ala Ser Pro Asp Val
                915                 920                 925

Pro Leu Pro Pro Met Leu Val Pro Leu Glu Asp Leu Ile Gly Tyr Thr
930                 935                 940

Met His Leu Leu Lys Thr Ala Ser Val Asn Gly Asp Leu Leu Gly Phe
945                 950                 955                 960

Leu Ala Leu Glu Cys His Ala Glu Glu Asp Glu Val Ile Ile Asp Ile
                    965                 970                 975

Asp Phe Ser Pro Ser Asp Thr Asp Phe Asn Pro Gln Asn Ser Ala Gly
                980                 985                 990

Val Glu Gln Lys Leu Lys Gln Thr Arg Arg Lys Ile Pro Leu Trp Lys
                995                 1000                1005

Phe Met Arg His Ser Ser Ile Glu Val Val Gln Gln Gln Thr Lys
    1010                1015                1020

Ala Ala Ser Val His Ala Asp Leu Arg Gly Gln Ile Met His Ala
    1025                1030                1035

Leu Glu His Gly Ser Ser Tyr Pro Trp Ser Leu Leu Ala Arg Leu
    1040                1045                1050

His Pro Ala Lys Phe Phe Ser Asp Met Val Glu Ala Val Leu Gly
    1055                1060                1065

Ala Val Trp Val Asp Ser Gly Asp Met Gly Ala Cys Ile Arg Val
    1070                1075                1080

Ala Glu Arg Leu Gly Ile Leu Pro Val Leu Ser Arg Leu Ala Lys
    1085                1090                1095
```

```
Glu Asp Val His Val Leu His Pro Lys Gln Glu Leu Gly Glu Ile
    1100                1105                1110

Ala Gly Pro Arg Thr Val Lys Tyr Leu Leu Thr Leu Pro Glu Asp
    1115                1120                1125

Ala Ala Gly Leu Gln Ser Ala Thr Arg Lys Tyr Ala Cys Lys Val
    1130                1135                1140

Met Val Gly Asp Arg Cys Val Ala Glu Val Asp Gly Val Ala
    1145                1150                1155

Arg Asp Glu Val Glu Thr Lys Ala Ala Glu Val Ala Val Gln Thr
    1160                1165                1170

Leu Lys Asn Glu Gln Ala Asp Ala Lys Gln Val Ala Glu His
    1175                1180                1185

<210> SEQ ID NO 9
<211> LENGTH: 260
<212> TYPE: DNA
<213> ORGANISM: Botrytis cinerea

<400> SEQUENCE: 9
tgcggaagaa cttgaaggtt tgctacacag tcaaatatgt actgcagaag atcccagctt      60
gctgcagtac tcaatcaaag gtaaacctga gactcttgcc tactatgatc ccttgggccc     120
gaaattcaat actcctcttt atcttcaaat gctcccgctt ctaaaagaca atcctatctt     180
tcggaagcca tttgtatttg ggacagaagc cagtagaact ctaggatctt ggtgtgttga     240
ccagatctgg actttctgtc                                                 260

<210> SEQ ID NO 10
<211> LENGTH: 296
<212> TYPE: DNA
<213> ORGANISM: Botrytis cinerea

<400> SEQUENCE: 10
tctttaagtg atatcgagga gactttggat gccatttgct gcacgccaaa atacatcga      60 gcagatcttc gccttcgagt aaagctacca cttctatcta ttatctacta tccccagag     120 tcaaatatca tcgtgacgaa aactgtggcg agcctgagaa agattgtgca agtctcaac     180 attttcgaag cccctacgt tttgacacta aaaggagtg atagcgaaaa aagtcaacgt     240
gagctggcga agtactcaa gagttttaag acatatagtc aaacccaatt aaagtc        296

<210> SEQ ID NO 11
<211> LENGTH: 293
<212> TYPE: DNA
<213> ORGANISM: Verticillium dahilae

<400> SEQUENCE: 11
ggcaagccca agagaatcgc ctttttcctc gtggaaaagg ttgctcttgc cctccaacag      60
cacgcggttc tggagtgcaa tctggaattt cccattgacc gggtatgcgg tgacatggta     120
cggtcggact ggatcaagga gtcatggatg aaaagatggg atgacaacat ggtcatggtc     180
tgcaccgccg ccatccttca gcaatgcctt gccagatcat tcatccgcat ggatcagatc     240
aacctgcttg tcttcgatga agcacatcac gccaagggaa atcatccgta cgc            293

<210> SEQ ID NO 12
<211> LENGTH: 319
<212> TYPE: DNA
<213> ORGANISM: Verticillium dahilae
```

<400> SEQUENCE: 12
acagacacgc cggaaaatcc ccctttggaa gtttatgcgc cactcctcaa tagaggttgt 60
gcagcagcag accaaagctg ccagcgttca tgccgatctc cgaggacaga tcatgcacgc 120
tctggaacat gggtcaagct accccctggtc tcttctcgcc cgtttacatc ccgcaaagtt 180
cttctccgac atggtcgaag ctgtactggg tgccgtctgg gtcgattcgg gcgacatggg 240
cgcgtgcatt cgtgtggcgg aacgactggg cattctgcct gtgctctccc gactggcaaa 300
ggaggacgtt catgtgctg 319

<210> SEQ ID NO 13
<211> LENGTH: 1021
<212> TYPE: DNA
<213> ORGANISM: Botrytis cinerea

<400> SEQUENCE: 13
ctcctggatc aggcagatga attagggaac tgatttcgac cttccagagt tctctttgcg 60
tgatgggtca cttgggtttg gttgtcggta tgctgtgggt tcggaggagt tgtcctttct 120
ggtttctttg ttggatagtc ctttttgggt agcttggtgt gatgcatgcg ttctgggtgt 180
gggtctcgtg aggtcttttt gtatcaagta tttttaagct tttttcttgt tctcttcttt 240
ttctgtattg gtaatgcttc ttctttatga tattctccca tcgctgcttt cgcattttct 300
aggttgtagg gtgcttccca cgtgtcttcc gccggttggt agcccttcca tcgcaccagg 360
tattgcacac ctctgcctct ttttctatgt gctaaaatcc tttccacctc atgctctatg 420
tgatcgtcaa tttcttctgg cggcggcggg tcggcggtac cctgtcgttc gtgccatggt 480
tcgagtaaag agacgtggaa tacattgtgg atcttgtagg tgggcggtaa tctaagttcg 540
tatgcttgcc cgctggtttt tatacccgtc acgacaaagg ggcctataaa tcgatcggag 600
aattttttct taggtcgcag ttgtttaatg ttctttgtgc ttagcatcac cttgtccccg 660
atgctatatc gctgtggtga ccccttcgta gtgttcttgt ttttctgatt ggttgccgat 720
ttccagaatt ctttcagctt ttctctttct ttctctaaag cgtcgatgcg ctcgcgtgct 780
gccggcgccc ttccctctaa atcggcgtcc tcgccgatat aatggaatgt gggttggaac 840
ccatacatag cctggaatgg gcttgtattg gttgtactgt gccatgtcgc gttatatgtg 900
aattcagcaa ggggcaatag cgatgcccag tcgtcttgcc tatagttggt gtagcaactt 960
atatagtgaa tcaaattttg gttttgtcgt tcggtttgac cgtcggtctg cgggtggaac 1020
g 1021

<210> SEQ ID NO 14
<211> LENGTH: 3927
<212> TYPE: DNA
<213> ORGANISM: Botrytis cinerea

<400> SEQUENCE: 14
atggcatcca gagctaccgc cacaggtcaa tctgccggag acaccaacga catcgagatg 60
accgacgccc caaaggagat cactatcaac gaaaccctta agatcgcctt accagacaag 120
taccaaggta gtcgacaaga gctcgatact ttcctcttac aacttgagat ctactttcga 180
ttcaatgagg acaagttcac taccaaggaa tccaagagta tatgggccgc atcatacctt 240
cgaggtgaag caaccaaatg gatccaacca tatttgcgcg actatttcga gcatgacgat 300
aaggatcgta tgcaacccac ccgaacaatc ttcaatagtt ttgaaggatt taagacagag 360
attcgtagaa tcttcggaaa ttccaacgag ttagaggtag cggaagataa gatcttcaac 420

```
ctcaagcaga caggatcagc attgaaatat gctacggaat ttcgaagata tgctggaaca    480
accaagtggg acgaaatcgc tatcatgagt cactaccgca agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaaa aatgagggta gaccacgtta caatccacag    720
agatacggag accccatgga actagacgcc acgcactaca caaacgggaa cgatgactcg    780
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc tacctttaca atcccagaaa atccaactaa atccgaaaat    960
actgagactt tcaccgttga ggaattccag caattactaa aggaattacc acgaaatcaa   1020
gagggcatga atgcaataga cttatgggag caagagtatt acagaacccc aacaccctct   1080
gtgacagaag aaagtcatca ggacgaggca gaagcagacc acgccacgat gagctggaca   1140
gcttgctatg atgaattctg cggaatccat cgatcagata agaagcaac cggatggtcc    1200
cctaagaaga gaaagacgaa gaaccatcag aataatgtaa catgcgagga tttaactccc   1260
aatataactt cgcaagaagt tcgcaaagtt acccagcagt taaatgctac gggacaggca   1320
ggacagatat actgcaaggt tcagataaat ggacacatac aatcagccat gatagattca   1380
ggggctacag gaaattttat tgcaccggaa gctgagacaa tcccaatacg aatgggcata   1440
acccaacata cagaggttat acagcttgac gttgtgccat gggccaaca acagatcatc    1500
ttaggaatgc catggttaaa ggcacataat ccgaaaatag attgggcaca aggaattgtg   1560
acatttgatc agtgcaaaag cggtcacagg gacacgctag aggcgttcgc gagacgtaac   1620
acgcgccaag gagagttgaa cgcgaacaac accggcgacg taggacaccc agtccagggt   1680
cctccattaa gagcgaaggc cagtacacct cctctacaaa tgcagaagcc aacgacacgg   1740
cacgaaatcg caatcgaggc aaaagaaaag cctacgatac cagaacagta caagaattat   1800
gaacatgttt tcaaagaacc agggatccat gaggctttac cggaacacaa gccatgggat   1860
catgagataa tattggagga aggcaagatg cctgtgcaca ccccaattta ttcaatgtca   1920
gccgatgagt taaagaggct cagagagtac atcgacgaca atttagccaa gggatggata   1980
agggaatccg cgtcccaagt ggccagtcca actatgtgga aggatcgata tccacttcca   2040
ttagctacgg aattaagaga tcgattaggc ggagctacga tatttaccaa gatggaccta   2100
cgtaatggtt accacttgat cagaatgaag gaaggcgaag aatggaaaac cgcttcaaaa   2160
caagatacgg gctatacgac tactttcatg aggcttatga acaatgtgtt gtcacaatat   2220
ttggatactt gctgtatatg ctacttggac gacatcctag tatattcaaa caacaaggtt   2280
caacacatta aggacgttag caacatcctc gaaagcctat ccaaggcaga cttgctgtgc   2340
aaaccaagca aatgcgaatt ccatgtcaca gagacagaat tcttgggatt caccgtatca   2400
agccaagggc tcaagatgag caaaggcaag gttaaggcag tgctcgaatg gaagcagccg   2460
accacaatca aggaagtaca atcctttcta gggttcgtca acttctacag aagattcatc   2520
aagggttatt cagggattac tacacccttg accacgttaa ccagaaaaga tcaaggaagc   2580
ttcgaatgga ctgccaaagc acaggagtca ttcgatacgc tcaaacaagc agtggcagaa   2640
gagccaaatac tgttgacttt tgacccgaga aaagaaatca tagtgagac ggactcctcg    2700
gatttcgcta taggagcagt tctgagccaa ccgggccaga atggaaaata ccagccaatc   2760
```

```
gcattctact cccgaaaact atcaccagcc gaattgaatt acgagatata tgacaaagaa   2820
ttactggcga tagtcgatgc atttagagaa tggcgagtgt atttggaagg atcgaaatac   2880
acggtacagg tgtatacaga tcataagaac ttggtttact tcaccacaac gaagcagtta   2940
aacagacgac aggtcagatg gtcggagacc atggccaact acaatttcag aatttcatat   3000
gtcaaaggat cagaaaacgc tagagccgac gctcttagcc gaaaaccaga atatcaagaa   3060
aacaaaacgt acgagtcata cgctatattc aagaaagacg gcgaatcact ggtttacaat   3120
gcaccacagc ttgcagcaac acacctgttg gaagacaacc acctcaggaa acagatccaa   3180
tcacactacg acaaggatgc tactgccaca cgcatacgca agacaataga accaggattc   3240
actatagaaa atgataccat atactttcat ggaaaagtat acattccgag tcaaatgacc   3300
aaggaatttg tgacggaaca acacgggttg ccggcacatg gacaccaagg aattgcaagg   3360
acatttgcaa gaatacggga aatcagttac ttcccacgaa tgagaacgat agttgaagaa   3420
gttgttggaa attgtgacac ctgcatacga aacaagtcat cacgacatgc tccgtatggt   3480
cagctccaga ccccagacat gccttctcag ccatggaagt ccatcacatg ggactttgtg   3540
gtcaaactac cactctcaaa agatcctact acaggaattg agtacgacgc gatactcaat   3600
atagtagaca ggctaacgaa atttgcatat atgataccat tcaaggaaac atgggatgct   3660
gagcaactag catatgtgtt cctaaggatc atagtaagca tacacggagt accagatgag   3720
ataatctcgg atcgagacaa gctctttacc tcgaaattct ggactacctt attagcactt   3780
atgggtatca agagaaagct atcgacatct ttccacccac aaacagatgg tcaaacagag   3840
aggaccaatc agacaatgga agcatatctt agatgctatc gtataaaatc ccgataccac   3900
aagaagttaa tgccgaatca gcgatag                                        3927
```

<210> SEQ ID NO 15
<211> LENGTH: 4857
<212> TYPE: DNA
<213> ORGANISM: Botrytis cinerea

<400> SEQUENCE: 15

```
atggcatcca gagatatcgc cacaggtcaa tctgccggag acaccaacga catcgagatg     60
accgatgccc caaaagagat cactatcaac gaaacactta agatcgcctt accagacaag    120
taccaaggta gtcgacaaga actcgatact ttcctcttac aacttgagat ctacttccga    180
ttcaatgagg acaagttcac taccaaggaa tccaagagta tatgggccgc atcatacctt    240
cgaggtgaag caaccaaatg gatccaacca tatttgcgcg actatttcga gcatgacgat    300
aaggatcgca tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactaccgta agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaag aatgagggta gaccacgtta caacccacag    720
agatacggag accccatgga actagacgct acgcactaca caaacgggaa cgatgactca    780
gaaaagagac gaagacgaga aaacaactta tgctttgaat gtggaaaagc agggcaccga    840
gcagcagaat gccgaagcaa gaagacagga ggaaaaaggg gcaacttcaa acctaagttc    900
ggcaagggcc aacttaatgc cacctttgca atctcagaaa actcaactaa acccgaaaat    960
```

```
actgagactt tcaccgttga ggaattccag caattattag aggaattacc acgaaaccaa    1020
gagggcatga atgcaataga cttatgggaa caagagtatt acagaactcc aacaccctct    1080
gtgacagaag aaagtcacca ggacgaggca gaagcggacc acgccacgat aagctggaca    1140
gcttgctatg acgaattctg cggaatccat cgatcagata aagaagcaac cggatggttc    1200
cctaagaaga gaaagacgaa gaaccatcag aataatgtaa catgcgagga tttaactccc    1260
aatataactt cgcaagaagt tcgcaaagtt acccagcagt taaatgctac gggacaggca    1320
ggacagatat actgcaaggt tcagataaat ggacacatac aatcagccat gatagattca    1380
ggggctacag gaaattttat tgcaccagaa gcggcaaagt acttggaaat accacttcag    1440
aggaaacaat accectatcg attgcagtta gttgacggac agctagcagg gtctgacgga    1500
aagatttcgc aggagacaat cccagtacga atgagcataa cccaacatac agaggttata    1560
cagcttgatg ttgtgccatt gggccaacaa cagatcatct taggaatgcc atggttaaag    1620
gcacataatc cgaaaataga ttgggcacaa ggagttgtga catttgatca gtgcaaaagc    1680
ggtcacaggg acacgataga ggcgtccgcg agacgtaaca cgcgccaagg agagttgaac    1740
gcgaacaaca ccggcgacgt aggacaccca gtccagggtc ctccattaag agcgaaggcc    1800
agtacacctc ctctacaaat gcagaagcca acgacacggc acgaaatcgc aatcgaggca    1860
aaagaaaggc ctacgatacc agaacagtac aagaaatatg aacatgtttt caaagaacca    1920
gggatccatg aggctttacc ggaacacaag ccatgggatc atgagataat attggaggaa    1980
ggcaagatgc ctgtgcacac cccaatttat tcaatgtcag ccgatgagtt aaagaggctc    2040
agagagtaca tcgacgacaa tttagccaag ggatggatca gggaatccgc gtcccaagtg    2100
gccagtccaa ctatgtgggt acccaagaag gatggacccg atagactagt tgtagactat    2160
agaaagctta acgcactcac taagaaggat cgatatccac ttccattagc tacggaatta    2220
agagatcgat taggcggagc tacgatattc accaagatgg acctacgtaa tggttaccac    2280
ttgatcagaa tgaaggaagg cgaagaatgg aaaaccgctt tcaaaacaag atacgggcta    2340
tacgagtacc aagttatgcc attcgggcta accaacgcac cagctacttt catgaggctt    2400
atgaacaatg tgttgtcaca atatttggat acttgctgta tatgctactt ggacgacatc    2460
ctagtatatt caaacaacaa ggttcaacac attaaggacg ttagcaacat cctcgaaagc    2520
ctatccaagg cagacttgct gtgcaaacca agcaaatgcg aattccatgt cacagagaca    2580
gaattcttgg gattcaccgt atcaagccaa gggctcaaga tgagcaaaga caaggttaag    2640
gcagtgctcg aatggaagca gccgaccaca atcaaggaag tacaatcctt tctagggttc    2700
gtcaacttct acagaagatt tatcaagggt tattcaggga ttactacacc cttgaccacg    2760
ttaaccagaa aagatcaagg aagcttcgaa tggactgcca agcacagga gtcattcgat    2820 acgctcaaac aagcagtggc agaagaacca atactgttga cttttgaccc agagaaagaa    2880
atcatagtgg agacggactc ctcggatttc gctataggag cagttctgag ccaaccgggc    2940
cagaatggaa ataccagcc aatcgcattc tactcccgaa actatcacc agccgaattg    3000 aattacgaga tatatgacaa agaattactg cgcgatagtcg atgcatttag agaatggcga    3060
gtgtatttgg aaggatcgaa atacacggta caggtgtata cagatcataa gaacttggtt    3120
tacttcacca caacgaagca gttaaacaga cgacaggtca gatggtcgga gaccatggcc    3180
aactacaatt tcagaatttc atatgtcaaa ggatcagaaa acgctagagc cgacgctctt    3240
agccgaaaac cagaatatca agaaaacaaa acgtacgagt catacgctat attcaagaaa    3300
```

-continued gacggcgaat cactggttta caatgcacca cagcttgcag caacacacct gttggaagac 3360
aaccacctca ggaaacagat ccaatcacac tacgacaagg atgctactgc cacacgcata 3420
cgcaagacaa tagaaccagg attcactata gaaaatgata ccatatactt tcatggaaaa 3480
gtatacattc cgagtcaaat gaccaaggaa tttgtgacgg aacaacacgg gttgccggca 3540
catggacacc aaggaattgc aaggacattt gcaagaatac gggaaatcag ttacttccca 3600
cgaatgagaa cgatagttga agaagttgtt ggaaattgtg acacctgcat acgaaacaag 3660
tcatcacgac atgctccgta tggtcagctc cagaccccag acatgccttc tcagccatgg 3720
aagtccatca catgggactt tgtggtcaaa ctaccactct caaaggatcc tactacagga 3780
attgagtacg acgcgatact caatatagta gacaggctaa cgaaatttgc atatatgata 3840
ccattcaagg aaacatggga tgctgagcaa ctagcatatg tgttcctaag gatcatagta 3900
agcatacacg gagtaccaga tgagataatc tcggatcgag acaagctctt tacctcaaaa 3960
ttctggacta ccttattagc acttatgggt atcaagagaa agctatcgac atctttccac 4020
ccacaaacag atggtcaaac agagaggacc aatcagacaa tggaagcata tcttagatgc 4080
tatgtaaatt atcgacaaga caattgggta gagctattac ccatggcaca gttcgcatac 4140
aatacatcag aaacggaaac cacgaaaatc acaccagcac gagctaattt tgggtttaat 4200
ccacaagcgt ataaaatccc gataccacaa gaagttaatg ccgaatcagc gatagtacaa 4260
atcgaacagc tgaaagatct ccaagagcaa ctggctcttg atctaagatt catatcttcc 4320
agaacagcag cgtactacaa tacgaaacgt agtatggaac ctacgcttaa agagggggat 4380
aaagtttatt tgctacgacg aaacatcgaa accaagagac caagcaataa actcgaccac 4440
aggaaactag gaccattcaa gattgataag gtaataggaa cggttaatta tcgattgaaa 4500
ttaccagaca caatgaatat ccacccagta ttccacatat ccttgctcga accagcacca 4560
ccaggagcgc caaatgcgcc atttacagaa attgaaccag tcaacccaaa cgccatatac 4620
gatgtcgaaa caatactaga ctgcaaatac gtcagaaaca aggtcaagta tttgatcaaa 4680
tggttagact acccacattc agaaaacaca tgggaactca aggaagatct cagctgccct 4740
gagaagctac gggcattcca cctgaagtac ccacacctgc caataaagcc tcaagatccg 4800
cttcggacaa ctcaggcaaa gaaggatcga agaaatcgaa ggaagaagaa tcaatag 4857

<210> SEQ ID NO 16
<211> LENGTH: 3909
<212> TYPE: DNA
<213> ORGANISM: Botrytis cinerea

<400> SEQUENCE: 16
atggcatcca gagctaccgc cacaggtcag tctaccggag ataccaacga catcgagatg 60
accgatgccc caaaggagat cactatcaac gaaacactta agatcgcctt accagacaag 120
taccaaggta gtcgacaaga gctcgatact ttcctcttac aacttgagat ctacttccga 180
ttcaatgagg acaagttcac taccaaggaa tccaagagca tatgggctgc atcatacctc 240
cgaggtgaag caaccaaatg gattcaacca tatttgcgcg actatttcga gcatgacgat 300
aaggatcgca tgcaacccac ccgaacaatc ttcaatagtt ttgaaggatt taagacagag 360
attcgtagaa tcttcggaaa ttccaacgag ttagaggtag cggaagataa gatcttcaac 420
ctcaagcaga caggatcagc attgaaatat gctacggaat ttcgaagata tgctggaaca 480
accaagtggg acgaaatcgc tatcatgagt cactatcgta agggactcaa accagaagtc 540
agactggaat tagaaagatc tgccgagagt acagatctga acgatctaat tcaggactcc 600

```
atcgaatcag atgatcgtct ctacagatat cgacaaagcc agagatcata caaaccccaa      660
ggaaatcaga agcaagggcg ttaccgcaaa aatgagggta gaccacgtta caatccacag      720
agatacggag accccatgga actagacgcc acgcactaca caaacgggaa cgatgactcg      780
gaaaagagac gaagacgaga aaacaactta tgctttgaat gtggaaaagc agggcaccga      840
gcagcagact gccgaagcaa gaagacagga ggaaaaaggg gcaacttcaa acctaagttc      900
ggcaaaggcc aacttaacgc tacctttaca atcccagaaa atccaactaa atccgaaaat      960
actgagactt tcaccgttga ggaattccag caattactaa aggaattacc acgaaatcaa     1020
gagggcatga atgcaataga cttatgggag caagagtatt acagaacccc aacaccctct     1080
gtgacagaag aaagtcatca ggacgaggca gaagcagacc acgccacgat gagctggaca     1140
gcttgctatg atgaattctg cggaatccat cgatcagata agaagcaac cggatggttc      1200 cctaagaaga gaaagacgaa gaaccatcag aataatgtaa catgcgagga tttaactccc     1260
aatataactt cgcaagaagt tcgcaaagtt acccagcagt taaatgctac gggacaggca     1320
ggacagatat actgcaaggt tcagataaat ggacacatac aatcagccat gatagattca     1380
ggggctacag gaattttat tgcaccggaa gctgtaaagt acttgggaat accacttcaa      1440
acgaaacaac accctatcg attgcaggac acgctagagg cgtccgcgag acgtaacacg      1500
cgccaaggag agttgaacgc gaacaacacc ggcgacgtag acacccagt ccagggtcct      1560 ccattaagag cgaaggccag tacacctcct ctacaaatgc agaagccaac gacacggcac     1620
gaaatcgcaa tcgaggcaaa agaaaggcct acgataccag aacagtacaa gaaatatgaa     1680
catgttttca aagaaccagg gatccatgag gctttaccag aacacaagcc atgggatcat     1740
gagataatat tggaggaagg caagatgcct gtgcacaccc caatttattc aatgtcagcc     1800
gatgagttaa aaaggctcag agaatacatc gacgacaatt tagccaaggg atggatcagg     1860
gaatccgcgt cccaagtggc cagtccaact atgtgggtac caagaagga tggacccgat     1920 agactagttg tagactatag aaagcttaac gcactcacta agaaggatcg atatccactt     1980
ccattagcta cggaattaag agatcgatta ggcggagcta cgatatttac caagatggac     2040
ctacgtaatg gttaccactt gatcagaatg aaggaaggcg aagaatggaa gaccgctttc     2100
aaaacaagat acgggctata cgagtaccaa gttatgccgt tcgggctaac caacgcacca     2160
gctactttca tgaggcttat gaacaatgtg ttgtcacaat acttggatac ttgctgtata     2220
tgctacttgg acgacatcct agtatattca aacaacaagg ttcaacacat taaggacgtt     2280
agcaacatcc tcgaaagcct atccaaggca gacttgctgt gcaaaccaag caatgcgaa     2340 ttccatgtca cagagacaga cttcttggga ttcaccgtat caagccaagg gctcaagatg     2400
agcaaagaca aggttaaggc agtgctcgaa tggaaacagc caaccacaat caaggaggta     2460
caatcctttc tagggttcgt caacttctac agaagattta tcaagggtta ttcagggatt     2520
actacaccct tgaccacgtt aaccagaaaa gatcaaggaa gcttcgaatg gactgccaaa     2580
gcacaggagt cattcgatac gctcaaacaa gcagtggcag aagagccaat actattgact     2640
tttgacccag agaagaaat catagtggag acggactcct cggatttcgc tataggagca     2700
gttctgagcc aacgggcca gaatggaaaa taccagccaa tcgcattcta ttcccgaaaa     2760
ctatcaccag ctgagttgaa ttacgagata tatgacaaag aattgctggc gatagtcgat     2820
gcatttagag aatggcgagt atatttggaa ggatcgaaat acacagtaca ggtgtataca     2880
gatcataaga acttggttta cttcaccaca acgaagcagt taaacagacg acaggtcaga     2940
```

-continued

```
tggtcggaga ccatggccaa ctacaatttc agaatttcat atgtcaaagg atcagaaaac   3000
gctagagccg acgctcttag ccgaaaacca gaatatcaag aaaacaaaac gtacgagtca   3060
tacgctatat tcaagaaaga cggcgaatca ctggtttaca atgcaccaca gcttgcagca   3120
acacacctgt tggaagacaa ctaccttagg aaacagatcc aatcacacta cgacaaggat   3180
gctactgcca cacgcatacg taagacaata gaaccaggat tcactataga aaatgatacc   3240
atatactttc atggaaaagt atacattccg agtcaaatga ccaaggaatt tgtgacggaa   3300
caacacggat tgccggcaca tggacaccaa ggaattgcaa ggacatttgc aagaatacgg   3360
gaaatcagtt acttcccacg aatgagaacg atagttgaag aagttgttgg aaattgtgac   3420
acctgcatac gaaacaagtc atcacgacat gctccgtatg gtcagctcca gaccccagac   3480
atgccttctc agccatggaa gtccatcaca tgggactttg tggtcaaact accactctcc   3540
aaggatccta ctacaggaat tgagtacgac gcgatactca atatagtaga caggctaacg   3600
aaatttgcat atatgatacc attcaaggaa acatgggatg ctgagcaact agcatatgtg   3660
ttccttagga tcatagtaag catacacgga gtaccagatg agataatctc ggatcgagac   3720
aagctcttta cctcgaaatt ctggactacc ttattagcac ttatgggtat caagagaaag   3780
ctatcgacat ctttccaccc acaaacagat ggtcaaacag agaggaccaa tcagacaatg   3840
gaagcatatc ttagatgcta tcgtataaaa tcccgatacc acaagaagtt aatgccgaat   3900
cagcgatag                                                          3909
```

<210> SEQ ID NO 17
<211> LENGTH: 4857
<212> TYPE: DNA
<213> ORGANISM: Botrytis cinerea

<400> SEQUENCE: 17

```
atggcatcca gagctaccgc cacaggtcag cctaccggag ataccaacga catcgagatg     60
accgatgccc caaaggagat cactatcaac gaaaccctta agatcgcctt accagacaag    120
taccaaggta gtcgacaaga gctcgatact ttcctcttac aacttgagat ctactttcga    180
ttcaatgagg acaagttcac taccaaggaa tccaagagta tatgggccgc atcatacctt    240
cgaggtgaag caaccaaatg gatccaacca tatttgcgcg actatttcga gcatgacgat    300
aaggatcgca tgcaacccac ccgaacaatc ttcaatagct ttgaaggatt taagacagag    360
attcgtagaa tcttcggaaa ttccaacgag ctagaggtag cggaagataa gatcttcaac    420
ctcaagcaga caggatcagc attgaaatat gctacggaat ttcgaagata cgctggaaca    480
accaagtggg acgaaatcgc tatcatgagt cactaccgca agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaag aatgagggta gaccacgtta caatccacaa    720
agatacggag accccatgga actagacgct acgcactaca caaacgggaa cgatgactca    780
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc taccttttaca atcccagaaa acccaactaa atccgaaaat    960
actgagactt tcaccgttga ggaattccag caattactaa aggaattacc acgaaataaa   1020
gagggcatga atgcaataga cttatgggaa caagagtatt acagaacccc aacaccctct   1080
gtgacagaag aaagtcacca ggacgaggca gaagcggacc acgccacgat gagctggaca   1140
```

-continued

```
gcttgctatg atgaattctg cggaatccat cgatcagata aagaagcaac cggatggttc    1200
cccaagaaaa ggaagacgaa gaaccatcag aataatgtaa catgcacgga tttaacttca    1260
aatataactt cgcgaaaagt tcgcaaagtt acccagcagt tgaatgctac gggacaagca    1320
ggacagatat actgcaaggt tcagataaat ggacacatac aatcagccat gatagattca    1380
ggggctacag gaaattttat tgcaccagaa gctgcaaagt acttggaaat accacttcag    1440
acgaaacaat acccctatcg attgcagtta gttgacggac agctagcagg gtctgacgga    1500
aagatttcgc aggagacaat cccagtacga atgggcataa cccaacatac agaggttata    1560
cagcttgacg ttgtgccatt gggccaacaa cagatcatct taggaatgcc atggttgaag    1620
gcacataatc cgaaaataga ttgggcacaa ggaattgtga catttgatca gtgcaaaagc    1680
ggtcacaggg acacgctaga ggcgtccgcg agacgtaaca cgcgccaagg agagttgaac    1740
gcgaacaaca ccggcgacgt aggacaccca gtccagggtc ctccattaag agcgaaggcc    1800
agtacacctc ctctacaaat gcagaagcca acgacacggc acgaaatcgc aatcgaggca    1860
aaagaaaggc ctacgatacc agaacagtac aagaaatatg aacatgtttt caaagaacca    1920
gggatccatg aggctttacc ggaacacaag ccatgggatc atgagataat attggaggaa    1980
ggcaagatgc ctgtgcacac cccaatttat tcaatgtcag ccgatgagtt aaaaaggctc    2040
agagaataca tcgacgacaa tttagccaag ggatggatca gggaatccgc gtcccaagtg    2100
gccagtccaa ctatgtgggt acccaagaag gatggacccg atagactagt tgtagactat    2160
agaaagctta acgcactcac taagaaggat cgatatccac ttccattagc tacgaattta    2220
agagatcgat taggcggagc tacgatattc accaagatgg acctacgtaa tggttaccac    2280
ttgatcagaa tgaaggaagg cgaagaatgg aaaaccgctt tcaaaacaag atacgggcta    2340
tacgagtacc aagttatgcc gttcgggcta accaacgcac cagctacttt catgaggctt    2400
atgaacaatg tgttgtcaca atatttggat acttgctgta tatgctactt ggacgacatc    2460
ctagtatatt caaacaacaa ggttcaacac attaaggacg ttagcagcat cctcgaaagt    2520
ctatccaaag cagacttgct gtgcaaacca agcaaatgcg aattccatgt cacagaaaca    2580
gaattcttgg gattcaccgt atcaagccaa gggctcaaga tgagcaagaa caaggttaag    2640
gcagtgctcg aatggaagca gccgaccaca atcaaggaag tacaatcctt tctaggattt    2700
gtcaacttct atagaagatt tatcaagggt tattcaggga ttactacacc cttgaccacg    2760
ttaaccagaa aagatcaagg aagcttcgaa tggactgcca aagcacagga gtcattcgat    2820
acactcaaac aagcagtggc agaagaacca atactgttga cttttgaccc agagaaagaa    2880
atcatagtgg aaacggattc ctcagatttc gctataggag cagttctgag ccaaccgggc    2940
cagaatggaa aataccagcc aatcgcattc tactcccgaa actatcacc agccgagttg    3000 aattacgaga tatatgacaa agaattactg gcgatagtcg atgcatttag agaatggcga    3060
gtatatttgg aaggatcgaa atacacagta caggtgtata cagatcataa gaacttggtt    3120
tacttcacca caacgaagca gttaaacaga cgacaggtca gatggtcgga gaccatggcc    3180
aactacaatt tcagaatttc atatgtcaaa ggatcagaaa cgctagagc cgacgctctt    3240 agccgaaaac cagaatatca agaaaacaaa acgtacgagt catacgctat attcaagaaa    3300
gacggcgaat cactggtcta caatgcacca cagcttgcag caacacacct gttggaagac    3360
aaccacctca gaaaacagat tcaatcacac tacgacaagg atgctactgc cacacgcata    3420
cgcaagacaa tagaaccagg attcactata gaaaatgata ccatatactt tcatggaaaa    3480
```

```
gtatacattc cgagtcaaat gaccaaggaa tttgtgacgg aacaacatgg gttgccggca   3540
catggacacc aaggaattgc aaggacattt gcaagaatac gggaaatcag ttacttccca   3600
cgaatgagaa cgatagttga agaagttgtt ggaaattgtg acacctgcat acgaaacaag   3660
tcatcacgac atgctccgta tggtcagctc cagaccccag acatgccttc tcagccatgg   3720
aagtccatca catgggactt tgtggtcaaa ctaccactct caaaggatcc tactacagga   3780
attgagtacg acgcgatact caatatagta gacaggctaa cgaaatttgc atatatgata   3840
ccattcaagg aaacatggga tgctgaacaa ctagcatatg tgttcctaag gatcatagta   3900
agcatacacg gagtaccaga tgagataatc tcggatcgag acaagctctt tacctcaaaa   3960
ttctggacta ccttattagc acttatgggt atcaagagaa agctatcgac atctttccac   4020
ccacaaacag atggtcaaac agagaggacc aatcagacaa tggaagcata tcttagatgc   4080
tatgtaaatt atcgacaaga caattgggta gaactattac ctatggcaca attcgcatat   4140
aatacatcgg aaacggaaac cacgaaaatc acaccagcac gagctaattt tgggtttaat   4200
ccacaagcgt ataaaatccc gataccacaa gaagttaatg ccgaatcagc aatagtacaa   4260
gtcgaacagc tgaaaaatct ccaagagcaa ctggctcttg atctaagatt catatcttcc   4320
agaacagcag cgtactacaa tacgaaacgt agtatggaac ctacgcttaa agagggggat   4380
aaagtttatt tgctacgacg aaacatcgaa accaagagac caagcaataa actcgaccac   4440
aggaaactag gaccattcaa gattgataag gtaataggaa cggttaatta tcgattgaaa   4500
ttaccagaca caatgaatat ccacccagta ttccacatat ccttgctcga accagcacca   4560
ccaggagcgc caaatgcgcc atttacagaa attgaaccag tcaacccaaa cgccatatac   4620
gatgtcgaaa caatactaga ctgcaaatac gtcagaaaca aggtcaagta tttgatcaaa   4680
tggttagact acccacattc agaaaacaca tgggaattca aggaggatct cagctgccct   4740
gagaagctac gggcattcca cctgaagtac ccacacctgc cagtaaagcc tcaagatccg   4800
cttcggacaa ctcaggcaaa gaaggatcga agaagtcgaa ggaagaagaa tcaatag      4857
```

<210> SEQ ID NO 18
<211> LENGTH: 3909
<212> TYPE: DNA
<213> ORGANISM: Botrytis cinerea

<400> SEQUENCE: 18

```
atggcatcca gagctaccgc cacaggtcaa tctgccggag acaccaacga catcgagatg     60
accgacgccc caaaggagat cactatcaac gaaaccctta agatcgcctt accagacaag    120
taccaaggta gtcgacaaga gctcgatact ttcctcttac aacttgagat ctactttcga    180
ttcaatgagg acaagttcac taccaaggaa tccaagagta tatgggccgc atcatacctt    240
cgaggtgaag caaccaaatg gatccaacca tatttgcgcg actatttcga gcatgacgat    300
aaggatcgta tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactaccgca agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaaa aatgagggta gaccacgtta caatccacag    720
agatacggag accccatgga actagacgcc acgcactaca caaacgggaa cgatgactcg    780
```

```
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc tacctttaca atcccagaaa atccaactaa atccgaaaat    960
actgagactt tcaccgttga ggaattccag caattactaa aggaattacc acgaaatcaa   1020
gagggcatga atgcaataga cttatgggag caagagtatt acagaacccc aacaccctct   1080
gtgacagaag aaagtcatca ggacgaggca gaagcagacc acgccacgat gagctggaca   1140
gcttgctatg atgaattctg cggaatccat cgatcagata agaagcaac cggatggtcc    1200 cctaagaaga gaaagacgaa gaaccatcag aataatgtaa catgcgagga tttaactccc   1260
aatataactt cgcaagaagt tcgcaaagtt acccagcagt taaatgctac gggacaggca   1320
ggacagatat actgcaaggt tcagataaat ggacacatac aatcagccat gatgattca    1380 ggggctacag gaaattttat tgcaccggaa gctgtaaagt acttgggaat accacttcaa   1440
acgaaacaac accctatcg attgcaggac acgctagagg cgtccgcgag acgtaacacg     1500
cgccaaggag agttgaacgc gaacaacacc ggcgacgtag gacacccagt ccagggtcct   1560
ccattaagag cgaaggccag tacacctcct ctacaaatgc agaagccaac gacacggcac   1620
gaaatcgcaa tcgaggcaaa agaaaggcct acgataccag aacagtacaa gaaatatgaa   1680
catgttttca aagaaccagg gatccatgag gctttaccgg aacacaagcc atgggatcat   1740
gagataatat tggaggaagg caagatgcct gtgcacaccc caatttattc aatgtcagcc   1800
gatgagttaa aaaggctcag agaatacatc gacgacaatt tagccaaggg atggatcagg   1860
gaatccgcgt cccaagtggc cagtccaact atgtgggtac caagaagga tggacccgat    1920 agactagttg tagactatag aaagcttaac acactcacta agaaggatcg atatccactt   1980
ccattagcta cggaattaag agatcggtta ggcggagcta cgatatttac caagatggac   2040
ctacgtaatg gttaccactt gatcagaatg aaggaaggcg aagaatgaa gaccgctttc     2100 aaaacaagat acgggctata cgagtaccaa gttatgccgt tcgggctaac caacgcacca   2160
gctactttca tgaggcttat gaacaatgtg ttgtcacaat acttggatac ttgctgtata   2220
tgctacttgg acgacatcct agtatattca acaacaagg ttcaacacat taaggacgtt     2280
agcaacatcc tcgaaagcct atccaaggca gacttgctgt gcaaaccaag caaatgcgaa   2340
ttccatgtca cagagacaga attcttggga ttcaccgtat caagccaagg gctcaagatg   2400
agcaaagaca aggttaaggc agtgctcgaa tggaagcagc caaccacaat caaggaagta   2460
caatcctttc tagggttcgt caacttctac agaagattta tcaagggtta ttcagggatt   2520
actacaccct tgaccacgtt aaccagaaaa gatcaagaaa gcttcgaatg gactgccata   2580
gcacaggagt cattcgatac gctcaaacaa gcagtggcag aagagccaat actattgact   2640
tttgacccag agaaagaaat catagtggag acggactcct cggatttcgc tataggagca   2700
gttctgagcc aaccgggcca gaatggaaaa taccagccaa tcgcattcta ctcccgaaaa   2760
ctatcaccag ccgaattgaa ttacgagata tatgacaaag aattgctggc gatagtcgat   2820
gcatttagag aatggcgagt atatttggaa ggatcgaaat acacagtaca ggtgtataca   2880
gatcataaga acttggttta cttcaccaca acgaagcagt taaacagacg acaggtcaga   2940
tggtcggaga ccatggccaa ctacaatttc agaatttcat atgtcaaagg atcagaaaac   3000
gctagagccg acgctcttag ccgaaaacca gaatatcaag aaaacaaaac gtacgagtca   3060
tacgctatat tcaagaaaga cggcgaatca ctggtttaca atgcaccaca gcttgcagca   3120
```

-continued

```
acacacctgt tggaagacaa ctaccttagg aaacagatcc aatcacacta cgacaaggat   3180
gctactgcca cacgcatacg caagacaata gaaccaggat tcactataga aaatgatacc   3240
atatactttc atggaaaagt atacattccg agtcaaatga ccaaggaatt tgtgacggaa   3300
caacatgggt tgccggcaca tggacaccaa ggaattgcaa ggacatttgc aagaatacgg   3360
gaaatcagtt acttcccacg aatgagaacg atagttgaag aagttgttgg aaattgtgac   3420
acctgcatac gaaacaagtc atcacggcat gctccgtatg gtcagctcca gaccccagac   3480
atgccttctc agccatggaa gtccatcaca tgggactttg tggtcaaact accactctca   3540
aaggatccta ctacaggaat tgagtacgac gcgatactca atatagtaga caggctaacg   3600
aaatttgcat atatgatacc attcaaggaa acatgggatg ctgaacaact agcatatgtg   3660
ttcctaagga tcatagtaag catacacgga gtaccagatg agataatctc ggatcgagac   3720
aagctcttta cctcgaaatt ctggactacc ttattagcac ttatgggtat caagagaaag   3780
ctatcgacat ctttccaccc acaaacagat ggtcaaacag agaggaccaa tcagacaatg   3840
gaagcatatc ttagatgcta tcgtataaaa tcccgatacc acaagaagtt aatgccgaat   3900
cagcaatag                                                           3909
```

```
<210> SEQ ID NO 19
<211> LENGTH: 3909
<212> TYPE: DNA
<213> ORGANISM: Botrytis cinerea

<400> SEQUENCE: 19
```

```
atggcatcca gagctaccgc cacaggtcag tctaccgaag ataccaacga catcgagatg     60
accgatgccc caaaggagat cactatcaac gaaacactta agatcgcctt accagacaag    120
taccaaggta gtcgacaaga gctcgatact ttcctcttac aacttgagat ctacttccga    180
ttcaatgaag acaagttcac taccaaggaa tccaagagca tatgggctgc atcatacctc    240
cgaggtgaag caaccaaatg gattcaacca tatttgcgcg actatttcga gcatgacgat    300
aaggatcgca tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactactgta agggactcaa accagaagtc    540
agactagagt tagaaagatc tgccgagagt acagatctga acgatctaat tcaggactcc    600
atcgaatcag atgatcgtct ctatagatat cgacaaagcc aaagatcata caaaccccaa    660
ggaaaccaaa agcaagggcg ttaccgcaag aatgagggta gaccacgtta caatccacag    720
agatacggag accccatgga actagacgcc acgcactaca caaacgggaa cgatgactca    780
gaaaagagac gaagacgaga aaacaactta tgctttgaat gtggaaaagc agggcaccga    840
gcagtagact gccgaagcaa gaagacagga ggaaaaaggg gcaacttcaa acctaagttc    900
ggcaagggcc aacttaacgc cacctttgcc atctcagaaa actcaactaa aaccgaaaat    960
actgagactt tcaccgttga ggaatttcag caattactaa aggaattacc acgaaataaa   1020
gagggcatga atgcaataga cttatgggaa caagagtatt acagaacccc aacaccctct   1080
gtgacagaag aaagtcacca ggacgaggca gaagcggacc acgccacgat gagctggaca   1140
gcttgctatg atgaattctg cggaatccat cgatcagata aagaagcaac cggatggttc   1200
cccaagaaaa ggaagacgaa gaaccatcag aataatgtaa catgcgagga tttaactccc   1260
aatataactt cgcaagaagt tcgcaaagtt acccagcagt tgaatgctac gggacaggca   1320
```

```
ggacaagtgt actgcaaggt ccagataaat ggacacatac aatcagccat gatagattca    1380 gggctacag  gaaattttat tgcaccagaa gctgcaaagt acttggaaat accacttcaa    1440
acgaaacaac  accctatcg attgcaggac acgctagagg cgtccgcgag acgtaacacg    1500
cgccaagggg agttgaacgc gaacaacacc ggcgacgtag acacccagt  ccagggtcct    1560 ccattaagag cgaaggccag tacacctcct ctacaaatgc agaagccaac gacacggcac    1620
gaaatcgcaa tcgaggcaaa agaaaggcct acgataccag aacagtacaa gaaatatgaa    1680
catgttttca aagaaccagg gatccatgag gctttaccgg aacacaagcc atgggatcat    1740
gagataatat tggaggaagg caagatgcct gtgcacaccc caatttattc aatgtcagcc    1800
gatgagttaa aaaggctcag agaatacatc gacgacaatt tagccaaggg atggatcagg    1860
gaatccgcgt cccaagtggc cagtccaact atgtgggtac caagaagga  tggacccgat    1920 agactagttg tagactatag aaagcttaac gcactcacta agaaggatcg atatccactt    1980
ccattagcta cggaattaag agatcgatta ggcggagcta cgatattcac caagatggac    2040
ctacgtaatg gttaccactt gatcagaatg aaggaaggcg aagaatggaa accgctttc    2100 aaaacaagat acgggctata cgagtaccaa gttatgccat cgggctaac  caacgcacca    2160 gctactttca tgaggcttat gaacaatgtg ttgtcacaat atttggatac ttgctgtata    2220
tgctacttgg acgacatcct agtatattca acaacaagg  ttcaacacat taaggacgtt    2280
agcaacatcc tcgaaagtct atccaaagca gacttgctgt gcaaaccaag caaatgcgaa    2340
ttccatgtca cagaaacaga attcttggga ttcaccgtat caagccaagg gctcaagatg    2400
agcaaagaca aggttaaggc agtgctcgaa tggaagcagc caaccacaat caaggaggta    2460
caatcctttc tagggttcgt caacttctac agaagattta tcaagggtta ttcagggatt    2520
actacaccct tgaccacgtt aaccagaaaa gatcaaggaa gcttcgaatg gactgccaaa    2580
gcacaggagt cattcgatac actcaaacaa gcagtggcag aagaaccaat actgttgact    2640
tttgacccag agaaagaaat catagtggaa acggattcct cagatttcgc tataggagca    2700
gttctgagcc aaccgggcca gaatggaaaa taccagccaa tcgcattcta ctcccgaaaa    2760
ctatcaccag ctgagttaaa ttacgagata tatgacaaag aattactggc aatagtcgat    2820
gcatttagag aatggcgagt atatttggaa ggatcgaaat acacagtaca ggtgtataca    2880
gatcataaga acttggttta cttcaccaca acgaagcagt taaacagacg acaggtcaga    2940
tggtcggaga ccatggccaa ctacaatttc agaatttcat atgtcaaagg atcagaaaac    3000
gctagagccg acgctcttag ccgaaaacca gaatatcaag aaaacaaaac gtacgagtca    3060
tacgctatat tcaagaaaga cggcgaatca ctggtctaca atgcaccaca gcttgcagca    3120
acacacctgt tggaagacaa ccacctcagg aaacagatcc aatcacacta caacaaggat    3180
gctactgcca cacgcatacg caagacaata gaaccaggat tcactataga agatgatacc    3240
atatactttc atgaaaaagt atacattccg agtcaaatga ccaaggaatt tgtgacggaa    3300
caacacggat tgccggcaca tggacaccaa ggaattgcaa ggacatttgc aagaatacgg    3360
gaaatcagtt acttcccacg aatgagaacg atagttgaag aagttgttgg aaattgtgac    3420
acctgcatac gaaacaagtc atcacgacat gctccgtatg tcagctcca  gaccccagac    3480 atgccttctc agccatggaa gtccatcaca tgggactttg tggtcaaact accactctca    3540
aaggatccta ctacaggaat tgagtacgac gcgatactca atatagtaga caggctaacg    3600
aaatttgcat atatgataac attcaaggaa acatgggatc ctgagcaact agcatatgtg    3660
```

```
ttcctaaggg tcatagtaag catacacgga gtaccagatg agataatctc ggatcgagac    3720
aagctcttta cctcgaaatt ctggactacc ttattagcac ttatgggtat caagagaaag    3780
ctatcgacat ctttccaccc acaaacagat ggtcaaacag agaggaccaa tcagacaatg    3840
gaagcatatc ttagatgcta tcgtataaaa tcccgatacc acaagaagtt aatgccgaat    3900
cagcaatag                                                            3909

<210> SEQ ID NO 20
<211> LENGTH: 4854
<212> TYPE: DNA
<213> ORGANISM: Botrytis cinerea

<400> SEQUENCE: 20
atggcatcca gagctaccgc cacaggtcaa tctgccggag acaccaacga catcgagatg      60
accgacgctc caaaggagat cactatcaac gaaacccctta agatcgcctt accagacaag    120
taccaaggta gtcgacaaga gctcgatact ttcctcttac aacttgagat ctacttccga    180
ttcaatgagg acaagttcac taccaaggaa tccaagagca tatgggccgc gtcataacctt   240 cgaggtgaag caaccaaatg gattcaacca tatttgcgcg actatttcga gcatgacgat    300
aaggatcgca tgcaacccac ccgaacaatc ttcaatagtt ttgaaggatt taagacagag    360
gttcgtagaa tcttcggaaa ttccaacgag ttagaggtag cggaagataa gatcttcaac    420
ctcaagcaga caggatcagc attgaaatat gctacgaaat tcgaagata tgctggaaca     480 accaagtggg acgaaatcgc tatcatgagt cactaccgca agggactcaa accagaagtc    540
agactagaat tagaaagatc tgccgagagt acagatctaa acgatctaat tcaggactcc    600
atcgaatcag atgatcgtct ctacagatat cgacaaagcc aaagatcata caaaccccaa    660
ggaaatcaga agcaagggcg ttaccgcaag aatgagggta gaccacgtta caatccacag    720
agatacggag accccatgga actagacgct acgcactaca caaacgggaa cgatgactca    780
gaaaagagac gaagacgaga taacaactta tgctttgaat gtggaaaagc agggcaccga    840
gcagcagact gccgaagcaa gaagacagga ggaaaaaggg gcaacttcaa acctaagttc    900
ggcaagggcc aacttaatgc caacctttgca atctcagaaa actcaactaa acccgaaaat    960
actgagactt tcaccgttga ggaattccag caattattag aggaattacc acgaaaccaa    1020
gagggcatga atgcaataga cttatgggaa caagagtatt acagaactcc aacaccctct    1080
gtgacagaag aaagtcacca ggacgaggca gaagcggacc acgccacgat aagctggaca    1140
gcttgctatg acgaattctg cggaatccat cgatcagata aagaagcaac cggatggttc    1200
cccaagaaga gaaagacgaa gaaccgacag aataatgtaa catgcaagga tttaactcca    1260
aatgtaactt cgcgaaaagt tcgcaaagtt acacagcaat tgaatgctac gggacaggca    1320
ggacaaatat actgcacggt tcagataaat ggacacatac aatcagccat gatagattca    1380
ggggctacag ggaatttttat tgcaccagaa gctgcaaagt acttggaaat accacttcaa    1440
acgaaacaac accctaccg attgcagtta gttgacggac agctagcagg gtctgacgga    1500
aagatttcgc aggagacaat cccagtacga atgggcataa cccaacatac agaggttata    1560
cagcttgacg ttgtgccatt gggccaacaa cagatcatct taggaatgcc atggttaaag    1620
gcacataatc cgaaaataga ttgggcacaa ggaattgtga catttgatca gtgcaaaagc    1680
ggtcacaggg acacgctaga ggcgttcgcg agacgtaaca cgcgccaagg agagttgaac    1740
gcgaacaaca ccggcgacgt aggacaccca gtccagggtc ctccattaag agcgaaggcc    1800
agtacacctc ctctacaaat gcagaagcca acgacacggc acgaaatcgc aatcgaggca    1860
```

```
aaagaaaagc ctacgatacc agaacagtac aagaattatg aacatgtttt caaagaacca    1920
gggatccatg aggctttacc ggaacacaag ccatgggatc atgagataat attggaggaa    1980
ggcaagatgc ctgtgcacac cccaatttat tcaatgtcag ccgatgagtt aaagaggctc    2040
agagagtaca tcgacgacaa tttagccaag ggatggatca gggaatccgc gtcccaagtg    2100
gccagtccaa ctatgtgggt acccaagaag gatggacccg atagactagt tgtagactat    2160
agaaagctta acgcactcac taagaaggat cgatatccac ttccattagc tacgaaatta    2220
agagatcgat taggcggagc tacgatattt accaagatgg acctacgtaa tggttaccac    2280
ttgatcagaa tgaaggaagg cgaagaatgg aaaaccgctt tcaaaacaag atacgggcta    2340
tacgagtacc aagttatgcc attcgggcta accaacgcac cagctacttt catgaggctt    2400
atgaacaatg tgttgtcaca atatttggat acttgctgta tatgctactt ggacgacatc    2460
ctagtatatt caaacaacaa ggttcaacac attaaggacg ttagcaacat cctcgaaagc    2520
ctatccaagg cagacttgct gtgcaaacca agcaaatgcg aattccatgt cacagagaca    2580
gaattcttgg gattcaccgt atcaagccaa gggctcaaga tgagcaaagg caaggttaag    2640
gcagtgctcg aatggaagca gccgaccaca atcaaggaag tacaatcctt tctagggttc    2700
gtcaacttct acagaagatt tatcaaaggt tattcaggga ttactacacc cttgaccacg    2760
ttaaccagaa aagatcaagg aagcttcgaa tggactgcca agcacagga gtcattcgat    2820 acgctcaaac aagcagtggc agaagagcca atactattga cttttgaccc agagaaagaa    2880
atcatagtgg agacggactc ctcggatttc gctataggag cagttctgag ccaaccgggt    2940
cagaatggaa aataccagcc aatcgcattc tactcccgaa aactatcacc agctgagttg    3000
aattacgaga tatatgacaa agaattactg gcgatagtcg atgcatttag agaatggcga    3060
gtatatttgg aaggatcgaa atacacagta caggtgtaca cagatcataa gaacttggtt    3120
tacttcacca caacgaagca gttaaacaga cgacaggtca gatggtcgga gaccatggcc    3180
aactacaact ttagaatttc atatgtcaaa ggatcagaaa atgctagagc cgacgctctt    3240
aaccgaaaac cagaatatca agaaaacaaa gcgtacgagt catacgctat attcaagaaa    3300
gacagcgaat cactggttta caatacacca cagcttgcaa caacacacct gttggaagac    3360
aaccacctca ggaaacagat ccaatcacac tacgacaagg atactactgc cacacgcata    3420
cgcaaaacaa tagaaccagg attcactata gaaaatgata ccatatactt tcatagaaaa    3480
gtatacattc cgagtcaaat gaccaaggaa tttgtgacgg aacaacacgg gttgccggca    3540
catgacacac aaggaattgc aaggacattt gcaagaatac gggaaatcag ttacttccca    3600
cgaatgagaa cgatagttga agaagttgtt ggaaattgtg acacctgcat acgaaacaag    3660
tcatcacgac atgctccgta tggtcagctc cagaccccag acatgccttc tcagccatgg    3720
aagtccatca catgggactt tgtggtcaaa ctaccactct caaaggatcc tactacagga    3780
attgagtacg acgcgatact caatatagta gacaggctaa cgaaatttgc atatatgata    3840
ccattcaagg aaacatggga tgctgagcaa ctagcatatg tgttcctaag gatcatagta    3900
agcatacacg gagtaccaga tgagataatc tcggatcgag acaagctctt tacctcgaaa    3960
ttctggacta ccttattagc acttatgggt atcaagagaa agctatcgac atctttccac    4020
ccacaaacag atggtcaaac agagaggacc aatcagacaa tggaagcata tcttagatgc    4080
tatgtaaatt atcgacaaga caattgggta gagctattac ccatggcaca gttcgcatac    4140
aatacatcag aaacggaaac cacgaaaatc acaccagcac gagctaattt tgggtttaat    4200
```

```
ccacaagcgt ataaaatccc gataccacaa gaagttaatg ccgaatcagc gatagtacaa    4260
gtcgaacagt tgaaagatct ccaagagcaa ctggctcttg atctaagatt catatcttcc    4320
agaacagcag cgtactacaa tacgaaacgt agtatggaac ctacgcttaa agaggggat     4380 aaagtttatt tgctacgacg aaacatcgaa accaagagac caagcaataa actcgaccac    4440
aggaaactag gaccattcaa gattgataag gtaataggaa cggttaatta tcaattgaaa    4500
ttaccagaca caatgaatat ccacccagta ttccacatat ccttgctcga accagcacca    4560
ccaggagcgc caaatgcgcc atttacagaa attgaaccag tcaacccaaa cgccatatac    4620
gatgtcgaaa caatactaga ctgcaaatac gtcagaaaca aggtcaagta tttgatcaaa    4680
tggttagact acccacattc agaaaacaca tgggaactca aggaagatct cagctgccct    4740
gagaaactac gggcattcca cctgaagtac ccacatctgc caacaaagcc tcaagctccg    4800
catcagacaa caaaggcaac gagggggtcga agaaaccaaa agaagaacca ctag          4854

<210> SEQ ID NO 21
<211> LENGTH: 1962
<212> TYPE: DNA
<213> ORGANISM: Botrytis cinerea

<400> SEQUENCE: 21
atgtgggtac ccaagaagga tggacccgat agactagttg tagactatag aaagcttaac      60
gcactcacta agaggatcg atatccactt ccattagcta cggaattaag agatcgatta     120
ggcggagcta cgatattcac caagatggac ctactatatt caaacaacaa ggttcaacac    180
attaaggacg ttagcaacat cctcgaaagc ctatccaagg cagacttgct gtgcaaacca    240
agcaaatgcg aattccatgt cacagagaca gaattcttgg gattcaccgt atcaagccaa    300
gggctcaaga tgagcaaagg caaggttaag gcagtgctcg aatggaagca gccgaccaca    360
atcaaggaag tacaatcctt tctagggttc gtcaacttct acagaagatt tatcaaaggt    420
tattcaggga ttactacacc cttgaccacg ttaaccagaa aagatcaagg aagcttcgaa    480
tggactgcca agcacagga gtcattcgat acgctcaaac aagcagtggc agaagagcca    540
atactattga cttttgaccc agagaaagaa atcatagtgg agacggactc ctcggatttc    600
gctataggag cagttctgag ccaaccgggt cagaatggaa aataccagcc aatcgcattc    660
tactcccgaa aactatcacc agctgagttg aattacgaga tatatgacaa agaattactg    720
gcgatagtcg atgcatttag agaatggcga gtatatttgg aaggatcgaa atacacagta    780
caggtgtaca cagatcataa gaacttggtt tacttcacca caacgaagca gttaaacaga    840
cgacaggtca gatggtcgga gaccatggcc aactacaact ttagaatttc atatgtcaaa    900
ggatcagaaa atgctagagc cgacgctctt agccgaaaac cagaatatca agaaaacaaa    960
acgtacgagt catacgctat attcaagaaa gacggcgaat cactggttta caatgcacca    1020
cagcttgcag caacacacct gttggaagac aaccacctca ggaaacagat ccaatcacac    1080
tacgacaagg atgctactgc cacacgcata cgcaagacaa tagaaccagg attcactata    1140
gaaaatgata ccatatactt tcatggaaaa gtatacattc cgagtcaaat gaccaaggaa    1200
tttgtgacgg aacaacacgg gttgccggca catggacacc aaggaattgc aaggacattt    1260
gcaagaatac gggaaatcag ttacttccca cgaatgagaa cgatagttga agaagttgtt    1320
ggaaattgtg acacctgcat acgaaacaag tcatcacgac atgctccgta tggtcagctc    1380
cagaccccag acatgccttc tcagccatgg aagtccatca catgggactt tgtggtcaaa    1440
ctaccactct caaaggatcc tactacagga attgagtacg acgcgatact caatatagta    1500
```
gacaggctaa cgaaatttgc atatatgata ccattcaagg aaacatggga tgctgagcaa 1560
ctagcatatg tgttcctaag gatcatagta agcatacacg gagtaccaga tgagataatc 1620
tcggatcgag acaagctctt tacctcgaaa ttctggacta ccttattagc acttatgggt 1680
atcaagagaa agctatcgac atctttccac ccacaaacag atggtcaaac agagaggacc 1740
aatcagacaa tggaagcata tcttagatgc tatgtaaatt atcgacaaga caattgggta 1800
gagctattac ccatggcaca gttcgcatac aatacatcag aaacggaaac cacgaaaatc 1860
acaccagcac gagctaattt tgggtttaat ccacaagcgt ataaaatccc gataccacaa 1920
gaagttaatg ccgaatcagc gatatatgga acctacgctt aa 1962

<210> SEQ ID NO 22
<211> LENGTH: 957
<212> TYPE: DNA
<213> ORGANISM: Botrytis cinerea

<400> SEQUENCE: 22
atggccaact acaattttag aatttcatat gtcaaaggat cagaaaacgc tagagccgac 60
gctcttagcc gaaaaccaga atatcaagaa aacaaaacgt acgagtcata cgctatattc 120
aagaaagacg gcgaatcact ggtctacaat gcaccacagc ttgcagcaac acacctgttg 180
gaagacaacc acctcaggaa acagatccaa tcacactaca acaaggatgc tactgccaca 240
cgcatacgca agacaataga accaggattc actatagaag atgataccat atactttcat 300
ggaaaagtat acattccgag tcaaatgacc aaggaatttg tgacggaaca acatgggttg 360
ccggcacacg gacatcaagg gattgcaaga acatttgcaa gaatccggga aatcagttac 420
ttcccacgaa tgagaacgat agttgaagaa gttgttggaa attgtgacac ctgcatacga 480
aacaagtcat cacgacatgc gccgtatggt cagctccaga ccccagacat gccttctcag 540
ccatggaagt ccatcacatg ggactttgtg gtcaaactac cactctcaaa ggatcctact 600
acaggaattg agtacgacgc gatactcaat atagtagaca ggctaacgaa attcgcatat 660
atgataccat tcaaggaaac atgggatgct gagcaactag catatgtgtt cctaaggatc 720
atagtaagca tacacggagt accagatgag ataatctcgg atcgagacaa gctctttacc 780
tcgaaattct ggactacctt attagcactt atgggtatca agagaaagct atcgacatct 840
ttccacccac aaacagatgg tcaaacagag aggaccaatc agacaatgga agcatatctt 900
agatgctatc gtataaaatc ccgataccac aagaagttaa tgccgaatca gcgatag 957

<210> SEQ ID NO 23
<211> LENGTH: 987
<212> TYPE: DNA
<213> ORGANISM: Botrytis cinerea

<400> SEQUENCE: 23
atccaatcac actacaacaa ggatgctact gccacacgca tacgcaagac aatagaacca 60
ggattcacta tagaagatga taccatatac tttcatggaa aagtatacat tccgagtcaa 120
atgaccaagg aatttgtgac ggaacaacat gggttgccgg cacacggaca tcaagggatt 180
gcaagaacat ttgcaagaat ccgggaaatc agttacttcc cacgaatgag aacgatagtt 240
gaagaagttg ttggaaattg tgacacctgc atacgaaaca agtcatcacg acatgcgccg 300
tatggtcagc tccagacccc agacatgcct tctcagccat ggaagtccat cacatgggac 360
tttgtggtca aactaccact ctcaaaggat cctactacag gaattgacat acacggagta 420
ccagatgaga taatctcgga tcgagacaag ctctttacct cgaaattctg gactacctta 480
ttagcactta tgggtatcaa gagaaagcta tcgacatctt tccacccaca aacagatggt 540
caaacagaga ggaccaatca gacaatggaa gcatatctta gatgctatgt aaattatcga 600
caagacaatt gggtagagct attacccatg gcacagttcg catacaatac atcggaaacg 660
gaaaccacga aaatcacccc agcacgagct aattttgggt ttaatccaca agcgtataaa 720
atcccgatac cacaagaagt taatgccgaa tcagcaatag tacaagtcga acagctgaaa 780
gatctccaag agcaactggc tcttgatcta agattcatat cttccagaac agcagcgtac 840
tacaatacga aacgtagtat ggaacctacg cttaaagagg gggataaagt ttatttgcta 900
caacgaaaca tcgaaaccaa gagaccaagc aataaactcg accacaggaa actaggacca 960
ttcaagattg ataaggtaat aggaacg 987

<210> SEQ ID NO 24
<211> LENGTH: 3573
<212> TYPE: DNA
<213> ORGANISM: Botrytis cinerea

<400> SEQUENCE: 24
atggcatcca gagccaccgc cacaggtcag tctaccggag ataccaacga catcgagatg 60
accgatgccc caaaggagat cactatcaac gaaacactta agatcgcctt accagacaag 120
taccaaggta gtcgacaaga gctcgatact ttcctcttac aacttgagat ctacttccga 180
ttcaatgaag acaagttcac taccaaggaa tccaagagca tatgggctgc atcatacctc 240
cgaggtgaag caaccaaatg gattcaacca tatttgcgcg actatttcga gcatgacgat 300
aaggatcgca tgcaacccac ccgaacaatc ttcaatagtt ttgaaggatt taagacagag 360
attcgtagaa tcttcggaaa ttccaacgag ttagaggtag cggaagataa gatcttcaac 420
ctcaagcaga caggatcagc attgaaatat gctacggaat ttcgaagata tgctggaaca 480
accaagtggg acgaaatcgc tatcatgagt cactaccgta agggactcaa accagaagtc 540
agactagagt tagaaagatc tgccgagagt acagatctga acgatctaat tcaggactcc 600
atcgaatcag atgatcgtct ctatagatat cgacaaagcc aaagatcata caaaccccaa 660
ggaaaccaaa agcaagggcg ttaccgcaag aatgagggta gaccacgtta caatccacag 720
agatacggag accccatgga actagacgcc acgcactaca caaacgggaa cgatgactca 780
gaaaagagac gaagacgaga aaacaactta tgctttgaat gtggaaaagc agggcaccga 840
gcagtagact gccgaagcaa gaagacagga ggaaaaaggg gcaacttcaa acctaagttc 900
ggcaagggcc aacttaacgc cacctttgcc atctcagaaa actcaactaa aaccgaaaat 960
actgagactt tcaccgttga ggaatttcag caattactaa aggaattacc acgaaataaa 1020
gagggcatga atgcaataga cttatgggaa caagagtatt acagaacccc aacaccctct 1080
gtgacagaag aaagtcacca ggacgaggca gaagcggacc acgccacgat gagctggaca 1140
gcttgctatg atgaattctg cggaatccat cgatcagata aagaagcaac cggatggttc 1200
cccaagaaaa ggaagacgaa gaaccatcag aataatgtaa catgcgagga tttaactccc 1260
aatataactt cgcaagaagt tcgcaaagtt acccagcagt tgaatgctac gggacaggca 1320
ggacaagtgt actgcaaggt ccagataaat ggacacatac aatcagccat gatagattca 1380
ggggctacag gaaattttat tgcaccagaa gctgcaaagt acttggaaat accacttcaa 1440
acgaaacaac atccctaccg attgcaggac acgctagagg cgtccgcgag acgtaacacg 1500
cgccaagggg agttgaacgc gaacaacacc ggcgacgtag gacacccagt ccagggtcct 1560

```
ccattaagag cgaaggccag tacacctcct ctacaaatgc agaagccaac gacacggcac    1620
gaaatcgcaa tcgaggcaaa agaaaggcct acgataccag aacagtacaa gaaatatgaa    1680
catgttttca agaaccagg gatccatgag gctttaccgg aacacaagcc atgggatcat     1740
gagataatat tggaggaagg caagatgcct gtgcacaccc caatttattc aatgtcagcc    1800
gatgagttaa aaaggctcag agaatacatc gacgacaatt tagccaaggg atggatcagg    1860
gaatccgcgt cccaagtggc cagtccaact atgtgggtac caagaagga tggacccgat     1920 agactagttg tagactatag aaagcttaac gcactcacta agaaggatcg atatccactt    1980
ccattagcta cggaattaag agatcgatta ggcggagcta cgatattcac caagatggac    2040
ctacgtaatg gttaccactt gatcagaatg aaggaaggcg aagaatggaa accgctttc    2100 aaaacaagat acgggctata cgagtaccaa gttatgccat cgggctaac caacgcacca    2160 gctactttca tgaggcttat gaacaatgtg ttgtcacaat atttggatac ttgctatcaa    2220
ggaagcttcg aatggactgc caaagcacag gagtcattcg atacgctcaa gcaagcagtg    2280
gcagaagaac caatactgtt gacttttgac ccagagaaag aaatcatagt ggagacggac    2340
tcctcggatt tcgctatagg agcagttctg agccaaccgg gccagaatgg aaaataccag    2400
ccaatcgcat tctactcccg aaaactatca ccagctgagt taaattacga gatatatgac    2460
aaagaattac tggcaatagt cgatgcattt agagaatggc gagcatattt ggaaggatcg    2520
aaatacacag tacaggtata tacagatcat aagaacttgg tttacttcac cacaacgaag    2580
cagttaaaca gacgacaggt cagatggtcg gagaccatgg ccaactacaa ctttagaatt    2640
tcatatgtca aggatcaga aaacgctaga gccgacgctc ttagccgaaa accagaatat    2700
caagaaaaca aaacgtacga gtcatacgct atattcaaga aagacggcga atcactggtc    2760
tacaatgcac cacagcttgc agcaacacac ctgttggaag acaaccacct caggaaacag    2820
atccaatcac actacaacaa ggatgctact gccacacgca tacgcaagac aatagaacca    2880
ggattcacta tagaagatga taccatatac tttcatggaa aagtatacat tccgagtcaa    2940
atgaccaagg aatttgtgac ggaacaacat gggttgccgg cacacggaca tcaagggatt    3000
gcaagaacat ttgcaagaat ccgggaaatc agttacttcc cacgaatgag aacgatagtt    3060
gaagaagttg ttggaaattg tgacacctgc atacgaaaca agtcatcacg acatgcgccg    3120
tatggtcagc tccagacccc agacatgcct tctcagccat ggaagtccat cacatgggac    3180
tttgtggtca aactaccact ctcaaaggat cctactacag gaattgagta cgacgcgata    3240
ctcaatatag tagacaggct aacgaaattt gcatatatga taccattcaa ggaaacatgg    3300
gatgctgagc aactagcata tgtgttccta agggtcatag taagcataca cggagtacca    3360
gatgagataa tctcggatcg agacaagctc tttacctcga aattctggac taccttatta    3420
gcacttatgg gtatcaagag aaagctatcg acatctttcc acccacaaac agatggtcaa    3480
acagagagga ccaatcagac aatggaagca tatcttagat gctatcgtat aaaatcccga    3540
taccacaaga agttaatgcc gaatcagcaa tag                                  3573
```

<210> SEQ ID NO 25
<211> LENGTH: 3909
<212> TYPE: DNA
<213> ORGANISM: Botrytis cinerea

<400> SEQUENCE: 25

```
atggcatcca gagataccgc cacaggtcaa tctgccggag acaccaacga catcgagatg    60
```

```
accgatgccc caaaggagat cactatcaac gaaaccctta agatcgcctt accagacaag      120
taccaaggta gtcgacaaga gctcgatact ttcctcttac aacttgagat ctacttccga      180
ttcaatgagg acaagttcac taccaaggaa tccaagagta tatgggccgc atcataccte      240 cgaggtgaag caaccaaatg gattcaacca tatttgcgcg actatttcga acatgacgat      300
aagaatcgca tgcaacccac ccgaacaatc ttcaatagtt ttgaaggatt taagacagag      360
attcgtagaa tcttcggaaa ttccaacgag ttagaggtag cggaagataa gatcttcaac      420
ctcaagcaga caggatcagc attgaaatat gctacggaat ttcgaagata tgctggaaca      480
accaagtggg acgaaatcgc tatcatgagt cactaccgca agggactcaa accagaagtc      540
agactggaat tagaaagatc tgccgagagt acagatctga acgatctaat tcaggactcc      600
atcgaatcag atgatcgtct ctacagatat cgacaaagcc agagatcata caaaccccaa      660
ggaaatcaga agcaagggcg ttaccgcaag aatgagggta gaccacgtta caatccacag      720
aggtacggag acccaatgga actagacgct acgcactaca caaacgggaa cgatgactca      780
gaaaagagac gaagacgaga aaacaactta tgctttgaat gtggaaaagc agggcaccga      840
gcagcagagt gccgaagcaa gaagacagga ggaaaaaggg gcaacttcaa acctaagttc      900
ggcaagggcc aacttaacgc caccttlgca atcccagaaa acccaactaa atccgaaaat      960
actgagactt tcaccattga agaattccag caattactag aggaattacc acgaaatcaa      1020
gagggcatga atgcaataga cttatgggaa caagagtatt cagaaccccc aacaccctct      1080
gtaacagaag aaagtcacca ggacgaggca gaagcagacc acgccacaat gagctggaca      1140
gcctgctatg atgaattctg cggaattcat cgatcagata agaagcaac cggatggttc      1200 cccaagaaaa ggaagacgaa gaaccatcag aataatgtaa catgcgagga tttaactccc      1260
aatcaacctt cgcaagaagt tcgcaaagtt acccagcagt tgaatgctac gggacaggca      1320
ggacagatat actgcaaagt tcagataaat ggacacatac aatcagccat gatagattca      1380
ggggctacag gaaattttat tgcaccagaa gctgcaaagt acttggaaat accacttcag      1440
acgaaacaac acccctaccg attgcaggac acgctagagg cgtccgcgag acgtaacacg      1500
cgccaaggag agttgaacgc gaacgacacc ggcgacgtag acacccagt ccagggtcct      1560 ccattaagag cgaaggccag tacacctcct ctacaaatgc agaagccaac gacacggcac      1620
gaaatcgcaa tcgaggcaaa agaaaagcct acgataccag aacagtacaa gaattatgaa      1680
catgttttca aagaaccagg gatccatgag gctttaccgg aacacaagcc atgggatcat      1740
gagataaatt ggaggaagg caagatgcct gtgcacaccc caatttattc aatgtcagcc      1800
gatgagttaa aaaggctcag agaatacatc gacgacaatt tagccaaggg atggatcagg      1860
gaatccgcgt cccaagtggc cagtccaact atgtgggtac caagaagga tggacccgat      1920 agactagttg tagactatag aaagcttaac gcactcacta gaaggatcg atatccactt      1980 ccattagcta cggaattaag agatcgatta ggcggagcta cgatatttac caagatggac      2040
ctacgtaatg gttaccactt gatcagaatg aaggaaggcg aagaatggaa aaccgcttc     2100 aaaacaagat acgggctata cgagtaccaa gttatgccat cgggctaac caacgcacca      2160 gctactttca tgaggcttat gaacaatgtg ttgtcacaat atttggatac ttgctgtata      2220
tgctacttgg acgacatcct agtatattca aacaacaagg ttcaacacat taaggacgtt      2280
agcaacatcc tcgaaagcct atccaaggca gacttgctgt gcaaaccaag caaatgcgaa      2340
ttccatgtca cagagacaga attcttggga ttcaccgtat caagccaagg gctcaagatg      2400
agcaaaggca aggttaaggc agtgctcgaa tggaagcagc cgaccacaat caaggaagta      2460
```

```
caatcctttc tagggttcgt caacttctac agaagattta tcaaaggtta ttcagggatt    2520
actacaccct tgaccacgtt aaccagaaaa gatcaaggaa gcttcgaatg gactgccaaa    2580
gcacaggagt cattcgatac gctcaaacaa gcagtggcag aagagccaat actattgact    2640
tttgacccag agaagaaat catagtggag acggactcct cggatttcgc tataggagca    2700
gttctgagcc aaccgggtca gaatggaaaa taccagccaa tcgcattcta ctcccgaaaa    2760
ctatcaccag ccgaattaaa ttatgaaata tacgacaaag aattactggc aatagtcgat    2820
gcatttagag aatggcgagt atatttggaa ggatcgaaat acacagtaca ggtgtacaca    2880
gatcataaga acttggttta cttcaccaca acgaagcagt taaacagacg acaggtcaga    2940
tggtcggaga ccatggccaa ctacaatttt agaatttcat atgtcaaagg atcagaaaac    3000
gctagagccg acgctcttag ccgaaaacca gaatatcaag aaaacaaaac gtacgagtca    3060
tacgctatat tcaagaaaga cggcgaatca ctggtttaca atgcaccaca gcttgcagca    3120
acacacctgt tggaagacaa ccacctcagg aaacagatcc aatcacacta cgacaaggat    3180
gctactgcca cacgcatacg caagacaata gaaccaggat tcactataga aaatgatacc    3240
atatactttc atggaaaagt atacattccg agtcaaatga ccaaggaatt tgtgacggaa    3300
caacatgggt tgccggcaca tggacatcaa ggaattgcaa ggacatttgc aagaatacgg    3360
ggaatcagtt acttcccacg aatgagaacg atagttgaag aagttgttgg aaattgtgac    3420
acctgcatac gaaacaagtc atcacgacat gctccgtatg gtcagctcca gccccagac    3480 atgccttctc agccatggaa gtccatcaca tgggactttg tgatcaaact accactctca    3540
aaggatccta ctacaggaat tgagtacgac gcgatactca atatagtaga caggctaacg    3600
aaatttgcat atatgatacc attcaaggaa acatgggatg ctgagcaact agcatatgtg    3660
ttcctaaggg tcatagtaag catacacgga gtaccagatg agataatctc ggatcgagac    3720
aagctcttta cctcgaaatt ctggactacc ttattagcac ttatgggtat caagagaaag    3780
ctatcgacat cttttccaccc acaaacagat ggtcaaacag agaggaccaa tcagacaatg    3840
gaagcatatc ttagatgcta tcgtataaaa tcccgatacc acaagaagtt aatgccgaat    3900
cagcgatag                                                           3909
```

<210> SEQ ID NO 26
<211> LENGTH: 288
<212> TYPE: DNA
<213> ORGANISM: Botrytis cinerea

<400> SEQUENCE: 26

```
atgaccaagg aatttgtgac ggaacaacat gggttgccgg cacacggaca tcaagggatt     60
gcaagaacat ttgcaagaat ccgggaaatc agttacttcc cacgaatgag aacgatagtt    120
gaagaagttg ttggaaattg tacacacctg catacgaaac aagtcatcac gacatgcgcc    180
gtatggtcag ctccagaccc cagacatgcc ttctcagcca tggaagtcca tcacatggga    240
ctttgtggtc aaactaccac tctcaaagga tcctactaca ggaattga                 288
```

<210> SEQ ID NO 27
<211> LENGTH: 11301
<212> TYPE: DNA
<213> ORGANISM: Botrytis cinerea

<400> SEQUENCE: 27

```
caaagggggc attacgcttc caactgccga aaccctgttg tatgtcaaca ctgtaaagga     60
```

| | |
|---|---|
| agtcacggat ccagagagtg cccaggaact atgtcacagc cttcccgaca gggaaacgct | 120 |
| tagacccagc tgttattctg agcgtcccac tgacgctggg tccccaaata gaaggacgta | 180 |
| ctacctttac cattatagca atgttccaac caaaagataa gccgatagcg cttcgatgcc | 240 |
| ttatcgactc aggagcacaa gccaacatca tccaacaatc caagtgtatc gaatgggact | 300 |
| ggctgcctat taagaaagga acagctttag tatctgcgaa cggtaccacg atgccgtcgt | 360 |
| atggtaacca tcagttcccc gtcgaagtaa aagatcaaaa gggagagaag agaaccttca | 420 |
| cccacgagtt tactgctgct gtactagact tacccaaaat cgatgctata tttggattac | 480 |
| cctggctaca agcggtaaac ccagatatcg actggaaatc gacgtctctt cactatcgcc | 540 |
| cctctcttag cgacctcgaa atgatttctg caagcgaact ctatagcgaa gtgaaaaagg | 600 |
| gcgtccatgt atatgttata ctaccagaga tccagcccca ttaccgtaga gacaacgggt | 660 |
| accgccgggt actcacgctc tccacactaa atatccccga agaataccaa gaataccaac | 720 |
| aagccttttc cgaggaagaa agcagtactc taccagaaca ccactcgatg gagcatcgca | 780 |
| ttgatctcga agccgattcg aaacctcctt gggggccaat ctattcttta tctgaagagg | 840 |
| aatcaatagt attaagggaa tacttagtag aatatcaaaa aaagggatgg ataaggaggt | 900 |
| ccattagttc ggcaggagcg ccaatcatgt ttgttcccaa gaagggggga ggctatcggc | 960 |
| tttgtgtcga ctaccggggt ctaaatagga taaccaaaaa ggatcgaacc ccgctacccc | 1020 |
| taatcagcga gtccttagac cgacttcgac aaggtgtcgt cttcactaaa ttggacctgc | 1080 |
| gagatgccta ccaccgtatt cgtatcaggg aaggcgacga atggaagacg gcgttccgca | 1140 |
| cgcggtacgg gcaattcgaa tacttagtta tgccattcgg cctgaccaat gctccagcaa | 1200 |
| cgttccaaac atacatcaat caagcactgt caggcttgac agacaccata tgcgtagtgt | 1260 |
| acctagatga tatcctgatt tactctgagg atagagaaag ccacacgcgg gatgtccgca | 1320 |
| gggtcctcga acgccttata gaatacaagc tgttcgcaaa actgaaaaaa tgtgtctttt | 1380 |
| acacccatga ggttgaattc ctaggattcg tcgtctcggg agcgggagtg acgatggaat | 1440 |
| ccagccgcat tcaaactatt atagaatggc caacacctac aaaccttagg gagctacagg | 1500 |
| tgttcctggg cttcgcgaac ttctatcgac ggtttatcag gacctattcg acggtagccc | 1560 |
| acgggatgac cgcccttatg aagggaacaa agaaggtaa aatggtaggg gagtttatat | 1620 |
| ggacaaagga ggcccaagat gcatttgagg cactaaagaa agcattcacc acggcaccga | 1680 |
| tactcaagca cttcgaacca tcgctccgca tcatggtcga aaccgactcg tcggtgtttg | 1740 |
| ctctaggatg catcctatcg caactattcg aaggagggac tgcagaagca ccgatacgac | 1800 |
| ggtggcaccc cgtcgcgttc tattcgagaa agctgaaccc tgcagaacaa cgatacttca | 1860 |
| ctcacgatca ggaattatta gcaatataca ctgcattcat gcaatggcgc cattacttga | 1920 |
| taggtagtcg gcacacaatc gtggtgaaat cggaccataa cagcttacaa cattttatgg | 1980 |
| tgaaaaagac cctcaatggc agacaagcta gatgggcgga agtactagca gcctacgact | 2040 |
| tcgaaatagt gtacagggca gggaaactga atccagccga cgggccatcg cgccgccccg | 2100 |
| actacgctac cgacacggag ggtatcaatg atatgctacc cacactccag aataaattaa | 2160 |
| aaagtaccgc agttatcgcg agtttatttt acgaatccac cgtgaaaacg gaaccccctgc | 2220 |
| gtattgctat tagtcgcttg caaagggaag ggtatagctt gccattacgt ggacagttag | 2280 |
| tttcactggt aaaaactggt tgcaaacagt cgataccacg tcggattgcc agtgttttcg | 2340 |
| catccgacga aacggcattc gaacctatat cggagtcgat gggaaaagct ttattgcggc | 2400 |
| ttcagaaaga agacgatttt ataaagaata aagagtacct aagacaaaga ttacgttccg | 2460 |

```
ccggagacgc ctcaccacgg caggtgggcg ccgacgagct ccttagacac aaggggagcg   2520
cgtacgtacc gccagacagc gctctcagag cagaaatctt agaaacgcat cacgatgacc   2580
ctattggagg tcattggggt gtcgctaaaa cattggaaat actgaagtct aaatattatt   2640
ggccttcaat gagaaaagac gtcaaacaac atgtcaaaac atgtgcggta tgccagcgaa   2700
ccgctatcaa aagacataag ccacacggcg agttacagac cctccctatt ccaaaaggac   2760
cctggaaaga gataactatg gattttatta cagatttacc tccttcgaaa cacggaaaac   2820
acgtatacga ttctattcta gtagtagtcg acaggttcac gaagctagcc cgatatatcg   2880
ccgtcaacaa gacgatatcg tctcctgaat tagctgacac tatggtcagc acagtattta   2940
aagactttgg tgtgccagag ggcatagtct ccgatagggg accgcaattc gtcagtaaat   3000
tttggagtag cctaatgttt tacttgcgaa tccgtcgtaa gctgtcgacg gcgttccacc   3060
cgcagaccga cggtcaaacc gaacgacaaa accaaaattt gattcactat ataagttgct   3120
acaccaacta taggcaagac gactgggcat cgctattgcc ccttgctgaa ttcacatata   3180
acgcgacatg gcacagtaca accaatacaa gcccattcca ggctatgtat gggttccaac   3240
ccacattcca ttatatcggc gaggacgccg atttagaggg aagggcgccg gcagcacgcg   3300
agcgcatcga cgctttagag aaagaaagag aaaagctgaa agaattctgg aaatcggcaa   3360
ccaatcagaa aaacaagaac actacgaagg ggtcaccaca gcgatatagc atcggggaca   3420
aggtgatgct aagcacaaag aacattaaac aactgcgacc taagaaaaaa ttctccgatc   3480
gatttatagg ccccttttgtc gtgacgggta taaaaaccag cgggcaagca tacgaactta   3540
gattaccgcc cacctacaag atccacaatg tattccacgt ctctttactc gaaccatggc   3600
acgaacgaca gggtaccgcc gacccgccgc cgccagaaga aattgacgat cacatagagc   3660
atgaggtgga aaggatttta gcacatagaa aaagaggcag aggtgtgcaa tacctggtgc   3720
gatggaaggg ctaccaaccg gcggaagaca cgtgggaagc accctacaac ctagaaaatg   3780
cgaaagcagc gatgggagaa tatcataaag aagaagcatt accaatacag aaaaagaaga   3840
gaacaagaaa aaagcttaaa aatacttgat acaaaaagac ctcacgagac ccacacccag   3900
aacgcatgca tcacaccaag ctacccaaaa aggactatcc aacaaagaaa ccagaaagga   3960
caactcctcc gaacccacag cataccgaca accaaaccca agtgacccat cacgcaaaga   4020
gaactctgga aggtcgaaat cagttcccta attcatctgc ctgatccagg aggtcagctg   4080
caatatctcg atcgccaaga aggacagaac ctacatcgct ggcatatccc ccgggactcg   4140
cgagcccgat ctgatcaacc tcacccccc cactgatctc atcttgatca ccgactcctt   4200
cctcctcgtt ctcgcgaatc tcgctgacag ggcgagctcc tgtcggaaaa ccagcggcaa   4260
cccgttgcct cttggagacc cgctccacat cagaattctc agagcgaagc ctttggggcg   4320
aatctgcttg actatcagac tcaccaatat agacttgttg aacagtgctg ggagccctct   4380
ttcgggattt aagagagcct acgggatgag agcggggtgt cggtgtgttg cgagaggcaa   4440
gctgcgacga cttagaagcg gaaagggaa tggcggatct agtcgcgagc ttatcggacc   4500
gagaacgacg aggcgtagca ggaggagcgt tctttctacc caagcttcca aacaataaag   4560
ccggtacact ctcatccaag gggtgacgcg gggcaccggt ggtctgatga ggttgatccg   4620
acacatcatc ctcttcagga gcagactctt cggattcatt gggatccacg attacactcc   4680
tcttcaactt cgcagaacct ttccggaggc cttgctgagc cgtcgtgaag acagcggggc   4740
ccgtccggct cgatgaagca gaagcatgac ggcgacctag ggaaccagct accatattca   4800
```

```
ggccctggtt accacctggg ggccccggag gagcttgaac accctgcagt gcgtcggcga    4860
cagcgcgcac agcgcgaggg tgtataaccg gagccatgaa ctccccttct tcgtccgagt    4920
ttaaggcggc gattaatggt gcagtaggag ctgcggcggc gacgtccaag gcaggcaggt    4980
tattctaaga accatcaaat cagctatcaa cagcaccaag gggcaagagc agggcaaccg    5040
acaacgaatc gatacgaatc cacaatgcgc tccataagat cgccaattct actcaatttg    5100
gacaccagaa gaagagtcaa ttcctctgcg gactgcggtt tgtgagtccc cccttgttta    5160
acctcttttc gaaggaaagc ctccactgcc ttgacgtatc gattacaccg gcgaatcacc    5220
acctcggagg cgtcctcatc ctcttggcta ttatccggag taaggcacca aaaggcatga    5280
gtctgatata agaggttcac gtcgggaaca aagcgaggag gtatcgggag gcagactttc    5340
ttttgtttgc gacaataact acatttagca gcaggacctt tatcaaaatg gcaaaattcg    5400
tcgttagaag agacggcaat tcgcttagaa catcgaaggc aagtagggat aactaacgcg    5460
gaaggggccg ctgcggaccg atcagcgata gcagccggag cgatgggttg cagtgcagcc    5520
atcttcgtat gagtaaataa gggggaataa tctgattgtg ggagatatat cagaggcaag    5580 aagaccccc ttatagaact atcggtgatc tgccggtaag gcggtgaggc gcgtaagaat    5640
gccgccgttt gcttgtttat tgtttgtaat gcctaaacaa gattggaatt gcttttggaa    5700
tgcggcgcag ggtcgggcat gcagcgacgc gacgacgcga cccacattcc gagtaaacaa    5760 tacgaagga agcaaacact tctcgggacg cgaagtgtaa agagaggggc tctgttacgg    5820
gacaaaacgt gaccggctca attaggcacg tgacagtgga cctctcgggt ctactgcgtg    5880
ccgaatgggg cccgcacacg tataaattgt ataatttgca tagttataga aaagcaatga    5940
aaagtcttgg tgccacaata tactagttga ttcatttgtt acggaggtac ccgcaccgca    6000
acatggatta taagataaac ctaaggcctt ggtgttggaa cctacgaaaa cagcactgta    6060
gggacagttg aattaaaggg taactaaaga tagcagtaac cgaatcaata agcaatgatt    6120
aaaagatagg tacctatctt ttgttggcac ctaccctaca gtaggcacag gagggatagc    6180
ggttataggt tatctagtaa gcacaggtta gataagcagt agtatcatgt aggtcacggg    6240
gcaagtgtca cgtgatggat agacaggata ggcaggctat ccaggctatc cgtggataga    6300
caggatagac agtctaccca agctatccag acgagaacga aggtctatat aagggaatgg    6360
gtttcattac aatgtagagc ttcgtgctca agaacaatca ttagtttcat tactatagtt    6420
acgagaattg caaccagtta caaccttatt gaattcctac ttgaagtcta gtctaaacca    6480
cctcgagaga tctctagaca cttccacgtg accctagagg cagctcccgt aacactttga    6540 gcacccttc tgcttcaagt accgattcga taaccaaccg ctaatatggc atccagagct    6600
accgccacag gtcagtctac cgaagatacc aacgacatcg agatgaccga tgccccaaag    6660
gagatcacta tcaacgaaac acttaagatc gccttaccag acaagtacca aggtagtcga    6720
caagagctcg atactttcct cttacaactt gagatctact tccgattcaa tgaagacaag    6780
ttcactacca aggaatccaa gagcatatgg gctgcatcat acctccgagg tgaagcaacc    6840
aaatggattc aaccatattt gcgcgactat ttcgagcatg acgataagga tcgcatgcaa    6900
cccacccgaa caatcttcaa tagttttgaa ggatttaaga cagagattcg tagaatcttc    6960
ggaaattcca acgagttaga ggtagcggaa gataagatct tcaacctcaa gcagacagga    7020
tcagcattga aatatgctac ggaatttcga agatatgctg gaacaaccaa gtgggacgaa    7080
atcgctatca tgagtcacta ctgtaaggga ctcaaaccag aagtcagact agagttagaa    7140
agatctgccg agagtacaga tctgaacgat ctaattcagg actccatcga atcagatgat    7200
```

```
cgtctctata gatatcgaca aagccaaaga tcatacaaac cccaaggaaa ccaaaagcaa    7260
gggcgttacc gcaagaatga gggtagacca cgttacaatc cacagagata cggagacccc    7320
atggaactag acgccacgca ctacacaaac gggaacgatg actcagaaaa gagacgaaga    7380
cgagaaaaca acttatgctt tgaatgtgga aaagcagggc accgagcagt agactgccga    7440
agcaagaaga caggaggaaa aaggggcaac ttcaaaccta agttcggcaa gggccaactt    7500
aacgccacct ttgccatctc agaaaactca actaaaaccg aaaatactga gactttcacc    7560
gttgaggaat ttcagcaatt actaaaggaa ttaccacgaa ataaagaggg catgaatgca    7620
atagacttat gggaacaaga gtattacaga accccaacac cctctgtgac agaagaaagt    7680
caccaggacg aggcagaagc ggaccacgcc acgatgagct ggacagcttg ctatgatgaa    7740
ttctgcggaa tccatcgatc agataaagaa gcaaccggat ggttccccaa gaaaaggaag    7800
acgaagaacc atcagaataa tgtaacatgc gaggatttaa ctcccaatat aacttcgcaa    7860
gaagttcgca aagttaccca gcagttgaat gctacgggac aggcaggaca agtgtactgc    7920
aaggtccaga taaatggaca catacaatca gccatgatag attcaggggc tacaggaaat    7980
tttattgcac cagaagctgc aaagtacttg gaaataccac ttcaaacgaa caacaccccc    8040
tatcgattgc agttagttga tggacagcta gcagggtctg acggaaagat ttcgcaggag    8100
acaatcccag tacgaatggg cataacccaa catacagagg ttatacagct tgacgttgtg    8160
ccattgggcc aacaacagat catcttagga atgccatggt tgaaggcaca taatccgaaa    8220
atagattggg cacaaggaat tgtgacattt gatcagtgca aaagcggtca cagggacacg    8280
ctagaggcgt ccgcgagacg taacacgcgc aaggggagt tgaacgcgaa caacaccggc    8340
gacgtaggac acccagtcca gggtcctcca ttaagagcga aggccagtac acctcctcta    8400
caaatgcaga agccaacgac acggcacgaa atcgcaatcg aggcaaaaga aaggcctacg    8460
ataccagaac agtacaagaa atatgaacat gtttttcaaag aaccagggat ccatgaggct    8520
ttaccggaac acaagccatg ggatcatgag ataatattgg aggaaggcaa gatgcctgtg    8580 cacacccccaa tttattcaat gtcagccgat gagttaaaaa ggctcagaga atacatcgac    8640
gacaatttag ccaagggatg gatcagggaa tccgcgtccc aagtggccag tccaactatg    8700
tgggtaccca agaaggatgg acccgataga ctagttgtag actatagaaa gcttaacgca    8760
ctcactaaga aggatcgata tccacttcca ttagctacgg aattaagaga tcgattaggc    8820
ggagctacga tattcaccaa gatggaccta cgtaatggtt accacttgat cagaatgaag    8880
gaaggcgaag aatggaaaac cgcttttcaaa acaagatacg ggctatacga gtaccaagtt    8940
atgccattcg ggctaaccaa cgcaccagct actttcatga ggcttatgaa caatgtgttg    9000
tcacaatatt tggatacttg ctgtatatgc tacttggacg acatcctagt atattcaaac    9060
aacaaggttc aacacattaa ggacgttagc aacatcctcg aaagtctatc caaagcagac    9120
ttgctgtgca aaccaagcaa atgcgaattc catgtcacag aaacagaatt cttgggattc    9180
accgtatcaa gccaagggct caagatgagc aaagacaagg ttaaggcagt gctcgaatgg    9240
aagcagccaa ccacaatcaa ggaggtacaa tcctttctag ggttcgtcaa cttctacaga    9300
agatttatca agggttattc agggattact acacccttga ccacgttaac cagaaaagat    9360
caaggaagct cgaatggac tgccaaagca caggagtcat tcgatacact caaacaagca    9420
gtggcagaag aaccaatact gttgactttt gacccagaga aagaaatcat agtgaaacg    9480 gattcctcag atttcgctat aggagcagtt ctgagccaac cgggccagaa tggaaaatac    9540
```

```
cagccaatcg cattctactc ccgaaaacta tcaccagctg agttaaatta cgagatatat    9600
gacaaagaat tactggcaat agtcgatgca tttagagaat ggcgagtata tttggaagga    9660
tcgaaataca cagtacaggt gtatacagat cataagaact tggtttactt caccacaacg    9720
aagcagttaa acagacgaca ggtcagatgg tcggagacca tggccaacta caatttcaga    9780
atttcatatg tcaaggatca agaaaacgct agagccgacg ctcttagccg aaaaccagaa    9840
tatcaagaaa acaaaacgta cgagtcatac gctatattca agaaagacgg cgaatcactg    9900
gtctacaatg caccacagct tgcagcaaca cacctgttgg aagacaacca cctcaggaaa    9960
cagatccaat cacactacaa caaggatgct actgccacac gcatacgcaa gacaatagaa   10020
ccaggattca ctatagaaga tgataccata tactttcatg gaaaagtata cattccgagt   10080
caaatgacca aggaatttgt gacggaacaa cacggattgc cggcacatgg acaccaagga   10140
attgcaagga catttgcaag aatacgggaa atcagttact tcccacgaat gagaacgata   10200
gttgaagaag ttgttggaaa ttgtgacacc tgcatacgaa acaagtcatc acgacatgct   10260
ccgtatggtc agctccagac cccagacatg ccttctcagc catggaagtc catcacatgg   10320
gactttgtgg tcaaactacc actctcaaag gatcctacta caggaattga gtacgacgcg   10380
atactcaata tagtagacag gctaacgaaa tttgcatata tgataccatt caaggaaaca   10440
tgggatgctg agcaactagc atatgtgttc ctaagggtca tagtaagcat acacggagta   10500
ccagatgaga taatctcgga tcgagacaag ctctttacct cgaaattctg gactaccttg   10560
ttagcactta tgggtatcaa gagaaagcta tcgacatctt tccacccaca aacagatggt   10620
caaacagaga ggaccaatca gacaatggaa gcatatctta gatgctatgt aaattatcga   10680
caagacaatt gggtagagct attacccatg gcacagttcg catacaatac atcggaaacg   10740
gaaaccacga aaatcacccc agcacgagct aattttgggt ttaatccaca gcgtataaaa   10800
atcccgatac acaagaagt taatgccgaa tcagcaatag tacaagtcga acagctgaaa   10860
gatctccaag agcaactggc tcttgatcta agattcatat cttccagaac agcagcgtac   10920
tacaatacga aacgtagtat ggaacctacg cttaagagg gggataaagt ttatttgcta   10980
caacgaaaca tcgaaaccaa gagaccaagc aataaactcg accacaggaa ataggacca   11040 ttcaagattg ataaggtaat aggaacggtt aattatcgat tgaaattacc agacacaatg   11100
aatatccacc cagtattcca catatccttg ctcgaaccag caccaccagg agcgccaaat   11160
gcgccattta cagaaatcga accagtcaac ccaaacgcca tatacgacgt tgaaacaata   11220
ctagattgta aatatgtcag gggcaaaatc aagtatttga tcaaatggtt agactaccca   11280
cattcggaaa acacatggga a                                             11301
```

<210> SEQ ID NO 28
<211> LENGTH: 936
<212> TYPE: DNA
<213> ORGANISM: Botrytis cinerea

<400> SEQUENCE: 28

```
gaagaggttg ttggcaatat tttgaagaaa gctgaggctg atttgaatgg agattaaaag      60
gggaatgaag ctgcggggcc accgatagca caaaaactac tgaagatttg aagcacgtta     120
aaattacact caggaataaa cggatggcaa gcttttcgat cgcccaaaca cggatctacg     180
actacgagtt acgcacgaca tgatttagcc ttttgtgtgc aatgatgatt agatagcatt     240
gcatttctcg aaattgacgg cacgactttt acgggcagat aatatcaaag attcctagtg     300
agcaagcggt gatgatacga tgtcattcca aaagttttt cctcgcgaat tttatttcat     360
```

```
ttcgaaggca tctttgctta gcagcatatt cacctttgat gtcctctgta ggggatggag    420
tctctaatct cgcggtcaca atgagacgtg atgcgctgcg aagtggtgac aatttcccct    480
tacttagaat agatcatgca cacatgcatg atgcatagct agctagtttt ttattcaatg    540
atagtttaat gacaaacacg tatctagata tcctcattca tgtatctgtg ggaggttgac    600
ttaagttatg gctgacttga tagtttcatt atatatgtat atgtgatatc taagtaaaga    660
ttaaagtgaa atcgaaatgc aacgccaaaa ttcattaat  tccatgaaat gatgtgatat    720
ggcatgacat gatatccaaa ctccgatttg aaatgctcca gcttcgcttt ctaaaattgg    780
taaaagggac attatttcgt ctggttgtgg gttttcattt ctgtgctcct actaggtgtg    840
aatgatagag tatgctgtgg tgtggtgtga tctcggaatt tggaaatttg agggctgtat    900
atcacctcat ttcgtgtgtc cgaatttcta cagact                              936

<210> SEQ ID NO 29
<211> LENGTH: 670
<212> TYPE: DNA
<213> ORGANISM: Botrytis cinerea

<400> SEQUENCE: 29
agagcatttg taggggaagg aggaaaaatt gaggaggagg ataagatgaa ttttgataaa     60
tttatttcct aacatcaggt cacaatctat gaattacatt tgatagtatt acgtatgccg    120
gtctgtacac aacacaacca tatagtaagg tatcaatcaa atgcgatgga tagtcatttc    180
aatttcttag tgaataatta caacgaacca gtaaaatagc aataactctg aaaagcttcc    240
ggactgccaa aaggtctcca ggacgagatt attacgaaga acccaagaat tcgcctagga    300
accaagataa acaaatcatc gacgtgttgc acttccatct atgcgacaat tatgccaagc    360
gagccgccag ttcttggggg tggagcgcta ggaatagggg gccggattgc catatcctta    420
tctagatcta gatggtatcg atatgataaa tcaatgcaat ggagagttaa aaagttatat    480
gccatatgat tgataattat tgacaatgca ggctatcgcg ggacaatggt aaatggttgt    540
aaaatatgga gtctatttcc ttagctagcg ataagatggg tggtttaaac acatcccgcc    600
ttctctttat cattctcctt ctcgtattca tatatcataa ttgcaaagta aggttgtatt    660
ttggactgtg                                                           670

<210> SEQ ID NO 30
<211> LENGTH: 345
<212> TYPE: DNA
<213> ORGANISM: Verticillium dahilae

<400> SEQUENCE: 30
aagctgtcaa ttgatgcgga gggtgagtga acgtctcgtc ggcggggccc cttgaggcga     60
gcgcccgttg gggggtgttg tggcactagg ttctctaggc cggcggtgac tttcattact    120
atattagaag caaatacggc gccttcatca caataataaa tatcgatctc gagtcgattc    180
cagacccgtt ataaacctat gtctgtgcaa ccagttgggt gctaatttct tgcattatca    240
tcatggatgt tgtctatttg agtctcaggt ccagctggtg cttataggtc atctccagta    300
tgcgactacc tctctcccctc tttgccattc ctaactgatt ctaac                   345

<210> SEQ ID NO 31
<211> LENGTH: 1000
<212> TYPE: DNA
<213> ORGANISM: Verticillium dahilae
```

<400> SEQUENCE: 31
cttcatcttc caaccgccat tacctccccc atacgcgtcc tgccaaagaa tcataactgg 60
ctaaaacata agacgggact ggtcatccgc tgaaccattc cgagctatgt gtcctgattg 120
acccatctcg gcttattcgc tctcaaatac gactgcaatc gcgtgtggct tggaaaccgt 180
ggaataccat cctcatattg tcagcacctg tagcgataca gcacaatgct tgacgattcg 240
gaatcatttt ccgcttcttt gcggagcagc ggatgtccaa ttgacgatga cttgactcca 300
gaaccaacgt ccgaatcacg cgactcaacc tccctaccgt atggccttca ggacgacatc 360
ggcccccttg ctgccacccc gagccagtcg agtaacgtca caatcaatgc acgggcatac 420
cagttggaga tgctggcgga aagtaggaag aggaatatca ttctagctgt gcgaaccttc 480
cctcttgcgc cagtcaacct cgattgacac ctccatagat ggacacaggc agtggcaaga 540
cccaagtgta cgttccctgc aagccgaacc tgattattga tactgatttt cccagtgccg 600
tcctccgaat tcgagcagag ctagaagaag gggcttcaga caaggtttga caaactccac 660
ttggtagctt cgcaatcact tacagggttt tagcttgtat ggttcgtggc tcacaatgtt 720
gagctttgcg ctcagcagca ttctgtactg cagtctcaga ttcctgcagt tcagaccaag 780
ctgcttcttg gcagcgataa tgttgattca tggtccaacc aagagacttg gaacgctgtg 840
cttctcaacg tcaaaattgt ggtgtcaacc cctcaagttc tctgcgatgc cttgagccac 900
ggctttgtcc agatgggttc attatccttg cttgtctttg atgaaggtat tcaatcagcg 960
cagtttatca agtgttcttg ccctaacaac ggtgtagcgc 1000

<210> SEQ ID NO 32
<211> LENGTH: 25
<212> TYPE: DNA
<213> ORGANISM: Verticillium dahilae

<400> SEQUENCE: 32
taaggatcgg aggttcgaat cagtt 25

<210> SEQ ID NO 33
<211> LENGTH: 26
<212> TYPE: DNA
<213> ORGANISM: Verticillium dahilae

<400> SEQUENCE: 33
gcgaggtgag aggacgacca gccaag 26

<210> SEQ ID NO 34
<211> LENGTH: 26
<212> TYPE: DNA
<213> ORGANISM: Verticillium dahilae

<400> SEQUENCE: 34
catctgagag gacgtcccgc catggc 26

<210> SEQ ID NO 35
<211> LENGTH: 26
<212> TYPE: DNA
<213> ORGANISM: Verticillium dahilae

<400> SEQUENCE: 35
gtccgggaaa tgaccagctt gagcag 26

<210> SEQ ID NO 36
<211> LENGTH: 28

<212> TYPE: DNA
<213> ORGANISM: Verticillium dahilae

<400> SEQUENCE: 36
atgtcgatgg tcggatgtat cctttct                                    28

<210> SEQ ID NO 37
<211> LENGTH: 18
<212> TYPE: DNA
<213> ORGANISM: Verticillium dahilae

<400> SEQUENCE: 37
gattggaacc tcagatcc                                              18

<210> SEQ ID NO 38
<211> LENGTH: 18
<212> TYPE: DNA
<213> ORGANISM: Verticillium dahilae

<400> SEQUENCE: 38
gcttggaacc tctgatcc                                              18

<210> SEQ ID NO 39
<211> LENGTH: 18
<212> TYPE: DNA
<213> ORGANISM: Verticillium dahilae

<400> SEQUENCE: 39
gactctaacc ttcgatct                                              18

<210> SEQ ID NO 40
<211> LENGTH: 19
<212> TYPE: DNA
<213> ORGANISM: Verticillium dahilae

<400> SEQUENCE: 40
tggttggaat ctctggtcc                                             19

<210> SEQ ID NO 41
<211> LENGTH: 19
<212> TYPE: DNA
<213> ORGANISM: Verticillium dahilae

<400> SEQUENCE: 41
tggttggaat ctctggtcc                                             19

<210> SEQ ID NO 42
<211> LENGTH: 18
<212> TYPE: DNA
<213> ORGANISM: Verticillium dahilae

<400> SEQUENCE: 42
ctggtcctcc tctcacca                                              18

<210> SEQ ID NO 43
<211> LENGTH: 18
<212> TYPE: DNA
<213> ORGANISM: Verticillium dahilae

<400> SEQUENCE: 43
ggtggaactt cttctcag                                              18

<210> SEQ ID NO 44

```
<210> SEQ ID NO 44
<211> LENGTH: 19
<212> TYPE: DNA
<213> ORGANISM: Verticillium dahilae

<400> SEQUENCE: 44
ttcaacctgg tgatttctc                                                19

<210> SEQ ID NO 45
<211> LENGTH: 19
<212> TYPE: DNA
<213> ORGANISM: Verticillium dahilae

<400> SEQUENCE: 45
ttcaacctgg tgatttctc                                                19

<210> SEQ ID NO 46
<211> LENGTH: 19
<212> TYPE: DNA
<213> ORGANISM: Verticillium dahilae

<400> SEQUENCE: 46
ttcaacctgg tgatttctc                                                19

<210> SEQ ID NO 47
<211> LENGTH: 19
<212> TYPE: DNA
<213> ORGANISM: Verticillium dahilae

<400> SEQUENCE: 47
gtcagactgg tcatttcca                                                19

<210> SEQ ID NO 48
<211> LENGTH: 22
<212> TYPE: DNA
<213> ORGANISM: Verticillium dahilae

<400> SEQUENCE: 48
aaaaagatgc atccgatctt cg                                            22

<210> SEQ ID NO 49
<211> LENGTH: 22
<212> TYPE: DNA
<213> ORGANISM: Verticillium dahilae

<400> SEQUENCE: 49
taaaagatat attcgaccat cc                                            22

<210> SEQ ID NO 50
<211> LENGTH: 56
<212> TYPE: DNA
<213> ORGANISM: Botrytis cinerea

<400> SEQUENCE: 50
ggggacaagt ttgtacaaaa aagcaggctt gcggaagaac ttgaaggttt gctaca       56

<210> SEQ ID NO 51
<211> LENGTH: 25
<212> TYPE: DNA
<213> ORGANISM: Botrytis cinerea

<400> SEQUENCE: 51
gtccagatct ggtcaacaca ccaag                                         25
```

```
<210> SEQ ID NO 52
<211> LENGTH: 45
<212> TYPE: DNA
<213> ORGANISM: Botrytis cinerea

<400> SEQUENCE: 52
cttggtgtgt tgaccagatc tggacggatg ccatttgctg cacgc            45

<210> SEQ ID NO 53
<211> LENGTH: 55
<212> TYPE: DNA
<213> ORGANISM: Botrytis cinerea

<400> SEQUENCE: 53
ggggaccact tgtacaaga aagctgggta ctcttgagta ctttcgccag ctcac   55

<210> SEQ ID NO 54
<211> LENGTH: 18
<212> TYPE: DNA
<213> ORGANISM: Verticillium dahilae

<400> SEQUENCE: 54
ggatcggagg ttcgaatc                                          18

<210> SEQ ID NO 55
<211> LENGTH: 18
<212> TYPE: DNA
<213> ORGANISM: Verticillium dahilae

<400> SEQUENCE: 55
ggatcggagg ttcgaatc                                          18

<210> SEQ ID NO 56
<211> LENGTH: 18
<212> TYPE: DNA
<213> ORGANISM: Verticillium dahilae

<400> SEQUENCE: 56
ggatcggagg ttcgaatc                                          18

<210> SEQ ID NO 57
<211> LENGTH: 19
<212> TYPE: DNA
<213> ORGANISM: Verticillium dahilae

<400> SEQUENCE: 57
ggatcggagg ttcgaatca                                         19

<210> SEQ ID NO 58
<211> LENGTH: 19
<212> TYPE: DNA
<213> ORGANISM: Verticillium dahilae

<400> SEQUENCE: 58
ggatcggagg ttcgaatca                                         19

<210> SEQ ID NO 59
<211> LENGTH: 18
<212> TYPE: DNA
<213> ORGANISM: Verticillium dahilae

<400> SEQUENCE: 59
aggtgagagg acgaccag                                          18
```

```
<210> SEQ ID NO 60
<211> LENGTH: 18
<212> TYPE: DNA
<213> ORGANISM: Verticillium dahilae

<400> SEQUENCE: 60
ctgagaggac gtcccgcc                                                 18

<210> SEQ ID NO 61
<211> LENGTH: 19
<212> TYPE: DNA
<213> ORGANISM: Verticillium dahilae

<400> SEQUENCE: 61
gggaaatgac cagcttgag                                                19

<210> SEQ ID NO 62
<211> LENGTH: 19
<212> TYPE: DNA
<213> ORGANISM: Verticillium dahilae

<400> SEQUENCE: 62
gggaaatgac cagcttgag                                                19

<210> SEQ ID NO 63
<211> LENGTH: 19
<212> TYPE: DNA
<213> ORGANISM: Verticillium dahilae

<400> SEQUENCE: 63
gggaaatgac cagcttgag                                                19

<210> SEQ ID NO 64
<211> LENGTH: 19
<212> TYPE: DNA
<213> ORGANISM: Verticillium dahilae

<400> SEQUENCE: 64
gggaaatgac cagcttgag                                                19

<210> SEQ ID NO 65
<211> LENGTH: 22
<212> TYPE: DNA
<213> ORGANISM: Verticillium dahilae

<400> SEQUENCE: 65
cgatggtcgg atgtatcctt tt                                            22

<210> SEQ ID NO 66
<211> LENGTH: 22
<212> TYPE: DNA
<213> ORGANISM: Verticillium dahilae

<400> SEQUENCE: 66
cgatggtcgg atgtatcctt tt                                            22
```

CONTROLLING FUNGAL PATHOGENS BY DISABLING THEIR SMALL RNA PATHWAYS USING RNAI-BASED STRATEGY

CROSS-REFERENCE TO RELATED APPLICATIONS

The present application claims priority to U.S. Provisional Application No. 62/028,776, filed Jul. 24, 2014, and to U.S. Provisional Application No. 62/153,440, filed Apr. 27, 2015, the entire content of each of which is incorporated by reference herein for all purposes.

STATEMENT AS TO RIGHTS TO INVENTIONS MADE UNDER FEDERALLY SPONSORED RESEARCH AND DEVELOPMENT

This invention was made with Government support under Grant No. MCB-0642843, IOS-1257576 awarded by the National Science Foundation, a NIH grant (R01 GM093008). The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SequenceListing_81906-951760.txt, created on Oct. 8, 2015, 160,282 bytes, machine format IBM-PC, MS-Windows operating system, is hereby incorporated by reference in its entirety for all purposes.

BACKGROUND OF THE INVENTION

In plants, pathogen attacks invoke multiple layers of host immune responses. Many pathogens of plants and animals deliver effectors into host cells to suppress host immunity, and many plants have evolved resistance proteins to recognize effectors and trigger robust resistance.

*Botrytis cinerea* is a fungal pathogen that infects almost all vegetable and fruit crops and annually causes $10-100 billion losses worldwide. With its broad host range, *B. cinerea* is a useful model for studying the pathogenicity of aggressive fungal pathogens.

BRIEF SUMMARY OF THE INVENTION

The present application provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that inhibits fungal expression of a fungal pathogen dicer-like (DCL) gene, wherein the plant has increased resistance to a fungal pathogen compared to a control plant lacking the expression cassette.

In some embodiments, the plant comprises two, three, four or more heterologous expression cassettes, wherein each expression cassette comprises a polynucleotide inhibits fungal expression of a distinct fungal pathogen DCL gene. In some embodiments, the plant comprises one or more heterologous expression cassettes for expressing two, three, four or more polynucleotides that inhibit fungal expression of distinct fungal pathogen DCL genes (e.g., two or more DCL genes from a species of fungal pathogen, or one or more DCL genes from each of two or more different species of fungal pathogens).

In some embodiments, the polynucleotide comprises an antisense nucleic acid or inhibitory RNA (RNAi) that targets the fungal pathogen DCL or a fragment thereof (e.g., a sequence of at least 15, 20, 30, 40, 50, 60, 70, 80, 90, 100, 150, 200, 250, 300, 350, 400, 450, 500 or more contiguous nucleotides of the DCL gene). In some embodiments, the polynucleotide comprises a nucleic acid having a sequence that is identical or complementary to at least 15 contiguous nucleotides of the fungal pathogen DCL. In some embodiments, the polynucleotide comprises an antisense nucleic acid that is complementary to any of SEQ ID NO:2, SEQ ID NO:4, SEQ ID NO:6, or SEQ ID NO:8 or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to any of SEQ ID NO:1, SEQ ID NO:3, SEQ ID NO:5, or SEQ ID NO:7 or a fragment thereof (e.g., at least 15, 16, 17, 18, 19, 20, 21, 22, 23, 24, 25, 26, 27, 28, 29, 30, 31, 32, 33, 34, 35, 36, 37, 38, 39, 40, at least 50, at least 60, at least 70, at least 80, at least 90, at least 100, at least 150, at least 200, at least 250, at least 300, at least 350, at least 400, at least 450, or at least 500 contiguous nucleotides thereof). In some embodiments, the polynucleotide comprises an inverted repeat of a fragment of any of SEQ ID NO:1, SEQ ID NO:3, SEQ ID NO:5, or SEQ ID NO:7, and further comprises a spacer region separating the inverted repeat nucleotide sequences. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:9, SEQ ID NO:10, SEQ ID NO:11, or SEQ ID NO:12, or a fragment thereof, or a complement thereof.

The present application also provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that inhibits fungal expression of a fungal pathogen LTR region, or comprising a promoter operably linked to a polynucleotide that targets an LTR promoter, wherein the plant has increased resistance to a fungal pathogen compared to a control plant lacking the expression cassette.

In some embodiments, the polynucleotide comprises an antisense nucleic acid or inhibitory RNA (RNAi) that targets the fungal pathogen LTR or a fragment thereof (e.g., a sequence of at least 15, 20, 30, 40, 50, 60, 70, 80, 90, 100, 150, 200, 250, 300, 350, 400, 450, 500 or more contiguous nucleotides of the LTR). In some embodiments, the polynucleotide comprises a nucleic acid having a sequence that is identical or complementary to at least 15 contiguous nucleotides of the fungal pathogen LTR. In some embodiments, the polynucleotide comprises an antisense nucleic acid that is complementary to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a fragment thereof. In some embodiments, the polynucleotide comprises an inverted repeat of a fragment of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27, and further comprises a spacer region separating the inverted repeat nucleotide sequences.

In some embodiments, the pathogen is *Botrytis*. In some embodiments, the pathogen is *Botrytis cines*. In some embodiments, the pathogen is *Verticillium*. In some embodiments, the pathogen is *V. dahilae*.

In some embodiments, the promoter is an inducible promoter. In some embodiments, the promoter is pathogen inducible. In some embodiments, the promoter is stress-inducible. In some embodiments, the promoter is a constitutive promoter.

In another aspect, the present invention provides for expression cassettes comprising: a promoter operably linked to a polynucleotide that inhibits expression of a fungal dicer-like (DCL) gene; or comprising a promoter operably linked a polynucleotide inhibits expression of a fungal LTR region. In some embodiments, the promoter is heterologous to the polynucleotide. Isolated nucleic acids comprising said expression cassettes are also provided.

In still another aspect, the present invention provides for expression vectors comprising an expression cassette as described herein.

In another aspect, methods of making a pathogen-resistant plant are provided. In some embodiments, the method comprises:

introducing the nucleic acid comprising an expression cassette as described herein into a plurality of plants; and selecting a plant comprising the expression cassette.

In some embodiments, the method of making a pathogen-resistant plant comprises: contacting a plant with a construct comprising a promoter operably linked to a polynucleotide that inhibits fungal expression of a fungal dicer-like (DCL) gene, wherein the plant has increased resistance to a fungal pathogen compared to a control plant that has not been contacted with the construct. In some embodiments, the construct further comprises a second polypeptide that inhibits fungal expression of a second fungal pathogen DCL gene. In some embodiments, the method further comprises contacting the plant with a second construct comprising a second promoter operably linked to a second polynucleotide that inhibits fungal expression of a second fungal pathogen DCL gene.

In some embodiments, the method of making a pathogen-resistant plant comprises:

contacting the plant or the part of the plant with a double-stranded RNA or a small RNA duplex or sRNA that targets a fungal dicer-like (DCL) gene, wherein the plant or the part of the plant has increased resistance to a fungal pathogen compared to a control plant or control plant part that has not been contacted with the double-stranded RNA or small RNA duplex.

In some embodiments, the double-stranded RNA or small RNA duplex or sRNA targets any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31 or a fragment thereof (e.g., at least 20, 30, 40, 50, 60, 70, 80, 90, 100, 150, 200, 250, 300, 350, 400, 450, 500 or more contiguous nucleotides thereof). In some embodiments, the double-stranded RNA or small RNA duplex comprises an inverted repeat of a sequence that is identical or substantially identical (e.g., at least 60%, 65%, 70%, 75%, 80%, 85%, 90%, 91%, 92%, 93%, 94%, 95%, 96%, 97%, 98%, or 99% identical) to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof, or a complement thereof. In some embodiments, the polynucleotide comprises a spacer in between the inverted repeat sequences.

In some embodiments, the method further comprises contacting the plant or the part of the plant with a second double-stranded RNA or a second small RNA duplex or a second sRNA that targets a second fungal pathogen DCL gene. In some embodiments, the method comprises contacting the plant or the part of the plant with one or more double-stranded RNAs or small RNA duplexes or sRNAs that target a DCL gene from a first species of fungal pathogen and further comprises contacting the plant or the part of the plant with one or more double-stranded RNAs or small RNA duplexes or sRNAs that target a DCL gene from a second species of fungal pathogen.

In some embodiments, the pathogen is *Botrytis* or *Verticillium*. In some embodiments, the double-stranded RNA is siRNA. In some embodiments, the double-stranded RNA or small RNA duplex or sRNA is sprayed or brushed onto the plant or the part of the plant (e.g., a leaf, fruit, vegetable, or flower).

In yet another aspect, methods of cultivating a plurality of pathogen-resistant plants are provided.

BRIEF DESCRIPTION OF THE DRAWINGS

The patent or patent application file contains at least one drawing executed in color. Copies of this patent or patent application publication with color drawing(s) will be provided by the U.S. Patent and Trademark Office upon request and payment of the necessary fee.

FIG. 3A-3D. *B. cinerea* DCLs are essential for its pathogenicity. *B. cinerea* dcl1 dcl2 double mutant, but not dcl1 or dcl2 single mutants, produced much weaker disease symptoms than did the wild type in both *Arabidopsis* (A-B) and *S. lycopersicum* (C-D).

FIG. 4A-4C. DCL-dependent small RNAs are important for fungal virulence. *B. cinerea* dcl1 dcl2 double mutant is much less virulent on fruits, vegetables and flowers as compared to a wild-type *Botrytis* strain. Tomato fruits and leaves (A), onions and lettuces (B), and rose flowers (C) were infected by *B. cinerea* wild type strain B05 (WT) or dcl1 dcl2 double mutant strain. Photographs were taken after 3 days for tomato leaves and 4 days for tomato fruits, onion, lettuce and rose.

FIG. 5A-5B. *Botrytis* DCLs are responsible for generating long terminal repeat (LTR)-derived sRNAs. Genome-wide comparative sRNA analysis on dcl1 dcl2 and wild-type revealed that *Botrytis* DCLs are responsible for generating LTR-derived sRNAs, many of which are sRNA effectors.

FIG. 9A-9B. Knocking down BcDCLs by host induced gene silencing (HIGS) in *Arabidopsis* enhances plant resistance to *B. cinerea*. (A) Three selected *B. cinerea* dcl1dcl2 (HIGS-BcDCL) lines as well as wild type plants were infected with *B. cinerea*. Photographs were taken 4 days post infection (dpi). Three biological repeats indicated similar results. (B) The expression level of siRBcDCLs from wild type and three selected transgenic lines transformed with HIGS-BcDCLs as measured by Northern blot. U6 was used as loading control.

Figure 1:
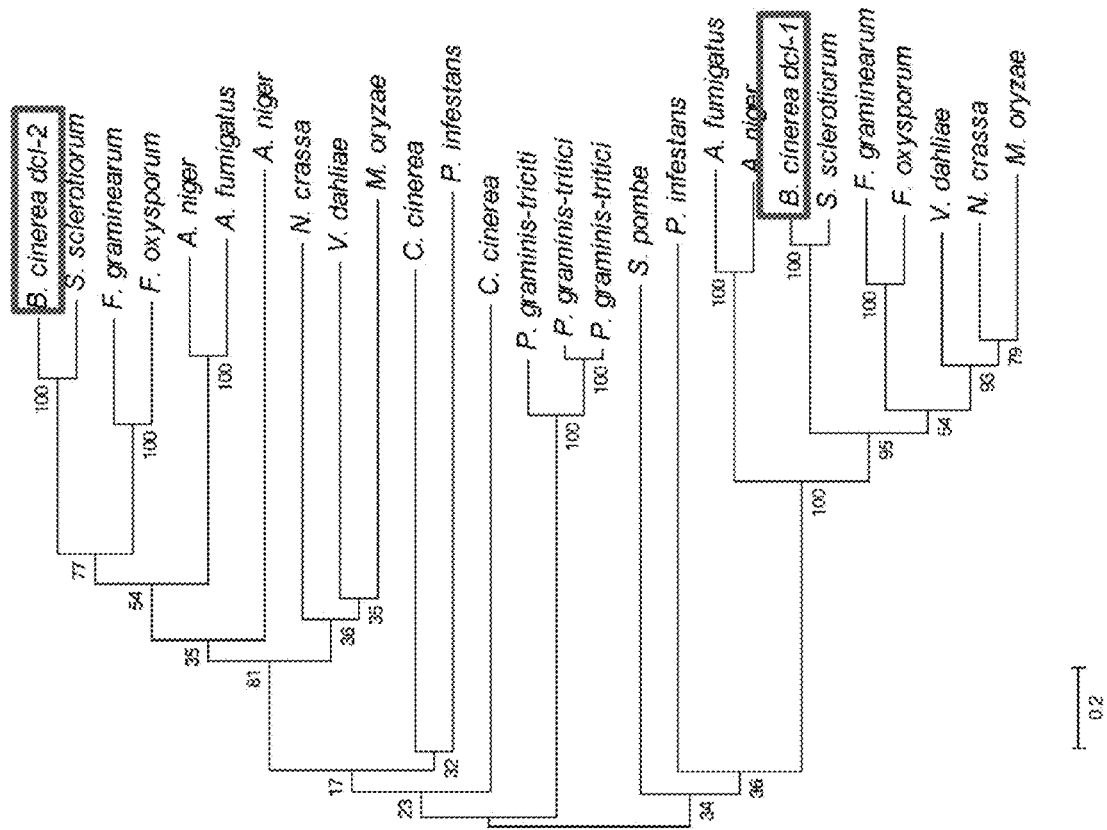
FIG. 1. The *B. cinerea* genome has two dicer-like (DCL) genes. The phylogenetic tree of DCL proteins from different pathogenic fungal species, the DCL proteins from an oomycete pathogen *Phytophthora infestans* are also included. *Schizosaccharomyces pombe* and *Neurospora crassa* were used as references.

The phrase "nucleic acid encoding" or "polynucleotide encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

Two nucleic acid sequences or polypeptides are said to be "identical" if the sequence of nucleotides or amino acid residues, respectively, in the two sequences is the same when aligned for maximum correspondence as described below. "Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" or "substantially identical," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "complementary to" is used herein to mean that a polynucleotide sequence is complementary to all or a portion of a reference polynucleotide sequence. In some embodiments, a polynucleotide sequence is complementary to at least 15, at least 20, at least 25, at least 30, at least 40, at least 50, at least 75, at least 100, at least 125, at least 150, at least 175, at least 200, or more contiguous nucleotides of a reference polynucleotide sequence. In some embodiments, a polynucleotide sequence is "substantially complementary" to a reference polynucleotide sequence if at least 70%, at least 75%, at least 80%, at least 85%, at least 90%, or at least 95% of the polynucleotide sequence is complementary to the reference polynucleotide sequence.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct, which when introduced into a host cell, results in transcription and/or translation of a RNA or polypeptide, respectively.

Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

DETAILED DESCRIPTION OF THE INVENTION

I. Introduction

It has been found that aggressive eukaryotic fungal pathogens, such as *Botrytis* and *verticillium*, have evolved a novel virulence mechanism by employing small RNAs as effector molecules to suppress host immune responses to achieve successful infection. It has also been found that the majority of the small RNA effectors are generated from transposon regions, mainly the retrotransposon long terminal repeats (LTRs). As reported in genome studies of other fungal and oomycete pathogens, many fungal protein effector genes are also enriched in the transposon regions, including LTRs. These LTR-derived small RNAs, including most small RNA effectors, are generated by fungal Dicer-like proteins (DCLs).

As shown herein, DCL genes are essential for the pathogenicity of eukaryotic pathogens, such as the fungal pathogens *Botrytis* and *Verticillium*, with small RNA effectors. Thus, DCL genes are excellent targets for controlling those eukaryotic pathogens that use small RNAs as effectors. For example, *Botrytis* is a significant pathogen not only in the field, but also at post-harvesting stages, and can infect many different fruit, vegetable, and flowering plants.

Thus, one aspect of the present invention relates to controlling the diseases caused by aggressive fungal and oomycete pathogens by silencing their DCL genes and LTRs (e.g., using a host-induced gene silencing (HIGS) mechanism). In some embodiments, silencing is achieved by generating transgenic plants that express antisense (e.g., RNAi) constructs that target fungal or oomycete DCLs. In some embodiments, silencing is achieved by contacting (e.g., spraying) plants with small RNA duplexes or double stranded RNAs that target pathogen DCLs. *Botrytis* and *Verticillium* DCLs are exemplary genes that can be targeted.

II. Fungal Pathogen DCL Genes and LTR Regions

In one aspect, methods of inhibiting or silencing expression of fungal pathogen dicer-like (DCL) genes or long terminal repeat (LTR) regions are provided. In some embodiments, the method comprises expressing in a plant an expression cassette comprising a promoter operably linked to a polynucleotide that inhibits expression of a fungal pathogen DCL gene or an expression cassette comprising a promoter operably linked to a polynucleotide that inhibits expression of a fungal pathogen LTR region. In some embodiments, the method comprises contacting the plant with a construct comprising a promoter operably linked to a polynucleotide that inhibits expression of a fungal pathogen DCL gene or a construct comprising a promoter operably linked to a polynucleotide that inhibits expression of a fungal pathogen LTR region. In some embodiments, the polynucleotide comprises an antisense nucleic acid that is complementary to the DCL gene or a fragment thereof. In some embodiments, the polynucleotide comprises a small RNA duplex or a double-stranded RNA that targets the DCL gene or a fragment thereof. In some embodiments, the polynucleotide sequence comprises an inverted repeat of a sequence targeting the DCL gene, optionally with a spacer present between the inverted repeat sequences. In some embodiments, the polynucleotide comprises an antisense nucleic acid that is complementary to the LTR region or a fragment thereof. In some embodiments, the polynucleotide comprises a small RNA duplex or a double-stranded RNA that targets the LTR region or a fragment thereof. In some embodiments, the polynucleotide sequence comprises an inverted repeat of a sequence targeting the LTR region, optionally with a spacer present between the inverted repeat sequences. In some embodiments, the promoter is an inducible promoter. In some embodiments, the promoter is a constitutively active promoter.

In another aspect, plants having inhibited or silenced expression of pathogen DCL genes or LTR region are provided. In some embodiments, the plant is contacted with a polynucleotide that inhibits expression of a pathogen DCL gene or a pathogen LTR region, wherein the plant has increased pathogen resistance relative to a control plant that is not contacted with the polynucleotide. In some embodiments, the plant comprises a heterologous expression cassette, the expression cassette comprising a polynucleotide that inhibits expression of a pathogen DCL or LTR region, wherein the plant has increased pathogen resistance relative to a control plant lacking the expression cassette. In some embodiments, the polynucleotide comprises an antisense nucleic acid that is complementary to the DCL gene or LTR region or a fragment thereof. In some embodiments, the polynucleotide comprises a double stranded nucleic acid that targets the DCL gene or LTR region or a fragment thereof.

In yet another aspect, expression cassettes comprising a promoter operably linked to a polynucleotide that inhibits expression of a pathogen DCL gene, or isolated nucleic acids comprising said expression cassettes, are provided. In some embodiments, the expression cassette comprises a promoter operably linked to a polynucleotide comprising an antisense nucleic acid that is complementary to the DCL gene or a fragment thereof. In some embodiments, the expression cassette comprises a promoter operably linked to a polynucleotide comprising a double stranded nucleic acid that targets the DCL gene or a fragment thereof. In some embodiments, a plant in which the expression cassette is introduced has increased resistance to the pathogen compared to a control plant lacking the expression cassette.

Pathogen DCL Genes and Polynucleotides Targeting Pathogen DCL Genes

In some embodiments, the pathogen DCL gene or DCL promoter to be targeted or silenced is from a viral, bacterial, fungal, nematode, oomycete, or insect pathogen. In some embodiments, the DCL gene is from a fungal pathogen. Examples of plant fungal pathogens include, but are not limited to, *Botyritis, Verticillium, Magnaporthe, Sclerotinia, Puccinia, Fusarium, Mycosphaerella, Blumeria, Colletotrichum, Ustilago,* and *Melampsora.* See, e.g., Dean et al., *Mol Plant Pathol* 13:804 (2012). In some embodiments, the pathogen is *Botyritis.* In some embodiments, the pathogen is *Botyritis cines.* In some embodiments, the pathogen is *Verticillium.* In some embodiments, the pathogen is *V. dahilae.*

In some embodiments, one or more pathogen DCL genes is targeted, silenced, or inhibited in order to increase resistance to the pathogen in a plant by expressing in the plant, or contacting to the plant, a polynucleotide that inhibits expression of the pathogen DCL gene or that is complementary to the DCL gene or a fragment thereof. In some embodiments, the polynucleotide comprises an antisense nucleic acid that is complementary to the DCL gene or a fragment thereof. In some embodiments, the polynucleotide comprises a double stranded nucleic acid that targets the DCL gene, or its promoter, or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to the DCL gene or a fragment thereof. In some embodiments, a "fragment" of a DCL gene or promoter comprises a sequence of at least 15, 16, 17, 18, 19, 20, 21, 22, 23, 24, 25, 26, 27, 28, 29, 30, 20, 30, 40, 50, 60, 70, 80, 90, 100, 150, 200, 250, 300, 350, 400, 450, 500 or more contiguous nucleotides of the DCL gene or promoter (e.g., comprises at least (e.g., at least 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500 or more contiguous nucleotides of any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31). In some embodiments, the double stranded nucleic acid is a small RNA duplex or a double stranded RNA.

In some embodiments, the polynucleotide inhibits expression of a fungal pathogen DCL gene that encodes a *Botrytis* or *Verticillium* DCL protein. In some embodiments, the polynucleotide inhibits expression of a fungal DCL gene that encodes a *Botrytis* DCL protein that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:2 or SEQ ID NO:4, or a fragment thereof. In some embodiments, the polynucleotide inhibits expression of a fungal DCL gene that encodes a *Verticillium* DCL protein that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:6 or SEQ ID NO:8, or a fragment thereof.

In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:1 or SEQ ID NO:3 or a fragment thereof, or a complement thereof. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:5 or SEQ ID NO:7 or a fragment thereof, or a complement thereof. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:9, SEQ ID NO:10, SEQ ID NO:11, or SEQ ID NO:12, or a fragment thereof, or a complement thereof.

In some embodiments, the polynucleotide comprises an inverted repeat of a sequence that is identical or substantially identical (e.g., at least 60%, 65%, 70%, 75%, 80%, 85%, 90%, 91%, 92%, 93%, 94%, 95%, 96%, 97%, 98%, or 99% identical) to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof, or a complement thereof. In some embodiments, the polynucleotide comprises a spacer in between the inverted repeat sequences.

In some embodiments, the polynucleotide targets a promoter region of a fungal pathogen DCL gene. For example, in some embodiments, the polynucleotide targets a promoter region within the sequence of any of SEQ ID NO:28, SEQ ID NO:29, SEQ ID NO:30, or SEQ ID NO:31.

In some embodiments, two or more fungal pathogen DCL genes or promoters are targeted (e.g., two, three, four or more DCL genes or promoters from the same fungal pathogen or from two or more fungal pathogens). In some embodiments, two or more *Botrytis* DCL genes or promoters are targeted. For example, in some embodiments, two or more of SEQ ID NO:1, SEQ ID NO:3, SEQ ID NO:28, and SEQ ID NO:29, or a fragment of any thereof, are targeted for inhibition of expression. In some embodiments, two or more *Verticillium* DCL genes or promoters are targeted. For example, in some embodiments, two or more of SEQ ID NO:5, SEQ ID NO:7, SEQ ID NO:30, or SEQ ID NO:31, or a fragment of any thereof, are targeted for inhibition of expression.

Pathogen LTR Regions and Polynucleotides Targeting Pathogen LTR Regions

The LTR regions that generate most small RNA effectors can be targeted for silencing. In some embodiments, such as for *B. cinerea*, sRNA effectors are derived from LTR retrotransposon regions. Additionally, the promoter regions of LTRs can also be targeted for silencing. Targeting of LTR promoter regions can trigger transcriptional gene silencing, which would avoid random silencing of host genes by LTR small RNAs.

In some embodiments, the polynucleotide targets or inhibits expression of a pathogen LTR region or of a promoter region of a pathogen LTR, wherein the pathogen is a fungal pathogen. In some embodiments, the pathogen is *Botyritis*. In some embodiments, the pathogen is *Botyritis cines*. In some embodiments, the pathogen is *Verticillium*. In some embodiments, the pathogen is *V. dahilae*.

In some embodiments, the polynucleotide targets a sequence of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a fragment thereof, or a complement thereof. In some embodiments, a "fragment" of a LTR region or LTR promoter comprises a sequence of at least 15, 20, 30, 40, 50, 60, 70, 80, 90, 100, 150, 200, 250, 300, 350, 400, 450, 500 or more contiguous nucleotides of the LTR region or LTR promoter (e.g., comprises at least 15, 20, 30, 40, 50, 60, 70, 80, 90, 100, 150, 200, 250, 300, 350, 400, 450, 500 or more contiguous nucleotides of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27).

In some embodiments, the polynucleotide comprises an antisense nucleic acid that is complementary to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a fragment thereof. In some embodiments, the polynucleotide comprises an inverted repeat of a fragment of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27, and further comprises a spacer region separating the inverted repeat nucleotide sequences.

In some embodiments, the polynucleotide targets a promoter region of a fungal LTR. For example, in some embodiments, the polynucleotide targets a promoter region within the sequence of SEQ ID NO:27.

Host-Induced Gene Silencing

In some embodiments, the methods of inhibiting or silencing expression of fungal pathogen DCL genes or LTR regions utilizes a host-induced gene silencing (HIGS) mechanism for producing in a host plant inhibitory RNA that subsequently moves into the pathogen to inhibit expression of a pathogen gene or region. In some embodiments, HIGS is used to produce in a plant inhibitory RNAs (e.g., sRNAs) that target one or more pathogen DCLs or LTRs. In some embodiments, wherein a pathogen has more than one DCL, HIGS is used to produce inhibitory RNAs (e.g., sRNAs) that target each of the DCLs of the pathogen (e.g., for *Botrytis*, targeting DCL1 and DCL2). In some embodiments, HIGS is used to produce inhibitory RNAs (e.g., sRNAs) against DCLs or LTRs of multiple pathogens.

The use of HIGS for silencing expression of pathogen genes in plants is described, e.g., in Nowara et al. (*Plant Cell* (2010) 22:3130-3141); Nunes et al. (*Mol Plant Pathol* (2012) 13:519-529); and Govindarajulu et al. (*Plant Biotechnology Journal* (2014) 1-9). Pathogen sRNAs are described, for example, in US 2015/0203865, incorporated by reference herein.

Antisense Technology

In some embodiments, antisense technology is used to silence or inactive the pathogen DCL gene or LTR. The antisense nucleic acid sequence transformed into plants will be substantially identical to at least a fragment of the gene to be silenced. In some embodiments, the antisense nucleic acid sequence that is transformed into plants is identical or substantially identical to the pathogen DCL sequence or LTR sequence to be blocked. In some embodiments, the antisense polynucleotide sequence is complementary to the pathogen DCL sequence or LTR sequence to be blocked. However, the sequence does not have to be perfectly identical to inhibit expression. Thus, in some embodiments, an antisense polynucleotide sequence that is substantially complementary (e.g., at least 70%, at least 75%, at least 80%, at least 85%, at least 90%, or at least 95% complementary) to the pathogen DCL sequence or LTR sequence to be blocked can be used (e.g., in an expression cassette under the control of a heterologous promoter, which is then transformed into plants such that the antisense nucleic acid is produced).

In some embodiments, an antisense or sense nucleic acid molecule comprising or complementary to only a fragment of the pathogen DCL gene sequence or LTR sequence can be useful for producing a plant in which pathogen gene expression is silenced. For example, a sequence of about 15, 20, 30, 40, 50, 100, 150, 200, 250, 300, 350, 400, 450, or 500 nucleotides can be used.

Catalytic RNA molecules or ribozymes can also be used to inhibit expression of a pathogen DCL gene or LTR. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the sequence intended to be repressed. This minimal identity will typically be greater than about 65% to the target gene sequence (e.g., DCL or LTR sequence), but a higher identity can exert a more effective repression of expression of the endogenous sequences. In some embodiments, sequences with substantially greater identity are used, e.g., at least about 80%, at least about 95%, or 100% identity are used. As with antisense regulation, the effect can be designed and tested so as to not significantly affect expression of other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. In some embodiments, a sequence of the size ranges noted above for antisense regulation is used, e.g., at least about 15, 20, 30, 40, 50, 60, 70, 80, 90, 100, 150, 200, 250, 300, 350, 400, 450, 500 or more nucleotides.

Gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is also known to be effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct. Genom.* 5: 240-244 (2004); Lu, et al., *Nucleic Acids Research* 32(21):e171 (2004)). For example, to achieve suppression of pathogen DCL expression using RNAi, a gene fragment (e.g., from a DCL gene) in an inverted repeat orientation with a spacer could be expressed in plants to generate double-stranded RNA having the sequence of an mRNA encoding the DCL protein, or a substantially similar sequence thereof (including those engineered not to translate the protein) or fragment thereof, is introduced into a plant or other organism of interest. The resulting plants/organisms can then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S., Patent Publication No. 2004/0029283 for an example of a non-identical siRNA sequence used to suppress gene expression. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211. Gene silencing in plants by the expression of small RNA duplexes is also described, e.g., in Lu et al., *Nucleic Acids Res.* 32(21):e171 (2004).

The RNAi polynucleotides can encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 10, 15, 20, 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected cells have been engineered to express small hairpin RNAs, which get processed in vivo into siRNAs molecules capable of carrying out gene-specific silencing (Brummelkamp et al., *Science* 296: 550-553 (2002), and Paddison, et al., *Genes & Dev.* 16:948-958 (2002)). Post-transcriptional gene silencing by double-stranded RNA is discussed in further detail by Hammond et al., *Nature Rev Gen* 2: 110-119 (2001), Fire et al., *Nature* 391: 806-811 (1998) and Timmons and Fire, *Nature* 395: 854 (1998).

Yet another way to suppress expression of a gene in a plant is by recombinant expression of a microRNA that suppresses the target gene. Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial micro-RNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Another way to suppress expression of a gene in a plant is by application of a dsRNA to a surface of a plant or part of a plant (e.g., onto a leaf, flower, fruit, or vegetable), for example by spraying the dsRNA onto the surface or brushing the dsRNA onto the surface. Methods of applying dsRNA onto external plant parts are described, for example, in WO 2013/02560 and in Gan et al., *Plant Cell Reports* 29:1261-1268 (2010).

In some embodiments, antisense sequences such as dsRNA or sRNA can be synthesized in planta and extracted from the plant for subsequent use on a target plant. As a non-limiting example, constructs for producing one or more dsRNA or sRNA sequences of interest can be transiently introduced into a plant (e.g., *N. benthamiana*), for example by infiltration with *Agrobacterium*. The dsRNA or sRNA sequences are produced by the plant and then RNA is extracted from one or more tissues of the plant in order to extract the dsRNA or sRNA sequences of interest. An exemplary method of expressing and extracting antisense sequences from *N. benthamiana* is described in the Examples section below.

III. Methods of Making Plants Having Increased Pathogen Resistance

In another aspect, methods of making plants having increased pathogen resistance are provided. In some embodiments, the method comprises:
 introducing into a plant a heterologous expression cassette comprising a promoter operably linked to a polynucleotide that inhibits fungal expression of a pathogen DCL gene; and
 selecting a plant comprising the expression cassette.

In some embodiments, the method further comprises introducing into the plant a second heterologous expression cassette comprising a second promoter operably linked to a second polynucleotide that inhibits fungal expression of a second pathogen DCL gene; and selecting a plant comprising the second expression cassette.

In some embodiments, the polynucleotide that inhibits fungal expression of the pathogen DCL gene is described herein (e.g., in Section II above). For example, in some embodiments, the polynucleotide inhibits the expression of one, two, three, four or more *Botrytis* or *Verticillium* DCL genes. In some embodiments, inhibits the expression of one, two, three, four or more of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31.

In some embodiments, a plant into which the expression cassette(s) has been introduced has increased pathogen resistance relative to a control plant lacking the expression cassette(s). In some embodiments, a plant into which the expression cassette has been introduced has enhanced resistance to a fungal pathogen (e.g., *Botyritis* or *Verticillium*) relative to a control plant lacking the expression cassette.

In some embodiments, the promoter is heterologous to the polynucleotide. In some embodiments, the polynucleotide encoding the sRNA-resistant target is operably linked to an inducible promoter. In some embodiments, the promoter is pathogen inducible (e.g., a *Botrytis* inducible promoter). In some embodiments, the promoter is stress inducible (e.g., an abiotic stress inducible promoter).

In some embodiments, the method comprises:
 contacting a plurality of plants with a construct comprising a promoter operably linked to a polynucleotide that inhibits fungal expression of a pathogen DCL gene or pathogen LTR region, wherein the plant has increased resistance to a pathogen compared to a control plant that has not been contacted with the construct.

In some embodiments, the method further comprises selecting a plant having increased pathogen resistance.

In some embodiments, the method comprises:
 contacting a plant or a part of a plant with a double-stranded RNA, a small RNA duplex, or a small RNA (sRNA) that targets a pathogen DCL gene or pathogen LTR region, wherein the plant or part of the plant has increased resistance to the pathogen compared to a control plant that has not been contacted with the double-stranded RNA or small RNA duplex.

In some embodiments, the double-stranded RNA or small RNA duplex (e.g., siRNA) or sRNA targets *Botrytis* DCLs or *Verticillium* DCLs. In some embodiments, the double-stranded RNA or small RNA duplex or sRNA targets any of SEQ ID NO:1, SEQ ID NO:3, SEQ ID NO:5, or SEQ ID NO:7 or a fragment thereof. In some embodiments, the double-stranded RNA is an siRNA. In some embodiments, the siRNA comprises a sequence that is identical to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof (e.g., a fragment of at least 15, 16, 17, 18, 19, 20, 21, 22, 23, 24, 25, 26, 27, 28, 29, 30, or more contiguous nucleotides) or a complement thereof.

In some embodiments, the method comprises contacting the plant or the part of the plant with two, three, four, five, or more double-stranded RNAs or small RNA duplexes (e.g., siRNAs) or sRNAs for targeting two, three, four, five, or more pathogen DCL genes or pathogen LTR regions from one, two, three or more different pathogens. As a non-limiting example, in some embodiments, the plant is contacted with a double-stranded RNA or small RNA duplex (e.g., siRNA) or sRNA that targets *Botrytis* DCL1 and a double-stranded RNA or small RNA duplex (e.g., siRNA) or sRNA that targets *Botrytis* DCL2. As another non-limiting example, in some embodiments, the plant is contacted with a double-stranded RNA or small RNA duplex (e.g., siRNA) or sRNA that targets *Verticillium* DCL1 and a double-stranded RNA or small RNA duplex (e.g., siRNA) or sRNA that targets *Verticillium* DCL2. As yet another non-limiting example, in some embodiments, the plant is contacted with a double-stranded RNA or small RNA duplex (e.g., siRNA) or sRNA that targets one or more DCLs of *Botrytis* (e.g., *Botrytis* DCL1 and/or *Botrytis* DCL2) and with a double-stranded RNA or small RNA duplex (e.g., siRNA) or sRNA that targets one or more DCLs of *Verticillium* (e.g., *Verticillium* DCL1 and *Verticillium* DCL2).

In some embodiments, the double-stranded RNA or small RNA duplex (e.g., siRNA) or sRNA is sprayed or brushed onto the plant or part of the plant (e.g., onto a leaf, a fruit, or a vegetable).

IV. Polynucleotides and Recombinant Expression Vectors

The isolation of polynucleotides of the invention may be accomplished by a number of techniques. For instance, oligonucleotide probes based on the sequences disclosed here can be used to identify the desired polynucleotide in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon a sequence disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Polynucleotides can also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Once a polynucleotide sequence that inhibits expression of a fungal dicer-like (DCL) gene or LTR region, or that is complementary to a fungal pathogen DCL gene or LTR region or a fragment thereof, is obtained, it can be used to prepare an expression cassette for expression in a plant. In some embodiments, expression of the polynucleotide is directed by a heterologous promoter.

Any of a number of means well known in the art can be used to drive expression of the polynucleotide sequence of interest in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, expression can be conditioned to only occur under certain conditions (e.g., using an inducible promoter).

For example, a plant promoter fragment may be employed to direct expression of the polynucleotide sequence of interest in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide sequence of interest in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653,535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include the presence of a pathogen, anaerobic conditions, elevated temperature, or the presence of light.

In some embodiments, the promoter is a constitutive promoter. In some embodiments, the promoter is an inducible promoter. In some embodiments, the promoter is stress inducible (e.g., inducible by abiotic stress). In some embodiments, the promoter is pathogen inducible. In some embodiments, the promoter is induced upon infection by *Botyrtis*. Non-limiting examples of pathogen inducible promoters include *Botyritis*-Induced Kinase 1 (BIK1) and the plant defensing gene PDF1.2. See, e.g., Penninckx et al., *Plant Cell* 10:2103-2113 (1998); see also Veronese et al., *Plant Cell* 18:257-273 (2006).

In some embodiments, a polyadenylation region at the 3'-end of the coding region can be included. The polyadenylation region can be derived from a NH3 gene, from a variety of other plant genes, or from T-DNA.

The vector comprising the sequences will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

V. Production of Transgenic Plants

As detailed herein, embodiments of the present invention provide for transgenic plants comprising recombinant expression cassettes for expressing a polynucleotide sequence as described herein (e.g., a polynucleotide that inhibits expression of a fungal pathogen dicer-like (DCL) gene or a polynucleotide that inhibits expression of a fungal pathogen LTR region). In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

In some embodiments, the transgenic plants comprising recombinant expression cassettes for expressing a polynucleotide sequence as described herein have increased or enhanced pathogen resistance compared to a plant lacking the recombinant expression cassette, wherein the transgenic plants comprising recombinant expression cassettes for expressing the polynucleotide sequence have about the same growth as a plant lacking the recombinant expression cassette. Methods for determining increased pathogen resistance are described, e.g., in Section VI below.

A recombinant expression vector as described herein may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the polynucleotide sequence of interest is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced pathogen resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes and antisense constructs (e.g., siRNAs) of the invention can be used to confer increased or enhanced pathogen resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and *Zea*. In some embodiments, the plant is a tomato plant. In some embodiments, the plant is a vining plant, e.g., a species from the genus *Vitis*. In some embodiments, the plant is an ornamental plant. In some embodiments, the plant is a vegetable- or fruit-producing plant. In some embodiments, the plant is a monocot. In some embodiments, the plant is a dicot.

VI. Selecting for Plants with Increased Pathogen Resistance

Plants (or parts of plants) with increased pathogen resistance can be selected in many ways. One of ordinary skill in the art will recognize that the following methods are but a few of the possibilities. One method of selecting plants or parts of plants (e.g., fruits and vegetables) with increased pathogen resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen, compound, or plant is used. Generally, increased resistance is measured by the reduction or elimination of disease symptoms (e.g., reduction in the number or size of lesions or reduction in the amount of fungal biomass on the plant or a part of the plant) when compared to a control plant. In some embodiments, resistance is increased when the number or sizes of lesions or amount of fungal biomass on the plant or on a part of the plant is decreased by at least about 10%, 20%, 30%, 40%, 50%, 60%, 70%, 80%, 90% or more relative to a control (e.g., relative to a plant in which a heterologous polynucleotide targeting a fungal pathogen DCL or LTR has not been expressed).

In some cases, increased resistance can also be measured by the production of the hypersensitive response (HR) of the plant (see, e.g., Staskawicz et al. (1995) *Science* 268(5211): 661-7). Plants with increased pathogen resistance can produce an enhanced hypersensitive response relative to control plants.

Increased pathogen resistance can also be determined by measuring the increased expression of a gene operably linked a defense related promoter. Measurement of such expression can be measured by quantifying the accumulation of RNA or subsequent protein product (e.g., using northern or western blot techniques, respectively (see, e.g., Sambrook et al. and Ausubel et al.).

VII. Examples

Example 1: Targeting DCL Genes to Attenuate Fungal Virulence

Eukaryotic small RNAs (sRNAs) are short regulatory noncoding RNAs that induce silencing of target genes at transcriptional and posttranscriptional levels. The endoribonuclease Dicer or Dicer-like proteins (DCLs) process double-stranded RNAs (dsRNAs) or RNAs with hairpin structures, giving rise to mostly 20-30-nt long sRNAs, which are loaded into Argonaute (AGO) proteins to induce gene silencing of their complementary targets by guiding mRNA cleaving or degradation, translational inhibition, DNA methylation, and histone modification. The role of sRNAs in plant-pathogen interactions, including the role of noncoding sRNAs from bacterial and eukaryotic plant pathogens in pathogenicity, is described in Weiberg et al., *Annu. Rev. Phytopathol.* 2014, 52:22.1-22.22, incorporated by reference herein.

sRNA effectors, like those found in *B. cinerea*, are transcribed from transposable elements (TEs) and suppress host immune-related genes. Host plant resistance genes are often clustered in genomic loci enriched with TEs. Similarly, protein effector genes are often found in clusters and interspersed with TEs. See, e.g., Weiberg at FIG. 2.

Because most of the *Botrytis* small RNA effectors are generated from LTR regions, there are multiple copies for each LTR, which makes Bc-sRNA knockouts impractical if not impossible. Therefore, to solve this problem, *Botrytis* DCL knockout mutants were generated.

Figure 2A:
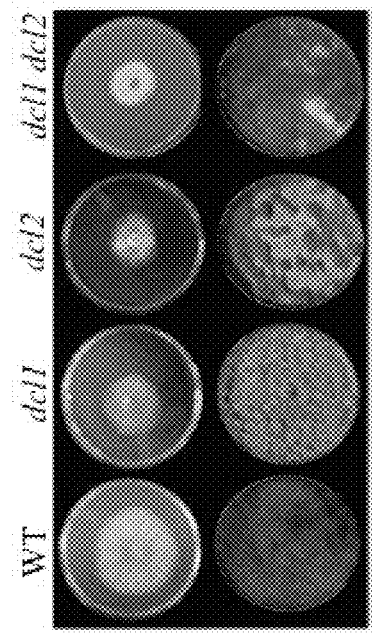
FIG. 2A-2C. *B. cinerea* (Bc)-sRNAs are dependent on both *B. cinerea* DCL proteins. All of the *B. cinerea* dcl1, dcl2, and dcl1 dcl2 mutant strains showed growth retardation and delayed development of conidiospores (A), but only the double mutant strain could not produce Bc-sRNA effectors (B). DCL-independent sRNAs were used as a control (C).
Figure 2B:
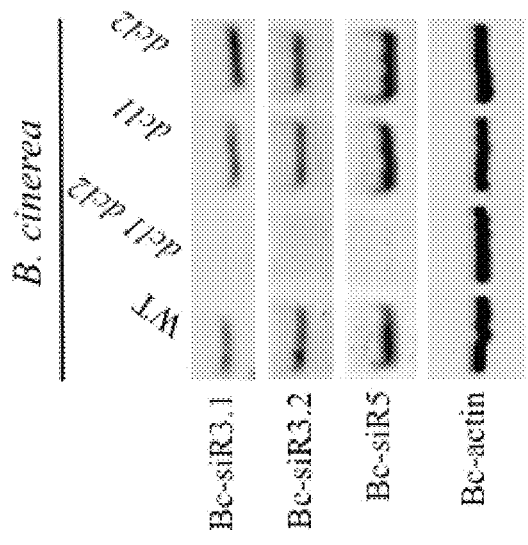
Figure 2C:
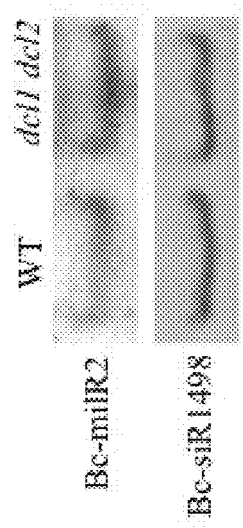
Figure 5A:
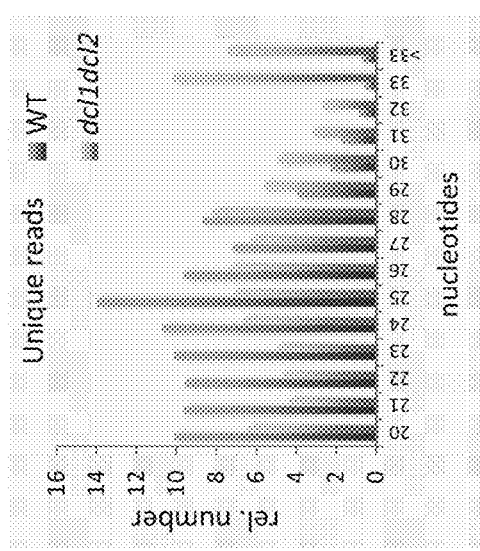
Figure 5A:
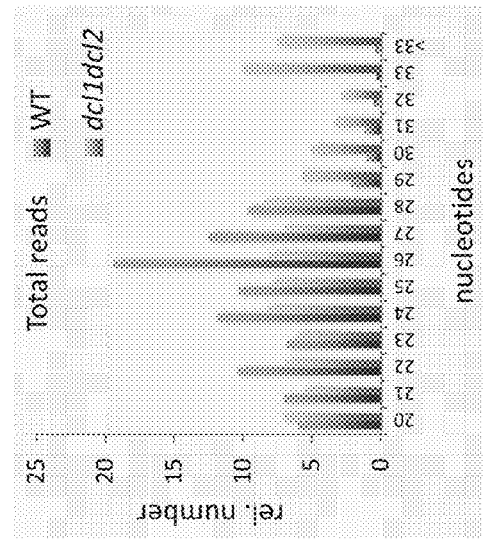
Figure 6:
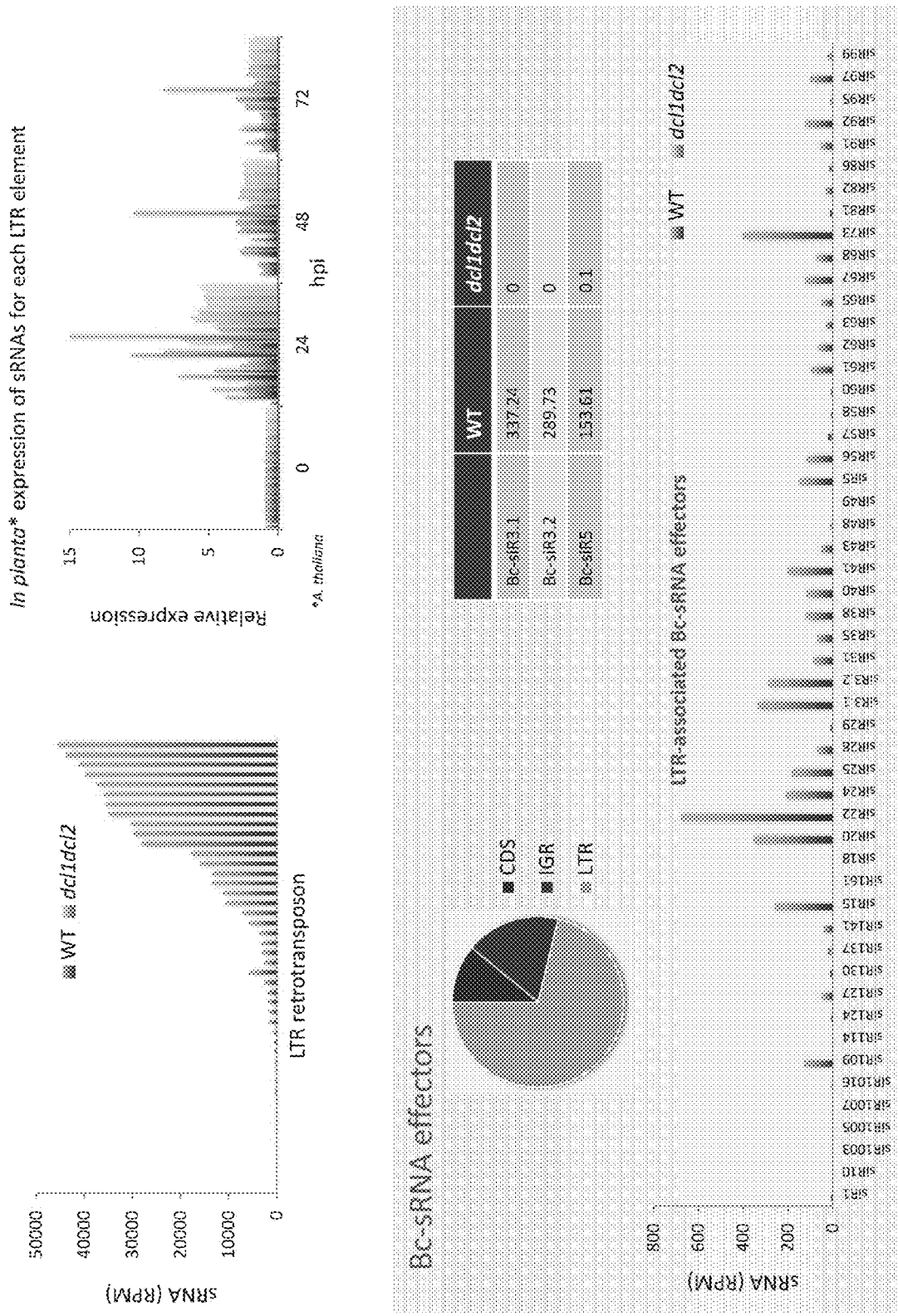
FIG. 6. LTR-derived Bc-sRNA effectors are dependent on DCL1 and DCL2.
Figure 7:
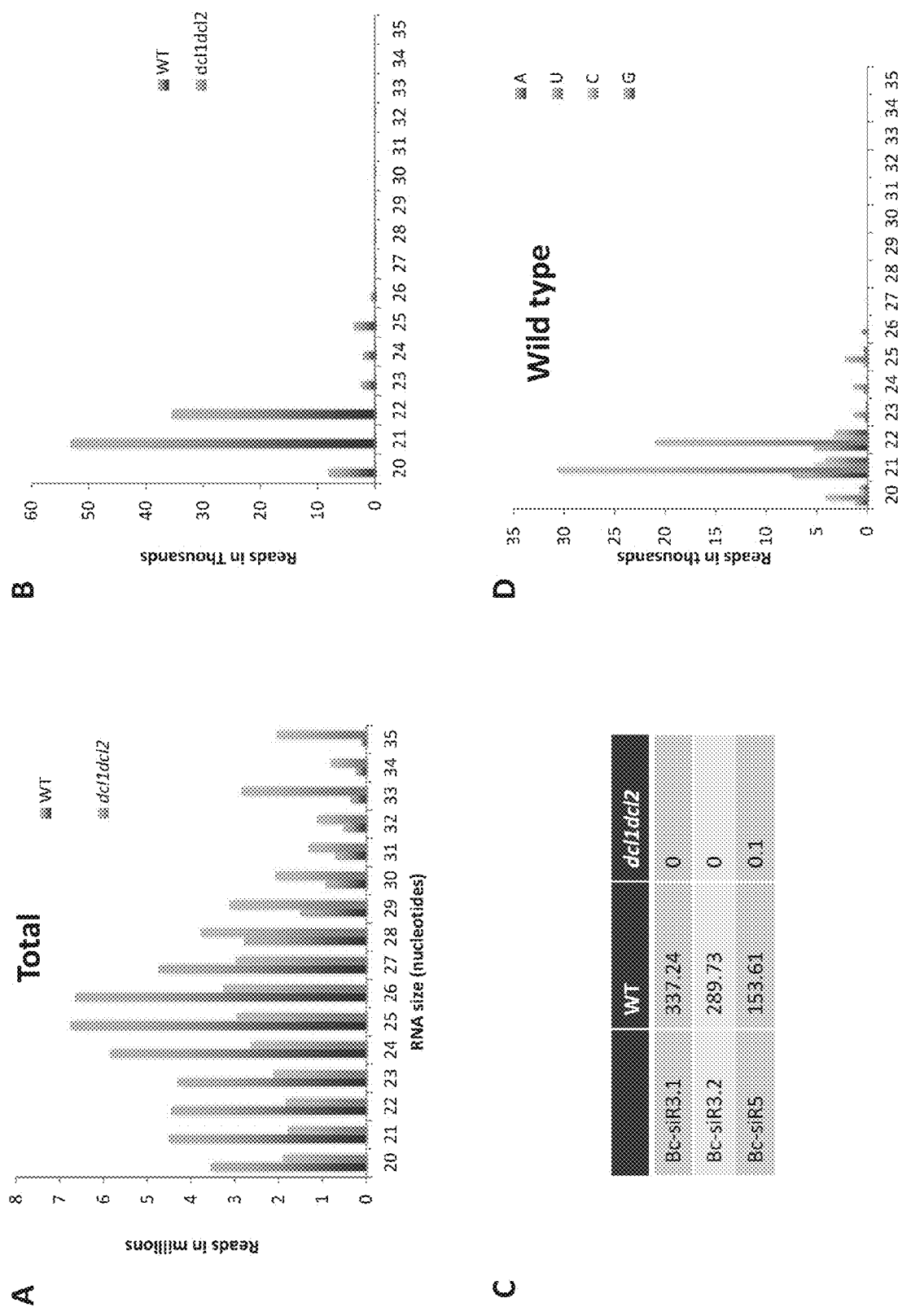
FIG. 7. Retrotransposon-derived Bc-sRNAs are mostly BcDCL-dependent. Two libraries were constructed from wild type *B. cinerea* and the dcl1 dcl2 double mutant and sequenced using Illumina deep sequencing. (A) The read numbers of all Bc-sRNA reads from the two libraries according to sRNA size. (B) The read numbers of retrotransposon-derived Bc-sRNA from the two libraries according to sRNA size. (C) The normalized read numbers of Bc-siR3.1, Bc-siR3.2, and Bc-siR5 from the two libraries. (D) The read numbers of retrotransposon-derived Bc-sRNAs according to 5' nucleotide (A, U, C, or G) and sRNA size. The X-axis in A, B, and D indicates RNA size in nucleotides.
Figure 8:
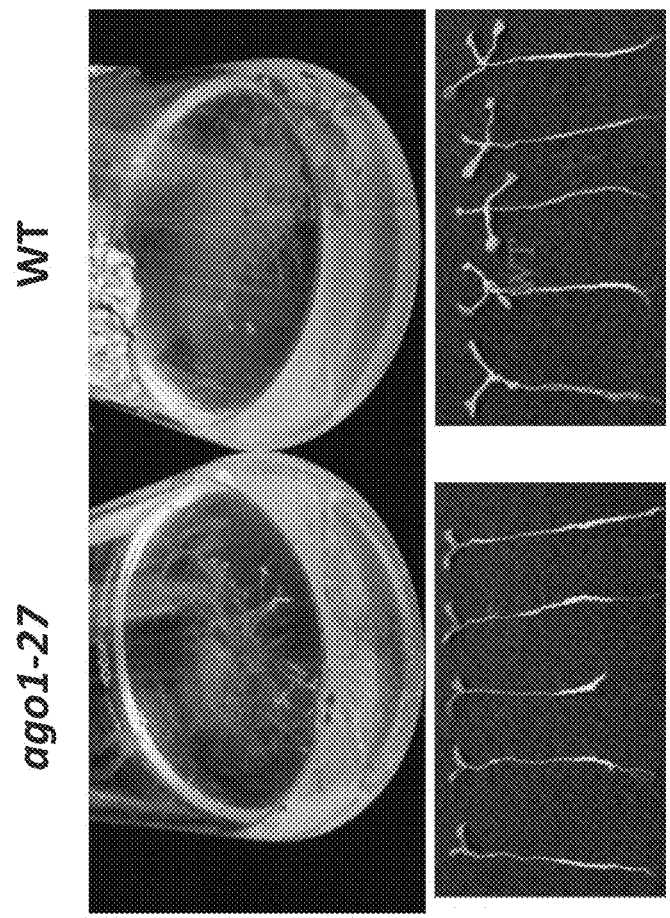
FIG. 8. Some *Verticillium* small RNAs were highly enriched in AGO1 pull-down fraction after infection. Root culture was performed to obtain material for immunoprecipitation of AGO1-associated small RNA in wild-type (WT) and ago1-27 mtuant *Arabidopsis* following infection. sRNAs that are associated with *Arabidopsis* AGO1 were pulled down and subjected to deep sequencing.

As shown in FIG. 1, the *B. cinerea* genome has two DCLs (dcl-1 and dcl-2). Single- and double-mutant (dcl1, dcl2, and dcl1 dcl2 mutant) strains were generated. As shown in FIG. 2, all of the *B. cinerea* dcl1, dcl2, and dcl1 dcl2 mutant strains showed growth retardation and delayed development of conidiospores (FIG. 2A), but only the double mutant strain (dcl1 dcl2) could not produce Bc-sRNA effectors (FIG. 2B).

*B. cinerea* DCLs are essential for the pathogenicity of *B. cinerea*. As shown in FIG. 3, dcl1 dcl 2 double mutants, but not dcl1 or dcl2 single mutants, produced much weaker disease symptoms than did the wild type in both *Arabidopsis* and *S. lycopersicum*, and largely attenuated the virulence of *B. cinerea*. Similarly, FIG. 4 shows that *B. cinerea* dcl1 dcl2 double mutants are much less virulent on fruit, vegetables, and flowers.

A genome-wide comparative sRNA analysis on a dcl1 dcl2 mutant strain and wild-type revealed that *Botrytis* DCLs are responsible for generating LTR-derived sRNAs, many of which are sRNA effectors. See, FIG. 5A-B, FIG. 6, and FIG. 7A-D.

*B. cinerea* delivers small RNAs into host cells (e.g., plant cells) to suppress host immune systems. See, e.g., Weiberg at FIG. 2. Another fungal plant pathogen, *Verticillium dahliae*, also depends on AGO1 function for its pathogenicity. See, e.g., Ellendorf et al., *J. Exp Bot* 2009; 60:591-602. This suggests that *Verticillium* is likely to have a similar RNAi virulence mechanism as *B. cinerea*. Because *Verticillium* infects the plants through roots, we used root culture to get more material for immunoprecipitation of *Arabidopsis* AGO1-associated small RNA. sRNAs that are associated with *Arabidopsis* AGO1 were pulled down and subjected to deep sequencing. We found that some of the *Verticillium* small RNAs were highly enriched after infection. We found that 41 Vd-sRNAs had *A. thaliana* (At) targets (using 100 rpm and 10 fold enrichment as a cutoff). Table 1 below shows examples of infection-enriched *Verticillium* small RNAs that have potential host targets.

Figure 10A:
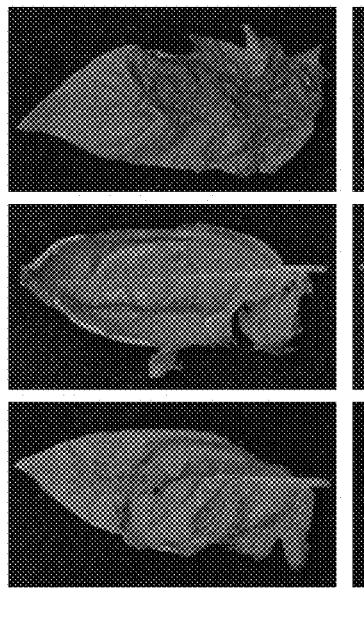
FIG. 10A-10B. Knocking down BcDCLs by virus induced gene silencing (VIGS) in tomato enhances plant resistance to *B. cinerea*. (A) The fifth, sixth, and seventh leaves of tomato VIGS-RB and VIGS-BcDCLs plants were detached and infected with *B. cinerea* using spray inoculation. Photographs were taken 3 dpi. Three biological repeats indicated similar results. (B) The levels of siRBcDCLs from the corresponding infected leaves were measured by Northern blot. U6 was used as loading control.
Figure 10B:
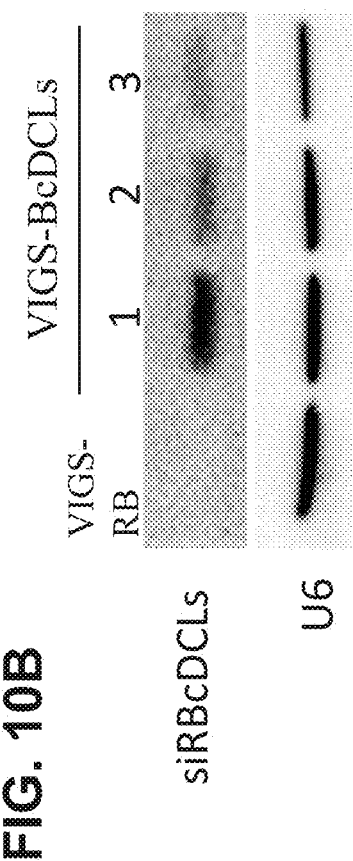

These results suggest that RNAi constructs, which target fungal Dicer-like protein genes to attenuate fungal virulence, can be expressed in host plants (including, but not limited to, tomato, grape and other commercially important crops). Alternatively, the RNAi constructs can be contacted to the plant, such as by being sprayed on a surface of the plant (e.g., onto the surface of a leaf) for promoting fungal resistance. As shown in FIG. 9, host induced gene silencing (HIGS) against *B. cinerea* dcl1 dcl2 (drop inoculation) increased plant tolerance against *B. cinerea*. Additionally, as shown in FIG. 10, virus induced gene silencing (VIGS) against *B. cinerea* dcl1dcl2 (spray inoculation) increased plant tolerance against *B. cinerea*.

TABLE 1

Infection-enriched *Verticillium* small RNAs have potential host targets

| Verticillium Small RNA Sequences | Reads in Infected | Reads in control | Enriched fold | Score | Targeting sequences (SEQ ID NO:) | | Target Genes |
|---|---|---|---|---|---|---|---|
| TAAGGATCGGAGG TTCGAATCAGTT SEQ ID NO: 32 | 724.7 | 0/0 | U/A | 3 | 3'-CTAAGCTTGGAGGCTAGG-5' \|\|\|\|x\|\|\|\|\|\|\|x\|\|\|\|\| 5'-GATTGGAACCTCAGATCC-3' | (54) (37) | Cysteine/Histidine-rich C1 domain family protein |
| | | | | 3 | 3'-CTAAGCTTGGAGGCTAGG-3' \|x\|\|x\|\|\|\|\|\|\|\|:\|\|\|\|\| 5'-GCTTGGAACCTCTGATCC-3' | (55) (38) | Cysteine/Histidine-rich C1 domain family protein |
| | | | | 3.5 | 3'-CTAAGCTTGGAGGCTAGG-5' \|\|x\|\|x\|\|\|\|\|:\|\|\|\|\|: 5'-GACTCTAACCTTCGATCT-3' | (56) (39) | WRKY DNA-binding protein 2 |
| | | | | 4.5 | 3'-ACTAAGCTTGGAGGCTAGG-5' \|\|:\|\|x\|\|\|:\|\|\|:\|:\|\|\| 5'-TGGTTGGAATCTCTGGTCC-3' | (57) (40) | Disease resistance protein (TIR-NBS-LRR class) |
| | | | | 4.5 | 3'-ACTAAGCTTGGAGGCTAGG-5' \|\|:\|\|x\|\|\|:\|\|\|:\|:\|\|\| 5'-TGGTTGGAATCTCTGGTCC-3' | (58) (41) | Disease resistance protein (TIR-NBS-LRR class) |
| GCGAGGTGAGAG GACGACCAGCCA AG SEQ ID NO: 33 | 10116.0 | 5.2 | 1938 | 3 | 3'-GACCAGCAGGAGAGTGGA-5' \|\|\|\|\|\|x\|\|\|\|\|\|\|\|\|\|x 5'-CTGGTCCTCCTCTCACCA-3' | (59) (42) | mitogen-activated protein kinase kinase kinase 5 |
| CATCTGAGGACG TCCCGCCATGGC SEQ ID NO: 34 | 5785.1 | 4.6 | 1266 | 4.5 | 3'-CCGCCCTGCAGGAGAGTC-5' \|\|:\|\|x\|\|x\|\|:\|\|\|\|\|\| 5'-GGTGGAACTTCTTCTCAG-3' | (60) (43) | Leucine-rich repeat protein kinase family protein |

TABLE 1-continued

Infection-enriched *Verticillium* small RNAs have potential host targets

| Verticillium Small RNA Sequences | Reads in Infected | Reads in control | Enriched fold | Score | Targeting sequences (SEQ ID NO:) | | Target Genes |
|---|---|---|---|---|---|---|---|
| GTCCGGGAAATG ACCAGCTTGAGC AG SEQ ID NO: 35 | 2717.7 | 4.6 | 595 | 4.5 | 3'-GAGTTCGACCAGTAAAGGG-5' :\|\|\|\|x\|\|\|\|x\|\|\|\|:\| 5'-TTCAACCTGGTGATTTCTC-3' | (61) (44) | Cysteine/Histidine-rich C1 domain family protein |
| | | | | 4.5 | 3'-GAGTTCGACCAGTAAAGGG-5' :\|\|\|\|x\|\|\|\|x\|\|\|\|:\| 5'-TTCAACCTGGTGATTTCTC-3' | (62) (45) | Cysteine/Histidine-rich C1 domain family protein |
| | | | | 4.5 | 3'-GAGTTCGACCAGTAAAGGG-5' :\|\|\|\|x\|\|\|\|x\|\|\|\|:\| 5'-TTCAACCTGGTGATTTCTC-3' | (63) (46) | Cysteine/Histidine-rich C1 domain family protein |
| | | | | 4.25 | 3'-GAGTTCGACCAGTAAAGGG-5' x\|\|\|:x\|\|\|\|\|\|\|\|\|\|\|\|x 5'-GTCAGACTGGTCATTTCCA-3' | (64) (47) | AGD2-like defense response protein 1 |
| ATGTCGATGGTC GGATGTATCCTT TTCT SEQ ID NO: 36 | 3164.0 | 46.3 | 68 | 4.5 | 3'-TTTTCCTATGTAGGCTGGTAGC-5' \|\|\|\|x\|\|\|:\|\|\|\|\|\|\|\|:\|x\|\|\| 5'-AAAAAGATGCATCCGATCTTCG-3' | (65) (48) | Ankyrin repeat family protein |
| | | | | 4.5 | 3'-TTTTCCTATGTAGGCTGGTAGC-5' x\|\|\|x\|\|\|\|:\|\|:\|\|\|\|\|\|\|\|\|x 5'-TAAAAGATATATTCGACCATCC-3' | (66) (49) | Cysteine/Histidine-rich C1 domain family protein |

Example 2: Increasing Fungal Resistance or Tolerance in Fruits and Vegetables by In Vitro Silencing of Fungal Pathogen DCLs Enhanced fungal resistance was observed when fruits, leaves, and vegetables were treated with sRNAs targeting fungal pathogen DCL genes. The following protocol was used for treating fruits, leaves, or vegetables with RNAs extracted from *N. Benthamiana* expressing Bc-DCL-targeting sRNAs.

Protocol

1. Plasmid Construction.

*B. cinerea* DCL1 (BcDCL1) RNAi fragment was amplified by using *B. cinerea* cDNAs as template, forward primer BcDCL1RNAi-F: 5'-GGGGACAAGTTTGTA-CAAAAAAGCAGGCTTGCGGAAGAACTT-GAAGGTTTGCTACA-3' SEQ ID NO: 50 and reverse primer BcDCL1RNAi-R: 5'-GTCCAGATCTGGTCAACA-CACCAAG-3' SEQ ID NO: 51, 252 bp. BcDCL2 RNAi fragment was amplified by the forward primer BcDCL2RNAi-F: 5'-CTTGGTGTGTTGACCAGATCTG-GACGGATGCCATTTGCTGCACGC-3' SEQ ID NO: 52 and reverse primer BcDCL2RNAi-R: 5'-GGGGAC-CACTTTGTACAAGAAAGCTGGGTACTCTTGAG-TACTTTCGC CAGCTCAC-3' SEQ ID NO: 53, 238 bp. These two RNAi fragments were integrated together by overlapping PCR as BcDCL-RNAi, which was cloned into pDONR207 by BP reactions (Life Technologies), and finally to destination vector pHELLSGATE 8.0 by LR reactions (Life Technologies) as pHELLSGATE-BcDCL-RNAL This vector as well as a negative control pHELLSGATE 8.0 empty vector were transformed into *A. tumefaciens* GV3101 strain.

2. Generate DCL-Targeting sRNAs in *N. benthamiana*.

The *A. tumethciens* GV3101 strain carrying pHELLS-GATE-BcDCL-RNAi (RNAi strain) and pHELLSGATE 8.0 empty vector (EV strain) were cultured in liquid LB with antibiotics (100 µg/µl Spectinomycin, 50 µg/µl Gentamycin and 50 µg/µl Rifampicin) overnight at 28° C. shaker. Both EV and RNAi *A. tumefilciens* cultures were centrifuged at 4000 rpm for 15 min at room temperature, and resuspended bacterial pellets with 5 mL infiltration buffer (10 mM MgCl2, 10 mM MES, and 0.2 mM Acetosyringone). The OD600 of both EV and RNAi strain solutions were adjusted to 1.0, and kept on room temperature for 4 hours. Both solutions were diluted to OD600=0.5 by infiltration buffer right before infiltration. Then, the EV and RNAi strain solutions were used to infiltrate the 4 weeks old leaves of *N. benthamiana*, and allowed 2 days infection to over express DCL-targeting sRNAs in RNAi strain treated tissues.

3. Extract the sRNAs from *N. benthamiana*.

The infiltrated *T. benthamiana* leaf tissues were harvested separately based on the strains (EV or RNAi) that infiltrated, and freeze them immediately in liquid nitrogen. 10 g of each tissue were ground into fine powder in the liquid nitrogen with mortars and pestles, and total RNAs were extracted by using TRIzol Reagent (Lift Technologies), Resolved the RNA pellets in 5000 DEPC treated $H_2O$, and the concentration of both EV and RNAi total RNAs was examined by nanodrop. The final concentration of these two RNAs samples were both adjusted to 50 ng/µl for further use. The sRNAs targeting Bc-DCLs were only present in the RNAi set, but not in the EV set, which was used as a negative control.

4. Treat the Vegetables or Fruits with the RNA Extracts.

2 sets of vegetables or fruits under similar conditions, (e.g., similar freshness, maturity, size, shape, etc.) were gently washed and put in a plastic box with a wetted filter paper on the bottom to keep moisture. The first set was evenly treated with RNA extracts from EV strain infiltrated tissues, the other set was evenly treated with RNA extracts from RNAi strain infiltrated tissues. RNA extracts were applied by spray or by drop inoculation.

5. *B. cinerea* Infection.

*B. cinerea* infection was carried out after the spray of RNA extracts. The spores from 10 days old *B. cinerea* grown on Malt Extract Agar medium were eluted in sterile $H_2O$, and the fungal mycelia were filtered from the spores by nylon cloth. *B. cinerea* spore concentration was calculated by hemocytometer and diluted in B5 medium (10 mM Sucrose, 10 mM KH2PO4, Tween-20 0.025%). 15 µl of *Botrytis* spore solution ($2\times10^{-5}$) was sprayed on the surface of the sprayed fruits or vegetable, and allowed 2-4 days *B. cinerea* inoculation. Different vegetables or fruits took different time to obtain obvious disease symptoms.

Alternatively, a "mix" method was used for administering a 1:1 mixture of total RNAs as described above and *Botrytis* spore solution (4×10⁻⁵). 15 ul of the mixed solution was directly dropped on the surface of 2 sets of fruits or vegetables under similar conditions.

Results

Figure 11:
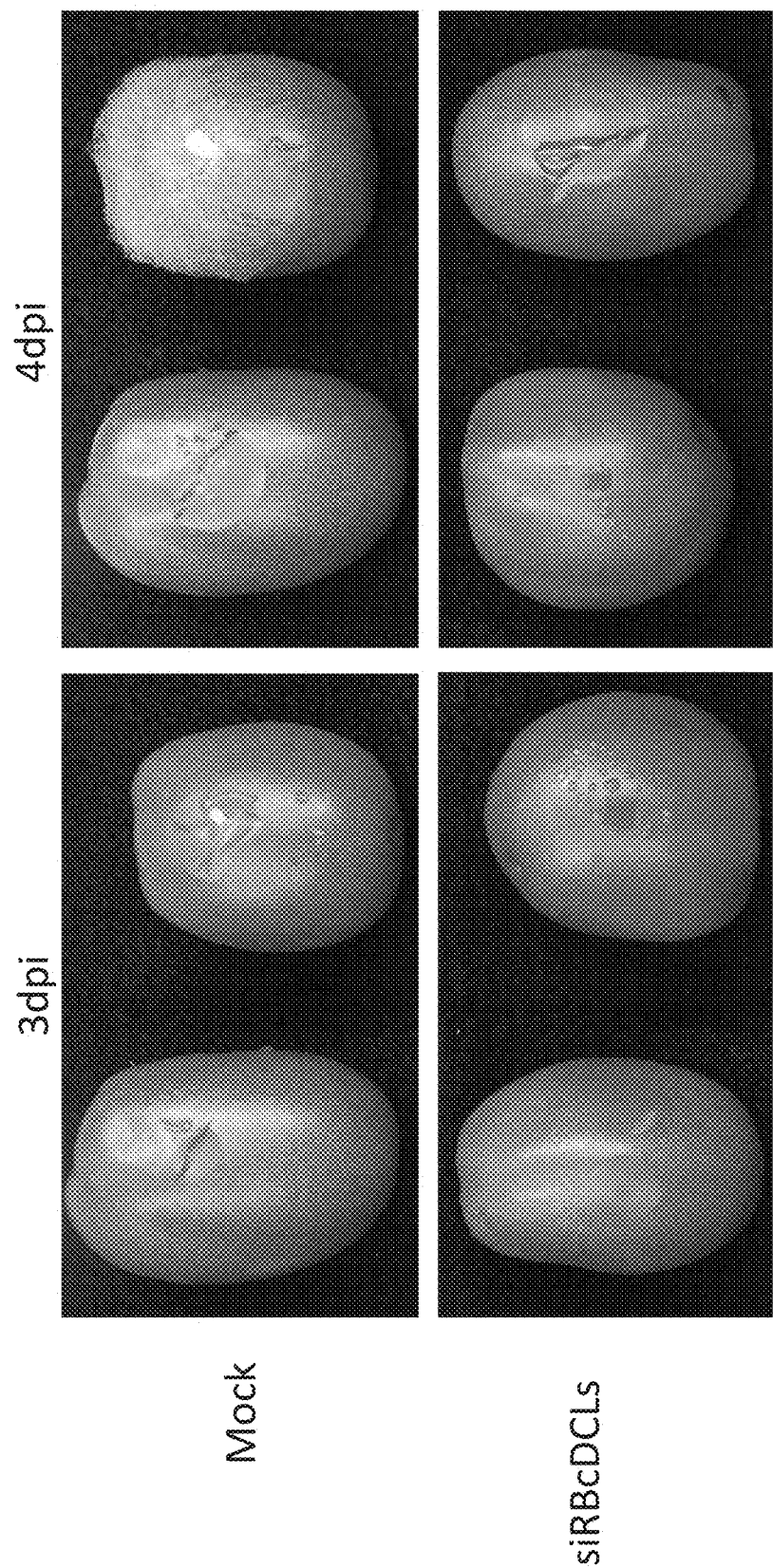
FIG. 11. Tomato was more resistant against *B. cinerea* when sprayed with RNA containing siRBcDCLs. Mock RNA: Total RNA extracted from tobacco infiltrated by mock. siRBcDCLs RNA: Small RNA extracted from tobacco infiltrated by Agrobacteria carrying siRBcDCLs producing vector (pHellsgate8-B052DCLs).
Figure 12:
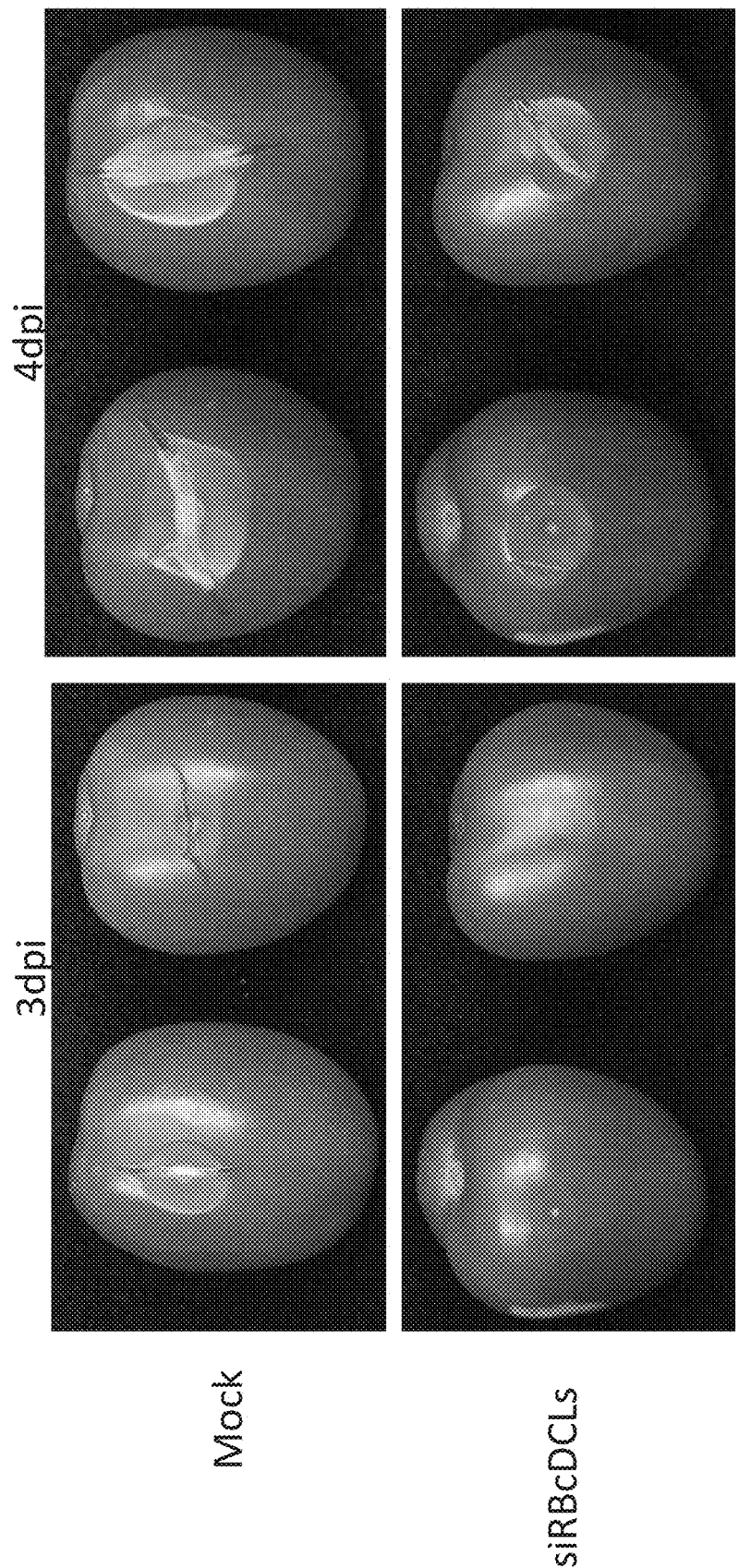
FIG. 12. *B. cinerea* was less virulent to tomatoes when mixed with *N. benthamiana* total RNA containing siRBcDCLs. Mock RNA: Total RNA extracted from tobacco infiltrated by mock. siRBcD permit correct read through by a polymerase and do not significantly alter expression of a polypeptide encoded by that nucleic acid.
Figure 13:
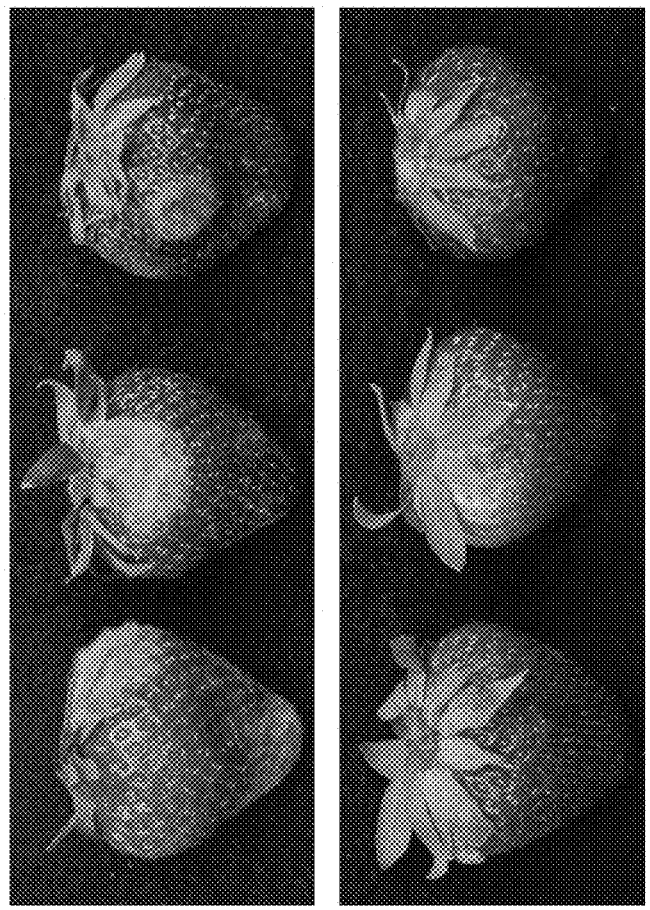
Figure 14:
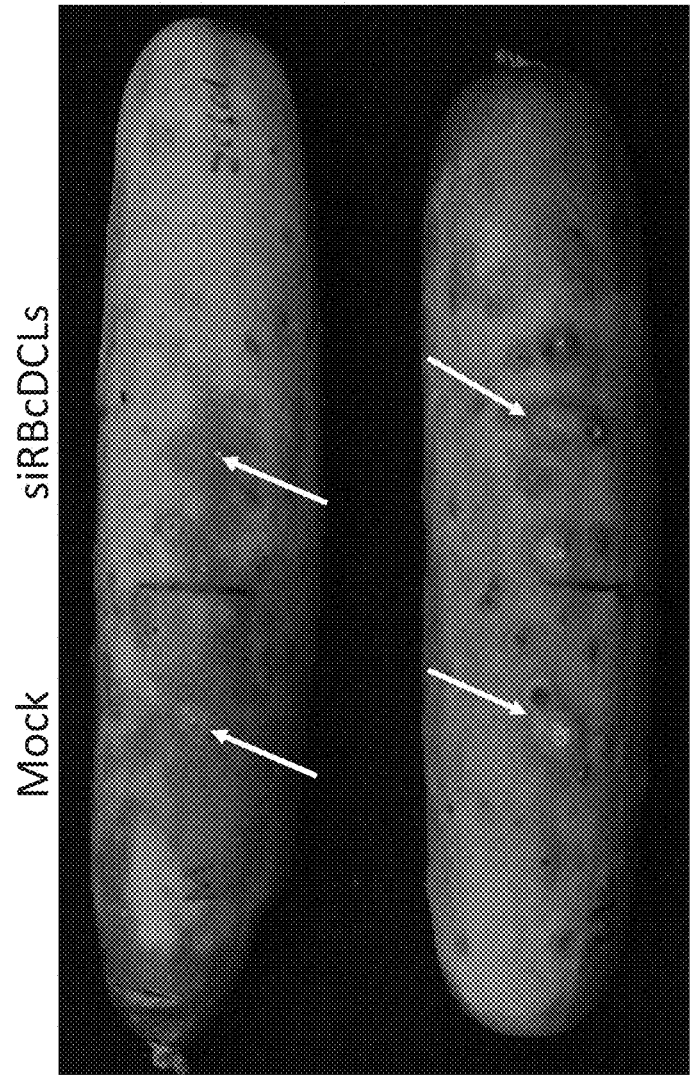

As shown in FIG. 11, tomato was more resistant against *B. cinerea* when sprayed with RNA containing siRBcDCLs. Additionally, FIGS. 12-14 show that *B. cinerea* was less virulent when mixed with *N. benthamiana* total RNA containing siRBcDCLs and applied to tomato (FIG. 12), strawberry (FIG. 13), or cucumber (FIG. 14).

In another experiment, pretreating tomato leaves and fruits, strawberry fruits, and grape fruits with the total RNA from *N. Benthamiana* infiltrated with pHELLSGATE-BcD-CLs and pHELLSGATE-EV by spray for 24 hours, followed by *B. cinerea* drop inoculation on the sprayed area of the fruits, reduced gray mold disease symptoms caused by *B. cinerea*. See, FIG. 15A-B.

Figure 16:
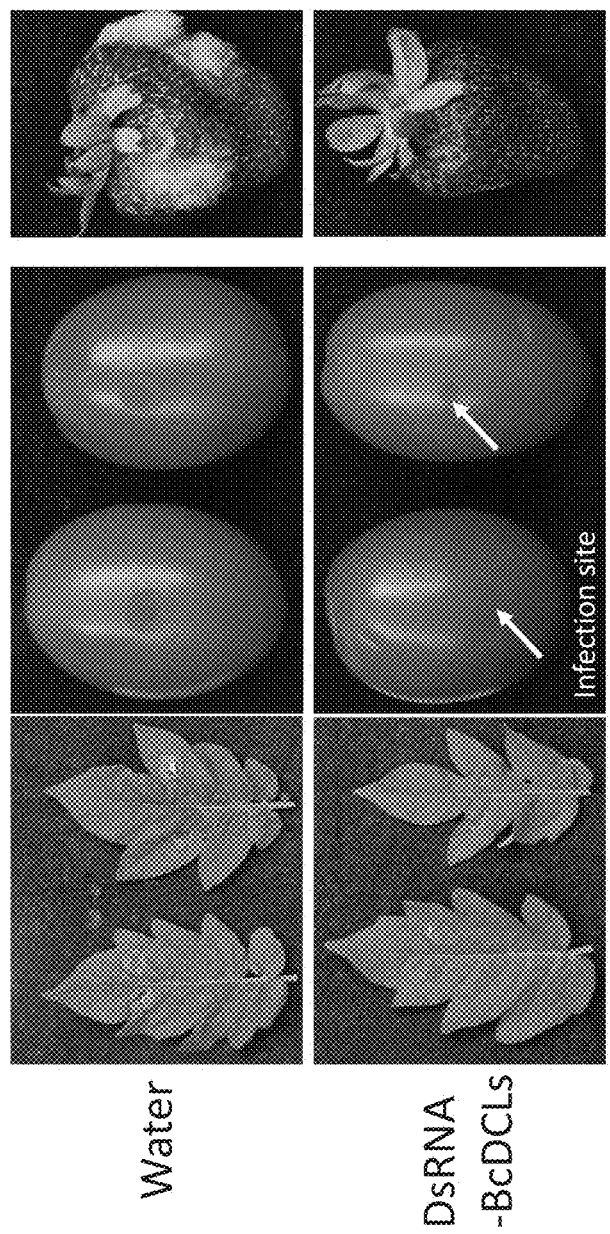

In yet another experiment, Spraying tomato leaves and fruits with in vitro transcribed dsRNA against BcDCLs reduced gray mold disease caused by *B. cinerea* on tomato and strawberry. Tomato leaves and fruits and strawberry fruits were pre-treated with water or in vitro transcribed long dsRNA against BcDCLs for 24 hours, followed by *B. cinerea* drop inoculation right on the pretreated area of the leaves or fruits. See, FIG. 16.

Example 3: Increasing Plant Tolerance to Multiple Pathogens

Figure 17:
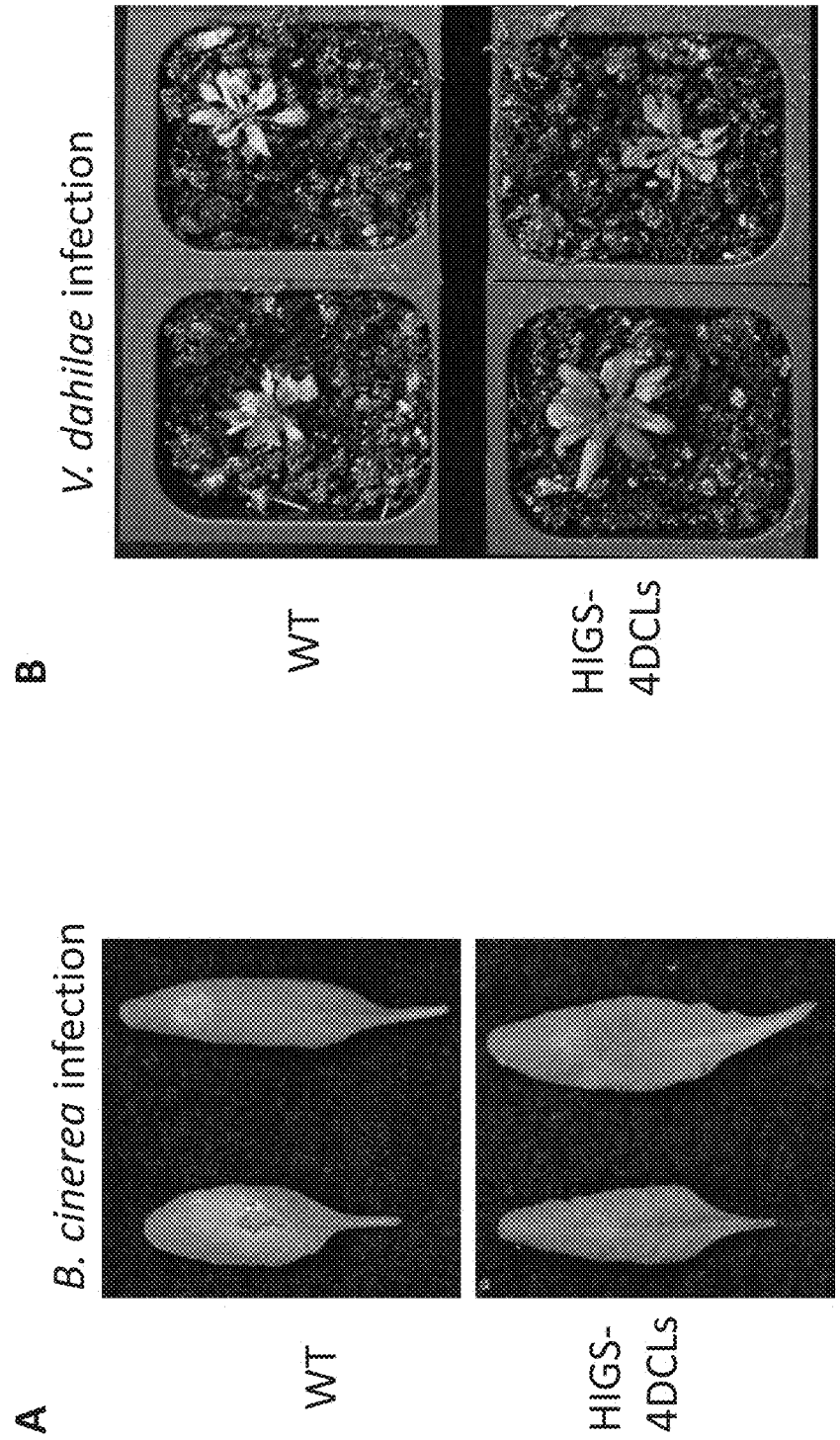

Host induced gene silencing (HIGS) was used to silence the dicer-like protein (DCL) genes of two fungal pathogens in plants. An RNAi approach for targeting two DCLs from *Botrytis* and two DCLs from *Verticillium* was used in *Arabidopsis*, resulting in the generation of "HIGS-4DCLs" lines. The HIGS-4DCLs lines, as well as wild type *Arabidopsis* plants, were infected with *B. cinerea* by drop inoculation on the leaves and were infected with *V. dahilae* by root inoculation. Three weeks after infection, the HIGS-4DCLs lines exhibited increased tolerance to both pathogens relative to the wild-type plants. See, FIG. 17. Thus, the gene targeting approaches described herein can be utilized for targeting multiple pathogens at the same time.

Example 4: Exemplary DCL Gene and Protein Sequences

```
SEQ ID NO:1 - Botrytis cinerea DCL1 genomic DNA sequence (selected RNAi fragment
marked by bolded text)

ATGACGAGAGACGCAGCAGCAGCAAAAAGTCTCTACCATTGGCGAAGAAAAGGCGTCACTC

CTTCAGCCGAAGAGGATCTTCTATCGTTTGATGATATTGTTACTGCCGTTCCACCTACAATCT

TGTCTTCGTCTGTCGCTCCATATACTTCTCGAGATAAGATACCTTCTGCATCTGGCAACGGAG

ATGCTATAGCAGATGTTAGCAGTGGTTACCTCAAACAGGCTACCGTATCTTCTCATTCTGCTC

AAGTCCGATCATCTTCAAACGGCAATCAAGGTGATGCCAAAAGTTCTCCCTCTCTTTCACCT

GATAGTAAACTGGAATTCATCTTTGGGCCTCCTTTAAGGGAGCCAGAGAAGCCATTCTTTAA

TAAATCTTCTTATTCGTTTCGAGATTCGAGAGGGTTGAGCAGAAATCGGGCTTCTTCTTCTAT

GGAAAATTCGAGAACTCTCGATCCAAAGATACTCAAACCAGTTATCATCAATAATCACCAGG

GCGAATGCTTCCAAGAGGCTTCCAGAACAGGTATACCTCAGGCTGATACTTTTGATAAATCT

TCCCTTGCTAAGACTGCGGATATGGATTTGTCACCAGTTTCTCACCATGCGGATGTGCTTGCG

ACGACGGTCACTGCACAGCATTCTGCAATAGCCGCCCAGAACGCAGCTCAAAGCTCTAAGA

TGCCAGGTCCTGAAGCTTTTTTACTTGCCGAAAAGGACGAGGCAGGTTCTCCCGTTGTTATAT

CACTGGGTTCTGCAAACCAAATTCCTTCTGGAAACATTTCTTTGCAGCTTGATTCACCATCTC

TGGAAAACCATTCTCCAAATGTGACCCCAATCAACAAAGTCCCTACACCATTCGCACTTTCT

ACAAGGACAACCGATGACGTTTTCGCAGAACTTAGGCGGCCTTTGCATCCCCAAGCTATTCA

GAGCCAGATTGATATCAAGACTTCCTCTTGTGTTGATAGTTATAACACGAATGATGAGATTC

TAGACAACAATCAAGGTTCCAATCAAAAAGATCTGCATGTTGTTGAAAAGGATAAGGAAGA

GGAAGAGGAAGAGGATATGAACCAAGCCATACCCGATATCAAACGTATCTCAGCACGAAAA

CAAAAGAACGCTGCCATATTTGACGTTTTTCTTAAGGAAGCTACCAAACTACCAAAGACAGA

AAAGACTTCACATGCGAATGATGAAGCAATTCAGTCTACTAGGTGGTTGATTGACCAAGCAG

AAAAACAGCATATTATAGAAAGTCCCAGGGACTATCAACTTGAATTGTTTGAGAAGGCAAA

GAAACAGAACATTATAGCTGTACTTGATACAGGATCTGGCAAGACATTCATTGCAGTTCTCT

TACTTCGGTGGATCATAGACCAAGAGCTTGAAGATAGAGCTATTGGCAAGCCTCATCGTGTT

TCATTCTTCCTGTGGAAGAAACGACTGGATACGAATATGGTCATTGTCTGCACTGCAGAAAT
```

TTTGCGCCAATGCCTGCACCATTCGTTTGTTACAATGGCTCAAATAAATCTGCTAATTTTCGA

TGAAGCCCACCATGCAAAGAAGGATCATCCTTATGCTAGGATTATTAAAGATTTTTATCGCA

ATGACACGGAAAAGGATATCGCTCTGCCTAAAATATTTGGGATGACAGCATCACCGGTAGA

TGCTAGAGATAATGTCAAGAAAGCTGCGGAAGAACTTGAAGGTTTGCTACACAGTCAAA

TATGTACTGCAGAAGATCCCAGCTTGCTGCAGTACTCAATCAAAGGTAAACCTGAGACT

CTTGCCTACTATGATCCCTTGGGCCCGAAATTCAATACTCCTCTTTATCTTCAAATGCT

CCCGCTTCTAAAAGACAATCCTATCTTTCGGAAGCCATTTGTATTTGGGACAGAAGCCA

GTAGAACTCTAGGATCTTGGTGTGTTGACCAGATCTGGACTTTCTGTCTTCAAGAAGAA

GAGTCTAAGAAACTACAAGCAAGGACGGAGCAGGCGCATCATAAGAAGAGAGTCCCGGAG

CCACTTGAAGTGCTAGAGAAACGCAAGGAACAACTTGAACAAGCCAAATCCATTGTCGAAA

ATCACACTTTCGAGCCACCACACTTTGCATCAAGATTATTGGATGATTTCACAACAAAGTT

CACTATTCGAATAATTTATCTACTAAAGTCGTTGCTCTCTTGAGTATTCTCAAAGATCGTTTC

CAACGACCCACCAATGACAAGTGTATTGTATTTGTCAAAGAAAGATACACCGCACGCCTTCT

AGCCTCACTTCTCTCCACACC

TGAAGCTGGGACACCATTCTTGAAGGCTGCACCGCTGGTTGGTACTACGTCTGCTTCAGCCG

GGGAAATGCATATCACATTTAGATCACAAACTCTTACTATGCACAACTTTCGCAATGGTAAA

ATCAACTGCCTTATCGCAACATCAGTTGCTGAAGAAGGTCTTGACATTCCTGACTGTAACCT

CGTTGTCAGATTCGATTTGTACAATACAGTCATTCAGTACATTCAATCTAGAGGTCGTGCTAG

GCATATCAATTCAAGGTACTACCATATGGTAGAGAGCCACAACGAGGAACAGATTCGTACA

ATCAAAGAGGTTTTGAAGCATGAGAAAATGCTAAAGCTTTTTGCTTCTGCTCTTCCAGAAGA

TCGAAAATTGACCGGAAACAACTTCAATATGGATTACTTCCTCAGAAAAGAACGAGGCCAC

AGAATTTACCCTGTCCCGAATAGTGACGCAAAACTTACTTACAGAATGAGCTTAACGGTCCT

ATCTGCCTTCGTTGACTCACTTCCTCGAGCCCCAGAGTCGGTTCTTCGAGTGGATTATGTCGT

CACAACTGTCGATAAGCAGTTTATCTGTGAGGCCATTTTGCCAGAAGAAGCACCCATACGCG

GAGCAATTGGTCGGCCAGCAACAACTAAACAAGTGGCCAAATGCTCAGCAGCCTTTGAAAC

TTGTGTGATTCTGCACCAGAAAGGATACATCAACGACTACCTACTTTCTACATTTAAAAGAT

CAGCACACATGATGAGAAATGCACTTTTGGCTGTGGATGGAAAGAAGCAAGAAGCTTATGA

TATGCAGACTAAACCAACTTTATGGTCTTCGAAAGGGAAACAAGGCATATTTTATATGACTG

TCTTGTCTCTCAAATCTCCAGATAATCTTGACAGAGCATCTCAGCCATTGGGCTTACTGACAA

GATCACCCTTGCCTGATTTGCCAGAATTTGTTCTTCATTTCGGAGCAGGGCGAAACTCTCCAA

CCTCGTGCGTACCTCTCGCTTCCTCAATTACGCTCGAAAAAAACAAGCTTGACCAAGTTAAT

ATGTTCACCCTATGTTTATTCCAAGATGTGTTCAGTAAAGCATACAAATCAGATCCGGATAG

TATGCCATACTTTCTGGTTCCTATCAACTGCCTGAATGCTATTGTCGACTGGAAATCACAAAA

CCCAATGTCAATAATCGATTGGGAGACAGTTGAATATGTCCAAGACTTCGAGAATAAGCAA

GCTGATAAGCCATGGGAGCACAAGCCATGGTTAGGAAAGCCTGACGATTATTTCAAAGACA

AATTCATAACTGATCCCTTTGACGGGTCTCGAAAATTGTGGTCCGTTGGAATCACAAAAGAA

TACAGACCATTGGATCCAGTCCCACCAAACACGGCGCCCAGGAAGGGAGCTAGAAAGAACA

ATAGTAATATCATGGAGTATAGTTGTAGTCTCTGGGCAAAGGCTAGAGCAAAACGAACTTTT

GATGAAGAACAGCCTGTTATTGAAGCAACCTACATTTCACTTCGGAGAAATTTGCTTGATGA

-continued

ATTTGATGGAGGTGAGCTCGAGACTTCAAAGAAGAGTTTTATTATTTTAGAACCATTGAAGG
TATCACCTCTTCCAACTACCGTGGGTGCAATGGCCTATCTTTTACCTGCAATTATTCATCGAG
TTGAGTCATATCTCATTGCTCTTGAAGCAACAGACTTGTTACATCTTGATATCCGTCCTGATC
TTGCGCTAGAGGCTGTTACCAAGGATTCCGACAATTCTGGAGAGCATGGTGAGGAACAGAC
AAACTTTCAACGTGGAATGGGCAATAATTATGAACGATTGGAATTTCTTGGGGACTGCTTCT
TGAAGATGGGAACGTCAATATCTCTATACGGTCTAAATCCTGATAGTGATGAATTCCGCTAC
CATGTTGATCGTATGTGTCTGATTTGCAACAAAAATCTGTTCAATACGGCTTTGAAATTAGA
GCTTTACAAATACATTCGGTCGGCAGCCTTCAACCGACGAGCTTGGTATCCCGAAGGCCCCG
AATTATTAAGAGGAAAGACAGCCACGGCACCAAATACCCACAAGCTCGGCGATAAGTCAGT
TGCAGATGTTTGTGAAGCAATGATTGGAGCTGCTTTACTAAGCCACCACGAAAGCAAGTCCA
TGGATAATGCGGTTCGCGCCGTTACTGAAGTTGTCAATAGTGACAACCACAATGCTGTTGTA
TGGTCTGATTATTACAAATTGTATGAGAAACCAAAATGGCAAACTGCTACAGCTACAGCTGC
ACAAATAG
ATATGGCAAGACAAGTTGAAATGAAACATCCATATCATTTCAAACACCCACGCCTGTTAAGA
TCAGCTTTCATCCATCCGGCATACTTGTTCATCTATGAACAAATTCCTTGTTATCAACGTCTC
GAATTTTTGGGTGATTCGCTACTCGATATGGCATGTGTCAACTTCCTTTTTCACAACCACCCA
ACAAAAGATCCTCAGTGGCTCACTGAGCACAAGATGGCTATAGTATCCAATCAGTTTCTTGG
AGCTCTTTGTGTCAAATTAGGCTTCCACAAACATCTACTGACACTCGATTCTCAAGTTCAAAA
AATGATTGCAGATTACTCCTCAGATATCAATGAAGCTCTCATTCAAGCCAAAACGGACGCAA
AGAGAGTCGGCAAAGTAGAAGATGATTACGCTCGTGATTATTGGATTGCCGTCCGTCAACCT
CCTAAATGTCTTCCCGATATTGTAGAAGCATTCATTGGTGCCATTTTTGTCGACTCTGAGTAT
GACTACGGTGAAGTTGAGAAGTTCTTTGAAATGCATATCAGATGGTACTTTGAGGATATGGG
CATCTACGATACCTATGCTAACAAGCACCCAACCACTTTCCTTACTAATTTCTTGCAAAAGA
ACATGGGATGTGAGGACTGGGCACCAGTTAGTAAGGAAGTACCTGGAGAGGATGGTAGAAA
GAATGTTGTAGTTTGCGGGGTCATCATACACAATAAGGTGGTATCAACTGCCACTGCCGAAA
GTATGAGATATGCTAGGGTCGGAGCAGCGAGGAATGCCTTGAGAAAATTGGAGGGAATGAG
TGTCCGAGAATTCAGGGATGAATACGGGTGCTCATGTGAAGGTGATGTTGTTGATGAAGAG
GGCAATATTGAATTTGTTGAACGTGAAGACGGGATGGAGGGGATCGGTATGGGATATTGA

SEQ ID NO:2 - *Botrytis cinerea* DCL1 protein sequence

MTRDAAAAKSLYHWRRKGVTPSAEEDLLSFDDIVTAVPPTILSSSVAPYTSRDKIPSASGNGDA

IADVSSGYLKQATVSSHSAQVRSSSNGNQGDAKSSPSLSPDSKLEFIFGPPLREPEKPFFNKSS

YSFRDSRGLSRNRASSSMENSRTLDPKILKPVIINNHQGECFQEASRTGIPQADTFDKSSLAKT

ADMDLSPVSHHADVLATTVTAQHSAIAAQNAAQSSKMPGPEAFLLAEKDEAGSPVVISLGSANQ

IPSGNISLQLDSPSLENHSPNVTPINKVPTPFALSTRTTDDVFAELRRPLHPQAIQSQIDIKTS

SCVDSYNTNDEILDNNQGSNQKDLHVVEKDKEEEEEEDMNQAIPDIKRISARKQKNAAIFDVFL

KEATKLPKTEKTSHANDEAIQSTRWLIDQAEKQHIIESPRDYQLELFEKAKKQNIIAVLDTGSG

KTFIAVLLLRWIIDQELEDRAIGKPHRVSFFLWKKRLDTNMVIVCTAEILRQCLHHSFVTMAQI

NLLIFDEAHHAKKDHPYARIIKDFYRNDTEKDIALPKIFGMTASPVDARDNVKKAAEELEGLLH

SQICTAEDPSLLQYSIKGKPETLAYYDPLGPKFNTPLYLQMLPLLKDNPIFRKPFVFGTEASRT

LGSWCVDQIWTFCLQEEESKKLQARTEQAHHKKRVPEPLEVLEKRKEQLEQAKSIVENHTFEPP

HFASRLLDDFTTKVHYSNNLSTKVVALLSILKDRFQRPTNDKCIVFVKERYTARLLASLLSTPE

AGTPFLKAAPLVGTTSASAGEMHITFRSQTLTMHNFRNGKINCLIATSVAEEGLDIPDCNLVVR

FDLYNTVIQYIQSRGRARHINSRYYHMVESHNEEQIRTIKEVLKHEKMLKLFASALPEDRKLTG

NNFNMDYFLRKERGHRIYPVPNSDAKLTYRMSLTVLSAFVDSLPRAPESVLRVDYVVTTVDKQF

ICEAILPEEAPIRGAIGRPATTKQVAKCSAAFETCVILHQKGYINDYLLSTFKRSAHMMRNALL

AVDGKKQEAYDMQTKPTLWSSKGKQGIFYMTVLSLKSPDNLDRASQPLGLLTRSPLPDLPEFVL

HFGAGRNSPTSCVPLASSITLEKNKLDQVNMFTLCLFQDVFSKAYKSDPDSMPYFLVPINCLNA

IVDWKSQNPMSIIDWETVEYVQDFENKQADKPWEHKPWLGKPDDYFKDKFITDPFDGSRKLWSV

GITKEYRPLDPVPPNTAPRKGARKNNSNIMEYSCSLWAKARAKRTFDEEQPVIEATYISLRRNL

LDEFDGGELETSKKSFIILEPLKVSPLPTTVGAMAYLLPAIIHRVESYLIALEATDLLHLDIRP

DLALEAVTKDSDNSGEHGEEQTNFQRGMGNNYERLEFLGDCFLKMGTSISLYGLNPDSDEFRYH

VDRMCLICNKNLFNTALKLELYKYIRSAAFNRRAWYPEGPELLRGKTATAPNTHKLGDKSVADV

CEAMIGAALLSHHESKSMDNAVRAVTEVVNSDNHNAVVWSDYYKLYEKPKWQTATATAAQIDMA

RQVEMKHPYHFKHPRLLRSAFIHPAYLFIYEQIPCYQRLEFLGDSLLDMACVNFLFHNHPTKDP

QWLTEHKMAIVSNQFLGALCVKLGFHKHLLTLDSQVQKMIADYSSDINEALIQAKTDAKRVGKV

EDDYARDYWIAVRQPPKCLPDIVEAFIGAIFVDSEYDYGEVEKFFEMHIRWYFEDMGIYDTYAN

KHPTTFLTNFLQKNMGCEDWAPVSKEVPGEDGRKNVVVCGVIIHNKVVSTATAESMRYARVGAA

RNALRKLEGMSVREFRDEYGCSCEGDVVDEEGNIEFVEREDGMEGIGMGY*

SEQ ID NO:3 - *Botrytis cinerea* DCL2 genomic DNA sequence (selected RNAi fragment marked by bolded text)

ATGGAATACACTTCGGAACCTGACACTGACCCGGATACACGCGGTAGCCTTATCGATGGTCG

AGATGGGATTGAAGGGGATCTTATTGCTTTGACGTCTGGGGAACGACTTAATGAGACTGTAG

AGGATTTATGTAGTGACTCATCAGGATTGATTGTTGAGAATGAAGATGATGATAACAGCGCA

GGGGAGAAGGGAGAGATTGTGATAGTAACACCAAGAACATACCAACTGGAAATGTTGGAA

GAGAGTTTGAAAAGGAATGTCATCGTTGCGATGGATACAGGAAGTGGCAAGACACATGTGG

CCGTTCTCCGAATACTAGCGGAACTTGAGCGGATGAAGCCTGGCAAGATAATATGGTTTCTT

GCGCCTACCGTTGCGCTCTGTGCTCAGCATCACGAATATCTCCAGCTGAATATTCCCTCTGTT

TTGATCAAAATGCTTATTGGTGCTGATGGTGTGGATCGATGGACAGAGCAGAGACAGTGGG

ATACGGTCTTGAAGGATGTCAAGGTAGTCGTATCTTCCTATCAAGTTCTTCTAGATGCCCTTA

CACACGGATTCGTACGCATGGGGCGTCTGTCCTTGATCATTTTTGATGAAGCACATAATTGT

GTAAATAAAGCGCCAGGGGCTAAAATTATGAAATCTTTCTATCATCCGTATAAATCGATATT

CCCACTTCCCCACATTCTGGGCCTCTCGGCCAGCCCTGTCATGAGATCCAGTCCACAATCTT

TAAGTGATATCGAGGAGACTTTGGATGCCATTTGCTGCACGCCAAAAATACATCGAGC

AGATCTTCGCCTTCGAGTAAAGCTACCACTTCTATCTATTATCTACTATACCCCAGAGT

CAAATATCATCGTGACGAAAACTGTGGCGAGCCTGAGAAAGATTGTGCAAAGTCTCAA

CATTTTCGAAGACCCCTACGTTTTGACACTAAAAAGGAGTGATAGCGAAAAAAGTCAAC

GTGAGCTGGCGAAAGTACTCAAGAGTTTTAAGACATATAGTCAAACCCAATTAAAGTCA

ATCGACAAAACTAGCAACGAGATTATTCTTGTAGAGCTAGGCCCATGGGCTGCAGATTACTA

TATCTCAACAGTGGTGACGAGATACTTGAAGGCAATGTCGGCAAAGGACACTTTCATTGTTG

AAGATTCACCAGCTGCCGAGAAGCTATATATTGCCAAGGCTCTCAGACAAGTCGAAATCTCT

```
CCTTCAACTCTCTCAGATACAGGCAAAATTTCTAACAAGGTTGAAAAGCTACTGGGGATAAT
TGCGCAACAGAAGCCTCCCTTTTCCGCTATTATATTTGTCCAAGAAAGAGCCACGGTGTCTG
TGCTAGCCCATCTATTATCGCATCATCCATTGACAAAGGATCGTTTTAAGATTGGAACCATG
GTTGGCACATCCTTAAATGGCAAGCGTACAGACCAAATAGGAGAGCTTGTCGATGTTAATCA
ACAAAAAGACACTTTGTCAAGTTTCAAGCGTGGAAAAATTGATATCCTTATAGCTACAAATG
TATTGGAAGAGGGAATTGATGTTCCTGCCTGTAATCTAGTGATCTGCTTTAGTAAACCAGCA
AACCTCAAATCTTTCGTACAAAGACGAGGGCGAGCAAGACAGCAAGATTCTAAGCTGATTC
TTCTTGATGCTTCAGGTGATAAAGCGACAAATTGGCATGAGCTTGAAAGAAAAATGCGAGA
GGAGTACGGAAAGGAAATGCGAGAATTGCAACACATCTACGAAATTGAGACAGCTGATGAA
CAGTCGGAAGATGATAGGGTCTTGCAATAGAAAGCACTGGGGCTCAATTAGACCTTGACA
GTGCTTTACCACATCTCTATCATTTCTGTTCAGTCTTAACAACAAAAGATTTTGTTGACCTCA
GGCCAGACTTCGTCTACTCCTCCGAACTGGGATCGGAATATGTTCGAGCAAAGGTCATCCTG
CCTGGATCGGTTTCTAAACCCCTGCGAGTCCATGAAAGCCGCGGATCGTGGTTGAGCGAGAG
GTCGGCTGCAAAAGATGCAGCGTTTGAGGCGTATTCCGCATTATACAGGGGGGCTTAGTGA
ATGATAACCTACTGCCCCTGATGGTGCACGACAAAGTCATCGATGAGTTGACTTCAAAGCCC
GTGGATACTCGCGCGTCTCTTCTGGAGGTGAAGGAAAGATTAAATCCATGGATTGACATTGC
TAGAGCATGGAAAGAGGCAGAACACCATGCTGGAATTGTTCGCACATCGGTAATGATCTTC
AATGGGATGAAGCTGGAACTCTGTCTTCC
AATTGATCCACCGGCAATACCCCCATTAAAGCTTTATTGGGATGCTGACACCGAGTTCTTTGT
TGACTTTACAAACGATATCGAGATCGGCACCAGCGAGAATATGTTGGCACAGGCGTTGAAC
GATACCAATCTACTATTATCAGATCGTGGTCGTAAAGTTCACATCCAGTCACGTCGAACAGT
TGTGCAATTTATCTTGCTTCAAGATTCGGGCTCGCTCAGTTCAGATTGTTTTCCGGTTGACCC
CAACGGTAATATTAAAAGTACAGGTTTTATCAGAGAAGTCGGTAAACTAGAATCGCCCTACA
TCTTTGAAAAATGGTTGCCCAATGCACCAGAAGACGTCCCATATCTAGCTGTGGTTAAAGTA
AGTCGCCGTGCAGACTTTTTGCACAAGGTACAGAACGAAAAACCCTCGTCATTCACTAAACA
ATTCTCGTCTGTTCTACCTGCCTCGACATGTGTACAGGATGTAATGCCCGCACAGTTGTCTCG
GTTCGGCATGATGATTCCTTCCATCACACACCACATTGAGGTGCAACTCGTTGTAGACCGAC
TATCCAGGACCATCCTCAAGGATCTCGAAATTAGTGACCAGAGTCTTATTCAGACCGCCATC
ACACATGCCAGTTATTCGTTAGACTCGAATTATCAGCGTCTCGAATTTCTGGGCGACTCAATT
CTCAAATTGTGTACATCGGTACAATTGGTGGCAGAGCATCTAGATTGGCACGAAGGATATTT
GTCGGCTATGAAGGATCGTATCGTGTCCAATTCACGGTCATCAAGAGCGGCGGCTGAAGTCG
GTTTGGATGAGTATATAATGACCAAGAAATTCACAGGTGCAAAATGGCGACCAATGTACGT
GGATGATCTGGTCGTCACAGAACAAAAAACAAGAGAAATGTCCTCCAAAATTCTTTCCGAC
GTTGTGGAAGCACTCATCGGCGCATCTCTCCGGCCCGTCGAGCAAATCCTCGCATATACCTT
CACCAAAAAATCTCTCCTCGTCGAAGCCATGACGCACCCCTCTTACACCAGCGGCACGCAAT
CCCTCGAGCGACTCGAGTTCCTCGGCGATTCCATTCTCGACAACATCATCGTCACAGCCATG
TGGTCGCACTCGACGCCGCTCTCCCACTTCCACATGCATCTCCTGCGCTCTGCGCTCGTCAAC
GCCGATTTCCTCGCCTTTTCTCTGCATGGAAATGAGCATCGACCAAAACGTCACCAATCTGAC
CGAAGGAAAAAACCATCGCATCCACGAAACCCACTCGCGACGCCGCGTTTCCCTCGTCAGTT
```

-continued

```
TTCTCCGTCACTCAAGCGTTCGTCTCTCTATCTATCAAAAAGAAGCGCTTTCTCGCCATGCAG

AATTGCGCGATCAGATCCTCGAGGCAATATACACCGGTGATACATTCCCCTGGGCTCTATTA

TCCCGATTGGACGCGCGGAAATTTTTCTCCGATATGATTGAGAGTTTGCTGGGCGCGGTATG

GATTGATAGCGGCTCGATGGAAGTGTGCACGCAGCTGATCGAAAGAATGGGCGTCCTGAGA

TACATGCGACGGATTTTGAAAGATGGCGTGCGCATCATGCATCCGAAGGAGGAACTGGGCA

TCGTGGCCGATTCTGAAAACGTCAGGTACGTTTTGCGGCGGGAGAAGATGGGTGGGGATGC

TACCGAGGTAAATGCGGACGCGGATGAAGAGGTACGCACGGAGTACCGGTGCACAGTATTT

GTGGGCGGGGAGGAAATTGTAGAGGTGAGGGGTGGAGCGAGGAAAGAGGAGATTCAGGCA

AGGGCTGCGGAGCAGGCGGTGCGGATTTTGAAGGCGAGGGGTCATGAGAAGAGGAATGGG

GGTGCGGGGGAGGGGAAAAAGAGAAAATCGCTGGATGAATAG
```

SEQ ID NO:4 - *Botrytis cinerea* DCL2 protein sequence

```
MEYTSEPDTDPDTRGSLIDGRDGIEGDLIALTSGERLNETVEDLCSDSSGLIVENEDDDNSAGE

KGEIVIVTPRTYQLEMLEESLKRNVIVAMDTGSGKTHVAVLRILAELERMKPGKIIWFLAPTVA

LCAQHHEYLQLNIPSVLIKMLIGADGVDRWTEQRQWDTVLKDVKVVVSSYQVLLDALTHGFVRM

GRLSLIIFDEAHNCVNKAPGAKIMKSFYHPYKSIFPLPHILGLSASPVMRSSPQSLSDIEETLD

AICCTPKIHRADLRLRVKLPLLSIIYYTPESNIIVTKTVASLRKIVQSLNIFEDPYVLTLKRSD

SEKSQRELAKVLKSFKTYSQTQLKSIDKTSNEIILVELGPWAADYYISTVVTRYLKAMSAKDTF

IVEDSPAAEKLYIAKALRQVEISPSTLSDTGKISNKVEKLLGIIAQQKPPFSAIIFVQERATVS

VLAHLLSHHPLTKDRFKIGTMVGTSLNGKRTDQIGELVDVNQQKDTLSSFKRGKIDILIATNVL

EEGIDVPACNLVICFSKPANLKSFVQRRGRARQQDSKLILLDASGDKATNWHELERKMREEYGK

EMRELQHIYEIETADEQSEDDRVLRIESTGAQLDLDSALPHLYHFCSVLTTKDFVDLRPDFVYS

SELGSEYVRAKVILPGSVSKPLRVHESRGSWLSERSAAKDAAFEAYSALYRGGLVNDNLLPLMV

HDKVIDELTSKPVDTRASLLEVKERLNPWIDIARAWKEAEHHAGIVRTSVMIFNGMKLELCLPI

DPPAIPPLKLYWDADTEFFVDFTNDIEIGTSENMLAQALNDTNLLLSDRGRKVHIQSRRTVVQF

ILLQDSGSLSSDCFPVDPNGNIKSTGFIREVGKLESPYIFEKWLPNAPEDVPYLAVVKVSRRAD

FLHKVQNEKPSSFTKQFSSVLPASTCVQDVMPAQLSRFGMMIPSITHHIEVQLVVDRLSRTILK

DLEISDQSLIQTAITHASYSLDSNYQRLEFLGDSILKLCTSVQLVAEHLDWHEGYLSAMKDRIV

SNSRSSRAAAEVGLDEYIMTKKFTGAKWRPMYVDDLVVTEQKTREMSSKILSDVVEALIGASLR

PVEQILAYTFTKKSLLVEAMTHPSYTSGTQSLERLEFLGDSILDNIIVTAMWSHSTPLSHFHMH

LLRSALVNADFLAFLCMEMSIDQNVTNLTEGKNHRIHETHSRRRVSLVSFLRHSSVRLSIYQKE

ALSRHAELRDQILEAIYTGDTFPWALLSRLDARKFFSDMIESLLGAVWIDSGSMEVCTQLIERM

GVLRYMRRILKDGVRIMHPKEELGIVADSENVRYVLRREKMGGDATEVNADADEEVRTEYRCTV

FVGGEEIVEVRGGARKEEIQARAAEQAVRILKARGHEKRNGGAGEGKKRKSLDE*
```

SEQ ID NO:5 - *Verticillium dahilae* DCL (VAD_00471.1) genomic DNA sequence (selected RNAi fragment marked by bolded text)

```
ATGACGACTGACGAGCTCTCTGTTGGTCTGGACGCCACCGGCATCTCAATCCTCGCAGATGG

ACCGGAAAACATATCGTCCAGCACATCAACATCTACGACTGGAAAGGAAGATGGATACCTC

TGTATCAACAGATTCACTCAGAATACCGCCACGACCCAGGACAACCAGAGCCGAGATTCTG

ACGACGATGAGGATGACTGCGGCAGCCACGATGAAGCTGACGAAGATTCAGACGAAAGAC

AGTACAGCATGACCCCAGAAAGGCCTCATAAAATTACCGAGAAGAAGCGCGCAGATCATGC
```

```
TGCCTTTCACGACTGGCTTCAGAGCAACTCCAGCGAGATTGCTCAGTCAACCCCTCAGCCGG

CTCAAAACCTCAACCACACCTCCACGGCCCTGATGGTACGCGAGAGTGAGAATCGTAAGAT

CATCGAAAATCCTCGGGAGTATCAGATTGAGCTCTTCGAGCGGGCGAAGCGAAAGAACATC

ATTGCCGTGTTACCCACTGGATCAGGAAAGACCTTAATCGCAGCCCTTCTTCTGCGACACAC

CCTCGAACAAGAAACCGCGGATCGACGCGCGGGCAAGCCCAAGAGAATCGCCTTTTTCCT

CGTGGAAAAGGTTGCTCTTGCCCTCCAACAGCACGCGGTTCTGGAGTGCAATCTGGAA

TTTCCCATTGACCGGGTATGCGGTGACATGGTACGGTCGGACTGGATCAAGGAGTCAT

GGATGAAAAGATGGGATGACAACATGGTCATGGTCTGCACCGCCGCCATCCTTCAGCA

ATGCCTTGCCAGATCATTCATCCGCATGGATCAGATCAACCTGCTTGTCTTCGATGAAG

CACATCACGCCAAGGGAAATCATCCGTACGCCCGGATCATCAAGGACTACTACATTACGG

AACCTGACAAAGAAAGGCGCCCCAAGATCTTCGGCATGACTGCCTCTCCGGTGGATGCCCTC

ACCGACGTCAAGATTGCTGCCGCTCAACTCGAAGGTTTGTTGCATAGTGAGATTGCGACAAT

CGAGGAGGACTCTGTATCATTCAAACAAATCCAGAAAGAGGTCGTCGAACAAGACTGCAAG

TACCCTGCCCTCGAACCACCCTTCACCACCAATCTTCATAAGAAGATCCAAGAACAGGTGCG

CTACAACAAGAACTTCGCAAAGGCGCTGAGCAATTCTTTAGAAATGTCGAGCTCCCTTGGCA

GCTGGTGTGTCGATCGCTTCTGGCAGATATTTCTGACCGAAGAAACCCTCGCGAGATTGGCA

GCGCAAACTGCACAAGACAACATTTTTGCCGATCGCGCCGAAAAGGAGCGCGTTGCCATTG

AGGAGGTCCGCAACATCATCAAGCAACATCAGTTCCTCCCAATCACCAAAACCCTGCAAGA

CTTGTCGTCCAAAGTGCTGTGCCTCCTCGGCCAACTGGAATTGCGCTTCAGTGCCCCTACCGA

TCACAAGTGCATCATCTTCGTGGAGAAACGAAACACAGCCATGATTCTGGCTCACCTCCTCT

CCTTGCCTGGTATTGGACCTCTATATCTGAAACCGGCTGCGCTTGTCGGGAACCCATCTGAC

AACAGCCCTCTTGCCATGTCGTACAAAGAGCAAGTGATGACAATAACAAAGTTCAGACGTG

GTGAATACAACTGTCTTCTCGCCACTTCTGTGGCCGAGGAGGGCATTGACATCGCAGACTGC

AACATTGTCATTCGATTCGATCTTTTCAACTCGGTGATTCAGTACATACAATCCAAAGGCCGC

GCTCGGCACTTGAACTCGGAGTATATTTGCATGGCCGAGCTAGGCAACGGCAAGCATACAA

GGGCGAAGATACAAGCAAATTATGACCTCTCCCTCATCCGCCAATTCTGCAGCACACTGCCA

GAAGACCGCAAGATCGTGGGCTGGGACCCCGAGGCAGCTCTTCACCATGGCGAGCGCGACC

ATAAGTTCCACATCGTTCCATCCACCGGGGCCAAACTCACCTGGAC

CGGCAGCCTCGTGGTTCTGTCAAATTTTGCCTCTTCTCTACAGGTGAACGACGAAACACTAA

GTCCTTCCTATATGGTCTCTCTCATCGGTAGCGAGTACATCTGCGAGGTCCAGCTTCCGAGCA

AGTCTCCCATTTTGAGCGTGTCAGGCACGCTCCAAAAGAACAAAGCAGAGGCCAGGTGCTC

CGCAGCGTTTGAGATGTGCATGAAGCTCATCAAAGGTGGGTTCATCAGCAGTCACCTTCAGC

CGACGTTTACCAGGAAGCTCCCGGCCATGCGAAACGCACGCCTAGCCATCAGCTCCAAGAA

GCGTGAACGGTACAATATGAGGGTCAAGCCAGAGGTATGGTCACGGCGTGGACCGGCATCC

TCTCTGTTCCTCACAGTCCTGAAGCTTCGTACACCTGGTGCATTGAACAGACCATCACAGCC

ACTCGCCCTCCTCACACGAGAGGCACTGCCAGAGCTTCCAGGAGTTCCGCTATTTTTCGGTA

ACTGTGGTCGGTCCATAGCGGAGGTAGTATCTGTGGCGAAACCCATGCACTTGGATGAAGTA

CGTCTAGACAGCCTCAGAGTATTCACCCTGCGCATTTTCAAAGATGTCTTCAGCAAGGTATA

CGATTCTCAAGTCGCAGACCTTCCATACTTCCTGGCACCTGCTGCTCATGACCACAGTCATGA

GTTCTCACCGAATGAAGACCCAGGGTCACTGATCGACTGGAGCCATCTGCTGTCGACCAAAG
```

```
AGGTTGAGTACTTGCCTTGGGATGAAGATCACAGTCCCAGCTTCTATCAAAGCAAGTTTGTG

ATTGATCCATACACGGGATCGCGCAAGCTGTTTCTCAGAGGTATTCGGACAGATCTCAAGCC

GACCGACTTGGTTCCAGATGGAGTTCCCGAACCCACATTCAGGCTCTGGAAGGACGTTGAGC

ATACCATAAAGGAATACAGCATCAGCCTCTGGGCAAAGAGTCGAGCCCGAGAGCTGGCGA

ATGGTTGGACACTCAACCCGTGGTAGAAGCCGAGTTGGTCTCGCTGCGCCGGAATCTTCTCG

ACGAATTTGCCGATTCCAAGCATGAAGGGTCTAGGGTCTGTTATGTGATTCTCCAGCCGCTA

CAGATCTCAACACTCCCTGTCGAGGTCGTCGCTATGGCCTACAACTTTCCCGCCATCATCCAT

CGGATTGAATCGAATATGATCGCCCTTGACGCCTGCCGTATGTTGAACCTTCGAGTTCGTCCC

GACCTGGCTCTCGAGGCGATGACCAAAGATTCAAGCAACAGTGAAGAGCACGATCAGGAAA

AGATTGATTTCCAGGCCGGCATGGGCAATAATTATGAGCGACTCGAGTTTCTCGGAGACTGC

TTTCTCAAAATGGCAACCACCATCGCACTTTTTACTCGGATCCCTGACAGCAACGAGTTTGA

GTGTCACGTCGAGCGAATGCTTCTTATTTGCAACCAGAATCTGTTCAATGTCGCATTAAAGA

AGAACTTGCAAGAGTACATTCGATCAAAGCAATTCGATCGACGCAGTTGGTACCCCCAGGGT

CTGAAGCAGAAGGCGGGCAAAGCCCAAGGAGCACAAAACTCACACTCATTGGCCGACAAGT

CTATTGCTGATGTATGCGAGGCCATCATTGGCGCCTCATATTTGTCGTACACTGACGAGGGC

AACTTTGACATGGCCGTACGCGCTGTGACGGCCGTCGTGAGGAACAAAAATCACGACATGA

AATCATACGAGGACTATTACAAAGCATTTAAGATGCCGATCTGGCAAGCGGCGGAGCCAAG

TGCTGTGCAGATGGAAGCGTCTTTACAGATTAAAGAGCAGATGGGATATGAGTTCAAGTCTC

CTGCCCTGCTGCGGAGTGCCTTCAAGCACCCGTCCTACCCCCGTCAGTTTGAGAGCGTGCCC

AATTATCAGCGCCTCGAGTTCCTCGGTGACGCGCTTCTAGACATGGTCTGCGTAGACTTTCTC

TTCAGGAAGTTTCCCGACG

CCGATCCTCAATGGCTCACTGAACACAAGATGGCCATGGTTTCGAACCACTTCCTCGGAAGT

CTGAGTGTAGAGTTGGGCTTCTACCGGCGTGTCCTTCACTTTAACAGCATCATGGCCAATCA

AATCAAGGACTACGTCGACGCACTTACTCATGCACGCCAAGAAGCCGAAGCGGTGGCCCAG

ATCTCTGGCACAGTCTCGCGAGATTACTGGCTCAACGTGAAGCACCCCCCCAAATTCCTCTC

AGACGTGGTCGAGGCATACATCGGTGCTATTTTCGTTGATTCAGGATACGATTATGCCAGG

TACAGGCGTTCTTCGAGAAGCATATCCGGCCTTTCTTCGCAGACATGGCGCTATATGATTCCT

TTGCCAGCAGCCACCCTGTCACAACGCTGGCGCGTATGATGCAGCAGGACTTTGGCTGCCAG

GACTGGCGGCTTCTTGTAAGTGAACTGCCGCCGAGCTGCGAAGACGGCGGGGCAGCTGCGA

TCACTGAGACGGAAGTGATTTGTGGGTTCATGGTCCACGGAAGAATCCTGCTACATGCCAAG

TCGTCGAGTGGACGGTACGCCAAAGTGGGTGCTGCAAAGAGAGCGGTCGAGAAGCTCATGG

GTCTCGGCAACGACAAAGAGGTCTTTCGGACGGACTTCGGCTGTGACTGTGACTGTGAAGGT

CAAGCAATCTAG
```

SEQ ID NO:6 - *Verticillium dahilae* DCL (VAD_00471.1) protein sequence

```
MTTDELSVGLDATGISILADGPENISSSTSTSTTGKEDGYLCINRFTQNTATTQDNQSRDSDDD

EDDCGSHDEADEDSDERQYSMTPERPHKITEKKRADHAAFHDWLQSNSSEIAQSTPQPAQNLNH

TSTALMVRESENRKIIENPREYQIELFERAKRKNIIAVLPTGSGKTLIAALLLRHTLEQETADR

RAGKPKRIAFFLVEKVALALQQHAVLECNLEFPIDRVCGDMVRSDWIKESWMKRWDDNMVVCT

AAILQQCLARSFIRMDQINLLVFDEAHHAKGNHPYARIIKDYYITEPDKERRPKIFGMTASPVD
```

ALTDVKIAAAQLEGLLHSEIATIEEDSVSFKQIQKEVVEQDCKYPALEPPFTTNLHKKIQEQVR

YNKNFAKALSNSLEMSSSLGSWCVDRFWQIFLTEETLARLAAQTAQDNIFADRAEKERVAIEEV

RNIIKQHQFLPITKTLQDLSSKVLCLLGQLELRFSAPTDHKCIIFVEKRNTAMILAHLLSLPGI

GPLYLKPAALVGNPSDNSPLAMSYKEQVMTITKFRRGEYNCLLATSVAEEGIDIADCNIVIRFD

LFNSVIQYIQSKGRARHLNSEYICMAELGNGKHTRAKIQANYDLSLIRQFCSTLPEDRKIVGWD

PEAALHHGERDHKFHIVPSTGAKLTWTGSLVVLSNFASSLQVNDETLSPSYMVSLIGSEYICEV

QLPSKSPILSVSGTLQKNKAEARCSAAFEMCMKLIKGGFISSHLQPTFTRKLPAMRNARLAISS

KKRERYNMRVKPEVWSRRGPASSLFLTVLKLRTPGALNRPSQPLALLTREALPELPGVPLFFGN

CGRSIAEVVSVAKPMHLDEVRLDSLRVFTLRIFKDVFSKVYDSQVADLPYFLAPAAHDHSHEFS

PNEDPGSLIDWSHLLSTKEVEYLPWDEDHSPSFYQSKFVIDPYTGSRKLFLRGIRTDLKPTDLV

PDGVPEPTFRLWKDVEHTIKEYSISLWAKSRARRAGEWLDTQPVVEAELVSLRRNLLDEFADSK

HEGSRVCYVILQPLQISTLPVEVVAMAYNFPAIIHRIESNMIALDACRMLNLRVRPDLALEAMT

KDSSNSEEHDQEKIDFQAGMGNNYERLEFLGDCFLKMATTIALFTRIPDSNEFECHVERMLLIC

NQNLFNVALKKNLQEYIRSKQFDRRSWYPQGLKQKAGKAQGAQNSHSLADKSIADVCEAIIGAS

YLSYTDEGNFDMAVRAVTAVVRNKNHDMKSYEDYYKAFKMPIWQAAEPSAVQMEASLQIKEQMG

YEFKSPALLRSAFKHPSYPRQFESVPNYQRLEFLGDALLDMVCVDFLFRKFPDADPQWLTEHKM

AMVSNHFLGSLSVELGFYRRVLHFNSIMANQIKDYVDALTHARQEAEAVAQISGTVSRDYWLNV

KHPPKFLSDVVEAYIGAIFVDSGYDYGQVQAFFEKHIRPFFADMALYDSFASSHPVTTLARMMQ

QDFGCQDWRLLVSELPPSCEDGGAAAITETEVICGFMVHGRILLHAKSSSGRYAKVGAAKRAVE

KLMGLGNDKEVFRTDFGCDCDCEGQAI*

SEQ ID NO:7 - *Verticillium dahilae* DCL (VAD_06945.1) genomic DNA sequence
(selected RNAi fragment marked by bolded text)

ATCACTCTACGGGTAAAAGCGCTGAGAGAATGATCATGATGAATTTCTATCATCCACGCAAA

CAATCGGCACTATCTGTTCCCCACGTCCTGGGACTGACCGCAAGCCCCATAATGCGATCTAG

GCTCGAAGGCCTTGAGGCACTGGAACAGACACTGGACTCGGTTTGCGTTACGCCCAGATTGC

ACCGAGATGACTTAATGACCCATGTCAAAAGGCCCACCGTCTGTTATGTCCATTACGAAACG

ACAGATGCTAAGGATGAGCCCAAGCCGGTCAGCATTTCAAGTCTTCGCGAAGCATGCAGAA

ATATGGACATCAGGCAAGATCCATACGTTATCTGTCTAAGAGACAAAGGCACTGATCGAGC

ACGACGTGAGCTCATCAAGGTCCTTACAAGCCATAAAACAGATTCGCAACAGCAAATGAAG

TCTTTCTTCAATCAAAGCTTGCGAGTCCTGCGAGATCTCGGGCCCTGGGCGGCCGAGTACTA

CATTTGGAAGGTTGTTACAGATTTTCTGGCAATCATTGAAGCAAGAGATCACCGCATGAATC

AACGGAATACCGAAGAAAAGCAGTATCTGGCCAACATCCTTCGACAAATCAGTATCAGCGA

GCCGCCAGTCAGCATGTTGAGTGCTCATAACACGTCGAACAAAGTAATGGTGCTCATGGAAT

ACTTGTCATCTAAAGCTACCGATGGTACTGTCGGGATCATATTTGTCAAAGAGCGATCAACT

GCGGCGATGCTTGCACACGTGATTGAGTCGCATCCACTGACACAGAATAGGCACTCGAGCGT

TGGGGTTGTTGTTGGTGCTTCCACTCATCTGGTAAGGAAGAAAGACATGTGGGATCTGTCTC

GAGCAGCCCACGAGACAGAGCCCCTTCTTCAGTTCAGATCTGGCCACCTCAATTTGCTCATC

GCCACGAGTGTGCTTGAAGAGGGCATCGACGTTCCTGCCTGCAACCTCGTGATCTGTTTTGA

TGAGCCCGAGAATCTCAAAGCCTTTGTCCAGCGGCGCGGCCGAGCCCGGAAGAAGGATTCT

AGCCTCGTGGTTCTTCTCCCCGGGACAGACCACGTGCCTCAGGACTGGGAAAGCATGGAAGC

```
GACAATGAGGACACACTACGAGAGAGAACAGCGCGAAATACAAATCATGGAGCAGATCGA
AGCATCCGAGTCTGCAAAGTACGAAGAGTACGTTGTCGAGAGTACTAATGCCAGACTCGAC
TTCGAGAACGCCAAAGCGCATCTCAGCAACTTTTGTGGGCAGCTCTCTCCCGGGGAGTTTAT
AGACAAGAGGCCCGAATACATACCCCGTGTGGTAGACAACGGAGTACCTCCATCTCTGAGG
GTCACGGTACTGTTGCCAAGCTATGTTCCAGCTGCCGTCCGCCATGCTGAGAGTCGTCGAAG
CTGGAAGTCGGAGCATCAGGCCTCAAAGGATGCCGCTTTTCAGGCATACGTGGCTCTTTACA
AAGCGGGACTGGTCAATGAACACATGCTTCCACTCACGGTAAAAGATATCGTACCCGCAAA
CGAACCTCGAGTAGCAACCTTGCAGGTCAATGGCCTCTTGAATGTCTGGCTTGGTATTGCCC
AGGCCTGGATCACGAGCACTGAAACCTGGTTAACTCCAGTGCACCTCCGAGACGCGACGGG
ATTGACGCGAGGAACGTATATCATGAGAATGCCGGTAGCATTGCCGGCACTGCCTTCCACGC
CGGTGTACTTCGATCGCGAAGGACCATGGCTTCTGGATTTTGGCCCACAAGAACGAAAGGA
GAATCTTGAAATGCCTGATCATACTTCAGTGCTGCTTGCACTCCACTTTGGCCATCACTGGTC
TATTGCTCATGGTCAGCAGCAGGTTATCAGCTTCGCTTCACAAGATGGCGA
ACTGAATATCAGGCAATTAAGTGCACGGGGTTTCACAACCGCAGATGCCGACCGAGAGGAA
ATGCTGTACCTGGTACGGGACGAGTCAGGATGCCCGTATGTGTACGACCACTTTCTAAATGG
CAAGCCGTCACTTGAACTTGTTCAACGACCTTTCCGGCGCATCGGGGACTCTCCAGGCTTTC
AAGACGCACCCAGTAACATCCCCTACTTGGCTCTCAGAAAGTGGCCGCGGTACCTGGCCCTC
TTGCACCAACAGAAGGTCAACGATCTACTGCCACAGGCGACAAACAAGAAGCCATATGCTA
GGGTTTATCCGGCACCGTGGGCGAAAGTCGACACGATTCCATTAGATCATGCTTACTTTGGG
GCGTTGATCCCTTTCATTTCACACATTGTCGAGGTTCGACTGGTTGCAGAACAGCTTTCCTCG
AGCCTACTTCGTGACCTCAATTTCTCAGATCCCTCTCTTGTCCTGGCGGCCATTAGCACTAAG
GGTTCCTTGGAAGCCACAAACTACGAGCGCCTTGAGCTTTTGGGTGACTCTATCCTCAAGCT
TTGCACCACGGCCAATGCCGCCGCTCTGCATGGCTTAGTGTCGAACTCGAGATTGTGTAGGG
CTGCACTGGATGCTGGCCTTGACAAATTTGTTCTAACTGAAAACTTCACTTGTCGCACGTGGC
GCCCTATCTACGTCAACGACATGATGGAAAAGGGTGCTCGCGACTCAGGACCCCGTATCATG
TCGACGAAGACGCTCGCCGATATTGTGGAAGCACTCATAGGGCCGCATACATTGACGGTG
GCCTCCCAAAGGCACTTGGGTGCATTTCGATCTTCCTGAGGGAGCTCGATTGGAAACCGTTG
CCAGCTTGCCAGGAGATCCTTTACAGTTTGGCGTCCCCTGATGTGCCTTTGCCGCCAATGCTT
GTTCCGCTGGAGGACCTGATCGGCTACACGATGCATCTCCTCAAGACTGCTTCGGTCAACGG
CGATCTTCTAGGCTTCCTTGCACTCGAGTGCCATGCCGAGGAAGACGAGGTGATCATTGATA
TCGATTTTTCTCCTTCCGATACGGACTTCAATCCTCAAAATTCCGCCGGGGTGGAACAGAAG
CTCAAACAGACACGCCGGAAAATCCCCCTTTGGAAGTTTATGCGCCACTCCTCAATAGA
GGTTGTGCAGCAGCAGACCAAAGCTGCCAGCGTTCATGCCGATCTCCGAGGACAGATC
ATGCACGCTCTGGAACATGGGTCAAGCTACCCCTGGTCTCTTCTCGCCCGTTTACATCC
CGCAAAGTTCTTCTCCGACATGGTCGAAGCTGTACTGGGTGCCGTCTGGGTCGATTCG
GGCGACATGGGCGCGTGCATTCGTGTGGCGGAACGACTGGGCATTCTGCCTGTGCTCT
CCCGACTGGCAAAGGAGGACGTTCATGTGCTGCATCCGAAGCAAGAGCTGGGAGAGATC
GCTGGTCCCCGGACAGTCAAATATCTCCTCACTTTGCCCGAGGACGCAGCCGGCCTGCAAAG
TGCAACAAGAAAATATGCCTGCAAGGTCATGGTCGGGGATCGCTGTGTTGCAGAGGTGGAT
```

GACGGGGTCGCTCGAGATGAGGTTGAGACAAAGGCTGCAGAGGTTGCGGTACAGACCTTGA

AGAATGAACAGGCTGACGCGAAACAAGTAGCAGAACACTAA

SEQ ID NO:8 - *Verticillium dahilae* DCL (VAD_06945.1) protein sequence

MIMMNFYHPRKQSALSVPHVLGLTASPIMRSRLEGLEALEQTLDSVCVTPRLHRDDLMTHVKRP

TVCYVHYETTDAKDEPKPVSISSLREACRNMDIRQDPYVICLRDKGTDRARRELIKVLTSHKTD

SQQQMKSFFNQSLRVLRDLGPWAAEYYIWKVVTDFLAIIEARDHRMNQRNTEEKQYLANILRQI

SISEPPVSMLSAHNTSNKVMVLMEYLSSKATDGTVGIIFVKERSTAAMLAHVIESHPLTQNRHS

SVGVVVGASTHLVRKKDMWDLSRAAHETEPLLQFRSGHLNLLIATSVLEEGIDVPACNLVICFD

EPENLKAFVQRRGRARKKDSSLVVLLPGTDHVPQDWESMEATMRTHYEREQREIQIMEQIEASE

SAKYEEYVVESTNARLDFENAKAHLSNFCGQLSPGEFIDKRPEYIPRVVDNGVPPSLRVTVLLP

SYVPAAVRHAESRRSWKSEHQASKDAAFQAYVALYKAGLVNEHMLPLTVKDIVPANEPRVATLQ

VNGLLNVWLGIAQAWITSTETWLTPVHLRDATGLTRGTYIMRMPVALPALPSTPVYFDREGPWL

LDFGPQERKENLEMPDHTSVLLALHFGHHWSIAHGQQQVISFASQDGELNIRQLSARGFTTADA

DREEMLYLVRDESGCPYVYDHFLNGKPSLELVQRPFRRIGDSPGFQDAPSNIPYLALRKWPRYL

ALLHQQKVNDLLPQATNKKPYARVYPAPWAKVDTIPLDHAYFGALIPFISHIVEVRLVAEQLSS

SLLRDLNFSDPSLVLAAISTKGSLEATNYERLELLGDSILKLCTTANAAALHGLVSNSRLCRAA

LDAGLDKFVLTENFTCRTWRPIYVNDMMEKGARDSGPRIMSTKTLADIVEALIGAAYIDGGLPK

ALGCISIFLRELDWKPLPACQEILYSLASPDVPLPPMLVPLEDLIGYTMHLLKTASVNGDLLGF

LALECHAEEDEVIIDIDFSPSDTDFNPQNSAGVEQKLKQTRRKIPLWKFMRHSSIEVVQQQTKA

ASVHADLRGQIMHALEHGSSYPWSLLARLHPAKFFSDMVEAVLGAVWVDSGDMGACIRVAERLG

ILPVLSRLAKEDVHVLHPKQELGEIAGPRTVKYLLTLPEDAAGLQSATRKYACKVMVGDRCVAE

VDDGVARDEVETKAAEVAVQTLKNEQADAKQVAEH*

SEQ ID NO:9 - RNAi fragment from *B. cinerea* DCL1 cDNA

TGCGGAAGAACTTGAAGGTTTGCTACACAGTCAAATATGTACTGCAGAAGATCCCAGCTTGC

TGCAGTACTCAATCAAAGGTAAACCTGAGACTCTTGCCTACTATGATCCCTTGGGCCCGAAA

TTCAATACTCCTCTTTATCTTCAAATGCTCCCGCTTCTAAAAGACAATCCTATCTTTCGGAAG

CCATTTGTATTTGGGACAGAAGCCAGTAGAACTCTAGGATCTTGGTGTGTTGACCAGATCTG

GACTTTCTGTC

SEQ ID NO:10 - RNAi fragment from *B. cinerea* DCL2 cDNA

TCTTTAAGTGATATCGAGGAGACTTTGGATGCCATTTGCTGCACGCCAAAAATACATCGAGC

AGATCTTCGCCTTCGAGTAAAGCTACCACTTCTATCTATTATCTACTATACCCCAGAGTCAAA

TATCATCGTGACGAAAACTGTGGCGAGCCTGAGAAAGATTGTGCAAAGTCTCAACATTTTCG

AAGACCCCTACGTTTTGACACTAAAAAGGAGTGATAGCGAAAAAAGTCAACGTGAGCTGGC

GAAAGTACTCAAGAGTTTTAAGACATATAGTCAAACCCAATTAAAGTC

SEQ ID NO:11 - RNAi fragment from *V. dahliae* DCL (VDAG_00471) cDNA

GGCAAGCCCAAGAGAATCGCCTTTTTCCTCGTGGAAAAGGTTGCTCTTGCCCTCCAACAGCA

CGCGGTTCTGGAGTGCAATCTGGAATTTCCCATTGACCGGGTATGCGGTGACATGGTACGGT

CGGACTGGATCAAGGAGTCATGGATGAAAAGATGGGATGACAACATGGTCATGGTCTGCAC

CGCCGCCATCCTTCAGCAATGCCTTGCCAGATCATTCATCCGCATGGATCAGATCAACCTGC

TTGTCTTCGATGAAGCACATCACGCCAAGGGAAATCATCCGTACGC

SEQ ID NO:12 - RNAi fragment from *V. dahliae* DCL (VDAG 06945.1) cDNA

ACAGACACGCCGGAAAATCCCCCTTTGGAAGTTTATGCGCCACTCCTCAATAGAGGTTGTGC

AGCAGCAGACCAAAGCTGCCAGCGTTCATGCCGATCTCCGAGGACAGATCATGCACGCTCT

GGAACATGGGTCAAGCTACCCCTGGTCTCTTCTCGCCCGTTTACATCCCGCAAAGTTCTTCTC

CGACATGGTCGAAGCTGTACTGGGTGCCGTCTGGGTCGATTCGGGCGACATGGGCGCGTGCA

TTCGTGTGGCGGAACGACTGGGCATTCTGCCTGTGCTCTCCCGACTGGCAAAGGAGGACGTT

CATGTGCTG

SEQ ID NO:13 - LTR for siR3
>B. cinerea (B05.10) Botrytis cinerea supercontig 1.56 [DNA]
218751-219771 -

CTCCTGGATCAGGCAGATGAATTAGGGAACTGATTTCGACCTTCCAGAGTTCTCTTTGCG

TGATGGGTCACTTGGGTTTGGTTGTCGGTATGCTGTGGGTTCGGAGGAGTTGTCCTTTCT

GGTTTCTTTGTTGGATAGTCCTTTTTGGGTAGCTTGGTGTGATGCATGCGTTCTGGGTGT

GGGTCTCGTGAGGTCTTTTTGTATCAAGTATTTTTAAGCTTTTTTCTTGTTCTCTTCTTT

TTCTGTATTGGTAATGCTTCTTCTTTATGATATTCTCCCATCGCTGCTTTCGCATTTTCT

AGGTTGTAGGGTGCTTCCCACGTGTCTTCCGCCGGTTGGTAGCCCTTCCATCGCACCAGG

TATTGCACACCTCTGCCTCTTTTTCTATGTGCTAAAATCCTTTCCACCTCATGCTCTATG

TGATCGTCAATTTCTTCTGGCGGCGGCGGGTCGGCGGTACCCTGTCGTTCGTGCCATGGT

TCGAGTAAAGAGACGTGGAATACATTGTGGATCTTGTAGGTGGGCGGTAATCTAAGTTCG

TATGCTTGCCCGCTGGTTTTTATACCCGTCACGACAAAGGGGCCTATAAATCGATCGGAG

AATTTTTTCTTAGGTCGCAGTTGTTTAATGTTCTTTGTGCTTAGCATCACCTTGTCCCCG

ATGCTATATCGCTGTGGTGACCCCTTCGTAGTGTTCTTGTTTTTCTGATTGGTTGCCGAT

TTCCAGAATTCTTTCAGCTTTTCTCTTTCTTTCTCTAAAGCGTCGATGCGCTCGCGTGCT

GCCGGCGCCCTTCCCTCTAAATCGGCGTCCTCGCCGATATAATGGAATGTGGGTTGGAAC

CCATACATAGCCTGGAATGGGCTTGTATTGGTTGTACTGTGCCATGTCGCGTTATATGTG

AATTCAGCAAGGGGCAATAGCGATGCCCAGTCGTCTTGCCTATAGTTGGTGTAGCAACTT

ATATAGTGAATCAAATTTTGGTTTTGTCGTTCGGTTTGACCGTCGGTCTGCGGGTGGAAC

G

SEQ ID NO:14 - LTR for siR5
>BC1G_08572.1 retrotransposable element Tf2 1 protein type 1
(Transcript:BC1T_08572)

ATGGCATCCAGAGCTACCGCCACAGGTCAATCTGCCGGAGACACCAACGACATCGAGATGA

CCGACGCCCCAAAGGAGATCACTATCAACGAAACCCTTAAGATCGCCTTACCAGACAAGTA

CCAAGGTAGTCGACAAGAGCTCGATACTTTCCTCTTACAACTTGAGATCTACTTTCGATTCAA

TGAGGACAAGTTCACTACCAAGGAATCCAAGAGTATATGGGCCGCATCATACCTTCGAGGT

GAAGCAACCAAATGGATCCAACCATATTTGCGCGACTATTTCGAGCATGACGATAAGGATC

GTATGCAACCCACCCGAACAATCTTCAATAGTTTTGAAGGATTTAAGACAGAGATTCGTAGA

ATCTTCGGAAATTCCAACGAGTTAGAGGTAGCGGAAGATAAGATCTTCAACCTCAAGCAGA

CAGGATCAGCATTGAAATATGCTACGGAATTTCGAAGATATGCTGGAACAACCAAGTGGGA

```
CGAAATCGCTATCATGAGTCACTACCGCAAGGGACTCAAACCAGAAGTCAGACTGGAATTA
GAAAGATCTGCCGAGAGTACAGATCTGAACGATCTAATTCAGGACTCCATCGAATCAGATG
ATCGTCTCTACAGATATCGACAAAGCCAGAGATCATACAAACCCCAAGGAAATCAGAAGCA
AGGGCGTTACCGCAAAAATGAGGGTAGACCACGTTACAATCCACAGAGATACGGAGACCCC
ATGGAACTAGACGCCACGCACTACACAAACGGGAACGATGACTCGGAAAAGAGACGAAGA
CGAGAAAACAACTTATGCTTTGAATGTGGAAAAGCAGGGCACCGAGCAGCAGACTGCCGAA
GCAAGAAGACAGGAGGAAAAAGGGGCAACTTCAAACCTAAGTTCGGCAAAGGCCAACTTA
ACGCTACCTTTACAATCCCAGAAAATCCAACTAAATCCGAAAATACTGAGACTTTCACCGTT
GAGGAATTCCAGCAATTACTAAAGGAATTACCACGAAATCAAGAGGGCATGAATGCAATAG
ACTTATGGGAGCAAGAGTATTACAGAACCCCAACACCCTCTGTGACAGAAGAAAGTCATCA
GGACGAGGCAGAAGCAGACCACGCCACGATGAGCTGGACAGCTTGCTATGATGAATTCTGC
GGAATCCATCGATCAGATAAAGAAGCAACCGGATGGTCCCCTAAGAAGAGAAAGACGAAG
AACCATCAGAATAATGTAACATGCGAGGATTTAACTCCCAATATAACTTCGCAAGAAGTTCG
CAAAGTTACCCAGCAGTTAAATGCTACGGGACAGGCAGGACAGATATACTGCAAGGTTCAG
ATAAATGGACACATACAATCAGCCATGATAGATTCAGGGGCTACAGGAAATTTTATTGCACC
GGAAGCTGAGACAATCCCAATACGAATGGGCATAACCCAACATACAGAGGTTATACAGCTT
GACGTTGTGCCATTGGGCCAACAACAGATCATCTTAGGAATGCCATGGTTAAAGGCACATAA
TCCGAAAATAGATTGGGCACAAGGAATTGTGACATTTGATCAGTGCAAAAGCGGTCACAGG
GACACGCTAGAGGCGTTCGCGAGACGTAACACGCGCCAAGGAGAGTTGAACGCGAACAACA
CCGGCGACGTAGGACACCCAGTCCAGGGTCCTCCATTAAGAGCGAAGGCCAGTACACCTCC
TCTACAAATGCAGAAGCCAACGACACGGCACGAAATCGCAATCGAGGCAAAAGAAAAGCCT
ACGATACCAGAACAGTACAAGAATTATGAACATGTTTTCAAAGAACCAGGGATCCATGAGG
CTTTACCGGAACACAAGCCATGGGATCATGAGATAATATTGGAGGAAGGCAAGATGCCTGT
GCACACCCCAATTTATTCAATGTCAGCCGATGAGTTAAAGAGGCTCAGAGAGTACATCGACG
ACAATTTAGCCAAGGGATGGATCAGGGAATCCGCGTCCCAAGTGGCCAGTCCAACTATGTG
GAAGGATCGATATCCACTTCCATTAGCTACGGAATTAAGAGATCGATTAGGCGGAGCTACG
ATATTTACCAAGATGGACCTACGTAATGGTTACCACTTGATCAGAATGAAGGAAGGCGAAG
AATGGAAAACCGCTTCAAAACAAGATACGGGCTATACGACTACTTTCATGAGGCTTATGAAC
AATGTGTTGTCACAATATTTGGATACTTGCTGTATATGCTACTTGGACGACATCCTAGTATAT
TCAAACAACAAGGTTCAACACATTAAGGACGTTAG
CAACATCCTCGAAAGCCTATCCAAGGCAGACTTGCTGTGCAAACCAAGCAAATGCGAATTCC
ATGTCACAGAGACAGAATTCTTGGGATTCACCGTATCAAGCCAAGGGCTCAAGATGAGCAA
AGGCAAGGTTAAGGCAGTGCTCGAATGGAAGCAGCCGACCACAATCAAGGAAGTACAATCC
TTTCTAGGGTTCGTCAACTTCTACAGAAGATTCATCAAGGGTTATTCAGGGATTACTACACCC
TTGACCACGTTAACCAGAAAAGATCAAGGAAGCTTCGAATGGACTGCCAAAGCACAGGAGT
CATTCGATACGCTCAAACAAGCAGTGGCAGAAGAGCCAATACTGTTGACTTTTGACCCAGAG
AAAGAAATCATAGTGGAGACGGACTCCTCGGATTTCGCTATAGGAGCAGTTCTGAGCCAAC
CGGGCCAGAATGGAAAATACCAGCCAATCGCATTCTACTCCCGAAAACTATCACCAGCCGA
ATTGAATTACGAGATATATGACAAAGAATTACTGGCGATAGTCGATGCATTTAGAGAATGGC
```

GAGTGTATTTGGAAGGATCGAAATACACGGTACAGGTGTATACAGATCATAAGAACTTGGTT

TACTTCACCACAACGAAGCAGTTAAACAGACGACAGGTCAGATGGTCGGAGACCATGGCCA

ACTACAATTTCAGAATTTCATATGTCAAAGGATCAGAAAACGCTAGAGCCGACGCTCTTAGC

CGAAAACCAGAATATCAAGAAAACAAAACGTACGAGTCATACGCTATATTCAAGAAAGACG

GCGAATCACTGGTTTACAATGCACCACAGCTTGCAGCAACACACCTGTTGGAAGACAACCAC

CTCAGGAAACAGATCCAATCACACTACGACAAGGATGCTACTGCCACACGCATACGCAAGA

CAATAGAACCAGGATTCACTATAGAAAATGATACCATATACTTTCATGGAA<u>AAGTTAATGCC</u>
<u>GAATCAGCGATAG</u>TGACCAAGGAATTTGTGACGGAACAACACGGGTTGCCGGCACATGGACAC

CAAGGAATTGCAAGGACATTTGCAAGAATACGGGAAATCAGTTACTTCCCACGAATGAGAA

CGATAGTTGAAGAAGTTGTTGGAAATTGTGACACCTGCATACGAAACAAGTCATCACGACAT

GCTCCGTATGGTCAGCTCCAGACCCCAGACATGCCTTCTCAGCCATGGAAGTCCATCACATG

GGACTTTGTGGTCAAACTACCACTCTCAAAAGATCCTACTACAGGAATTGAGTACGACGCGA

TACTCAATATAGTAGACAGGCTAACGAAATTTGCATATATGATACCATTCAAGGAAACATGG

GATGCTGAGCAACTAGCATATGTGTTCCTAAGGATCATAGTAAGCATACACGGAGTACCAG

ATGAGATAATCTCGGATCGAGACAAGCTCTTTACCTCGAAATTCTGGACTACCTTATTAGCA

CTTATGGGTATCAAGAGAAAGCTATCGACATCTTTCCACCCACAAACAGATGGTCAAACAGA

GAGGACCAATCAGACAATGGAAGCATATCTTAGATGCTATCGTATAAAATCCCGATACCAC

AAGAAGTTAATGCCGAATCAGCGATAG

SEQ ID NO:15 - LTR for siR5
>BC1G_15284.1 - enzymatic polyprotein

ATGGCATCCAGAGATATCGCCACAGGTCAATCTGCCGGAGACACCAACGACATCGAGATGA

CCGATGCCCCAAAAGAGATCACTATCAACGAAACACTTAAGATCGCCTTACCAGACAAGTA

CCAAGGTAGTCGACAAGAACTCGATACTTTCCTCTTACAACTTGAGATCTACTTCCGATTCA

ATGAGGACAAGTTCACTACCAAGGAATCCAAGAGTATATGGGCCGCATCATACCTTCGAGG

TGAAGCAACCAAATGGATCCAACCATATTTGCGCGACTATTTCGAGCATGACGATAAGGATC

GCATGCAACCCACCCGAACAATCTTCAATAGTTTTGAAGGATTTAAGACAGAGATTCGTAGA

ATCTTCGGAAATTCCAACGAGTTAGAGGTAGCGGAAGATAAGATCTTCAACCTCAAGCAGA

CAGGATCAGCATTGAAATATGCTACGGAATTTCGAAGATATGCTGGAACAACCAAGTGGGA

CGAAATCGCTATCATGAGTCACTACCGTAAGGGACTCAAACCAGAAGTCAGACTGGAATTA

GAAAGATCTGCCGAGAGTACAGATCTGAACGATCTAATTCAGGACTCCATCGAATCAGATG

ATCGTCTCTACAGATATCGACAAAGCCAGAGATCATACAAACCCCAAGGAAATCAGAAGCA

AGGGCGTTACCGCAAGAATGAGGGTAGACCACGTTACAACCCACAGAGATACGGAGACCCC

ATGGAACTAGCGCTACGCACTACACAAACGGGAACGATGACTCAGAAAAGAGACGAAGA

CGAGAAAACAACTTATGCTTTGAATGTGGAAAAGCAGGGCACCGAGCAGCAGAATGCCGAA

GCAAGAAGACAGGAGGAAAAAGGGGCAACTTCAAACCTAAGTTCGGCAAGGGCCAACTTA

ATGCCACCTTTGCAATCTCAGAAAACTCAACTAAACCCGAAAATACTGAGACTTTCACCGTT

GAGGAATTCCAGCAATTATTAGAGGAATTACCACGAAACCAAGAGGGCATGAATGCAATAG

ACTTATGGGAACAAGAGTATTACAGAACTCCAACACCCTCTGTGACAGAAGAAAGTCACCA

GGACGAGGCAGAAGCGGACCACGCCACGATAAGCTGGACAGCTTGCTATGACGAATTCTGC

GGAATCCATCGATCAGATAAAGAAGCAACCGGATGGTTCCCTAAGAAGAGAAAGACGAAG

AACCATCAGAATAATGTAACATGCGAGGATTTAACTCCCAATATAACTTCGCAAGAAGTTCG

```
CAAAGTTACCCAGCAGTTAAATGCTACGGGACAGGCAGGACAGATATACTGCAAGGTTCAG

ATAAATGGACACATACAATCAGCCATGATAGATTCAGGGGCTACAGGAAATTTTATTGCACC

AGAAGCGGCAAAGTACTTGGAAATACCACTTCAGAGGAAACAATACCCCTATCGATTGCAG

TTAGTTGACGGACAGCTAGCAGGGTCTGACGGAAAGATTTCGCAGGAGACAATCCCAGTAC

GAATGAGCATAACCCAACATACAGAGGTTATACAGCTTGATGTTGTGCCATTGGGCCAACAA

CAGATCATCTTAGGAATGCCATGGTTAAAGGCACATAATCCGAAAATAGATTGGGCACAAG

GAGTTGTGACATTTGATCAGTGCAAAAGCGGTCACAGGGACACGATAGAGGCGTCCGCGAG

ACGTAACACGCGCCAAGGAGAGTTGAACGCGAACAACACCGGCGACGTAGGACACCCAGTC

CAGGGTCCTCCATTAAGAGCGAAGGCCAGTACACCTCCTCTACAAATGCAGAAGCCAACGA

CACGGCACGAAATCGCAATCGAGGCAAAAGAAAGGCCTACGATACCAGAACAGTACAAGA

AATATGAACATGTTTTCAAAGAACCAGGGATCCATGAGGCTTTACCGGAACACAAGCCATG

GGATCATGAGATAATATTGGAGGAAGGCAAGATGCCTGTGCACACCCCAATTTATTCAATGT

CAGCCGATGAGTTAAAGAGGCTCAGAGAGTACATCGACGACAATTTAGCCAAGGGATGGAT

CAGGGAATCCGCGTCCCAAGTGGCCAGTCCAACTATGTGGGTACCCAAGAAGGATGGACCC

GATAGACTAGTTGTAGACTATAGAAAGCTTAACGCACTCACTAAGAAGGATCGATATCCACT

TCCATTAGCTACGGAATTAAGAGATCGATTAGGCGGAGCTACGATATTCACCAAGATGGACC

TACGTAATGGTTACCACTTGATCAGAATGAAGGAAGG

CGAAGAATGGAAAACCGCTTTCAAAACAAGATACGGGCTATACGAGTACCAAGTTATGCCA

TTCGGGCTAACCAACGCACCAGCTACTTTCATGAGGCTTATGAACAATGTGTTGTCACAATA

TTTGGATACTTGCTGTATATGCTACTTGGACGACATCCTAGTATATTCAAACAACAAGGTTCA

ACACATTAAGGACGTTAGCAACATCCTCGAAAGCCTATCCAAGGCAGACTTGCTGTGCAAAC

CAAGCAAATGCGAATTCCATGTCACAGAGACAGAATTCTTGGGATTCACCGTATCAAGCCAA

GGGCTCAAGATGAGCAAAGACAAGGTTAAGGCAGTGCTCGAATGGAAGCAGCCGACCACA

ATCAAGGAAGTACAATCCTTTCTAGGGTTCGTCAACTTCTACAGAAGATTTATCAAGGGTTA

TTCAGGGATTACTACACCCTTGACCACGTTAACCAGAAAAGATCAAGGAAGCTTCGAATGG

ACTGCCAAAGCACAGGAGTCATTCGATACGCTCAAACAAGCAGTGGCAGAAGAACCAATAC

TGTTGACTTTTGACCCAGAGAAAGAAATCATAGTGGAGACGGACTCCTCGGATTTCGCTATA

GGAGCAGTTCTGAGCCAACCGGGCCAGAATGGAAAATACCAGCCAATCGCATTCTACTCCC

GAAAACTATCACCAGCCGAATTGAATTACGAGATATATGACAAAGAATTACTGGCGATAGT

CGATGCATTTAGAGAATGGCGAGTGTATTTGGAAGGATCGAAATACACGGTACAGGTGTAT

ACAGATCATAAGAACTTGGTTTACTTCACCACAACGAAGCAGTTAAACAGACGACAGGTCA

GATGGTCGGAGACCATGGCCAACTACAATTTCAGAATTTCATATGTCAAAGGATCAGAAAA

CGCTAGAGCCGACGCTCTTAGCCGAAAACCAGAATATCAAGAAAACAAAACGTACGAGTCA

TACGCTATATTCAAGAAAGACGGCGAATCACTGGTTTACAATGCACCACAGCTTGCAGCAAC

ACACCTGTTGGAAGACAACCACCTCAGGAAACAGATCCAATCACACTACGACAAGGATGCT

ACTGCCACACGCATACGCAAGACAATAGAACCAGGATTCACTATAGAAAATGATACCATAT

ACTTTCATGGAAAAGTATACATTCCGAGTCAAATGACCAAGGAATTTGTGACGGAACAAC

ACGGGTTGCCGGCACATGGACACCAAGGAATTGCAAGGACATTTGCAAGAATACGGGAAAT

CAGTTACTTCCCACGAATGAGAACGATAGTTGAAGAAGTTGTTGGAAATTGTGACACCTGCA
```

-continued

```
TACGAAACAAGTCATCACGACATGCTCCGTATGGTCAGCTCCAGACCCCAGACATGCCTTCT

CAGCCATGGAAGTCCATCACATGGGACTTTGTGGTCAAACTACCACTCTCAAAGGATCCTAC

TACAGGAATTGAGTACGACGCGATACTCAATATAGTAGACAGGCTAACGAAATTTGCATAT

ATGATACCATTCAAGGAAACATGGGATGCTGAGCAACTAGCATATGTGTTCCTAAGGATCAT

AGTAAGCATACACGGAGTACCAGATGAGATAATCTCGGATCGAGACAAGCTCTTTACCTCA

AAATTCTGGACTACCTTATTAGCACTTATGGGTATCAAGAGAAAGCTATCGACATCTTTCCA

CCCACAAACAGATGGTCAAACAGAGAGGACCAATCAGACAATGGAAGCATATCTTAGATGC

TATGTAAATTATCGACAAGACAATTGGGTAGAGCTATTACCCATGGCACAGTTCGCATACAA

TACATCAGAAACGGAAACCACGAAAATCACACCAGCACGAGCTAATTTTGGGTTTAATCCA

CAAGCGTATAAAATCCCGATACCACAAGAAGTTAATGCCGAATCAGCGATAGTACAAATCG

AACAGCTGAAAGATCTCCAAGAGCAACTGGCTCTTGATCTAAGATTCATATCTTCCAGAACA

GCAGCGTACTACAATACGAAACGTAGTATGGAACCTACGCTTAAAGAGGGGGATAAAGTTT

ATTTGCTACGACGAAACATCGAAACCAAGAGACCAAGCAATAAACTCGACCACAGGAAACT

AGGACCATTCAAGATTGATAAGGTAATAGGAACGGTTAATTATCGATTGAAATTACCAGAC

ACAATGAATATCCACCCAGTATTCCACATATCCTTGCTCGAACCAGCACCACCAGGAGCGCC

AAATGCGCCATTTACAGAAATTGAACCAG

TCAACCCAAACGCCATATACGATGTCGAAACAATACTAGACTGCAAATACGTCAGAAACAA

GGTCAAGTATTTGATCAAATGGTTAGACTACCCACATTCAGAAAACACATGGGAACTCAAG

GAAGATCTCAGCTGCCCTGAGAAGCTACGGGCATTCCACCTGAAGTACCCACACCTGCCAAT

AAAGCCTCAAGATCCGCTTCGGACAACTCAGGCAAAGAAGGATCGAAGAAATCGAAGGAA

GAAGAATCAATAG

SEQ ID NO:16 - LTR for siR5
>BC1G_04408.1 retrotransposable element Tf2 1 protein type 1

ATGGCATCCAGAGCTACCGCCACAGGTCAGTCTACCGGAGATACCAACGACATCGAGATGA

CCGATGCCCCAAAGGAGATCACTATCAACGAAACACTTAAGATCGCCTTACCAGACAAGTA

CCAAGGTAGTCGACAAGAGCTCGATACTTTCCTCTTACAACTTGAGATCTACTTCCGATTCA

ATGAGGACAAGTTCACTACCAAGGAATCCAAGAGCATATGGGCTGCATCATACCTCCGAGG

TGAAGCAACCAAATGGATTCAACCATATTTGCGCGACTATTTCGAGCATGACGATAAGGATC

GCATGCAACCCACCCGAACAATCTTCAATAGTTTTGAAGGATTTAAGACAGAGATTCGTAGA

ATCTTCGGAAATTCCAACGAGTTAGAGGTAGCGGAAGATAAGATCTTCAACCTCAAGCAGA

CAGGATCAGCATTGAAATATGCTACGGAATTTCGAAGATATGCTGGAACAACCAAGTGGGA

CGAAATCGCTATCATGAGTCACTATCGTAAGGGACTCAAACCAGAAGTCAGACTGGAATTA

GAAAGATCTGCCGAGAGTACAGATCTGAACGATCTAATTCAGGACTCCATCGAATCAGATG

ATCGTCTCTACAGATATCGACAAAGCCAGAGATCATACAAACCCAAGGAAATCAGAAGCA

AGGGCGTTACCGCAAAAATGAGGGTAGACCACGTTACAATCCACAGAGATACGGAGACCCC

ATGGAACTAGACGCCACGCACTACACAAACGGGAACGATGACTCGGAAAAGAGACGAAGA

CGAGAAAACAACTTATGCTTTGAATGTGGAAAAGCAGGGCACCGAGCAGCAGACTGCCGAA

GCAAGAAGACAGGAGGAAAAAGGGGCAACTTCAAACCTAAGTTCGGCAAAGGCCAACTTA

ACGCTACCTTTACAATCCCAGAAAATCCAACTAAATCCGAAAATACTGAGACTTTCACCGTT

GAGGAATTCCAGCAATTACTAAAGGAATTACCACGAAATCAAGAGGGCATGAATGCAATAG
```

```
ACTTATGGGAGCAAGAGTATTACAGAACCCCAACACCCTCTGTGACAGAAGAAAGTCATCA
GGACGAGGCAGAAGCAGACCACGCCACGATGAGCTGGACAGCTTGCTATGATGAATTCTGC
GGAATCCATCGATCAGATAAAGAAGCAACCGGATGGTTCCCTAAGAAGAGAAAGACGAAG
AACCATCAGAATAATGTAACATGCGAGGATTTAACTCCCAATATAACTTCGCAAGAAGTTCG
CAAAGTTACCCAGCAGTTAAATGCTACGGGACAGGCAGGACAGATATACTGCAAGGTTCAG
ATAAATGGACACATACAATCAGCCATGATAGATTCAGGGGCTACAGGAAATTTTATTGCACC
GGAAGCTGTAAAGTACTTGGGAATACCACTTCAAACGAAACAACACCCCTATCGATTGCAG
GACACGCTAGAGGCGTCCGCGAGACGTAACACGCGCCAAGGAGAGTTGAACGCGAACAAC
ACCGGCGACGTAGGACACCCAGTCCAGGGTCCTCCATTAAGAGCGAAGGCCAGTACACCTC
CTCTACAAATGCAGAAGCCAACGACACGGCACGAAATCGCAATCGAGGCAAAAGAAAGGC
CTACGATACCAGAACAGTACAAGAAATATGAACATGTTTTCAAAGAACCAGGGATCCATGA
GGCTTTACCAGAACACAAGCCATGGGATCATGAGATAATATTGGAGGAAGGCAAGATGCCT
GTGCACACCCCAATTTATTCAATGTCAGCCGATGAGTTAAAAAGGCTCAGAGAATACATCGA
CGACAATTTAGCCAAGGGATGGATCAGGGAATCCGCGTCCCAAGTGGCCAGTCCAACTATG
TGGGTACCCAAGAAGGATGGACCCGATAGACTAGTTGTAGACTATAGAAAGCTTAACGCAC
TCACTAAGAAGGATCGATATCCACTTCCATTAGCTACGGAATTAAGAGATCGATTAGGCGGA
GCTACGATATTTACCAAGATGGACCTACGTAATGGTTACCACTTGATCAGAATGAAGGAAGG
CGAAGAATGGAAGACCGCTTTCAAAACAAGATACGGGCTATACGAGTACCAAGTTATGCCG
TTCGGGCTAACCAACGCACCAGCTACTTTCATGAGGCTTATGAACAATGTGTTGTCACAATA
CTTGGATACTTGCTGTATATGCTACTTGGACGACATCCTAGTATATTCAAACAACAAGGTTC
AACACATTAAGGACGTTAGCAACATCCTCGAAAGCCT
ATCCAAGGCAGACTTGCTGTGCAAACCAAGCAAATGCGAATTCCATGTCACAGAGACAGAC
TTCTTGGGATTCACCGTATCAAGCCAAGGGCTCAAGATGAGCAAAGACAAGGTTAAGGCAG
TGCTCGAATGGAAACAGCCAACCACAATCAAGGAGGTACAATCCTTTCTAGGGTTCGTCAAC
TTCTACAGAAGATTTATCAAGGGTTATTCAGGGATTACTACACCCTTGACCACGTTAACCAG
AAAAGATCAAGGAAGCTTCGAATGGACTGCCAAAGCACAGGAGTCATTCGATACGCTCAAA
CAAGCAGTGGCAGAAGAGCCAATACTATTGACTTTTGACCCAGAGAAAGAAATCATAGTGG
AGACGGACTCCTCGGATTTCGCTATAGGAGCAGTTCTGAGCCAACCGGGCCAGAATGGAAA
ATACCAGCCAATCGCATTCTATTCCCGAAAACTATCACCAGCTGAGTTGAATTACGAGATAT
ATGACAAAGAATTGCTGGCGATAGTCGATGCATTTAGAGAATGGCGAGTATATTTGGAAGG
ATCGAAATACACAGTACAGGTGTATACAGATCATAAGAACTTGGTTTACTTCACCACAACGA
AGCAGTTAAACAGACGACAGGTCAGATGGTCGGAGACCATGGCCAACTACAATTTCAGAAT
TTCATATGTCAAAGGATCAGAAAACGCTAGAGCCGACGCTCTTAGCCGAAAACCAGAATAT
CAAGAAAACAAAACGTACGAGTCATACGCTATATTCAAGAAAGACGGCGAATCACTGGTTT
ACAATGCACCACAGCTTGCAGCAACACACCTGTTGGAAGACAACTACCTTAGGAAACAGAT
CCAATCACACTACGACAAGGATGCTACTGCCACACGCATACGTAAGACAATAGAACCAGGA
TTCACTATAGAAAATGATACCATATACTTTCATGGAAAAGTATACATTCCGAGTCAAATGA
CCAAGGAATTTGTGACGGAACAACACGGATTGCCGGCACATGGACACCAAGGAATTGCAAG
GACATTTGCAAGAATACGGGAAATCAGTTACTTCCCACGAATGAGAACGATAGTTGAAGAA
GTTGTTGGAAATTGTGACACCTGCATACGAAACAAGTCATCACGACATGCTCCGTATGGTCA
```

-continued

```
GCTCCAGACCCCAGACATGCCTTCTCAGCCATGGAAGTCCATCACATGGGACTTTGTGGTCA

AACTACCACTCTCCAAGGATCCTACTACAGGAATTGAGTACGACGCGATACTCAATATAGTA

GACAGGCTAACGAAATTTGCATATATGATACCATTCAAGGAAACATGGGATGCTGAGCAAC

TAGCATATGTGTTCCTTAGGATCATAGTAAGCATACACGGAGTACCAGATGAGATAATCTCG

GATCGAGACAAGCTCTTTACCTCGAAATTCTGGACTACCTTATTAGCACTTATGGGTATCAA

GAGAAAGCTATCGACATCTTTCCACCCACAAACAGATGGTCAAACAGAGAGGACCAATCAG

ACAATGGAAGCATATCTTAGATGCTATCGTATAAAATCCCGATACCACAAGAAGTTAATGCC

GAATCAGCGATAG
```

SEQ ID NO:17 - LTR for siR5
>BC1G_12842.1 retrotransposable element Tf2 1 Protein type 1
(Transcript:BC1T_12842)

```
ATGGCATCCAGAGCTACCGCCACAGGTCAGCCTACCGGAGATACCAACGACATCGAGATGA

CCGATGCCCCAAAGGAGATCACTATCAACGAAACCCTTAAGATCGCCTTACCAGACAAGTA

CCAAGGTAGTCGACAAGAGCTCGATACTTTCCTCTTACAACTTGAGATCTACTTTCGATTCAA

TGAGGACAAGTTCACTACCAAGGAATCCAAGAGTATATGGGCCGCATCATACCTTCGAGGT

GAAGCAACCAAATGGATCCAACCATATTTGCGCGACTATTTCGAGCATGACGATAAGGATC

GCATGCAACCCACCCGAACAATCTTCAATAGCTTTGAAGGATTTAAGACAGAGATTCGTAGA

ATCTTCGGAAATTCCAACGAGCTAGAGGTAGCGGAAGATAAGATCTTCAACCTCAAGCAGA

CAGGATCAGCATTGAAATATGCTACGGAATTTCGAAGATACGCTGGAACAACCAAGTGGGA

CGAAATCGCTATCATGAGTCACTACCGCAAGGGACTCAAACCAGAAGTCAGACTGGAATTA

GAAAGATCTGCCGAGAGTACAGATCTGAACGATCTAATTCAGGACTCCATCGAATCAGATG

ATCGTCTCTACAGATATCGACAAAGCCAGAGATCATACAAACCCCAAGGAAATCAGAAGCA

AGGGCGTTACCGCAAGAATGAGGGTAGACCACGTTACAATCCACAAAGATACGGAGACCCC

ATGGAACTAGACGCTACGCACTACACAAACGGGAACGATGACTCAGAAAAGAGACGAAGA

CGAGAAAACAACTTATGCTTTGAATGTGGAAAAGCAGGGCACCGAGCAGCAGACTGCCGAA

GCAAGAAGACAGGAGGAAAAAGGGGCAACTTCAAACCTAAGTTCGGCAAAGGCCAACTTA

ACGCTACCTTTACAATCCCAGAAAACCCAACTAAATCCGAAAATACTGAGACTTTCACCGTT

GAGGAATTCCAGCAATTACTAAAGGAATTACCACGAAATAAAGAGGGCATGAATGCAATAG

ACTTATGGGAACAAGAGTATTACAGAACCCCAACACCCTCTGTGACAGAAGAAAGTCACCA

GGACGAGGCAGAAGCGGACCACGCCACGATGAGCTGGACAGCTTGCTATGATGAATTCTGC

GGAATCCATCGATCAGATAAAGAAGCAACCGGATGGTTCCCCAAGAAAAGGAAGACGAAG

AACCATCAGAATAATGTAACATGCACGGATTTAACTTCAAATATAACTTCGCGAAAAGTTCG

CAAAGTTACCCAGCAGTTGAATGCTACGGGACAAGCAGGACAGATATACTGCAAGGTTCAG

ATAAATGGACACATACAATCAGCCATGATAGATTCAGGGGCTACAGGAAATTTTATTGCACC

AGAAGCTGCAAAGTACTTGGAAATACCACTTCAGACGAAACAATACCCCTATCGATTGCAGT

TAGTTGACGGACAGCTAGCAGGGTCTGACGGAAAGATTTCGCAGGAGACAATCCCAGTACG

AATGGGCATAACCCAACATACAGAGGTTATACAGCTTGACGTTGTGCCATTGGGCCAACAAC

AGATCATCTTAGGAATGCCATGGTTGAAGGCACATAATCCGAAAATAGATTGGGCACAAGG

AATTGTGACATTTGATCAGTGCAAAAGCGGTCACAGGGACACGCTAGAGGCGTCCGCGAGA

CGTAACACGCGCCAAGGAGAGTTGAACGCGAACAACACCGGCGACGTAGGACACCCAGTCC
```

```
AGGGTCCTCCATTAAGAGCGAAGGCCAGTACACCTCCTCTACAAATGCAGAAGCCAACGAC

ACGGCACGAAATCGCAATCGAGGCAAAAGAAAGGCCTACGATACCAGAACAGTACAAGAA

ATATGAACATGTTTTCAAAGAACCAGGGATCCATGAGGCTTTACCGGAACACAAGCCATGG

GATCATGAGATAATATTGGAGGAAGGCAAGATGCCTGTGCACACCCCAATTTATTCAATGTC

AGCCGATGAGTTAAAAAGGCTCAGAGAATACATCGACGACAATTTAGCCAAGGGATGGATC

AGGGAATCCGCGTCCCAAGTGGCCAGTCCAACTATGTGGGTACCCAAGAAGGATGGACCCG

ATAGACTAGTTGTAGACTATAGAAAGCTTAACGCACTCACTAAGAAGGATCGATATCCACTT

CCATTAGCTACGGAATTAAGAGATCGATTAGGCGGAGCTACGATATTCACCAAGATGGACCT

ACGTAATGGTTACCACTTGATCAGAATGAAGGAAGG

CGAAGAATGGAAAACCGCTTTCAAAACAAGATACGGGCTATACGAGTACCAAGTTATGCCG

TTCGGGCTAACCAACGCACCAGCTACTTTCATGAGGCTTATGAACAATGTGTTGTCACAATA

TTTGGATACTTGCTGTATATGCTACTTGGACGACATCCTAGTATATTCAAACAACAAGGTTCA

ACACATTAAGGACGTTAGCAGCATCCTCGAAAGTCTATCCAAAGCAGACTTGCTGTGCAAAC

CAAGCAAATGCGAATTCCATGTCACAGAAACAGAATTCTTGGGATTCACCGTATCAAGCCAA

GGGCTCAAGATGAGCAAAGACAAGGTTAAGGCAGTGCTCGAATGGAAGCAGCCGACCACA

ATCAAGGAAGTACAATCCTTTCTAGGATTTGTCAACTTCTATAGAAGATTTATCAAGGGTTA

TTCAGGGATTACTACACCCTTGACCACGTTAACCAGAAAAGATCAAGGAAGCTTCGAATGG

ACTGCCAAAGCACAGGAGTCATTCGATACACTCAAACAAGCAGTGGCAGAAGAACCAATAC

TGTTGACTTTTGACCCAGAGAAAGAAATCATAGTGGAAACGGATTCCTCAGATTTCGCTATA

GGAGCAGTTCTGAGCCAACCGGGCCAGAATGGAAAATACCAGCCAATCGCATTCTACTCCC

GAAAACTATCACCAGCCGAGTTGAATTACGAGATATATGACAAAGAATTACTGGCGATAGT

CGATGCATTTAGAGAATGGCGAGTATATTTGGAAGGATCGAAATACACAGTACAGGTGTAT

ACAGATCATAAGAACTTGGTTTACTTCACCACAACGAAGCAGTTAAACAGACGACAGGTCA

GATGGTCGGAGACCATGGCCAACTACAATTTCAGAATTTCATATGTCAAAGGATCAGAAAA

CGCTAGAGCCGACGCTCTTAGCCGAAAACCAGAATATCAAGAAAACAAAACGTACGAGTCA

TACGCTATATTCAAGAAAGACGGCGAATCACTGGTCTACAATGCACCACAGCTTGCAGCAAC

ACACCTGTTGGAAGACAACCACCTCAGAAAACAGATTCAATCACACTACGACAAGGATGCT

ACTGCCACACGCATACGCAAGACAATAGAACCAGGATTCACTATAGAAAATGATACCATAT

ACTTTCATGGAAAAGTATACATTCCGAGTCAAATGACCAAGGAATTTGTGACGGAACAAC

ATGGGTTGCCGGCACATGGACACCAAGGAATTGCAAGGACATTTGCAAGAATACGGGAAAT

CAGTTACTTCCCACGAATGAGAACGATAGTTGAAGAAGTTGTTGGAAATTGTGACACCTGCA

TACGAAACAAGTCATCACGACATGCTCCGTATGGTCAGCTCCAGACCCCAGACATGCCTTCT

CAGCCATGGAAGTCCATCACATGGGACTTTGTGGTCAAACTACCACTCTCAAAGGATCCTAC

TACAGGAATTGAGTACGACGCGATACTCAATATAGTAGACAGGCTAACGAAATTTGCATAT

ATGATACCATTCAAGGAAACATGGGATGCTGAACAACTAGCATATGTGTTCCTAAGGATCAT

AGTAAGCATACACGGAGTACCAGATGAGATAATCTCGGATCGAGACAAGCTCTTTACCTCA

AAATTCTGGACTACCTTATTAGCACTTATGGGTATCAAGAGAAAGCTATCGACATCTTTCCA

CCCACAAACAGATGGTCAAACAGAGAGGACCAATCAGACAATGGAAGCATATCTTAGAT GC

TATGTAAATTATCGACAAGACAATTGGGTAGAACTATTACCTATGGCACAATTCGCATATAA

TACATCGGAAACGGAAACCACGAAAATCACACCAGCACGAGCTAATTTTGGGTTTAATCCA
```

```
CAAGCGTATAAAATCCCGATACCACAAGAAGTTAATGCCGAATCAGCAATAGTACAAGTCG

AACAGCTGAAAAATCTCCAAGAGCAACTGGCTCTTGATCTAAGATTCATATCTTCCAGAACA

GCAGCGTACTACAATACGAAACGTAGTATGGAACCTACGCTTAAAGAGGGGGATAAAGTTT

ATTTGCTACGACGAAACATCGAAACCAAGAGACCAAGCAATAAACTCGACCACAGGAAACT

AGGACCATTCAAGATTGATAAGGTAATAGGAACGGTTAATTATCGATTGAAATTACCAGAC

ACAATGAATATCCACCCAGTATTCCACATATCCTTGCTCGAACCAGCACCACCAGGAGCGCC

AAATGCGCCATTTACAGAAATTGAACCAG

TCAACCCAAACGCCATATACGATGTCGAAACAATACTAGACTGCAAATACGTCAGAAACAA

GGTCAAGTATTTGATCAAATGGTTAGACTACCCACATTCAGAAAACACATGGGAATTCAAGG

AGGATCTCAGCTGCCCTGAGAAGCTACGGGCATTCCACCTGAAGTACCCACACCTGCCAGTA

AAGCCTCAAGATCCG

CTTCGGACAACTCAGGCAAAGAAGGATCGAAGAAGTCGAAGGAAGAAGAATCAATAG

SEQ ID NO:18 - LTR for siR5
>BC1G_07532 - retrotransposable element Tf2 1 Protein type 1

ATGGCATCCAGAGCTACCGCCACAGGTCAATCTGCCGGAGACACCAACGACATCGAGATGA

CCGACGCCCCAAAGGAGATCACTATCAACGAAACCCTTAAGATCGCCTTACCAGACAAGTA

CCAAGGTAGTCGACAAGAGCTCGATACTTTCCTCTTACAACTTGAGATCTACTTTCGATTCAA

TGAGGACAAGTTCACTACCAAGGAATCCAAGAGTATATGGGCCGCATCATACCTTCGAGGT

GAAGCAACCAAATGGATCCAACCATATTTGCGCGACTATTTCGAGCATGACGATAAGGATC

GTATGCAACCCACCCGAACAATCTTCAATAGTTTTGAAGGATTTAAGACAGAGATTCGTAGA

ATCTTCGGAAATTCCAACGAGTTAGAGGTAGCGGAAGATAAGATCTTCAACCTCAAGCAGA

CAGGATCAGCATTGAAATATGCTACGGAATTTCGAAGATATGCTGGAACAACCAAGTGGGA

CGAAATCGCTATCATGAGTCACTACCGCAAGGGACTCAAACCAGAAGTCAGACTGGAATTA

GAAAGATCTGCCGAGAGTACAGATCTGAACGATCTAATTCAGGACTCCATCGAATCAGATG

ATCGTCTCTACAGATATCGACAAAGCCAGAGATCATACAAACCCCAAGGAAATCAGAAGCA

AGGGCGTTACCGCAAAAATGAGGGTAGACCACGTTACAATCCACAGAGATACGGAGACCCC

ATGGAACTAGACGCCACGCACTACACAAACGGGAACGATGACTCGGAAAAGAGACGAAGA

CGAGAAAACAACTTATGCTTTGAATGTGGAAAAGCAGGGCACCGAGCAGCAGACTGCCGAA

GCAAGAAGACAGGAGGAAAAAGGGGCAACTTCAAACCTAAGTTCGGCAAAGGCCAACTTA

ACGCTACCTTTACAATCCCAGAAAATCCAACTAAATCCGAAAATACTGAGACTTTCACCGTT

GAGGAATTCCAGCAATTACTAAAGGAATTACCACGAAATCAAGAGGGCATGAATGCAATAG

ACTTATGGGAGCAAGAGTATTACAGAACCCCAACACCCTCTGTGACAGAAGAAAGTCATCA

GGACGAGGCAGAAGCAGACCACGCCACGATGAGCTGGACAGCTTGCTATGATGAATTCTGC

GGAATCCATCGATCAGATAAAGAAGCAACCGGATGGTCCCCTAAGAAGAGAAAGACGAAG

AACCATCAGAATAATGTAACATGCGAGGATTTAACTCCCAATATAACTTCGCAAGAAGTTCG

CAAAGTTACCCAGCAGTTAAATGCTACGGGACAGGCAGGACAGATATACTGCAAGGTTCAG

ATAAATGGACACATACAATCAGCCATGATAGATTCAGGGGCTACAGGAAATTTTATTGCACC

GGAAGCTGTAAAGTACTTGGGAATACCACTTCAAACGAAACAACACCCCTATCGATTGCAG

GACACGCTAGAGGCGTCCGCGAGACGTAACACGCGCCAAGGAGAGTTGAACGCGAACAAC

ACCGGCGACGTAGGACACCCAGTCCAGGGTCCTCCATTAAGAGCGAAGGCCAGTACACCTC
```

```
CTCTACAAATGCAGAAGCCAACGACACGGCACGAAATCGCAATCGAGGCAAAAGAAAGGC

CTACGATACCAGAACAGTACAAGAAATATGAACATGTTTTCAAAGAACCAGGGATCCATGA

GGCTTTACCGGAACACAAGCCATGGGATCATGAGATAATATTGGAGGAAGGCAAGATGCCT

GTGCACACCCCAATTTATTCAATGTCAGCCGATGAGTTAAAAAGGCTCAGAGAATACATCGA

CGACAATTTAGCCAAGGGATGGATCAGGGAATCCGCGTCCCAAGTGGCCAGTCCAACTATG

TGGGTACCCAAGAAGGATGGACCCGATAGACTAGTTGTAGACTATAGAAAGCTTAACACAC

TCACTAAGAAGGATCGATATCCACTTCCATTAGCTACGGAATTAAGAGATCGGTTAGGCGGA

GCTACGATATTTACCAAGATGGACCTACGTAATGGTTACCACTTGATCAGAATGAAGGAAGG

CGAAGAATGGAAGACCGCTTTCAAAACAAGATACGGGCTATACGAGTACCAAGTTATGCCG

TTCGGGCTAACCAACGCACCAGCTACTTTCATGAGGCTTATGAACAATGTGTTGTCACAATA

CTTGGATACTTGCTGTATATGCTACTTGGACGACATCCTAGTATATTCAAACAACAAGGTTC

AACACATTAAGGACGTTAGCAACATCCTCGAAAGCCTATCCAAGGCAGACTTGCTGTGCAA

ACCAAGCAAATGCGAATTCCATGTCACAGAGACAGAATTCTTGGGATTCACCGTATCAAGCC

AAGGGCTCAAGATGAGCAAAGACAAGGTTAAGGCAGTGCTCGAATGGAAGCAGCCAACCA

CAATCAAGGAAGTACAATCCTTTCTAGGGTTCGTCAACTTCTACAGAAGATTTATCAAGGGT

TATTCAGGGATTACTACACCCTTGACCACGTTAACCAGAAAAGATCAAGAAAGCTTCGAATG

GACTGCCATAGCACAGGAGTCATTCGATACGCTCAAACAAGCAGTGGCAGAAGAGCCAATA

CTATTGACTTTTGACCCAGAGAAAGAAATCATAGTGGAGACGGACTCCTCGGATTTCGCTAT

AGGAGCAGTTCTGAGCCAACCGGGCCAGAATGGAAAATACCAGCCAATCGCATTCTACTCC

CGAAAACTATCACCAGCCGAATTGAATTACGAGATATATGACAAAGAATTGCTGGCGATAG

TCGATGCATTTAGAGAATGGCGAGTATATTTGGAAGGATCGAAATACACAGTACAGGTGTAT

ACAGATCATAAGAACTTGGTTTACTTCACCACAACGAAGCAGTTAAACAGACGACAGGTCA

GATGGTCGGAGACCATGGCCAACTACAATTTCAGAATTTCATATGTCAAAGGATCAGAAAA

CGCTAGAGCCGACGCTCTTAGCCGAAAACCAGAATATCAAGAAAACAAAACGTACGAGTCA

TACGCTATATTCAAGAAAGACGGCGAATCACTGGTTTACAATGCACCACAGCTTGCAGCAAC

ACACCTGTTGGAAGACAACTACCTTAGGAAACAGATCCAATCACACTACGACAAGGATGCT

ACTGCCACACGCATACGCAAGACAATAGAACCAGGATTCACTATAGAAAATGATACCATAT

ACTTTCATGGAAAAGTATACATTCCGAGTCAAATGACCAAGGAATTTGTGACGGAACAAC

ATGGGTTGCCGGCACATGGACACCAAGGAATTGCAAGGACATTTGCAAGAATACGGGAAAT

CAGTTACTTCCCACGAATGAGAACGATAGTTGAAGAAGTTGTTGGAAATTGTGACACCTGCA

TACGAAACAAGTCATCACGGCATGCTCCGTATGGTCAGCTCCAGACCCCAGACATGCCTTCT

CAGCCATGGAAGTCCATCACATGGGACTTTGTGGTCAAACTACCACTCTCAAAGGATCCTAC

TACAGGAATTGAGTACGACGCGATACTCAATATAGTAGACAGGCTAACGAAATTTGCATAT

ATGATACCATTCAAGGAAACATGGGATGCTGAACAACTAGCATATGTGTTCCTAAGGATCAT

AGTAAGCATACACGGAGTACCAGATGAGATAATCTCGGATCGAGACAAGCTCTTTACCTCG

AAATTCTGGACTACCTTATTAGCACTTATGGGTATCAAGAGAAAGCTATCGACATCTTTCCA

CCCACAAACAGATGGTCAAACAGAGAGGACCAATCAGACAATGGAAGCATATCTTAGATGC

TATCGTATAAAAATCCCGATACCACAAGAAGTTAATGCCGAATCAGCAATAG
```

SEQ ID NO:19 - LTR for siR5
>BC1G_09712 - enzymatic polyprotein

```
ATGGCATCCAGAGCTACCGCCACAGGTCAGTCTACCGAAGATACCAACGACATCGAGATGA
CCGATGCCCCAAAGGAGATCACTATCAACGAAACACTTAAGATCGCCTTACCAGACAAGTA
CCAAGGTAGTCGACAAGAGCTCGATACTTTCCTCTTACAACTTGAGATCTACTTCCGATTCA
ATGAAGACAAGTTCACTACCAAGGAATCCAAGAGCATATGGGCTGCATCATACCTCCGAGG
TGAAGCAACCAAATGGATTCAACCATATTTGCGCGACTATTTCGAGCATGACGATAAGGATC
GCATGCAACCCACCCGAACAATCTTCAATAGTTTTGAAGGATTTAAGACAGAGATTCGTAGA
ATCTTCGGAAATTCCAACGAGTTAGAGGTAGCGGAAGATAAGATCTTCAACCTCAAGCAGA
CAGGATCAGCATTGAAATATGCTACGGAATTTCGAAGATATGCTGGAACAACCAAGTGGGA
CGAAATCGCTATCATGAGTCACTACTGTAAGGGACTCAAACCAGAAGTCAGACTAGAGTTA
GAAAGATCTGCCGAGAGTACAGATCTGAACGATCTAATTCAGGACTCCATCGAATCAGATG
ATCGTCTCTATAGATATCGACAAAGCCAAAGATCATACAAACCCCAAGGAAACCAAAAGCA
AGGGCGTTACCGCAAGAATGAGGGTAGACCACGTTACAATCCACAGAGATACGGAGACCCC
ATGGAACTAGACGCCACGCACTACACAAACGGGAACGATGACTCAGAAAAGAGACGAAGA
CGAGAAAACAACTTATGCTTTGAATGTGGAAAAGCAGGGCACCGAGCAGTAGACTGCCGAA
GCAAGAAGACAGGAGGAAAAAGGGGCAACTTCAAACCTAAGTTCGGCAAGGGCCAACTTA
ACGCCACCTTTGCCATCTCAGAAAACTCAACTAAAACCGAAAATACTGAGACTTTCACCGTT
GAGGAATTTCAGCAATTACTAAAGGAATTACCACGAAATAAAGAGGGCATGAATGCAATAG
ACTTATGGGAACAAGAGTATTACAGAACCCCAACACCCTCTGTGACAGAAGAAAGTCACCA
GGACGAGGCAGAAGCGGACCACGCCACGATGAGCTGGACAGCTTGCTATGATGAATTCTGC
GGAATCCATCGATCAGATAAAGAAGCAACCGGATGGTTCCCCAAGAAAAGGAAGACGAAG
AACCATCAGAATAATGTAACATGCGAGGATTTAACTCCCAATATAAACTTCGCAAGAAGTTCG
CAAAGTTACCCAGCAGTTGAATGCTACGGGACAGGCAGGACAAGTGTACTGCAAGGTCCAG
ATAAATGGACACATACAATCAGCCATGATAGATTCAGGGGCTACAGGAAATTTTATTGCACC
AGAAGCTGCAAAGTACTTGGAAATACCACTTCAAACGAAACAACACCCCTATCGATTGCAG
GACACGCTAGAGGCGTCCGCGAGACGTAACACGCGCCAAGGGGAGTTGAACGCGAACAAC
ACCGGCGACGTAGGACACCCAGTCCAGGGTCCTCCATTAAGAGCGAAGGCCAGTACACCTC
CTCTACAAATGCAGAAGCCAACGACACGGCACGAAATCGCAATCGAGGCAAAAGAAAGGC
CTACGATACCAGAACAGTACAAGAAATATGAACATGTTTTCAAAGAACCAGGGATCCATGA
GGCTTTACCGGAACACAAGCCATGGGATCATGAGATAATATTGGAGGAAGGCAAGATGCCT
GTGCACACCCCAATTTATTCAATGTCAGCCGATGAGTTAAAAAGGCTCAGAGAATACATCGA
CGACAATTTAGCCAAGGGATGGATCAGGGAATCCGCGTCCCAAGTGGCCAGTCCAACTATG
TGGGTACCCAAGAAGGATGGACCCGATAGACTAGTTGTAGACTATAGAAAGCTTAACGCAC
TCACTAAGAAGGATCGATATCCACTTCCATTAGCTACGGAATTAAGAGATCGATTAGGCGGA
GCTACGATATTCACCAAGATGGACCTACGTAATGGTTACCACTTGATCAGAATGAAGGAAG
GCGAAGAATGGAAAACCGCTTTCAAAACAAGATACGGGCTATACGAGTACCAAGTTATGCC
ATTCGGGCTAACCAACGCACCAGCTACTTTCATGAGGCTTATGAACAATGTGTTGTCACAAT
ATTTGGATACTTGCTGTATATGCTACTTGGACGACATCCTAGTATATTCAAACAACAAGGTTC
AACACATTAAGGACGTTAGCAACATCCTCGAAAGTCT
```

```
ATCCAAAGCAGACTTGCTGTGCAAACCAAGCAAATGCGAATTCCATGTCACAGAAACAGAA
TTCTTGGGATTCACCGTATCAAGCCAAGGGCTCAAGATGAGCAAAGACAAGGTTAAGGCAG
TGCTCGAATGGAAGCAGCCAACCACAATCAAGGAGGTACAATCCTTTCTAGGGTTCGTCAAC
TTCTACAGAAGATTTATCAAGGGTTATTCAGGGATTACTACACCCTTGACCACGTTAACCAG
AAAAGATCAAGGAAGCTTCGAATGGACTGCCAAAGCACAGGAGTCATTCGATACACTCAAA
CAAGCAGTGGCAGAAGAACCAATACTGTTGACTTTTGACCCAGAGAAAGAAATCATAGTGG
AAACGGATTCCTCAGATTTCGCTATAGGAGCAGTTCTGAGCCAACCGGGCCAGAATGGAAA
ATACCAGCCAATCGCATTCTACTCCCGAAAACTATCACCAGCTGAGTTAAATTACGAGATAT
ATGACAAAGAATTACTGGCAATAGTCGATGCATTTAGAGAATGGCGAGTATATTTGGAAGG
ATCGAAATACACAGTACAGGTGTATACAGATCATAAGAACTTGGTTTACTTCACCACAACGA
AGCAGTTAAACAGACGACAGGTCAGATGGTCGGAGACCATGGCCAACTACAATTTCAGAAT
TTCATATGTCAAAGGATCAGAAAACGCTAGAGCCGACGCTCTTAGCCGAAAACCAGAATAT
CAAGAAAACAAAACGTACGAGTCATACGCTATATTCAAGAAAGACGGCGAATCACTGGTCT
ACAATGCACCACAGCTTGCAGCAACACACCTGTTGGAAGACAACCACCTCAGGAAACAGAT
CCAATCACACTACAACAAGGATGCTACTGCCACACGCATACGCAAGACAATAGAACCAGGA
TTCACTATAGAAGATGATACCATATACTTTCATGGAAAGGTATACATTCCGAGTCAAATGA
CCAAGGAATTTGTGACGGAACAACACGGATTGCCGGCACATGGACACCAAGGAATTGCAAG
GACATTTGCAAGAATACGGGAAATCAGTTACTTCCCACGAATGAGAACGATAGTTGAAGAA
GTTGTTGGAAATTGTGACACCTGCATACGAAACAAGTCATCACGACATGCTCCGTATGGTCA
GCTCCAGACCCCAGACATGCCTTCTCAGCCATGGAAGTCCATCACATGGGACTTTGTGGTCA
AACTACCACTCTCAAAGGATCCTACTACAGGAATTGAGTACGACGCGATACTCAATATAGTA
GACAGGCTAACGAAATTTGCATATATGATACCATTCAAGGAAACATGGGATGCTGAGCAAC
TAGCATATGTGTTCCTAAGGGTCATAGTAAGCATACACGGAGTACCAGATGAGATAATCTCG
GATCGAGACAAGCTCTTTACCTCGAAATTCTGGACTACCTTATTAGCACTTATGGGTATCAA
GAGAAAGCTATCGACATCTTTCCACCCACAAACAGATGGTCAAACAGAGAGGACCAATCAG
ACAATGGAAGCATATCTTAGATGCTATCGTATAAAATCCCGATACCACAAGAAGTTAATGCC
GAATCAGCAATAG
SEQ ID NO:20 - LTR for siR5
>BC1G_15972 - enzymatic Polyprotein ATGGCATCCAGAGCTACCGCCACAGGTCAATCTGCCGGAGACACCAACGACATCGAGATGA
CCGACGCTCCAAAGGAGATCACTATCAACGAAACCCTTAAGATCGCCTTACCAGACAAGTA
CCAAGGTAGTCGACAAGAGCTCGATACTTTCCTCTTACAACTTGAGATCTACTTCCGATTCA
ATGAGGACAAGTTCACTACCAAGGAATCCAAGAGCATATGGGCCGCGTCATACCTTCGAGG
TGAAGCAACCAAATGGATTCAACCATATTTGCGCGACTATTTCGAGCATGACGATAAGGATC
GCATGCAACCCACCCGAACAATCTTCAATAGTTTTGAAGGATTTAAGACAGAGGTTCGTAGA
ATCTTCGGAAATTCCAACGAGTTAGAGGTAGCGGAAGATAAGATCTTCAACCTCAAGCAGA
CAGGATCAGCATTGAAATATGCTACGGAATTTCGAAGATATGCTGGAACAACCAAGTGGGA
CGAAATCGCTATCATGAGTCACTACCGCAAGGGACTCAAACCAGAAGTCAGACTAGAATTA
GAAAGATCTGCCGAGAGTACAGATCTAAACGATCTAATTCAGGACTCCATCGAATCAGATG
ATCGTCTCTACAGATATCGACAAAGCCAAAGATCATACAAACCCCAAGGAAATCAGAAGCA
```

```
AGGGCGTTACCGCAAGAATGAGGGTAGACCACGTTACAATCCACAGAGATACGGAGACCCC
ATGGAACTAGACGCTACGCACTACACAAACGGGAACGATGACTCAGAAAAGAGACGAAGA
CGAGATAACAACTTATGCTTTGAATGTGGAAAAGCAGGGCACCGAGCAGCAGACTGCCGAA
GCAAGAAGACAGGAGGAAAAAGGGGCAACTTCAAACCTAAGTTCGGCAAGGGCCAACTTA
ATGCCACCTTTGCAATCTCAGAAAACTCAACTAAACCCGAAAATACTGAGACTTTCACCGTT
GAGGAATTCCAGCAATTATTAGAGGAATTACCACGAAACCAAGAGGGCATGAATGCAATAG
ACTTATGGGAACAAGAGTATTACAGAACTCCAACACCCTCTGTGACAGAAGAAAGTCACCA
GGACGAGGCAGAAGCGGACCACGCCACGATAAGCTGGACAGCTTGCTATGACGAATTCTGC
GGAATCCATCGATCAGATAAAGAAGCAACCGGATGGTTCCCCAAGAAGAGAAAGACGAAG
AACCGACAGAATAATGTAACATGCAAGGATTTAACTCCAAATGTAACTTCGCGAAAAGTTC
GCAAAGTTACACAGCAATTGAATGCTACGGGACAGGCAGGACAAATATACTGCACGGTTCA
GATAAATGGACACATACAATCAGCCATGATAGATTCAGGGGCTACAGGGAATTTTATTGCAC
CAGAAGCTGCAAAGTACTTGGAAATACCACTTCAAACGAAACAACACCCCTACCGATTGCA
GTTAGTTGACGGACAGCTAGCAGGGTCTGACGGAAAGATTTCGCAGGAGACAATCCCAGTA
CGAATGGGCATAACCCAACATACAGAGGTTATACAGCTTGACGTTGTGCCATTGGGCCAACA
ACAGATCATCTTAGGAATGCCATGGTTAAAGGCACATAATCCGAAAATAGATTGGGCACAA
GGAATTGTGACATTTGATCAGTGCAAAAGCGGTCACAGGGACACGCTAGAGGCGTTCGCGA
GACGTAACACGCGCCAAGGAGAGTTGAACGCGAACAACACCGGCGACGTAGGACACCCAGT
CCAGGGTCCTCCATTAAGAGCGAAGGCCAGTACACCTCCTCTACAAATGCAGAAGCCAACG
ACACGGCACGAAATCGCAATCGAGGCAAAAGAAAAGCCTACGATACCAGAACAGTACAAG
AATTATGAACATGTTTTCAAAGAACCAGGGATCCATGAGGCTTTACCGGAACACAAGCCATG
GGATCATGAGATAATATTGGAGGAAGGCAAGATGCCTGTGCACACCCCAATTTATTCAATGT
CAGCCGATGAGTTAAAGAGGCTCAGAGAGTACATCGACGACAATTTAGCCAAGGGATGGAT
CAGGGAATCCGCGTCCCAAGTGGCCAGTCCAACTATGTGGGTACCCAAGAAGGATGGACCC
GATAGACTAGTTGTAGACTATAGAAAGCTTAACGCACTCACTAAGAAGGATCGATATCCACT
TCCATTAGCTACGGAATTAAGAGATCGATTAGGCGGAGCTACGATATTTACCAAGATGGACC
TACGTAATGGTTACCACTTGATCAGAATGAAGGAAGG
CGAAGAATGGAAAACCGCTTTCAAAACAAGATACGGGCTATACGAGTACCAAGTTATGCCA
TTCGGGCTAACCAACGCACCAGCTACTTTCATGAGGCTTATGAACAATGTGTTGTCACAATA
TTTGGATACTTGCTGTATATGCTACTTGGACGACATCCTAGTATATTCAAACAACAAGGTTCA
ACACATTAAGGACGTTAGCAACATCCTCGAAAGCCTATCCAAGGCAGACTTGCTGTGCAAAC
CAAGCAAATGCGAATTCCATGTCACAGAGACAGAATTCTTGGGATTCACCGTATCAAGCCAA
GGGCTCAAGATGAGCAAAGGCAAGGTTAAGGCAGTGCTCGAATGGAAGCAGCCGACCACA
ATCAAGGAAGTACAATCCTTTCTAGGGTTCGTCAACTTCTACAGAAGATTTATCAAAGGTTA
TTCAGGGATTACTACACCCTTGACCACGTTAACCAGAAAAGATCAAGGAAGCTTCGAATGG
ACTGCCAAAGCACAGGAGTCATTCGATACGCTCAAACAAGCAGTGGCAGAAGAGCCAATAC
TATTGACTTTTGACCCAGAGAAAGAAATCATAGTGGAGACGGACTCCTCGGATTTCGCTATA
GGAGCAGTTCTGAGCCAACCGGGTCAGAATGGAAAATACCAGCCAATCGCATTCTACTCCC
GAAAACTATCACCAGCTGAGTTGAATTACGAGATATATGACAAAGAATTACTGGCGATAGT
```

CGATGCATTTAGAGAATGGCGAGTATATTTGGAAGGATCGAAATACACAGTACAGGTGTAC

ACAGATCATAAGAACTTGGTTTACTTCACCACAACGAAGCAGTTAAACAGACGACAGGTCA

GATGGTCGGAGACCATGGCCAACTACAACTTTAGAATTTCATATGTCAAAGGATCAGAAAAT

GCTAGAGCCGACGCTCTTAACCGAAAACCAGAATATCAAGAAAACAAAGCGTACGAGTCAT

ACGCTATATTCAAGAAAGACAGCGAATCACTGGTTTACAATACACCACAGCTTGCAACAAC

ACACCTGTTGGAAGACAACCACCTCAGGAAACAGATCCAATCACACTACGACAAGGATACT

ACTGCCACACGCATACGCAAAACAATAGAACCAGGATTCACTATAGAAAATGATACCATAT

ACTTTCATAGAAAAGTATACATTCCGAGTCAAATGACCAAGGAATTTGTGACGGAACAAC

ACGGGTTGCCGGCACATGGACACCAAGGAATTGCAAGGACATTTGCAAGAATACGGGAAAT

CAGTTACTTCCCACGAATGAGAACGATAGTTGAAGAAGTTGTTGGAAATTGTGACACCTGCA

TACGAAACAAGTCATCACGACATGCTCCGTATGGTCAGCTCCAGACCCCAGACATGCCTTCT

CAGCCATGGAAGTCCATCACATGGGACTTTGTGGTCAAACTACCACTCTCAAAGGATCCTAC

TACAGGAATTGAGTACGACGCGATACTCAATATAGTAGACAGGCTAACGAAATTTGCATAT

ATGATACCATTCAAGGAAACATGGGATGCTGAGCAACTAGCATATGTGTTCCTAAGGATCAT

AGTAAGCATACACGGAGTACCAGATGAGATAATCTCGGATCGAGACAAGCTCTTTACCTCG

AAATTCTGGACTACCTTATTAGCACTTATGGGTATCAAGAGAAAGCTATCGACATCTTTCCA

CCCACAAACAGATGGTCAAACAGAGAGGACCAATCAGACAATGGAAGCATATCTTAGATGC

TATGTAAATTATCGACAAGACAATTGGGTAGAGCTATTACCCATGGCACAGTTCGCATACAA

TACATCAGAAACGGAAACCACGAAAATCACACCAGCACGAGCTAATTTTGGGTTTAATCCA

CAAGCGTATAAAATCCCGATACCACAAGAAGTTAATGCCGAATCAGCGATAGTACAAGTCG

AACAGTTGAAAGATCTCCAAGAGCAACTGGCTCTTGATCTAAGATTCATATCTTCCAGAACA

GCAGCGTACTACAATACGAAACGTAGTATGGAACCTACGCTTAAAGAGGGGGATAAAGTTT

ATTTGCTACGACGAAACATCGAAACCAAGAGACCAAGCAATAAACTCGACCACAGGAAACT

AGGACCATTCAAGATTGATAAGGTAATAGGAACGGTTAATTATCAATTGAAATTACCAGAC

ACAATGAATATCCACCCAGTATTCCACATATCCTTGCTCGAACCAGCACCACCAGGAGCGCC

AAATGCGCCATTTACAGAAATTGAACCAG

TCAACCCAAACGCCATATACGATGTCGAAACAATACTAGACTGCAAATACGTCAGAAACAA

GGTCAAGTATTTGATCAAATGGTTAGACTACCCACATTCAGAAAACACATGGGAACTCAAG

GAAGATCTCAGCTGCCCTGAGAAACTACGGGCATTCCACCTGAAGTACCCACATCTGCCAAC

AAAGCCTCAAGCTCCG

CATCAGACAACAAAGGCAACGAGGGGTCGAAGAAACCAAAAGAAGAACCACTAG

SEQ ID NO:21 - LTR for siR5
>BC1G_13999 retrotransposable element Tf2 1 protein type 1

ATGTGGGTACCCAAGAAGGATGGACCCGATAGACTAGTTGTAGACTATAGAAAGCTTAACG

CACTCACTAAGAAGGATCGATATCCACTTCCATTAGCTACGGAATTAAGAGATCGATTAGGC

GGAGCTACGATATTCACCAAGATGGACCTACTATATTCAAACAACAAGGTTCAACACATTAA

GGACGTTAGCAACATCCTCGAAAGCCTATCCAAGGCAGACTTGCTGTGCAAACCAAGCAAA

TGCGAATTCCATGTCACAGAGACAGAATTCTTGGGATTCACCGTATCAAGCCAAGGGCTCAA

GATGAGCAAAGGCAAGGTTAAGGCAGTGCTCGAATGGAAGCAGCCGACCACAATCAAGGA

AGTACAATCCTTTCTAGGGTTCGTCAACTTCTACAGAAGATTTATCAAAGGTTATTCAGGGA

-continued

```
TTACTACACCCTTGACCACGTTAACCAGAAAAGATCAAGGAAGCTTCGAATGGACTGCCAA
AGCACAGGAGTCATTCGATACGCTCAAACAAGCAGTGGCAGAAGAGCCAATACTATTGACT
TTTGACCCAGAGAAAGAAATCATAGTGGAGACGGACTCCTCGGATTTCGCTATAGGAGCAG
TTCTGAGCCAACCGGGTCAGAATGGAAAATACCAGCCAATCGCATTCTACTCCGAAAACTA
TCACCAGCTGAGTTGAATTACGAGATATATGACAAAGAATTACTGGCGATAGTCGATGCATT
TAGAGAATGGCGAGTATATTTGGAAGGATCGAAATACACAGTACAGGTGTACACAGATCAT
AAGAACTTGGTTTACTTCACCACAACGAAGCAGTTAAACAGACGACAGGTCAGATGGTCGG
AGACCATGGCCAACTACAACTTTAGAATTTCATATGTCAAAGGATCAGAAAATGCTAGAGCC
GACGCTCTTAGCCGAAAACCAGAATATCAAGAAAACAAAACGTACGAGTCATACGCTATAT
TCAAGAAAGACGGCGAATCACTGGTTTACAATGCACCACAGCTTGCAGCAACACACCTGTTG
GAAGACAACCACCTCAGGAAACAGATCCAATCACACTACGACAAGGATGCTACTGCCACAC
GCATACGCAAGACAATAGAACCAGGATTCACTATAGAAAATGATACCATATACTTTCATGG
AAAAGTATACATTCCGAGTCAAATGACCAAGGAATTTGTGACGGAACAACACGGGTTGCC
GGCACATGGACACCAAGGAATTGCAAGGACATTTGCAAGAATACGGGAAATCAGTTACTTC
CCACGAATGAGAACGATAGTTGAAGAAGTTGTTGGAAATTGTGACACCTGCATACGAAACA
AGTCATCACGACATGCTCCGTATGGTCAGCTCCAGACCCCAGACATGCCTTCTCAGCCATGG
AAGTCCATCACATGGGACTTTGTGGTCAAACTACCACTCTCAAAGGATCCTACTACAGGAAT
TGAGTACGACGCGATACTCAATATAGTAGACAGGCTAACGAAATTTGCATATATGATACCAT
TCAAGGAAACATGGGATGCTGAGCAACTAGCATATGTGTTCCTAAGGATCATAGTAAGCAT
ACACGGAGTACCAGATGAGATAATCTCGGATCGAGACAAGCTCTTTACCTCGAAATTCTGGA
CTACCTTATTAGCACTTATGGGTATCAAGAGAAAGCTATCGACATCTTTCCACCCACAAACA
GATGGTCAAACAGAGAGGACCAATCAGACAATGGAAGCATATCTTAGATGCTATGTAAATT
ATCGACAAGACAATTGGGTAGAGCTATTACCCATGGCACAGTTCGCATACAATACATCAGA
AACGGAAACCACGAAAATCACACCAGCACGAGCTAATTTTGGGTTTAATCCACAAGCGTAT
AAAATCCCGATACCACAAGAAGTTAATGCCGAATCAGCGATATATGGAACCTACGCTTAA
```

SEQ ID NO:22 - LTR for siR5
>BC1G_04888.1 retrotransposable element Tf2 1 protein type 1
(Transcript:BC1T_04888)

```
ATGGCCAACTACAATTTTAGAATTTCATATGTCAAAGGATCAGAAAACGCTAGAGCCGACGC
TCTTAGCCGAAAACCAGAATATCAAGAAAACAAAACGTACGAGTCATACGCTATATTCAAG
AAAGACGGCGAATCACTGGTCTACAATGCACCACAGCTTGCAGCAACACACCTGTTGGAAG
ACAACCACCTCAGGAAACAGATCCAATCACACTACAACAAGGATGCTACTGCCACACGCAT
ACGCAAGACAATAGAACCAGGATTCACTATAGAAGATGATACCATATACTTTCATGGAAAA
GTATACATTCCGAGTCAAATGACCAAGGAATTTGTGACGGAACAACATGGGTTGCCGGCA
CACGGACATCAAGGGATTGCAAGAACATTTGCAAGAATCCGGGAAATCAGTTACTTCCCAC
GAATGAGAACGATAGTTGAAGAAGTTGTTGGAAATTGTGACACCTGCATACGAAACAAGTC
ATCACGACATGCGCCGTATGGTCAGCTCCAGACCCCAGACATGCCTTCTCAGCCATGGAAGT
CCATCACATGGGACTTTGTGGTCAAACTACCACTCTCAAAGGATCCTACTACAGGAATTGAG
TACGACGCGATACTCAATATAGTAGACAGGCTAACGAAATTCGCATATATGATACCATTCAA
GGAAACATGGGATGCTGAGCAACTAGCATATGTGTTCCTAAGGATCATAGTAAGCATACAC
GGAGTACCAGATGAGATAATCTCGGATCGAGACAAGCTCTTTACCTCGAAATTCTGGACTAC
```

CTTATTAGCACTTATGGGTATCAAGAGAAAGCTATCGACATCTTTCCACCCACAAACAGATG

GTCAAACAGAGAGGACCAATCAGACAATGGAAGCATATCTTAGATGCTATCGTATAAAATC

CCGATACCACAAGAAGTTAATGCCGAATCAGCGATAG

SEQ ID NO:23 - LTR for siR5
>BC1G_16375.1 hypothetical protein sitrilar to truncated Pol
(Transcript:BC1T_16375)

ATCCAATCACACTACAACAAGGATGCTACTGCCACACGCATACGCAAGACAATAGAACCAGG

ATTCACTATAGAAGATGATACCATATACTTTCATGGAAAAGTATACATTCCGAGTCAAATGAC

CAAGGAATTTGTGACGGAACAACATGGGTTGCCGGCACACGGACATCAAGGGATTGCAAGA

ACATTTGCAAGAATCCGGGAAATCAGTTACTTCCCACGAATGAGAACGATAGTTGAAGAAGTT

GTTGGAAATTGTGACACCTGCATACGAAACAAGTCATCACGACATGCGCCGTATGGTCAGCTC

CAGACCCCAGACATGCCTTCTCAGCCATGGAAGTCCATCACATGGGACTTTGTGGTCAAACTA

CCACTCTCAAAGGATCCTACTACAGGAATTGACATACACGGAGTACCAGATGAGATAATCTCG

GATCGAGACAAGCTCTTTACCTCGAAATTCTGGACTACCTTATTAGCACTTATGGGTATCAAGA

GAAAGCTATCGACATCTTTCCACCCACAAACAGATGGTCAAACAGAGAGGACCAATCAGACA

ATGGAAGCATATCTTAGATGCTATGTAAATTATCGACAAGACAATTGGGTAGAGCTATTACCCAT

GGCACAGTTCGCATACAATACATCGGAAACGGAAACCACGAAAATCACCCCAGCACGAGCTA

ATTTTGGGTTTAATCCACAAGCGTATAAAATCCCGATACCACAAGAAGTTAATGCCGAATCAGC

AATAGTACAAGTCGAACAGCTGAAAGATCTCCAAGAGCAACTGGCTCTTGATCTAAGATTCAT

ATCTTCCAGAACAGCAGCGTACTACAATACGAAACGTAGTATGGAACCTACGCTTAAAGAGGG

GGATAAAGTTTATTTGCTACAACGAAACATCGAAACCAAGAGACCAAGCAATAAACTCGACC

ACAGGAAACTAGGACCATTCAAGATTGATAAGGTAATAGGAACG

SEQ ID NO:24 - LTR for siR5
>BC1G_06254.1 retrotransposable element Tf2 1 Protein type 1
(Transcrpt :BC1T_06254)

ATGGCATCCAGAGCCACCGCCACAGGTCAGTCTACCGGAGATACCAACGACATCGAGATGAC

CGATGCCCCAAAGGAGATCACTATCAACGAAACACTTAAGATCGCCTTACCAGACAAGTACC

AAGGTAGTCGACAAGAGCTCGATACTTTCCTCTTACAACTTGAGATCTACTTCCGATTCAATGA

AGACAAGTTCACTACCAAGGAATCCAAGAGCATATGGGCTGCATCATACCTCCGAGGTGAAG

CAACCAAATGGATTCAACCATATTTGCGCGACTATTTCGAGCATGACGATAAGGATCGCATGCA

ACCCACCCGAACAATCTTCAATAGTTTTGAAGGATTTAAGACAGAGATTCGTAGAATCTTCGG

AAATTCCAACGAGTTAGAGGTAGCGGAAGATAAGATCTTCAACCTCAAGCAGACAGGATCAG

CATTGAAATATGCTACGGAATTTCGAAGATATGCTGGAACAACCAAGTGGGACGAAATCGCTA

TCATGAGTCACTACCGTAAGGGACTCAAACCAGAAGTCAGACTAGAGTTAGAAAGATCTGCC

GAGAGTACAGATCTGAACGATCTAATTCAGGACTCCATCGAATCAGATGATCGTCTCTATAGAT

ATCGACAAAGCCAAAGATCATACAAACCCCAAGGAAACCAAAAGCAAGGGCGTTACCGCAA

GAATGAGGGTAGACCACGTTACAATCCACAGAGATACGGAGACCCCATGGAACTAGACGCCA

CGCACTACACAAACGGGAACGATGACTCAGAAAAGAGACGAAGACGAGAAAACAACTTATG

CTTTGAATGTGGAAAAGCAGGGCACCGAGCAGTAGACTGCCGAAGCAAGAAGACAGGAGGA

AAAGGGGCAACTTCAAACCTAAGTTCGGCAAGGGCCAACTTAACGCCACCTTTGCCATCTC

AGAAAACTCAACTAAAACCGAAAATACTGAGACTTTCACCGTTGAGGAATTTCAGCAATTACT

-continued

```
AAAGGAATTACCACGAAATAAAGAGGGCATGAATGCAATAGACTTATGGGAACAAGAGTATTA
CAGAACCCCAACACCCTCTGTGACAGAAGAAAGTCACCAGGACGAGGCAGAAGCGGACCAC
GCCACGATGAGCTGGACAGCTTGCTATGATGAATTCTGCGGAATCCATCGATCAGATAAAGAA
GCAACCGGATGGTTCCCCAAGAAAAGGAAGACGAAGAACCATCAGAATAATGTAACATGCGA
GGATTTAACTCCCAATATAACTTCGCAAGAAGTTCGCAAAGTTACCCAGCAGTTGAATGCTAC
GGGACAGGCAGGACAAGTGTACTGCAAGGTCCAGATAAATGGACACATACAATCAGCCATGA
TAGATTCAGGGGCTACAGGAAATTTTATTGCACCAGAAGCTGCAAAGTACTTGGAAATACCAC
TTCAAACGAAACAACATCCCTACCGATTGCAGGACACGCTAGAGGCGTCCGCGAGACGTAAC
ACGCGCCAAGGGGAGTTGAACGCGAACAACACCGGCGACGTAGGACACCCAGTCCAGGGTC
CTCCATTAAGAGCGAAGGCCAGTACACCTCCTCTACAAATGCAGAAGCCAACGACACGGCAC
GAAATCGCAATCGAGGCAAAAGAAAGGCCTACGATACCAGAACAGTACAAGAAATATGAACA
TGTTTTCAAAGAACCAGGGATCCATGAGGCTTTACCGGAACACAAGCCATGGGATCATGAGAT
AATATTGGAGGAAGGCAAGATGCCTGTGCACACCCCAATTTATTCAATGTCAGCCGATGAGTT
AAAAAGGCTCAGAGAATACATCGACGACAATTTAGCCAAGGGATGGATCAGGGAATCCGCGT
CCCAAGTGGCCAGTCCAACTATGTGGGTACCCAAGAAGGATGGACCCGATAGACTAGTTGTA
GACTATAGAAAGCTTAACGCACTCACTAAGAAGGATCGATATCCACTTCCATTAGCTACGGAAT
TAAGAGATCGATTAGGCGGAGCTACGATATTCACCAAGATGGACCTACGTAATGGTTACCACTT
GATCAGAATGAAGGAAGGCGAAGAATGGAAAACCGCTTTCAAAACAAGATACGGGCTATACG
AGTACCAAGTTATGCCATTCGGGCTAACCAACGCACCAGCTACTTTCATGAGGCTTATGAACA
ATGTGTTGTCACAATATTTGGATACTTGCTATCAAGGAAGCTTCGAATGGACTGCCAAAGCAC
AGGAGTCATTCGATACGCTCAAGCAAGCAGTGGCAGAAGAACCAATACTGTT
GACTTTTGACCCAGAGAAAGAAATCATAGTGGAGACGGACTCCTCGGATTTCGCTATAGGAGC
AGTTCTGAGCCAACCGGGCCAGAATGGAAAATACCAGCCAATCGCATTCTACTCCCGAAAACT
ATCACCAGCTGAGTTAAATTACGAGATATATGACAAAGAATTACTGGCAATAGTCGATGCATTT
AGAGAATGGCGAGCATATTTGGAAGGATCGAAATACACAGTACAGGTATATACAGATCATAAG
AACTTGGTTTACTTCACCACAACGAAGCAGTTAAACAGACGACAGGTCAGATGGTCGGAGAC
CATGGCCAACTACAACTTTAGAATTTCATATGTCAAAGGATCAGAAAACGCTAGAGCCGACGC
TCTTAGCCGAAAACCAGAATATCAAGAAAACAAAACGTACGAGTCATACGCTATATTCAAGAA
AGACGGCGAATCACTGGTCTACAATGCACCACAGCTTGCAGCAACACACCTGTTGGAAGACA
ACCACCTCAGGAAACAGATCCAATCACACTACAACAAGGATGCTACTGCCACACGCATACGC
AAGACAATAGAACCAGGATTCACTATAGAAGATGATACCATATACTTTCATGGAAAAGTATAC
ATTCCGAGTCAAATGACCAAGGAATTTGTGACGGAACAACATGGGTTGCCGGCACACGGAC
ATCAAGGGATTGCAAGAACATTTGCAAGAATCCGGGAAATCAGTTACTTCCCACGAATGAGA
ACGATAGTTGAAGAAGTTGTTGGAAATTGTGACACCTGCATACGAAACAAGTCATCACGACAT
GCGCCGTATGGTCAGCTCCAGACCCCAGACATGCCTTCTCAGCCATGGAAGTCCATCACATGG
GACTTTGTGGTCAAACTACCACTCTCAAAGGATCCTACTACAGGAATTGAGTACGACGCGATA
CTCAATATAGTAGACAGGCTAACGAAATTTGCATATATGATACCATTCAAGGAAACATGGGATG
CTGAGCAACTAGCATATGTGTTCCTAAGGGTCATAGTAAGCATACACGGAGTACCAGATGAGA
TAATCTCGGATCGAGACAAGCTCTTTACCTCGAAATTCTGGACTACCTTATTAGCACTTATGGG
TATCAAGAGAAAGCTATCGACATCTTTCCACCCACAAACAGATGGTCAAACAGAGAGGACCA
```

ATCAGAC

AATGGAAGCATATCTTAGATGCTATCGTATAAAATCCCGATACCACAAGAAGTTAATGCCGAAT

CAGCAATAG

SEQ ID NO:25 - LTR for siR5
>BC1G_08449.1 retrotransposable element Tf2 1 protein type 1
(Transcript:BC1T_08449)

ATGGCATCCAGAGATACCGCCACAGGTCAATCTGCCGGAGACACCAACGACATCGAGATGAC

CGATGCCCCAAAGGAGATCACTATCAACGAAACCCTTAAGATCGCCTTACCAGACAAGTACCA

AGGTAGTCGACAAGAGCTCGATACTTTCCTCTTACAACTTGAGATCTACTTCCGATTCAATGAG

GACAAGTTCACTACCAAGGAATCCAAGAGTATATGGGCCGCATCATACCTCCGAGGTGAAGCA

ACCAAATGGATTCAACCATATTTGCGCGACTATTTCGAACATGACGATAAGAATCGCATGCAAC

CCACCCGAACAATCTTCAATAGTTTTGAAGGATTTAAGACAGAGATTCGTAGAATCTTCGGAA

ATTCCAACGAGTTAGAGGTAGCGGAAGATAAGATCTTCAACCTCAAGCAGACAGGATCAGCA

TTGAAATATGCTACGGAATTTCGAAGATATGCTGGAACAACCAAGTGGGACGAAATCGCTATC

ATGAGTCACTACCGCAAGGGACTCAAACCAGAAGTCAGACTGGAATTAGAAAGATCTGCCGA

GAGTACAGATCTGAACGATCTAATTCAGGACTCCATCGAATCAGATGATCGTCTCTACAGATAT

CGACAAAGCCAGAGATCATACAAACCCCAAGGAAATCAGAAGCAAGGGCGTTACCGCAAGA

ATGAGGGTAGACCACGTTACAATCCACAGAGGTACGGAGACCCAATGGAACTAGACGCTACG

CACTACACAAACGGGAACGATGACTCAGAAAAGAGACGAAGACGAGAAAACAACTTATGCT

TTGAATGTGGAAAAGCAGGGCACCGAGCAGCAGAGTGCCGAAGCAAGAAGACAGGAGGAA

AAAGGGGCAACTTCAAACCTAAGTTCGGCAAGGGCCAACTTAACGCCACCTTTGCAATCCCA

GAAAACCCAACTAAATCCGAAAATACTGAGACTTTCACCATTGAAGAATTCCAGCAATTACTA

GAGGAATTACCACGAAATCAAGAGGGCATGAATGCAATAGACTTATGGGAACAAGAGTATTAC

AGAACCCCAACACCCTCTGTAACAGAAGAAAGTCACCAGGACGAGGCAGAAGCAGACCACG

CCACAATGAGCTGGACAGCCTGCTATGATGAATTCTGCGGAATTCATCGATCAGATAAAGAAG

CAACCGGATGGTTCCCCAAGAAAAGGAAGACGAAGAACCATCAGAATAATGTAACATGCGAG

GATTTAACTCCCAATACAACTTCGCAAGAAGTTCGCAAAGTTACCCAGCAGTTGAATGCTACG

GGACAGGCAGGACAGATATACTGCAAAGTTCAGATAAATGGACACATACAATCAGCCATGATA

GATTCAGGGCTACAGGAAATTTTATTGCACCAGAAGCTGCAAAGTACTTGGAAATACCACTT

CAGACGAAACAACACCCCTACCGATTGCAGGACACGCTAGAGGCGTCCGCGAGACGTAACA

CGCGCCAAGGAGAGTTGAACGCGAACGACACCGGCGACGTAGGACACCCAGTCCAGGGTCC

TCCATTAAGAGCGAAGGCCAGTACACCTCCTCTACAAATGCAGAAGCCAACGACACGGCACG

AAATCGCAATCGAGGCAAAAGAAAAGCCTACGATACCAGAACAGTACAAGAATTATGAACAT

GTTTTCAAAGAACCAGGGATCCATGAGGCTTTACCGGAACACAAGCCATGGGATCATGAGATA

ATATTGGAGGAAGGCAAGATGCCTGTGCACACCCCAATTTATTCAATGTCAGCCGATGAGTTA

AAAAGGCTCAGAGAATACATCGACGACAATTTAGCCAAGGGATGGATCAGGGAATCCGCGTC

CCAAGTGGCCAGTCCAACTATGTGGGTACCCAAGAAGGATGGACCCGATAGACTAGTTGTAG

ACTATAGAAAGCTTAACGCACTCACTAAGAAGGATCGATATCCACTTCCATTAGCTACGGAATT

AAGAGATCGATTAGGCGGAGCTACGATATTTACCAAGATGGACCTACGTAATGGTTACCACTT

GATCAGAATGAAGGAAGGCGAAGAATGGAAAACCGCTTTCAAAACAAGATACGGGCTATACG

AGTACCAAGTTATGCCATTCGGGCTAACCAACGCACCAGCTACTTTCATGAGGCTTATGAACA

ATGTGTTGTCACAATATTTGGATACTTGCTGTATATGCTACTTGGACGACATCCTAGTATATTCA

AACAACAAGGTTCAACACATTAAGGACGTTAGCAACATCCTCGAAAGCCT

ATCCAAGGCAGACTTGCTGTGCAAACCAAGCAAATGCGAATTCCATGTCACAGAGACAGAAT

TCTTGGGATTCACCGTATCAAGCCAAGGGCTCAAGATGAGCAAAGGCAAGGTTAAGGCAGTG

CTCGAATGGAAGCAGCCGACCACAATCAAGGAAGTACAATCCTTTCTAGGGTTCGTCAACTTC

TACAGAAGATTTATCAAAGGTTATTCAGGGATTACTACACCCTTGACCACGTTAACCAGAAAA

GATCAAGGAAGCTTCGAATGGACTGCCAAAGCACAGGAGTCATTCGATACGCTCAAACAAGC

AGTGGCAGAAGAGCCAATACTATTGACTTTTGACCCAGAGAAAGAAATCATAGTGGAGACGG

ACTCCTCGGATTTCGCTATAGGAGCAGTTCTGAGCCAACCGGGTCAGAATGGAAAATACCAGC

CAATCGCATTCTACTCCCGAAAACTATCACCAGCCGAATTAAATTATGAAATATACGACAAAGA

ATTACTGGCAATAGTCGATGCATTTAGAGAATGGCGAGTATATTTGGAAGGATCGAAATACACA

GTACAGGTGTACACAGATCATAAGAACTTGGTTTACTTCACCACAACGAAGCAGTTAAACAG

ACGACAGGTCAGATGGTCGGAGACCATGGCCAACTACAATTTTAGAATTTCATATGTCAAAGG

ATCAGAAAACGCTAGAGCCGACGCTCTTAGCCGAAAACCAGAATATCAAGAAAACAAAACGT

ACGAGTCATACGCTATATTCAAGAAAGACGGCGAATCACTGGTTTACAATGCACCACAGCTTG

CAGCAACACACCTGTTGGAAGACAACCACCTCAGGAAACAGATCCAATCACACTACGACAA

GGATGCTACTGCCACACGCATACGCAAGACAATAGAACCAGGATTCACTATAGAAATGATAC

CATATACTTTCATGGAAAAGTATACATTCCGAGTCAAATGACCAAGGAATTTGTGACGGAAC

AACATGGGTTGCCGGCACATGGACATCAAGGAATTGCAAGGACATTTGCAAGAATACGGGGA

ATCAGTTACTTCCCACGAATGAGAACGATAGTTGAAGAAGTTGTTGGAAATTGTGACACCTGC

ATACGAAACAAGTCATCACGACATGCTCCGTATGGTCAGCTCCAGACCCCAGACATGCCTTCT

CAGCCATGGAAGTCCATCACATGGACTTTGTGATCAAACTACCACTCTCAAAGGATCCTACT

ACAGGAATTGAGTACGACGCGATACTCAATATAGTAGACAGGCTAACGAAATTTGCATATATGA

TACCATTCAAGGAAACATGGGATGCTGAGCAACTAGCATATGTGTTCCTAAGGGTCATAGTAA

GCATACACGGAGTACCAGATGAGATAATCTCGGATCGAGACAAGCTCTTTACCTCGAAATTCT

GGACTACCTTATTAGCACTTATGGGTATCAAGAGAAAGCTATCGACATCTTTCCACCCACAAAC

AGATGGTCAAACAGAGAGGACCAATCAGACAATGGAAGCATATCTTAGATGCTATCGTATAAA

ATCCCGATACCACAAGAAGTTAATGCCGAATCAGCGATAG

SEQ ID NO:26 - LTR for siR5
>BC1G_16170.1 hypothetical protein similar to integrase
(Transcript:BC1T_16170)

<u>ATG</u>ACCAAGGAATTTGTGACGGAACAACATGGGTTGCCGGCACACGGACATCAAGGGATTG

CAAGAACATTTGCAAGAATCCGGGAAATCAGTTACTTCCCACGAATGAGAACGATAGTTGA

AGAAGTTGTTGGAAATTGTACACACCTGCATACGAAACAAGTCATCACGACATGCGCCGTAT

GGTCXAGCTCCAGACCCCAGACATGCCTTCTCAGCCATGGAAGTCCATCACATGGACTTTGT

GGTCAAACTACCACTCTCAAAGGATCCTACTACAGGAATTGA

SEQ ID NO:27 - Botrytis LTR genomic DNA sequence
>B. cinerea (B05.10) Botrytis cinerea supercontig 1.56 [DNA] 215700-227000 +

CAAAGGGGGCATTACGCTTCCAACTGCCGAAACCCTGTTGTATGTCAACACTGTAAAGGA

AGTCACGGATCCAGAGAGTGCCCAGGAACTATGTCACAGCCTTCCCGACAGGGAAACGCT

TAGACCCAGCTGTTATTCTGAGCGTCCCACTGACGCTGGGTCCCCAAATAGAAGGACGTA

```
CTACCTTTACCATTATAGCAATGTTCCAACCAAAAGATAAGCCGATAGCGCTTCGATGCC

TTATCGACTCAGGAGCACAAGCCAACATCATCCAACAATCCAAGTGTATCGAATGGGACT

GGCTGCCTATTAAGAAAGGAACAGCTTTAGTATCTGCGAACGGTACCACGATGCCGTCGT

ATGGTAACCATCAGTTCCCCGTCGAAGTAAAAGATCAAAAGGGAGAGAAGAGAACCTTCA

CCCACGAGTTTACTGCTGCTGTACTAGACTTACCCAAAATCGATGCTATATTTGGATTAC

CCTGGCTACAAGCGGTAAACCCAGATATCGACTGGAAATCGACGTCTCTTCACTATCGCC

CCTCTCTTAGCGACCTCGAAATGATTTCTGCAAGCGAACTCTATAGCGAAGTGAAAAAGG

GCGTCCATGTATATGTTATACTACCAGAGATCCAGCCCCATTACCGTAGAGACAACGGGT

ACCGCCGGGTACTCACGCTCTCCACACTAAATATCCCCGAAGAATACCAAGAATACCAAC

AAGCCTTTTCCGAGGAAGAAAGCAGTACTCTACCAGAACACCACTCGATGGAGCATCGCA

TTGATCTCGAAGCCGATTCGAAACCTCCTTGGGGGCCAATCTATTCTTTATCTGAAGAGG

AATCAATAGTATTAAGGGAATACTTAGTAGAATATCAAAAAAAGGGATGGATAAGGAGGT

CCATTAGTTCGGCAGGAGCGCCAATCATGTTTGTTCCCAAGAAGGGGGAGGCTATCGGC

TTTGTGTCGACTACCGGGGTCTAAATAGGATAACCAAAAAGGATCGAACCCCGCTACCCC

TAATCAGCGAGTCCTTAGACCGACTTCGACAAGGTGTCGTCTTCACTAAATTGGACCTGC

GAGATGCCTACCACCGTATTCGTATCAGGGAAGGCGACGAATGGAAGACGGCGTTCCGCA

CGCGGTACGGGCAATTCGAATACTTAGTTATGCCATTCGGCCTGACCAATGCTCCAGCAA

CGTTCCAAACATACATCAATCAAGCACTGTCAGGCTTGACAGACACCATATGCGTAGTGT

ACCTAGATGATATCCTGATTTACTCTGAGGATAGAGAAAGCCACACGCGGGATGTCCGCA

GGGTCCTCGAACGCCTTATAGAATACAAGCTGTTCGCAAAACTGAAAAAATGTGTCTTTT

ACACCCATGAGGTTGAATTCCTAGGATTCGTCGTCTCGGGAGCGGGAGTGACGATGGAAT

CCAGCCGCATTCAAACTATTATAGAATGGCCAACACCTACAAACCTTAGGGAGCTACAGG

TGTTCCTGGGCTTCGCGAACTTCTATCGACGGTTTATCAGGACCTATTCGACGGTAGCCC

ACGGGATGACCGCCCTTATGAAGGGAACAAAGAAAGGTAAAATGGTAGGGGAGTTTATAT

GGACAAAGGAGGCCCAAGATGCATTTGAGGCACTAAAGAAAGCATTCACCACGGCACCGA

TACTCAAGCACTTCGAACCATCGCTCCGCATCATGGTCGAAACCGACTCGTCGGTGTTTG

CTCTAGGATGCATCCTATCGCAACTATTCGAAGGAGGGACTGCAGAAGCACCGATACGAC

GGTGGCACCCCGTCGCGTTCTATTCGAGAAAGCTGAACCCTGCAGAACAACGATACTTCA

CTCACGATCAGGAATTATTAGCAATATACACTGCATTCATGCAATGGCGCCATTACTTGA

TAGGTAGTCGGCACACAATCGTGGTGAAATCGGACCATAACAGCTTACAACATTTTATGG

TGAAAAAGACCCTCAATGGCAGACAAGCTAGATGGGCGGAAGTACTAGCAGCCTACGACT

TCGAAATAGTGTACAGGGCAGGGAAACTGAATCCAGCCGACGGGCCATCGCGCCGCCCG

ACTACGCTACCGACACGGAGGGTATCAATGATATGCTACCCACACTCCAGAATAAATTAA

AAAGTACCGCAGTTATCGCGAGTTTATTTTACGAATCCACCGTGAAAACGGAACCCCTGC

GTATTGCTATTAGTCGCTTGCAAAGGGAAGGGTATAGCTTGCCATTACGTGGACAGTTAG

TTTCACTGGTAAAAACTGGTTGCAAACAGTCGATACCACGTCGGATTGCCAGTGTTTTCG

CATCCGACGAAACGGCATTCGAACCTATATCGGAGTCGATGGGAAAAGCTTTATTGCGGC

TTCAGAAAGAAGACGATTTTATAAAGAATAAAGAGTACCTAAGACAAAGATTACGTTCCG

CCCGGAGACGCCTCACCACGGCAGGTGGGCGCCGACGAGCTCCTTAGACACAAGGGGAGCG

CGTACGTACCGCCAGACAGCGCTCTCAGAGCAGAAATCTTAGAAACGCATCACGATGACC
```

```
CTATTGGAGGTCATTGGGGTGTCGCTAAAACATTGGAAATACTGAAGTCTAAATATTATT

GGCCTTCAATGAGAAAAGACGTCAAACAACATGTCAAAACATGTGCGGTATGCCAGCGAA

CCGCTATCAAAAGACATAAGCCACACGGCGAGTTACAGACCCTCCCTATTCCAAAAGGAC

CCTGGAAAGAGATAACTATGGATTTTATTACAGATTTACCTCCTTCGAAACACGGAAAAC

ACGTATACGATTCTATTCTAGTAGTAGTCGACAGGTTCACGAAGCTAGCCCGATATATCG

CCGTCAACAAGACGATATCGTCTCCTGAATTAGCTGACACTATGGTCAGCACAGTATTTA

AAGACTTTGGTGTGCCAGAGGGCATAGTCTCCGATAGGGGACCGCAATTCGTCAGTAAAT

TTTGGAGTAGCCTAATGTTTTACTTGCGAATCCGTCGTAAGCTGTCGACGGCGTTCCACC

CGCAGACCGACGGTCAAACCGAACGACAAAACCAAAATTTGATTCACTATATAAGTTGCT

ACACCAACTATAGGCAAGACGACTGGGCATCGCTATTGCCCCTTGCTGAATTCACATATA

ACGCGACATGGCACAGTACAACCAATACAAGCCCATTCCAGGCTATGTATGGGTTCCAAC

CCACATTCCATTATATCGGCGAGGACGCCGATTTAGAGGGAAGGGCGCCGGCAGCACGCG

AGCGCATCGACGCTTTAGAGAAAGAAAGAGAAAAGCTGAAAGAATTCTGGAAATCGGCAA

CCAATCAGAAAAACAAGAACACTACGAAGGGGTCACCACAGCGATATAGCATCGGGGACA

AGGTGATGCTAAGCACAAAGAACATTAAACAACTGCGACCTAAGAAAAAATTCTCCGATC

GATTTATAGGCCCCTTTGTCGTGACGGGTATAAAAACCAGCGGGCAAGCATACGAACTTA

GATTACCGCCCACCTACAAGATCCACAATGTATTCCACGTCTCTTTACTCGAACCATGGC

ACGAACGACAGGGTACCGCCGACCCGCCGCCGCCAGAAGAAATTGACGATCACATAGAGC

ATGAGGTGGAAAGGATTTTAGCACATAGAAAAAGAGGCAGAGGTGTGCAATACCTGGTGC

GATGGAAGGGCTACCAACCGGCGGAAGACACGTGGGAAGCACCCTACAACCTAGAAAATG

CGAAAGCAGCGATGGGAGAATATCATAAAGAAGAAGCATTACCAATACAGAAAAAGAAGA

GAACAAGAAAAAAGCTTAAAAATACTTGATACAAAAAGACCTCACGAGACCCACACCCAG

AACGCATGCATCACACCAAGCTACCCAAAAAGGACTATCCAACAAAGAAACCAGAAAGGA
CAACTCCTCCGAACCCACAGCATACCGACAACCAAACCCAAGTGACCCATCACGCAAAGA

GAACTCTGGAAGGTCGAAATCAGTTCCCTAATTCATCTGCCTGATCCAGGAGGTCAGCTG

CAATATCTCGATCGCCAAGAAGGACAGAACCTACATCGCTGGCATATCCCCCGGGACTCG

CGAGCCCGATCTGATCAACCTCACCCCCCCCACTGATCTCATCTTGATCACCGACTCCTT

CCTCCTCGTTCTCGCGAATCTCGCTGACAGGGCGAGCTCCTGTCGGAAAACCAGCGGCAA

CCCGTTGCCTCTTGGAGACCCGCTCCACATCAGAATTCTCAGAGCGAAGCCTTTGGGGCG

AATCTGCTTGACTATCAGACTCACCAATATAGACTTGTTGAACAGTGCTGGGAGCCCTCT

TTCGGGATTTAAGAGAGCCTACGGGATGAGAGCGGGGTGTCGGTGTGTTGCGAGAGGCAA

GCTGCGACGACTTAGAAGCGGAAAGGGGAATGGCGGATCTAGTCGCGAGCTTATCGGACC

GAGAACGACGAGGCGTAGCAGGAGGAGCGTTCTTTCTACCCAAGCTTCCAAACAATAAAG

CCGGTACACTCTCATCCAAGGGGTGACGCGGGCACCGGTGGTCTGATGAGGTTGATCCG

ACACATCATCCTCTTCAGGAGCAGACTCTTCGGATTCATTGGGATCCACGATTACACTCC

TCTTCAACTTCGCAGAACCTTTCCGGAGGCCTTGCTGAGCCGTCGTGAAGACAGCGGGGC

CCGTCCGGCTCGATGAAGCAGAAGCATGACGGCGACCTAGGGAACCAGCTACCATATTCA

GGCCCTGGTTACCACCTGGGGGCCCCGGAGGAGCTTGAACACCCTGCAGTGCGTCGGCGA

CAGCGCGCACAGCGCGAGGGTGTATAACCGGAGCCATGAACTCCCCTTCTTCGTCCGAGT

TTAAGGCGGCGATTAATGGTGCAGTAGGAGCTGCGGCGGCGACGTCCAAGGCAGGCAGGT

TATTCTAAGAACCATCAAATCAGCTATCAACAGCACCAAGGGGCAAGAGCAGGGCAACCG
```

-continued

```
ACAACGAATCGATACGAATCCACAATGCGCTCCATAAGATCGCCAATTCTACTCAATTTG
GACACCAGAAGAAGAGTCAATTCCTCTGCGGACTGCGGTTTGTGAGTCCCCCCTTGTTTA
ACCTCTTTTCGAAGGAAAGCCTCCACTGCCTTGACGTATCGATTACACCGGCGAATCACC
ACCTCGGAGGCGTCCTCATCCTCTTGGCTATTATCCGGAGTAAGGCACCAAAAGGCATGA
GTCTGATATAAGAGGTTCACGTCGGGAACAAAGCGAGGAGGTATCGGGAGGCAGACTTTC
TTTTGTTTGCGACAATAACTACATTTAGCAGCAGGACCTTTATCAAAATGGCAAAATTCG
TCGTTAGAAGAGACGGCAATTCGCTTAGAACATCGAAGGCAAGTAGGGATAACTAACGCG
GAAGGGGCCGCTGCGGACCGATCAGCGATAGCAGCCGGAGCGATGGGTTGCAGTGCAGCC
ATCTTCGTATGAGTAAATAAGGGGGAATAATCTGATTGTGGGAGATATATCAGAGGCAAG
AAGACCCCCCTTATAGAACTATCGGTGATCTGCCGGTAAGGCGGTGAGGCGCGTAAGAAT
GCCGCCGTTTGCTTGTTTATTGTTTGTAATGCCTAAACAAGATTGGAATTGCTTTTGGAA
TGCGGCGCAGGGTCGGGCATGCAGCGACGCGACGACGCGACCCACATTCCGAGTAAACAA
TACGGAAGGAAGCAAACACTTCTCGGGACGCGAAGTGTAAAGAGAGGGGCTCTGTTACGG
GACAAAACGTGACCGGCTCAATTAGGCACGTGACAGTGGACCTCTCGGGTCTACTGCGTG
CCGAATGGGGCCCGCACACGTATAAATTGTATAATTTGCATAGTTATAGAAAAGCAATGA
AAAGTCTTGGTGCCACAATATACTAGTTGATTCATTTGTTACGGAGGTACCCGCACCGCA
ACATGGATTATAAGATAAACCTAAGGCCTTGGTGTTGGAACCTACGAAAACAGCACTGTA
GGGACAGTTGAATTAAAGGGTAACTAAAGATAGCAGTAACCGAATCAATAAGCAATGATT
AAAAGATAGGTACCTATCTTTTGTTGGCACCTACCCTACAGTAGGCACAGGAGGGATAGC
GGTTATAGGTTATCTAGTAAGCACAGGTTAGATAAGCAGTAGTATCATGTAGGTCACGGG
GCAAGTGTCACGTGATGGATAGACAGGATAGGCAGGCTATCCAGGCTATCCGTGGATAGA
CAGGATAGACAGTCTACCCAAGCTATCCAGACGAGAACGAAGGTCTATATAAGGGAATGG
GTTTCATTACAATGTAGAGCTTCGTGCTCAAGAACAATCATTAGTTTCATTACTATAGTT
ACGAGAATTGCAACCAGTTACAACCTTATTGAATTCCTACTTGAAGTCTAGTCTAAACCA
CCTCGAGAGATCTCTAGACACTTCCACGTGACCCTAGAGGCAGCTCCCGTAACACTTTGA
GCACCCTTTCTGCTTCAAGTACCGATTCGATAACCAACCGCTAATATGGCATCCAGAGCT
ACCGCCACAGGTCAGTCTACCGAAGATACCAACGACATCGAGATGACCGATGCCCCAAAG
GAGATCACTATCAACGAAACACTTAAGATCGCCTTACCAGACAAGTACCAAGGTAGTCGA
CAAGAGCTCGATACTTTCCTCTTACAACTTGAGATCTACTTCCGATTCAATGAAGACAAG
TTCACTACCAAGGAATCCAAGAGCATATGGGCTGCATCATACCTCCGAGGTGAAGCAACC
AAATGGATTCAACCATATTTGCGCGACTATTTCGAGCATGACGATAAGGATCGCATGCAA
CCCACCCGAACAATCTTCAATAGTTTTGAAGGATTTAAGACAGAGATTCGTAGAATCTTC
GGAAATTCCAACGAGTTAGAGGTAGCGGAAGATAAGATCTTCAACCTCAAGCAGACAGGA
TCAGCATTGAAATATGCTACGGAATTTCGAAGATATGCTGGAACAACCAAGTGGGACGAA
ATCGCTATCATGAGTCACTACTGTAAGGGACTCAAACCAGAAGTCAGACTAGAGTTAGAA
AGATCTGCCGAGAGTACAGATCTGAACGATCTAATTCAGGACTCCATCGAATCAGATGAT
CGTCTCTATAGATATCGACAAAGCCAAAGATCATACAAACCCCAAGGAAACCAAAAGCAA
GGGCGTTACCGCAAGAATGAGGGTAGACCACGTTACAATCCACAGAGATACGGAGACCCC
ATGGAACTAGACGCCACGCACTACACAAACGGGAACGATGACTCAGAAAAGAGACGAAGA
CGAGAAAACAACTTATGCTTTGAATGTGGAAAAGCAGGGCACCGAGCAGTAGACTGCCGA
```

```
AGCAAGAAGACAGGAGGAAAAAGGGGCAACTTCAAACCTAAGTTCGGCAAGGGCCAACTT

AACGCCACCTTTGCCATCTCAGAAAACTCAACTAAAACCGAAAATACTGAGACTTTCACC

GTTGAGGAATTTCAGCAATTACTAAAGGAATTACCACGAAATAAAGAGGGCATGAATGCA

ATAGACTTATGGGAACAAGAGTATTACAGAACCCCAACACCCTCTGTGACAGAAGAAAGT

CACCAGGACGAGGCAGAAGCGGACCACGCCACGATGAGCTGGACAGCTTGCTATGATGAA

TTCTGCGGAATCCATCGATCAGATAAAGAAGCAACCGGATGGTTCCCCAAGAAAAGGAAG

ACGAAGAACCATCAGAATAATGTAACATGCGAGGATTTAACTCCCAATATAACTTCGCAA

GAAGTTCGCAAAGTTACCCAGCAGTTGAATGCTACGGGACAGGCAGGACAAGTGTACTGC

AAGGTCCAGATAAATGGACACATACAATCAGCCATGATAGATTCAGGGGCTACAGGAAAT

TTTATTGCACCAGAAGCTGCAAAGTACTTGGAAATACCACTTCAAACGAAACAACACCCC

TATCGATTGCAGTTAGTTGATGGACAGCTAGCAGGGTCTGACGGAAAGATTTCGCAGGAG

ACAATCCCAGTACGAATGGGCATAACCCAACATACAGAGGTTATACAGCTTGACGTTGTG

CCATTGGGCCAACAACAGATCATCTTAGGAATGCCATGGTTGAAGGCACATAATCCGAAA

ATAGATTGGGCACAAGGAATTGTGACATTTGATCAGTGCAAAAGCGGTCACAGGGACACG

CTAGAGGCGTCCGCGAGACGTAACACGCGCCAAGGGGAGTTGAACGCGAACAACACCGGC

GACGTAGGACACCCAGTCCAGGGTCCTCCATTAAGAGCGAAGGCCAGTACACCTCCTCTA

CAAATGCAGAAGCCAACGACACGGCACGAAATCGCAATCGAGGCAAAAGAAAGGCCTACG

ATACCAGAACAGTACAAGAAATATGAACATGTTTTCAAAGAACCAGGGATCCATGAGGCT

TTACCGGAACACAAGCCATGGGATCATGAGATAATATTGGAGGAAGGCAAGATGCCTGTG

CACACCCCAATTTATTCAATGTCAGCCGATGAGTTAAAAAGGCTCAGAGAATACATCGAC

GACAATTTAGCCAAGGGATGGATCAGGGAATCCGCGTCCCAAGTGGCCAGTCCAACTATG

TGGGTACCCAAGAAGGATGGACCCGATAGACTAGTTGTAGACTATAGAAAGCTTAACGCA

CTCACTAAGAAGGATCGATATCCACTTCCATTAGCTACGGAATTAAGAGATCGATTAGGC

GGAGCTACGATATTCACCAAGATGGACCTACGTAATGGTTACCACTTGATCAGAATGAAG

GAAGGCGAAGAATGGAAAACCGCTTTCAAAACAAGATACGGGCTATACGAGTACCAAGTT

ATGCCATTCGGGCTAACCAACGCACCAGCTACTTTCATGAGGCTTATGAACAATGTGTTG

TCACAATATTTGGATACTTGCTGTATATGCTACTTGGACGACATCCTAGTATATTCAAAC

AACAAGGTTCAACACATTAAGGACGTTAGCAACATCCTCGAAAGTCTATCCAAAGCAGAC

TTGCTGTGCAAACCAAGCAAATGCGAATTCCATGTCACAGAAACAGAATTCTTGGGATTC

ACCGTATCAAGCCAAGGGCTCAAGATGAGCAAAGACAAGGTTAAGGCAGTGCTCGAATGG

AAGCAGCCAACCACAATCAAGGAGGTACAATCCTTTCTAGGGTTCGTCAACTTCTACAGA

AGATTTATCAAGGGTTATTCAGGGATTACTACACCCTTGACCACGTTAACCAGAAAAGAT

CAAGGAAGCTTCGAATGGACTGCCAAAGCACAGGAGTCATTCGATACACTCAAACAAGCA

GTGGCAGAAGAACCAATACTGTTGACTTTTGACCCAGAGAAAGAAATCATAGTGGAAACG

GATTCCTCAGATTTCGCTATAGGAGCAGTTCTGAGCCAACCGGGCCAGAATGGAAAATAC

CAGCCAATCGCATTCTACTCCCGAAAACTATCACCAGCTGAGTTAAATTACGAGATATAT

GACAAAGAATTACTGGCAATAGTCGATGCATTTAGAGAATGGCGAGTATATTTGGAAGGA

TCGAAATACACAGTACAGGTGTATACAGATCATAAGAACTTGGTTTACTTCACCACAACG

AAGCAGTTAAACAGACGACAGGTCAGATGGTCGGAGACCATGGCCAACTACAATTTCAGA
```

```
ATTTCATATGTCAAAGGATCAGAAAACGCTAGAGCCGACGCTCTTAGCCGAAAACCAGAA

TATCAAGAAAACAAAACGTACGAGTCATACGCTATATTCAAGAAAGACGGCGAATCACTG

GTCTACAATGCACCACAGCTTGCAGCAACACACCTGTTGGAAGACAACCACCTCAGGAAA

CAGATCCAATCACACTACAACAAGGATGCTACTGCCACACGCATACGCAAGACAATAGAA

CCAGGATTCACTATAGAAGATGATACCATATACTTTCATGGAAAAGTATACATTCCGAGT

CAAATGACCAAGGAATTTGTGACGGAACAACACGGATTGCCGGCACATGGACACCAAGGA

ATTGCAAGGACATTTGCAAGAATACGGGAAATCAGTTACTTCCCACGAATGAGAACGATA

GTTGAAGAAGTTGTTGGAAATTGTGACACCTGCATACGAAACAAGTCATCACGACATGCT

CCGTATGGTCAGCTCCAGACCCCAGACATGCCTTCTCAGCCATGGAAGTCCATCACATGG

GACTTTGTGGTCAAACTACCACTCTCAAAGGATCCTACTACAGGAATTGAGTACGACGCG

ATACTCAATATAGTAGACAGGCTAACGAAATTTGCATATATGATACCATTCAAGGAAACA

TGGGATGCTGAGCAACTAGCATATGTGTTCCTAAGGGTCATAGTAAGCATACACGGAGTA

CCAGATGAGATAATCTCGGATCGAGACAAGCTCTTTACCTCGAAATTCTGGACTACCTTA

TTAGCACTTATGGGTATCAAGAGAAAGCTATCGACATCTTTCCACCCACAAACAGATGGT

CAAACAGAGAGGACCAATCAGACAATGGAAGCATATCTTAGATGCTATGTAAATTATCGA

CAAGACAATTGGGTAGAGCTATTACCCATGGCACAGTTCGCATACAATACATCGGAAACG

GAAACCACGAAAATCACCCCAGCACGAGCTAATTTTGGGTTTAATCCACAAGCGTATAAA

ATCCCGATACCACAAGAAGTTAATGCCGAATCAGCAATAGTACAAGTCGAACAGCTGAAA

GATCTCCAAGAGCAACTGGCTCTTGATCTAAGATTCATATCTTCCAGAACAGCAGCGTAC

TACAATACGAAACGTAGTATGGAACCTACGCTTAAAGAGGGGATAAAGTTTATTTGCTA

CAACGAAACATCGAAACCAAGAGACCAAGCAATAAACTCGACCACAGGAAAATAGGACCA

TTCAAGATTGATAAGGTAATAGGAACGGTTAATTATCGATTGAAATTACCAGACACAATG

AATATCCACCCAGTATTCCACATATCCTTGCTCGAACCAGCACCACCAGGAGCGCCAAAT

GCGCCATTTACAGAAATCGAACCAGTCAACCCAAACGCCATATACGACGTTGAAACAATA

CTAGATTGTAAATATGTCAGGGGCAAAATCAAGTATTTGATCAAATGGTTAGACTACCCA

CATTCGGAAAACACATGGGAA

SEQ ID NO:28 - Botrytis DCL1 promoter sequence
>B. cinerea (B05.10) Botrytis cinerea supercontig 1.69 [DNA] 45790-46725 -

GAAGAGGTTGTTGGCAATATTTTGAAGAAAGCTGAGGCTGATTTGAATGGAGATTAAAAGG

GGAATGAAGCTGCGGGGCCACCGATAGCACAAAAACTACTGAAGATTTGAAGCACGTTAAA

ATTACACTCAGGAATAAACGGATGGCAAGCTTTTCGATCGCCCAAACACGGATCTACGACTA

CGAGTTACGCACGACATGATTTAGCCTTTTGTGTGCAATGATGATTAGATAGCATTGCATTTC

TCGAAATTGACGGCACGACTTTTACGGGCAGATAATATCAAAGATTCCTAGTGAGCAAGCG

GTGATGATACGATGTCATTCCAAAAGTTTTTTCCTCGCGAATTTTATTTCATTTCGAAGGCAT

CTTTGCTTAGCAGCATATTCACCTTTGATGTCCTCTGTAGGGGATGGAGTCTCTAATCTCGCG

GTCACAATGAGACGTGATGCGCTGCGAAGTGGTGACAATTTCCCTTTACTTAGAATAGATCA

TGCACACATGCATGATGCATAGCTAGCTAGTTTTTTATTCAATGATAGTTTAATGACAAACA

CGTATCTAGATATCCTCATTCATGTATCTGTGGGAGGTTGACTTAAGTTATGGCTGACTTGAT

AGTTTCATTATATATGTATATGTGATATCTAAGTAAAGATTAAAGTGAAATCGAAATGCAAC

GCCGAAATTCTATTAATTCCATGAAATGATGTGATATGGCATGACATGATATCCAAACTCCG

ATTTGAAATGCTCCAGCTTCGCTTTCTAAAATTGGTAAAAGGGACATTATTTCGTCTGGTTGT
```

```
GGGTTTTCATTTCTGTGCTCCTACTAGGTGTGAATGATAGAGTATGCTGTGGTGTGGTGTGAT

CTCGGAATTTGGAAATTTGAGGGCTGTATATCACCTCATTTCGTGTGTCCGAATTTCTACAGA

CT
```

SEQ ID NO:29 - Botrytis DCL2 promoter sequence
>B. cinerea (B05.10) Botrytis cinerea supercontig 1.78 [DNA] 26792-27461 -

```
AGAGCATTTGTAGGGGAAGGAGGAAAAATTGAGGAGGAGGATAAGATGAATTTTGATAAAT

TTATTTCCTAACATCAGGTCACAATCTATGAATTACATTTGATAGTATTACGTATGCCGGTCT

GTACACAACACAACCATATAGTAAGGTATCAATCAAATGCGATGGATAGTCATTTCAATTTC

TTAGTGAATAATTACAACGAACCAGTAAAATAGCAATAACTCTGAAAAGCTTCCGGACTGCC

AAAAGGTCTCCAGGACGAGATTATTACGAAGAACCCAAGAATTCGCCTAGGAACCAAGATA

AACAAATCATCGACGTGTTGCACTTCCATCTATGCGACAATTATGCCAAGCGAGCCGCCAGT

TCTTGGGGGTGGAGCGCTAGGAATAGGGGGCCGGATTGCCATATCCTTATCTAGATCTAGAT

GGTATCGATATGATAAATCAATGCAATGGAGAGTTAAAAAGTTATATGCCATATGATTGATA

ATTATTGACAATGCAGGCTATCGCGGGACAATGGTAAATGGTTGTAAAATATGGAGTCTATT

TCCTTAGCTAGCGATAAGATGGGTGGTTTAAACACATCCCGCCTTCTCTTTATCATTCTCCTT

CTCGTATTCATATATCATAATTGCAAAGTAAGGTTGTATTTTGGACTGTG
```

SEQ ID NO:30 - Verticillium DCL1 promoter sequence
>V. dahliae VdLs.17 supercontl.1 of Verticillium dahliae (VdLs.17) [DNA]
1574620-1574964 -

```
AAGCTGTCAATTGATGCGGAGGGTGAGTGAACGTCTCGTCGGCGGGCCCCTTGAGGCGAG

CGCCCGTTGGGGGGTGTTGTGGCACTAGGTTCTCTAGGCCGGCGGTGACTTTCATTACTATAT

TAGAAGCAAATACGGCGCCTTCATCACAATAATAAATATCGATCTCGAGTCGATTCCAGACC

CGTTATAAACCTATGTCTGTGCAACCAGTTGGGTGCTAATTTCTTGCATTATCATCATGGATG

TTGTCTATTTGAGTCTCAGGTCCAGCTGGTGCTTATAGGTCATCTCCAGTATGCGACTACCTC

TCTCCCTCTTTGCCATTCCTAACTGATTCTAAC
```

SEQ ID NO:31 - Verticillium DCL2 promoter sequence
>V. dahliae VdLs.17 supercontl.15 of Verticillium dahliae (VdLs.17) [DNA]
194566-195565 +

```
CTTCATCTTCCAACCGCCATTACCTCCCCCATACGCGTCCTGCCAAAGAATCATAACTGGCTA

AAACATAAGACGGGACTGGTCATCCGCTGAACCATTCCGAGCTATGTGTCCTGATTGACCCA

TCTCGGCTTATTCGCTCTCAAATACGACTGCAATCGCGTGTGGCTTGGAAACCGTGGAATAC

CATCCTCATATTGTCAGCACCTGTAGCGATACAGCACAATGCTTGACGATTCGGAATCATTTT

CCGCTTCTTTGCGGAGCAGCGGATGTCCAATTGACGATGACTTGACTCCAGAACCAACGTCC

GAATCACGCGACTCAACCTCCCTACCGTATGGCCTTCAGGACGACATCGGCCCCCTTGCTGC

CACCCCGAGCCAGTCGAGTAACGTCACAATCAATGCACGGGCATACCAGTTGGAGATGCTG

GCGGAAAGTAGGAAGAGGAATATCATTCTAGCTGTGCGAACCTTCCCTCTTGCGCCAGTCAA

CCTCGATTGACACCTCCATAGATGGACACAGGCAGTGGCAAGACCCAAGTGTACGTTCCCTG

CAAGCCGAACCTGATTATTGATACTGATTTTCCCAGTGCCGTCCTCCGAATTCGAGCAGAGC

TAGAAGAAGGGGCTTCAGACAAGGTTTGACAAACTCCACTTGGTAGCTTCGCAATCACTTAC

AGGGTTTTAGCTTGTATGGTTCGTGGCTCACAATGTTGAGCTTTGCGCTCAGCAGCATTCTGT

ACTGCAGTCTCAGATTCCTGCAGTTCAGACCAAGCTGCTTCTTGGCAGCGATAATGTTGATTC

ATGGTCCAACCAAGAGACTTGGAACGCTGTGCTTCTCAACGTCAAAATTGTGGTGTCAACCC
```

-continued

CTCAAGTTCTCTGCGATGCCTTGAGCCACGGCTTTGTCCAGATGGGTTCATTATCCTTGCTTG

TCTTTGATGAAGGTATTCAATCAGCGCAGTTTATCAAGTGTTCTTGCCCTAACAACGGTGTAG

CGC

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pathogen-resistant plant comprising:
a heterologous expression cassette, the expression cassette comprising a promoter operably linked to a first polynucleotide that encodes a first inhibitory RNA that targets a first fungal pathogen dicer-like (DCL) gene and a second polynucleotide that encodes a second inhibitory RNA that targets a second DCL gene of the same fungal pathogen, wherein the fungal pathogen is *Botrytis* or *Verticillium*, and wherein the plant has increased resistance to the fungal pathogen compared to a control plant lacking the expression cassette.

2. The pathogen-resistant plant of claim 1, wherein the pathogen is *Botrytis cinerea* or *Verticillium dahliae*.

3. The pathogen-resistant plant of claim 1, wherein the plant is a vegetable- or fruit-producing plant.

4. The pathogen-resistant plant of claim 1, wherein the plant is an ornamental plant.

5. The pathogen-resistant plant of claim 1, wherein the first inhibitory RNA targets the sequence of SEQ ID NO:9 and the second inhibitory RNA targets the sequence of SEQ ID NO:10.

6. The pathogen-resistant plant of claim 1, wherein the first inhibitory RNA targets the sequence of SEQ ID NO:11 and the second inhibitory RNA targets the sequence of SEQ ID NO:12.

7. A method of making a pathogen-resistant plant of claim 1, the method comprising introducing the expression cassette into a plurality of plants; and selecting a plant comprising the expression cassette.

8. An isolated nucleic acid comprising the expression cassette of claim 1.

9. A host cell comprising the nucleic acid of claim 8.

10. A method of making a pathogen-resistant plant, the method comprising:

introducing a construct into a plant, wherein the construct comprises a promoter operably linked to a first polynucleotide that encodes a first inhibitory RNA that targets a first fungal pathogen dicer-like (DCL) gene and a second polynucleotide that encodes a second inhibitory RNA that targets a second DCL gene of the same fungal pathogen, wherein the fungal pathogen is *Botrytis* or *Verticillium*, and wherein the plant has increased resistance to the fungal pathogen compared to a control plant that has not been contacted with the construct.

11. The method of claim 10, wherein the pathogen is *Botrytis cinerea* or *Verticillium dahliae*.

12. The method of claim 10, wherein the plant is a vegetable- or fruit-producing plant.

13. The method of claim 10, wherein the plant is an ornamental plant.

14. The method of claim 10, wherein the first inhibitory RNA targets the sequence of SEQ ID NO:9 and the second inhibitory RNA targets the sequence of SEQ ID NO:10.

15. The method of claim 10, wherein the first inhibitory RNA targets the sequence of SEQ ID NO:11 and the second inhibitory RNA targets the sequence of SEQ ID NO:12.

16. A method of increasing pathogen resistance in a plant, the method comprising:

contacting the plant with a mixture of double-stranded RNAs or small RNA duplexes that target fungal pathogen dicer-like (DCL) genes of *Botrytis* or *Verticillium*, wherein the plant has increased resistance to the fungal pathogen compared to a control plant that has not been contacted with the mixture.

17. The method of claim 16, wherein the pathogen is *Botrytis cinerea* or *Verticillium dahliae*.

18. The method of claim 16, wherein the mixture comprises small RNA duplexes.

19. The method of claim 16, wherein the mixture is sprayed onto the plant.

20. The pathogen-resistant plant of claim 1, wherein the plant is a species of the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, or *Zea*.

21. A plant part from the pathogen-resistant plant of claim 1, wherein the plant part comprises the heterologous expression cassette.

\* \* \* \* \*